US010854104B2

(12) United States Patent
Mettler May

(10) Patent No.: US 10,854,104 B2
(45) Date of Patent: Dec. 1, 2020

(54) SYSTEM FOR MOVEMENT SKILL ANALYSIS AND SKILL AUGMENTATION AND CUEING

(71) Applicant: ICUEMOTION, LLC, Minneapolis, MN (US)

(72) Inventor: Berenice Mettler May, San Francisco, CA (US)

(73) Assignee: iCueMotion LLC, San Francisco, CA (US)

(*) Notice: Subject to any disclaimer, the term of this patent is extended or adjusted under 35 U.S.C. 154(b) by 0 days.

(21) Appl. No.: 15/247,622

(22) Filed: Aug. 25, 2016

(65) Prior Publication Data

US 2017/0061817 A1 Mar. 2, 2017

Related U.S. Application Data

(60) Provisional application No. 62/211,281, filed on Aug. 28, 2015.

(51) Int. Cl.
*G09B 19/00* (2006.01)
*A61B 5/11* (2006.01)
(Continued)

(52) U.S. Cl.
CPC .......... *G09B 19/003* (2013.01); *A61B 5/1123* (2013.01); *A61B 5/1124* (2013.01);
(Continued)

(58) Field of Classification Search
CPC ............ A63B 24/0003; A63B 2220/62; A63B 2220/20; G09B 19/003; G09B 19/0015;
(Continued)

(56) References Cited

U.S. PATENT DOCUMENTS 4,257,594 A 3/1981 Conrey et al.
4,303,241 A 12/1981 Burroughs
(Continued)

FOREIGN PATENT DOCUMENTS

CN 104107134 A 10/2014
CN 104225890 A 12/2014
(Continued)

OTHER PUBLICATIONS

Communication Pursuant to Article 94(3) EPC dated Feb. 1, 2016 in connection with European Patent Application No. 12827395.0, 7 pages.

(Continued)

*Primary Examiner* — Malina D. Blaise
(74) *Attorney, Agent, or Firm* — Dorsey & Whitney LLP

(57) ABSTRACT

A cue processor uses one or more sensors to obtain motion data for a user performing a physical task in an environment. A cueing law is based on a model determined from the motion data, for example a movement and skill model where the collected motion data are parsed into one or more movement units used to accomplish a range of outcomes. The cue processor generates a movement phase estimation to predict a movement phase and associated movement feature, and applies the cueing law to generate a cue signal. The cue signal is communicated to the user as a visual, audio or haptic stimulus, selected to target the feature for the user to achieve or improve a desired outcome.

43 Claims, 35 Drawing Sheets

(51) Int. Cl.
*A61B 5/00* (2006.01)
*A61B 5/0488* (2006.01)

(52) U.S. Cl.
CPC ............ *A61B 5/1128* (2013.01); *A61B 5/486* (2013.01); *A61B 5/742* (2013.01); *A61B 5/7405* (2013.01); *A61B 5/7455* (2013.01); *G09B 19/0015* (2013.01); *A61B 5/0077* (2013.01); *A61B 5/0488* (2013.01); *A61B 5/1107* (2013.01); *A61B 5/1122* (2013.01); *A61B 2503/10* (2013.01)

(58) Field of Classification Search
CPC ... A61B 5/1123; A61B 5/1124; A61B 5/1128; A61B 5/486; A61B 5/7405; A61B 5/742; A61B 5/7455; A61B 5/0077; A61B 5/0488; A61B 5/1107; A61B 5/1122; A61B 2503/10
See application file for complete search history.

(56) References Cited

U.S. PATENT DOCUMENTS

| | | | |
|---|---|---|---|
| 4,508,510 | A | 4/1985 | Clifford |
| 5,031,909 | A | 7/1991 | Pecker |
| 5,154,427 | A | 10/1992 | Harlan et al. |
| 5,226,650 | A | 7/1993 | Suttner |
| 5,368,042 | A | 11/1994 | O'Neal et al. |
| 5,419,562 | A | 5/1995 | Cromarty |
| 5,610,590 | A | 3/1997 | Johnson et al. |
| 5,646,911 | A | 7/1997 | Davis |
| 5,694,340 | A | 12/1997 | Kim |
| 6,032,530 | A | 3/2000 | Hock |
| 6,219,032 | B1 | 4/2001 | Rosenberg et al. |
| 6,224,493 | B1 | 5/2001 | Lee et al. |
| 6,314,339 | B1 | 11/2001 | Rastegar et al. |
| 6,565,449 | B2 | 5/2003 | Buhler |
| 6,649,905 | B2 | 11/2003 | Grenlund |
| 7,021,140 | B2 | 4/2006 | Perkins |
| 7,160,200 | B2 | 1/2007 | Grober |
| 7,264,554 | B2 | 9/2007 | Bentley |
| 7,536,033 | B2 | 5/2009 | Kirby |
| 7,602,301 | B1 | 10/2009 | Stirling et al. |
| 7,891,666 | B2 | 2/2011 | Kuenzler et al. |
| 8,282,487 | B2 | 10/2012 | Wilson et al. |
| 8,323,107 | B2 | 12/2012 | Amit |
| 8,337,335 | B2 | 12/2012 | Dugan |
| 8,360,904 | B2 | 1/2013 | Oleson et al. |
| 8,556,267 | B2 | 10/2013 | Gobush |
| 8,589,114 | B2 | 11/2013 | Papadourakis |
| 8,602,922 | B2 | 12/2013 | Schwenger et al. |
| 8,622,795 | B2 | 1/2014 | Edis et al. |
| 8,831,905 | B2 | 9/2014 | Papadourakis |
| 8,903,521 | B2 | 12/2014 | Goree et al. |
| 8,905,855 | B2 | 12/2014 | Fitzpatrick et al. |
| 8,941,723 | B2 | 1/2015 | Bentley et al. |
| 8,944,928 | B2 | 2/2015 | Kaps et al. |
| 8,944,940 | B2 | 2/2015 | Mettler |
| 8,956,238 | B2 | 2/2015 | Boyd et al. |
| 8,989,441 | B2 | 3/2015 | Han et al. |
| 8,994,826 | B2 | 3/2015 | Bentley |
| 9,039,527 | B2 | 5/2015 | Bentley et al. |
| 9,656,122 | B2 | 5/2017 | Papadourakis |
| 9,694,267 | B1 | 7/2017 | Thornbrue et al. |
| 9,901,776 | B2* | 2/2018 | Mettler ............ A63B 24/0003 |
| 2001/0049890 | A1 | 12/2001 | Hirsch et al. |
| 2002/0077189 | A1 | 6/2002 | Tuer et al. |
| 2002/0107077 | A1 | 8/2002 | Buhler |
| 2002/0134153 | A1 | 9/2002 | Grenlund |
| 2003/0024311 | A1 | 2/2003 | Perkins |
| 2004/0243261 | A1 | 12/2004 | King |
| 2004/0259651 | A1 | 12/2004 | Storek |
| 2005/0017454 | A1 | 1/2005 | Endo et al. |
| 2005/0054457 | A1 | 3/2005 | Eyestone et al. |
| 2005/0196737 | A1 | 9/2005 | Mann |
| 2005/0227775 | A1 | 10/2005 | Cassady et al. |
| 2005/0261073 | A1 | 11/2005 | Farrington, Jr. et al. |
| 2006/0025229 | A1* | 2/2006 | Mahajan ............ A63B 24/0003 473/131 |
| 2006/0052173 | A1 | 3/2006 | Telford |
| 2006/0166737 | A1 | 7/2006 | Bentley |
| 2006/0166738 | A1 | 7/2006 | Eyestone et al. |
| 2006/0184336 | A1 | 8/2006 | Kolen |
| 2006/0277466 | A1 | 12/2006 | Anderson |
| 2007/0015611 | A1* | 1/2007 | Noble ................ A61B 5/1122 473/450 |
| 2007/0105664 | A1 | 5/2007 | Scheinert et al. |
| 2007/0111811 | A1 | 5/2007 | Grober |
| 2007/0135225 | A1* | 6/2007 | Nieminen .......... A63B 24/0006 473/212 |
| 2007/0207873 | A1 | 9/2007 | Rose |
| 2007/0265105 | A1 | 11/2007 | Barton et al. |
| 2008/0085778 | A1 | 4/2008 | Dugan |
| 2008/0200287 | A1* | 8/2008 | Marty ................ A63B 24/0003 473/459 |
| 2008/0312010 | A1* | 12/2008 | Marty ................ A63B 24/0003 473/447 |
| 2009/0143926 | A1 | 6/2009 | Almalki et al. |
| 2009/0209358 | A1 | 8/2009 | Niegowski |
| 2009/0210078 | A1 | 8/2009 | Crowley |
| 2010/0093463 | A1 | 4/2010 | Davenport et al. |
| 2010/0121228 | A1 | 5/2010 | Stirling et al. |
| 2010/0144414 | A1 | 6/2010 | Edis et al. |
| 2010/0173276 | A1 | 7/2010 | Vasin |
| 2010/0184564 | A1 | 7/2010 | Molyneux et al. |
| 2010/0323794 | A1 | 12/2010 | Su |
| 2011/0021280 | A1 | 1/2011 | Boroda et al. |
| 2011/0054290 | A1 | 3/2011 | Derchak |
| 2011/0143319 | A1 | 6/2011 | Bennett et al. |
| 2011/0183787 | A1 | 7/2011 | Schwenger et al. |
| 2011/0184225 | A1 | 7/2011 | Whitall et al. |
| 2011/0202152 | A1 | 8/2011 | Barton et al. |
| 2011/0230265 | A1 | 9/2011 | Amit |
| 2011/0230274 | A1 | 9/2011 | Lafortune et al. |
| 2012/0029666 | A1 | 2/2012 | Crowley et al. |
| 2012/0046119 | A1 | 2/2012 | Davenport |
| 2012/0050529 | A1* | 3/2012 | Bentley ................ G01S 19/19 348/139 |
| 2012/0052973 | A1 | 3/2012 | Bentley |
| 2012/0059297 | A1 | 3/2012 | Bentley |
| 2012/0136464 | A1 | 5/2012 | Saito et al. |
| 2012/0157241 | A1 | 6/2012 | Nomura et al. |
| 2012/0189996 | A1 | 7/2012 | Hager et al. |
| 2012/0236030 | A1* | 9/2012 | Border ............... G02B 27/0093 345/633 |
| 2013/0018493 | A1 | 1/2013 | Amini |
| 2013/0018494 | A1* | 1/2013 | Amini ................ A63B 24/0006 700/91 |
| 2013/0053190 | A1* | 2/2013 | Mettler ............ G09B 19/0038 473/463 |
| 2013/0095939 | A1 | 4/2013 | Meadows et al. |
| 2013/0095962 | A1 | 4/2013 | Yamamoto et al. |
| 2013/0128022 | A1* | 5/2013 | Bose ...................... H04N 7/18 348/77 |
| 2013/0266918 | A1* | 10/2013 | Tinjust ............... A63B 71/0622 434/247 |
| 2013/0267339 | A1 | 10/2013 | Boyd et al. |
| 2013/0302768 | A1 | 11/2013 | Webb |
| 2014/0031703 | A1 | 1/2014 | Rayner et al. |
| 2014/0047457 | A1 | 2/2014 | Nojima |
| 2014/0278219 | A1* | 9/2014 | Canavan ............ A63B 24/0062 702/150 |
| 2015/0019135 | A1 | 1/2015 | Kacyvenski et al. |
| 2015/0057111 | A1 | 2/2015 | Tremblay-munger et al. |
| 2015/0104768 | A1 | 4/2015 | Clark |
| 2015/0112464 | A1 | 4/2015 | Crowley et al. |
| 2015/0120021 | A1* | 4/2015 | Kerhuel ................ A63B 69/38 700/91 |
| 2015/0141178 | A1 | 5/2015 | Mettler |
| 2015/0196803 | A1 | 7/2015 | Shavit et al. |
| 2015/0317910 | A1* | 11/2015 | Daniels ................ G09B 21/00 84/485 R |
| 2016/0027325 | A1 | 1/2016 | Malhotra |

(56) References Cited

U.S. PATENT DOCUMENTS

| | | | |
|---|---|---|---|
| 2016/0086500 | A1 | 3/2016 | Kaleal |
| 2016/0303426 | A1 | 10/2016 | Martikka et al. |
| 2016/0361593 | A1 | 12/2016 | Elliott |
| 2017/0004358 | A1 | 1/2017 | Bose et al. |
| 2017/0011527 | A1 | 1/2017 | Matsunaga et al. |
| 2017/0021259 | A1* | 1/2017 | Dismuke ............... A63B 69/36 |
| 2017/0061817 | A1 | 3/2017 | Mettler May |
| 2017/0225033 | A1 | 8/2017 | Czaja |
| 2017/0232324 | A1* | 8/2017 | Mettler May .......... A63B 71/06 473/459 |
| 2018/0001173 | A1 | 1/2018 | Cupa |
| 2018/0229078 | A1 | 8/2018 | Mettler |
| 2019/0009133 | A1 | 1/2019 | Mettler May |
| 2019/0111327 | A1 | 4/2019 | Mochizuki |
| 2019/0126126 | A1 | 5/2019 | Knab |

FOREIGN PATENT DOCUMENTS

| | | | |
|---|---|---|---|
| EP | 2752224 | A1 | 7/2014 |
| FR | 2829700 | A1 | 3/2003 |
| RU | 2364436 | C2 | 8/2009 |
| WO | WO2006/004908 | A2 | 1/2006 |
| WO | 2009043558 | A1 | 4/2009 |
| WO | WO2011/036567 | A2 | 3/2011 |
| WO | 2015123474 | A1 | 8/2015 |
| WO | WO2016/025460 | A1 | 2/2016 |
| WO | 2017040242 | A1 | 3/2017 |

OTHER PUBLICATIONS

Extended European Search Report dated Apr. 21, 2015 in connection with European Patent Application No. 12827395.0, 6 pages.

International Search Report and Written Opinion dated Nov. 11, 2015 in connection with International Patent Application No. PCT/US2015/044620, 12 pages.

Extended European Search Report dated Nov. 29, 2017 in connection with European Patent Application No. 15831843.6, 10 pages.

International Search Report and Written Opinion dated Dec. 1, 2016 in connection with International Patent Application No. PCt/US2016/048871, 16 pages.

Abernathy et al., "Expertise and the perception of kinematic and situational probability information" Abstract, Perception, 2001; 30(2): 233-252.

Bernardi et al., "Mental practice promotes motor anticipation: evidence for skilled music performance" Abstract, Frontiers in Human Neuroscience, 2013; 7:451.

Bernstein, "The Co-ordination and Regulation of Movements", Science, Jan. 26, 1968: vol. 159, Issue 3813, p. 415.

Gibson, "The Ecological Approach to Visual Perception: Classic Edition" Introduction, Psychology Press, 1986.

Kugler et al., Information, natural law, and the self-assembly of rhythmic movement Abstract, Hillsdale, N.J., NJ Erlbaum Associates, (1987).

Landlinger et al., "Key factors and timing patterns in the tennis forehand of different skill levels", J. Sports Sc. & Med., 9(4): 643 (2010).

Lee et al., "Sensory and intrinsic coordination of movement", Royal Soc. of London, pp. 2029-2035 (1999).

Posner, "Orienting of Attention", The Quarterly Journal of Experimental Psychology, 1980, 32:3-35.

Warren, "The Dynamics of Perception and Action", Psychological Review, (2006), vol. 113, No. 2, pp. 358-389.

Williams et al., "Anticipation skill in a real-world task: Measurement, raining, and transfer in tennis" Abstract, Journal of Experimental Psychology: Applied, vol. 8(4), Dec. 2002, pp. 259-270.

Extended European Search Report dated Jun. 21, 2018 in connection with European Patent Application No. 18173631.5, 4 pages.

Office Action dated Jul. 25, 2019 in connection with Chinese Patent Application No. 2016800641099, 17 pages including English translation.

Decision Denying Institution of Inter Partes Review; IPR2016-00675, U.S. Pat. No. 8,941,723. 16 pages, Aug. 14, 2017.

Final Written Decision of Inter Partes Review; IPR2016-00676, U.S. Pat. No. 8,905,855. 38 pages, Aug. 14, 2017.

Final Written Decision of Inter Partes Review; IPR2016-00677, U.S. Pat. No. 8,944,928. 30 pages, Aug. 14, 2017.

Decision Denying Institution of Inter Partes Review; IPR2016-00672, U.S. Pat. No. 8,903,521. 20 pages, Aug. 29, 2016.

Decision Denying Institution of Inter Partes Review; IPR2016-00674, U.S. Pat. No. 9,039,527. 11 pages, Aug. 29, 2016.

Otto, et al. "System Architecture of a Wireless Body Area Sensor Network for Ubiquitous Health Monitoring," Journal of Mobile Multimedia, vol. 1, No. 4, 2006, pp. 307-326.

Decision Denying Request for Rehearing; IPR20198-00537, U.S. Pat. No. 8,831,905. 8 pages, Oct. 7, 2019.

Decision Denying Petitioner's Request for Rehearing of Decision Denying Institution of Inter Partes Review; IPR2019-00538, U.S. Pat. No. 8,589,114. 12 pages, Oct. 10, 2019.

Decision Denying Petitioner's Request for Rehearing of Decision Denying Institution of Inter Partes Review; IPR2019-00536, U.S. Pat. No. 9,656,122. 14 pages, Oct. 24, 2019.

Extended European Search Report dated Apr. 8, 2019 in connection with European Patent Application No. 16842664.1, 13 pages.

International Search Report and Written Opinion dated Nov. 20, 2018 in connection with International Patent Application No. PCT/US2018/041118, 12 pages.

Communication pursuant to Article 94(3) EPC dated May 22, 2019 in connection with European Patent Application No. 15831843.6, 6 pages.

Second Office Action dated May 19, 2020 in connection with Chinese Patent Application No. 2016800641099, 23 pages including English translation.

* cited by examiner

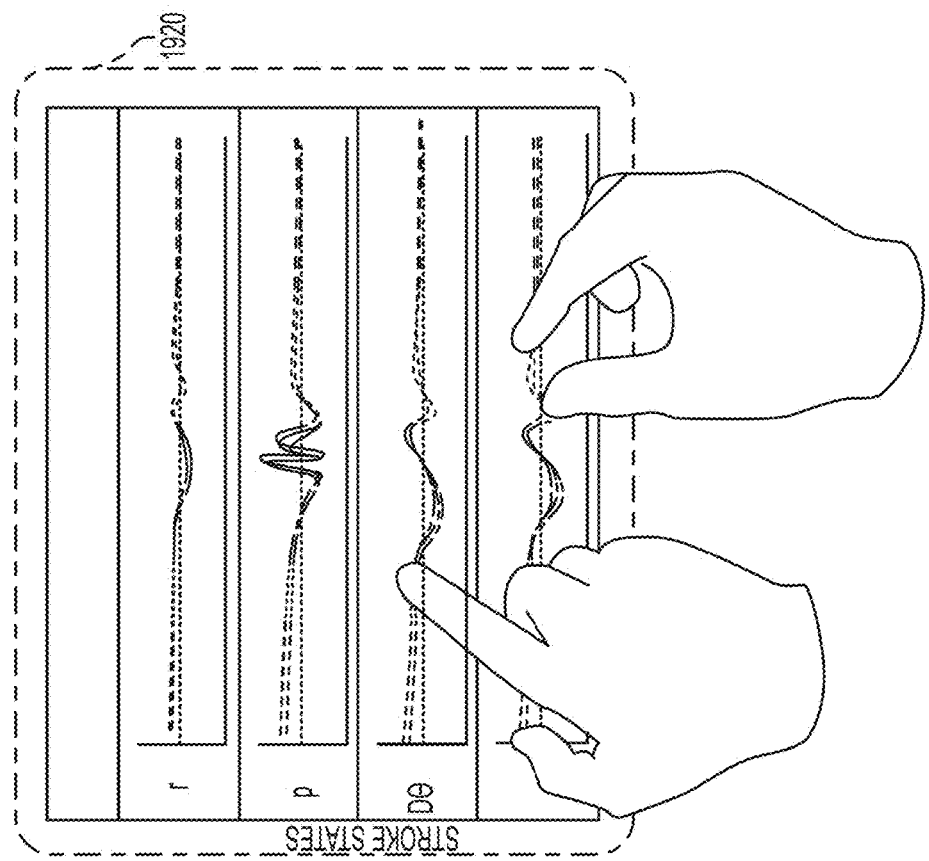
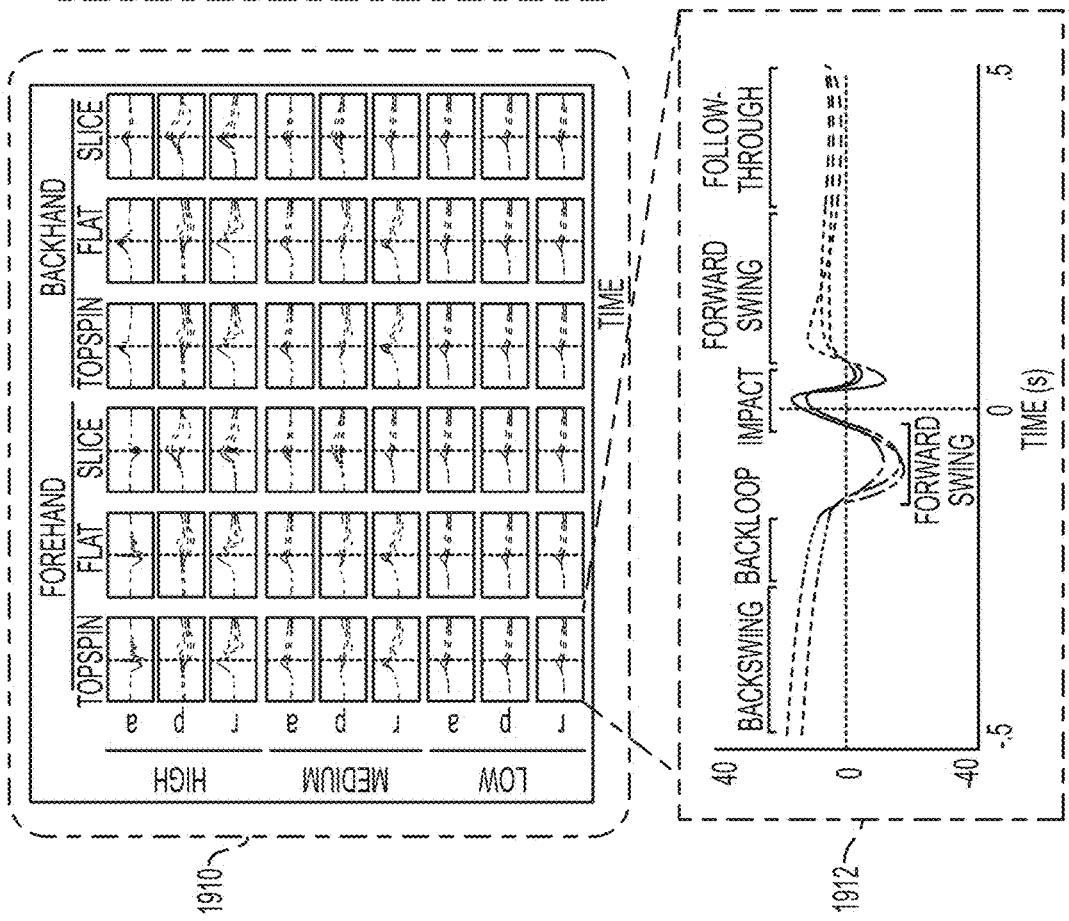
FIG. 19A
FIG. 19B

SYSTEM FOR MOVEMENT SKILL ANALYSIS AND SKILL AUGMENTATION AND CUEING

CROSS REFERENCE TO RELATED APPLICATIONS

This application claims the benefit of U.S. Provisional Application No. 62/211,281, filed Aug. 28, 2015, entitled PLATFORM SYSTEM FOR MOVEMENT SKILL ANALYSIS AND SKILL AUGMENTATION AND CUEING, which application is incorporated herein by reference.

BACKGROUND

Field

Disclosed are devices, systems and methods for movement skill analysis, movement skill augmentation and movement cueing using decomposed movement elements for modeling and analysis.

Description of Related Art

Humans rely on motion skills to perform daily tasks ranging from actions essential to our autonomy to more specialized domains requiring highly refined motion skills. Professional athletes, musicians, surgeons, and even elite amateurs require thousands of hours of systematical and focused training, as well as continued training to maintain high skill levels. Even simple daily acts involve complex coordination of a range of processes, from sensing and motor-control to perception and cognition. Learning, maintaining, and rehabilitating movement skills are valuable, but at the same time, complex and challenging tasks. Acquiring and maintaining specialized movement skills takes time. Progress of movement skills does not develop linearly with training time. Rather, skills progress exponentially with what is left to learn in order to be proficient at the movement. Movement performance relies on a broad range of functions (e.g., sensory, perceptual, planning, cognition). Many movement skills within the category of complex movement are unnatural and therefore require adaptation of innate functions to the specific task requirement and familiarization with the external task elements. Complex movement requires coordinating large numbers of muscles and body segments. The computational requirements for movement need to be initiated within short time-frames and often need to be adapted during performance. Movement is typically learned by trial and error, focusing on the outcome. The specific details regarding how movement is organized are only known implicitly in procedural memory. Explicit knowledge surrounding movement details are typically not used during practice and execution. Movements often unfold too quickly to even be perceived. Complex movements involve too many dimensions. For example, the path of a piece of equipment, such as a tennis racket, involves combining three translational and rotational variables (e.g., six degrees of freedom).

This complexity grows exponentially when various body segments and biomechanical and neuro-motor constraints are included. To make matters even more complex, these variables are constrained by the dynamics, which constrain their spatial and temporal evolution. Finally, there are very few feedback stimuli, or signals, available to a user during the training process. As a result, for most people who don't have access to coaching, movement skill relies on self-observation and tedious repetition. In many domains, proficiency cannot be achieved without the assistance of an expert coach or trainer.

Challenges exist in characterizing and assessing movement. First, human movement is variable. Each repeated trial of the same task results in a slightly different execution. Second, technique is idiosyncratic. Individuals with the same general level of ability have a different approach and style. Third, movement is fast. Often an action unfolds within a fraction of a second, with relevant details only spanning a few milliseconds. Fourth, movement is complex. It often focuses on the control of an end effector, such as a tool (e.g. surgical instrument) or piece of equipment (e.g., tennis racket, baseball bat, golf club), which need to be controlled in three dimensional workspaces. The execution of such movements, however, requires controlling the various limbs, joints, and muscles, which add many more additional degrees of freedom.

Moreover, coordinated motion patterns are typically too complex and execute too quickly to be perceived and processed consciously. Therefore, it is usually impossible to make training interventions in real time. Moreover, athletes or operators usually don't have a sufficiently explicit awareness of the details of their motion execution. These characteristics explain why it difficult to improve skills once basic motion patterns are acquired. External feedback from a trainer or coach becomes necessary in order to improve.

Movement skills also depend on a perceptual understanding of the external task elements. These characteristics are much harder to assess from observations of the movement performance. They manifest indirectly in the performance. A good instructor will call his attention to important perceptual cues and response characteristics and give diagnostic knowledge of results.

Finally, an important requirement for effective training is to account for individual differences in body type, skill level, health, etc. Such characteristics are much harder to explicitly take into account during training. It is particularly critical for rehabilitation or when working with injured or aging athletes. A training approach should also leverage the properties and natural learning principles and processes of skill development.

Popular wearable and embedded devices currently primarily focus on the identification and tracking of activity (e.g. Fitbit® fitness tracker (available from Fitbit, Inc.) or Jawbone® fitness tracker (available from Aliphcom doing business as Jawbone)). Popular examples of fitness trackers include devices for counting steps and tracking distance covered. More advanced capabilities can be found in devices that are specialized for a particular sport. Tennis, badminton, and golf represent the largest market segments (see e.g. BABOLAT® (from Babolat (France)), ZEPP® tennis swing analyzer (available from Zepp US, Inc.), and the SMART TENNIS SENSOR (available from Sony)). These products aim to provide an analysis of players' technical performance. Typical features include tracking the type of actions; reconstructing movements, such as the path of the tennis racket during a stroke; tracking key outcome variables of actions such as the racket head speed, the distribution of impacts on the sting bed, and the amount of spin.

The outputs of these assessments are typically provided after a training or play session. The data is presented as summaries of session performance, as well as time. The data is also aggregated to provide statistical trends. The main shortcoming of these products is that the analysis is based on outcome variables (referred to as knowledge of results in the human skill literature) and thus does not provide actionable information that can be leveraged directly for training.

What is needed are systems and methods that provide real-time and post-performance training and rehabilitation to a user which provides augmentation of human movement and takes into consideration various components of the movement.

SUMMARY

A human movement augmentation system is disclosed that provides various forms of feedback, including real-time feedback and post-performance feedback for training and rehabilitation. The devices, systems and methods are configurable to augment human movement behavior in order to accelerate complex movement skill acquisition, improve outcome and performance, and mitigate injuries and wear from poor or maladaptive movement technique.

A difficulty with skilled human movement behavior is that the data needed to describe the performance is high-dimensional and includes other complexities such as nonlinearities arising from movement dynamics. Moreover, human performance is highly variable, even for a single individual. In addition, humans present a broad range of skill levels, styles, body types, ages, physical conditions, and medical conditions. All of these variables affect movement performance. The movement complexity has long eluded researchers who study the human nervous system (see e.g., Bernstein's degree of freedom problem).

A method is disclosed that decomposes movement into elements that follow the natural structure and organization of the human nervous system. These elements are used to model and analyze movement behavior systematically, and subsequently can be used to synthesize and implement various forms of movement augmentation to improve skills consistent with natural human movement control principles.

Additionally, an environment that enables systematic and comprehensive improvement of capabilities through the integration of its components. On the input side, the invention assumes a method for collecting movement measurement data of the equipment and various body segments in relationship to task and environmental elements that are relevant to the level of analysis considered in that activity. The measurements encompass data from wearable sensors, such as MEMS IMUs, and/or data from technologies including a vision or optical based tracking system. On the output side, the invention uses various modalities to communicate feedback, including visual, haptic, and audio; these are embedded either in pieces of equipment or in accessories (smart watches, smart glasses, etc.).

The components of the movement skill augmentation system include: A Movement Processing System (MPS) to decompose movement data according to the hierarchical movement system organization. The first step extracts movement segments that correspond to movement profiles of the primary movement units (PMU) used in performing a task. The second step of MPS delineates movement data into movement categories and classes according to movement intrinsic characteristics, interactions with the task environment, and/or the movement's outcomes. The collection of PMU defines the subject movement repertoire. The PMU movement profiles from each class are then segmented into phases. Finally, the phase profiles are decomposed into movement components that can be related to the muscular activation patterns and joint motions underlying the movement coordination.

The Motion Model (MM) captures movement behavior following the three levels of organization of the human movement system used for the MPS processing stages. The repertoire of PMU formed by aggregating the categories or classes describes how a subject partitions the space of outcomes required to perform a task into distinct families of movement patterns with their associated outcomes. The phase-segmented PMUs are used to define a finite-state model that describes movement pattern as a sequence of states with specific dynamics. The states correspond to the individual movement phases, which are driven by the underlying continuous movement process. State-transition conditions determine the sequencing of the phases. This model describes how complex movement patterns are achieved in the face of musculoskeletal and other biological constraints. Finally, the individual movement components, obtained by decomposing the phase profiles, are mapped to the musculoskeletal system to describe how the movement profiles are achieved by combining body segments and muscle synergies.

The Skill Model (SM) extracts attributes from the motion model. The skill model is divided into two levels. The task performance assessment level describes the range of outcomes and reliability of the movement in achieving these outcomes. The functional assessment level describes how the subject uses movement technique to achieve various outcomes, and how movement technique is adapted to compensate for variations and uncertainties in task conditions and movement execution. The movement phase elements provide a sparse description of the high-dimensional movement data. Since it is grounded in human structure, it plays a central role in functional analysis. The elements of the movement model, including phase transition configuration, phase profile characteristics, etc. are used to identify what features are most predictive of the outcome. Similarly, movement adaptation mechanisms can be analyzed by studying patterns of coupling between movement component features that have no effect on the outcome. The skill model is used to determine the individual's Skill Status (SS), which provides a comprehensive skill assessment. At the activity performance level, it encompasses repertoire, statistical characteristics of movement pattern profiles, and associated outcomes. At the functional level, it encompasses the outcome feature sets and adaptation feature sets for each movement pattern and their associated movement model. Finally, the biological details include muscle and joint coordination and performance, which are described by the movement synergies and biomechanical models.

A method for the synthesis of feedback augmentation. The augmentations are divided into Instructions, which operate at the knowledge level, and Feedback Cues, which operate at the signal and cue level of the human information processing and skill hierarchy. The Instructions operate at the knowledge level and are implemented through various visualization methods that describe the elements of the motion and skill models such as maps of the repertoire, graphs of the movement profiles for different movement patterns, and detailed graphs of the phase-segmented movement profiles, and at the lowest level, the movement synergies and associated movement biomechanics. The visual instructions are also accompanied by verbal instructions that explain the relevant quantities. At the functional level, the instructions detail the role of the elements of the movement model in generating outcomes, including the features related to movement configuration at phase transitions, and profile features of the various phase segments. The synthesis of Feedback Cues is based on Cueing Mechanisms that are derived from the motion model and its various functional features that are related to the natural movement implementation.

A method and system to realize or implement the different forms of feedback augmentations for training and rehabilitation and injury protection. The augmentation is divided between the Instructions and the Feedback Cues. The system components necessary for generating instructions are implemented by a host computer with the necessary display and user interface such as a smart phone or a tablet. The system components necessary for generating feedback cues are implemented by the Cueing System. The cueing relies on real-time movement data processing. The cueing system is divided into two subsystems: The Cue Processor (CP) and the Cue Generator (CG). The CP takes movement data from the available measurement systems or devices and generates a Cue Signal. The CG takes the Cues Signal and generates cue stimuli that can be perceived by the human individual. The CP is composed of a Phase-state Estimator (PE) and a Cueing Law (CL). The PE estimates the current and future movement phases and extracts relevant movement data. The CL takes the phase information and various movement data and computes a cue signal. The CG is composed of a Cue Encoder (CE) and a Cue Transducer (CT). The CE takes the cue signals and generates a feedback signal that can be interpreted by the human subject. The CT takes the feedback signal and generates physical stimuli (e.g., audio, visual, haptic).

The movement model and augmentation mechanisms provide the components for computer assisted training (CAT). CAT handles various aspects of the management and operation of the augmented training process. The CAT system has two primary subsystems: a Training Agent (TA), which serves as virtual coach that manages the training process, and a Cueing Agent (CA), which controls the Cueing System and manages the various cueing functions during play or performance. The Training Agent analyzes the diagnostic results to formulate a Training Schedule (TS). At the repertoire level, the TA determines which movement patterns must be optimized or refined, and also specifies what new movement patterns must be formed. The former improves the skills of specific movement patterns and the latter is directed at broadening the repertoire either through the introduction of a new pattern or by helping the differentiation of movement within an existing pattern.

The Training Schedule is encoded as a sequence of Training Elements (TE). These are either target motion pattern refinement or movement pattern formation. The TE are formalized as a hierarchical tree that spans the various Training Paths. The information about the hierarchical relationships between the patterns in the repertoire and the relative importance of the various patterns for the activity domain is used to define the ordering and timing of the TE. The Training Agent tracks the Skill Status and the progress along the training schedule and updates the TEs. The longitudinal changes in Skill Status corresponds to the individual's learning curve. The Cueing Agent manages the cueing process for a particular Training Element of the TS. The TEs typically consist of pattern refinement or pattern formation. The Feedback Cue that can be activated to augment training of the Training Element consists of a set of Cueing Elements that constitute the Cueing Profile (CPr). Each Cueing Element is characterized by a Cueing Mechanism and is realized by the Cueing System through a cueing law. The Cueing Agent tracks the effectiveness of the Cueing Profile and the individual Cueing Elements.

In addition to these capabilities, the data structure associated with the motion and skill models provide features to support efficient management, organization and communication of movement data. The quantities that are described above can be managed for various populations of individual along with any relevant parameters such as body type, size, age, injuries, equipment, etc. The metadata extracted from this system can be used to optimize models, algorithms and cueing mechanisms, and provide long-term optimization of training. The extracted metadata can also improve the understanding of other long-term movement characteristics such as aging, wear, development of injuries, etc.

Other functionalities and systems related to the overall environment include the Cue Designer. This system provides user interactions at the training agent level to optimize training schedule and cueing laws and cue profiles for professionals.

An aspect of the disclosure is directed to a motion analysis system. The motion analysis system comprises: one or more sensors configured to obtain motion data; a processor in communication with one or more sensors, the processor configured to: collect a motion data from the one or more sensors; parse the collected motion data into one or more movement units; model the one or more movement units; analyze the one or more movement units; compare the one or more movement units to one or more of each of a prior movement measurement and a library of movement measurements to generate a comparison; identify one or more aspects of the motion data for change based on the comparison; and provide feedback to a user. The one or more sensors can obtain motion data with two or more degrees of freedom that are selected from three axes in Euclidean space or selected from three measured quantities. Additionally, the motion data obtained can be a movement within a repertoire of user movements. Moreover, one or more sensors can be selected from one or more of each of a wearable sensor and a remote sensor. Wearable sensors can further be configurable to sense one or more of each of a velocity of the motion, an orientation for the motion, a gravitational force, and an electrical activity of a muscle. Feedback provided to the user can be one or more of each of visible, haptic, and audible. Additionally, one or more movement features can be computed that impact a quality or outcome of the feedback. Moreover, the one or more movement features are one of a phase transition or phase profile attribute. The feedback provided to the user can be one or more of each of a phase transition cue, a phase profile cue, an alert, and an outcome validation cue. Additionally, the feedback can be provided real-time, near real-time, or at a time remote to an actual movement session. Alerts can be computed from the map of movement feature to biomechanical features (e.g. to protect from injury or wear). One or more movement units can be further segmented into two or more movement phases. Two or more movement phases can be decomposed into two or more synergies wherein the two or more synergies are one or more of each of biomechanical relationships and neuro-muscular relationships. A local host device, such as a local computing device, can be configurable to communicate one or more of each of a training information and a cueing information to the user. One or more parsed motion data for change can be prioritized based on whether a feature of the movement unit is changeable and will impact a quality or outcome of a repeated movement. Additionally, the collected motion data can be one or more of a user motion data and a user controlled device motion data.

Another aspect of the disclosure is directed to a means for motion analysis. The means for motion analysis comprises: one or more sensor means configured to obtain motion data; a processor means in communication with one or more sensor means, the processor means configured to: collect a motion data from the one or more sensor means; parse the collected motion data into one or more movement units; model the one or more movement units; analyze the one or more movement units; compare the one or more movement units to one or more of a prior movement measurement and a library of movement measurements to generate a comparison; identify one or more aspects of the motion data for change based on the comparison; and provide feedback to a user. The one or more sensor means can obtain motion data with two or more degrees of freedom that are selected from three axes in Euclidean space or selected from three measured quantities. Additionally, the motion data obtained can be a movement within a repertoire of user movements. Moreover, one or more sensor means can be selected from one or more of each of a wearable sensor means and a remote sensor means. Wearable sensor means can further be configurable to sense one or more of a velocity of the motion, an orientation for the motion, a gravitational force, and an electrical activity of a muscle. Feedback provided to the user can be one or more of visible, haptic, and audible. Additionally, one or more movement features can be computed that impact a quality or outcome of the feedback. Moreover, the one or more movement features are one of a phase transition or phase profile attribute. The feedback provided to the user can be one or more of a phase transition cue, a phase profile cue, an alert, and an outcome validation cue. Additionally, the feedback can be provided real-time, near real-time, or at a time remote to an actual movement session. Alerts can be computed from the map of movement feature to biomechanical features (e.g. to protect from injury or wear). One or more movement units can be further segmented into two or more movement phases. Two or more movement phases can be decomposed into two or more synergies wherein the two or more synergies are one or more of each of biomechanical relationships and neuro-muscular relationships. A local host device means, such as a local computing device means, can be configurable to communicate one or more of a training information and a cueing information to the user. One or more parsed motion data for change can be prioritized based on whether a feature of the movement unit is changeable and will impact a quality or outcome of a repeated movement. Additionally, the collected motion data can be one or more of a user motion data and a user controlled device motion data.

Still another aspect of the disclosure is directed to a cue processors. Suitable cue processors are configurable to: generate a movement phase estimation which provides a prediction of a movement phase and an associated feature, extract a movement phase feature, apply a movement cueing law; and generate a movement cue, wherein the movement phase estimation and the movement phase feature extraction includes one or more of each of a phase initiation predictor, an initial phase state extractor, a phase profile parameter extractor, and an outcome extractor. The cueing law is further configurable to at least one of compare a reference timing, compare a target state value, compare a reference profile, and compare a target outcome. Additionally, the cue generator is configurable to generate one or more of each of a phase transition cue, a phase profile cue, an alert and an outcome validation cue. Moreover, the cue processor can be incorporated into a stand-alone device. The cue processor can be part of a cueing system having a phase state estimator, a cue encoder and a transducer. One or more cues generated can be prioritized based on one or more of each of decomposed motion data for change based on whether a movement feature is changeable and will impact a quality of a repeated movement.

Yet another aspect of the disclosure is directed to a cue processor means. Suitable cue processor means are configurable to: generate a movement phase estimation which provides a prediction of a movement phase and an associated feature, extract a movement phase feature, apply a movement cueing law; and generate a movement cue, wherein the movement phase estimation and the movement phase feature extraction includes one or more of a phase initiation predictor, an initial phase state extractor, a phase profile parameter extractor, and an outcome extractor. The cueing law is further configurable to at least one of compare a reference timing, compare a target state value, compare a reference profile, and compare a target outcome. Additionally, the cue generator means is configurable to generate one or more of a phase transition cue, a phase profile cue, an alert and an outcome validation cue. Moreover, the cue processor means can be incorporated into a stand-alone device. The cue processor means can be part of a cueing system means having a phase state estimator, a cue encoder and a transducer. One or more cues generated can be prioritized based on one or more of decomposed motion data for change based on whether a movement feature is changeable and will impact a quality of a repeated movement.

Still another aspect of the disclosure is directed to motion training programs. Suitable motion training programs comprise: one or more sensor inputs configurable to collect motion data; a computerized motion training program, wherein the computerized motion training program is configured to: parse the collected motion data into one or more movement units, compare the one or more movement units to one or more of a prior movement measurement and a library of movement measurements to generate a comparison, and present at least one of a training assessment and training instruction to the user about one or more of a repertoire movement, a motion phase segment, and a movement synergy. Additionally, the motion training program is configurable to provide a plurality of prompts to a user during a sensed motion. In at least some configurations, the computerized motion training is iterative. An output of the motion training program includes a training schedule and one or more instructions. The training schedule can identify one or more patterns in a repertoire movement to be practiced by a user. The collected motion data can include one or more of a user motion data and a user controlled device motion data.

Another aspect of the disclosure is directed to motion training programs. Suitable motion training programs comprise: one or more sensor input means configurable to collect motion data; a computerized motion training program, wherein the computerized motion training program is configured to: parse the collected motion data into one or more movement units, compare the one or more movement units to one or more of a prior movement measurement and a library of movement measurements to generate a comparison, and present at least one of a training assessment and training instruction to the user about one or more of a repertoire movement, a motion phase segment, and a movement synergy. Additionally, the motion training program is configurable to provide a plurality of prompts to a user during a sensed motion from a prompting means. In at least some configurations, the computerized motion training is iterative. An output of the motion training program includes a training schedule and one or more instructions. The training schedule can identify one or more patterns in a repertoire movement to be practiced by a user. The collected motion data can include one or more of a user motion data and a user controlled device motion data.

A method of training is also disclosed. Suitable methods of training comprise: collecting a motion data from one or more sensors; parsing the collected motion data into one or more movement units; modeling the one or more movement units; analyzing the one or more movement units; comparing the one or more movement units to one or more of a prior movement measurement and a library of movement measurements; and identifying one or more aspects of the motion data for change based on the comparison. Additionally, the methods can include the step of providing feedback to the user, such as real-time feedback, near real-time feedback or feedback provided at a later time. In at least some configurations, the feedback is at least one of an instruction and a cue, such as one or more of each of visible, haptic, and audible cues. Additionally, the method can include generating a training schedule based on the one or more parsed motion data identified for change. The one or more movement units can further be segmented into two or more movement phases. Additionally, the two or more movement phases can be decomposed into two or more synergies wherein the two or more synergies are one or more of each of biomechanical relationships and neuro-muscular relationships. In some configurations, a local host device is configurable to communicate one or more of each of a training information and a cueing information to the user. The collected motion data can be one or more of each of a user motion data and a user controlled device motion data.

INCORPORATION BY REFERENCE

All publications, patents, and patent applications mentioned in this specification are herein incorporated by reference to the same extent as if each individual publication, patent, or patent application was specifically and individually indicated to be incorporated by reference. See, for example, US 2013/0053190 A1 published Feb. 28, 2013 for RACKET SPORT INERTIAL SENSOR MOTION TRACKING AND ANALYSIS now U.S. Pat. No. 8,944,940 B2 issued Feb. 3, 2015; U.S. Pat. No. 8,602,922 B2 issued Dec. 10, 2013, for METHOD AND APPARATUSES FOR ENHANCING PERFORMANCE IN RACKET SPORTS, US 2005/0017454 A1 published Jan. 27, 2005, for INTERACTIVE GAMING SYSTEMS WITH HAPTIC FEEDBACK; US 2007/0105664 A1 published May 10, 2007 for RACQUET WITH ENTERTAINMENT AND PERFORMANCE FEEDBACK; U.S. Pat. No. 4,257,594 A issued Mar. 24, 1981 for ELECTRONIC ATHLETIC EQUIPMENT; U.S. Pat. No. 8,337,335 B2 issued Dec. 25, 2012, for SYSTEMS AND METHODS FOR MEASURING AND/OR ANALYZING SWING INFORMATION; U.S. Pat. No. 5,646,911 A issued Jul. 8, 1997 for TENNIS PACER; U.S. Pat. No. 5,226,650 A issued Jul. 13, 1993 for TENNIS RACKET; US 2002/0077189 A1 published Jun. 20, 2002, for PROPRIOCEPTIVE GOLF CLUB WITH ANALYSIS, CORRECTION AND CONTROL CAPABILITIES; U.S. Pat. No. 5,031,909 A issued Jul. 16, 1991 for ELECTRONIC ATHLETIC EQUIPMENT; US 2006/0025229 A1 published Feb. 2, 2006, for MOTION TRACKING AND ANALYSIS APPARATUS AND METHOD AND SYSTEM IMPLEMENTATIONS THEREOF; U.S. Pat. No. 4,303,241 A issued Dec. 1, 1981, for SPORTS VISION TRAINING DEVICE; U.S. Pat. No. 7,891,666 B2 issued Feb. 22, 2011, for DEVICE AND METHOD FOR MEASURING SHOT FORCE EXERTED ON A MOVEABLE GAME DEVICE; and WO 2009/043558 A1 published Apr. 9, 2009, for FORCE SENSOR FOR RACQUET HANDLE.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIGS. 16C-1 to 16C-2 illustrate a 3-dimensional angular rate phase portrait for an ensemble of forehand/backhand, topspin/slice strokes;

FIGS. 19A-19B illustrate exemplar user interfaces;

DETAILED DESCRIPTION

The disclosure is directed to a system which provides systematic, data-driven, computer-assisted movement skill training, maintenance and rehabilitation. The systems and methods use objective and quantitative methods of skill level assessment, the use of these assessments are then used to identify specific deficiencies, followed by the formal specification of a training intervention. Once it is possible to translate these components and their interactions quantitatively by decomposing the movement into decomposed movement data, it is then possible to analyze the decomposed movement to identify specifically where change is required. This enables a user to close the training or rehabilitation loop and run it as an iterative scheme.

Figure 1:
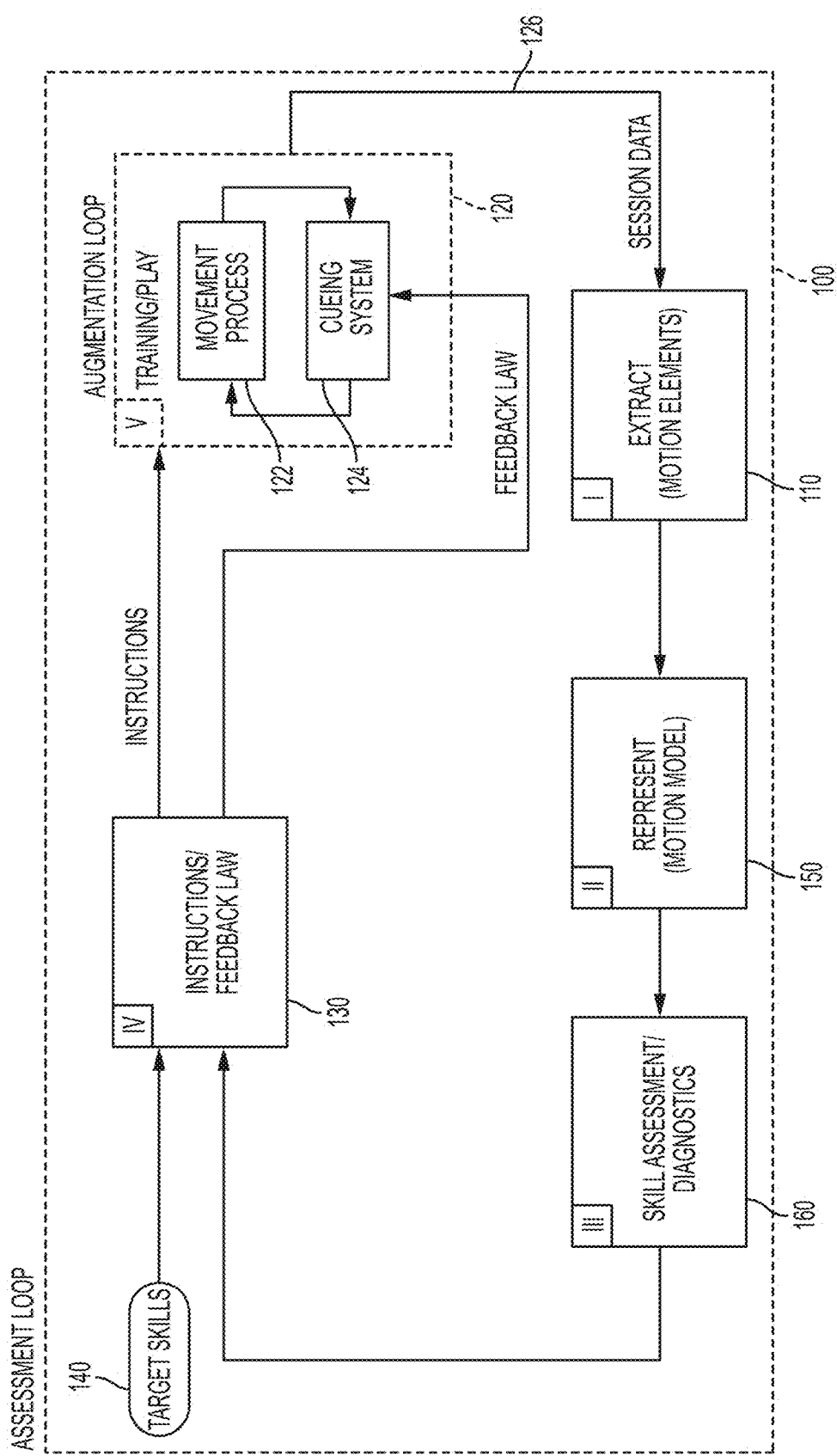
FIG. 1 illustrates an exemplar training process showing main processes in a closed-loop system with training loop and an augmentation loop.

FIG. 1 illustrates an assessment loop 100. The assessment loop 100 is configurable to have five components. An extractor 110 extracts motion elements from a target motion. The extracted motion elements can be directed from an augmentation loop 120 which collects information from user training or play. The augmentation loop 120 can have a feedback loop between a movement process 122 and a cueing system 124. Additionally, the augmentation loop 120 can received information from an instruction module 130. The instruction module 130 may receive a set of target skills 140 from a user or a trainer. Session data 126 can be provided to the extractor 110. The extractor 110 output generates a motion model 150 which can then be used for skill assessment and diagnostics 160. A measurement process can be provided that maps aspects of behavior or movement into one or more measurement signals. A control algorithm is configurable to generate a control action based on the measurement of the current behavior or movement and a desired behavior or movement. An actuator that transforms the measurement signal into an input signal can be provided that will help steer the system. The system operationalizes the training process and creates a systematic schedule that builds skills in following logical development, consistent with human learning principles. The training starts from a user's existing motor skills and proceed by shaping these skills towards the specified goal skills.

The cueing system 124 can include two components: a cue processor and a cue generator. The cue processor translates movement data into cue signals. The cue processor implements a finite state estimator and a cueing law calculator. The finite-state estimator is an approximation of the user's movement model (which is itself represented as a finite state machine). The cue generator translates cue signals into physical stimuli; the system operates in real-time to provide feedback as the user participates in an activity. The cueing law calculator takes the state estimate and the motion data and operates on them to calculate if a cue will be delivered and what the cue should communicate. The feedback synthesis model determines how the cueing law calculator operates, whereas the finite-state estimator is defined by the user's current movement model. The cue generator takes the cue signal and translates it into a feedback stimuli generated by a transducer (audio, visual, haptic, symbolic, or other type). The form of transducer is determined by the platform implementation details, user characteristics, equipment parameters, environment status, and/or other concerns.

The system receives input from a user's physical movement that takes place during a use or play session. The measurements can capture a range of movement behavior that performed to complete the activity (e.g., all the motion associated with a tennis stroke, all the motion associated with a golf swing, etc.), associated task conditions, as well as the elements relevant to the broader functional components such as perception of task elements.

MEMS IMUs (e.g., available from ST Microelectronics and InvenSense) typically include 6-axes acceleration and angular rates and 3-axes magnetometers, which are often used to estimate absolute orientation in space (Attitude and Heading Reference System or AHRS). To render useful information from collected movement measurement data collected, structural characteristics are identified that can then be related to particular motor events or actions. For computational analysis of technique and skills and ultimately synthesis of effective feedback for training instructions, it is necessary to break down movement into movement elements.

Movement characteristics can be represented as geometrical and topological properties, which can be related to specific aspects of movement organization and skill. For example, movement characteristics can be observed in movement phase portraits such as that of the racket angular rate. Ensembles of movement data can be analyzed for patterns (e.g. using principle component analysis, phase-space analysis and nonlinear time series analysis techniques such as state-space embedding). In addition, machine learning techniques can be applied to analyze the distribution of features and characteristics of the movement, as well as to aggregate and classify the data to determine patterns which in turn can be used to determine a deeper organization of the overall system. Given the variety of movement types and the variability in human performance. Typically, the system is configurable to distinguish between different movement types before proceeding to deeper analysis of any individual movement or component thereof.

One or more motion sensors, either embedded, or deployed in the user's environment, can be used with the system to provide measurements of movement dynamics encompassing one or more users, actors and their associated equipment (if any). As will be appreciated by those skilled in the art, given the depth of hierarchical levels of the movement system, the scope of motion analysis can be conducted at multiple levels. For example, it could focus on neuro-motor aspects, movement technique and structure, and outcomes, all the way up to tactical and strategic levels.

Figure 2:
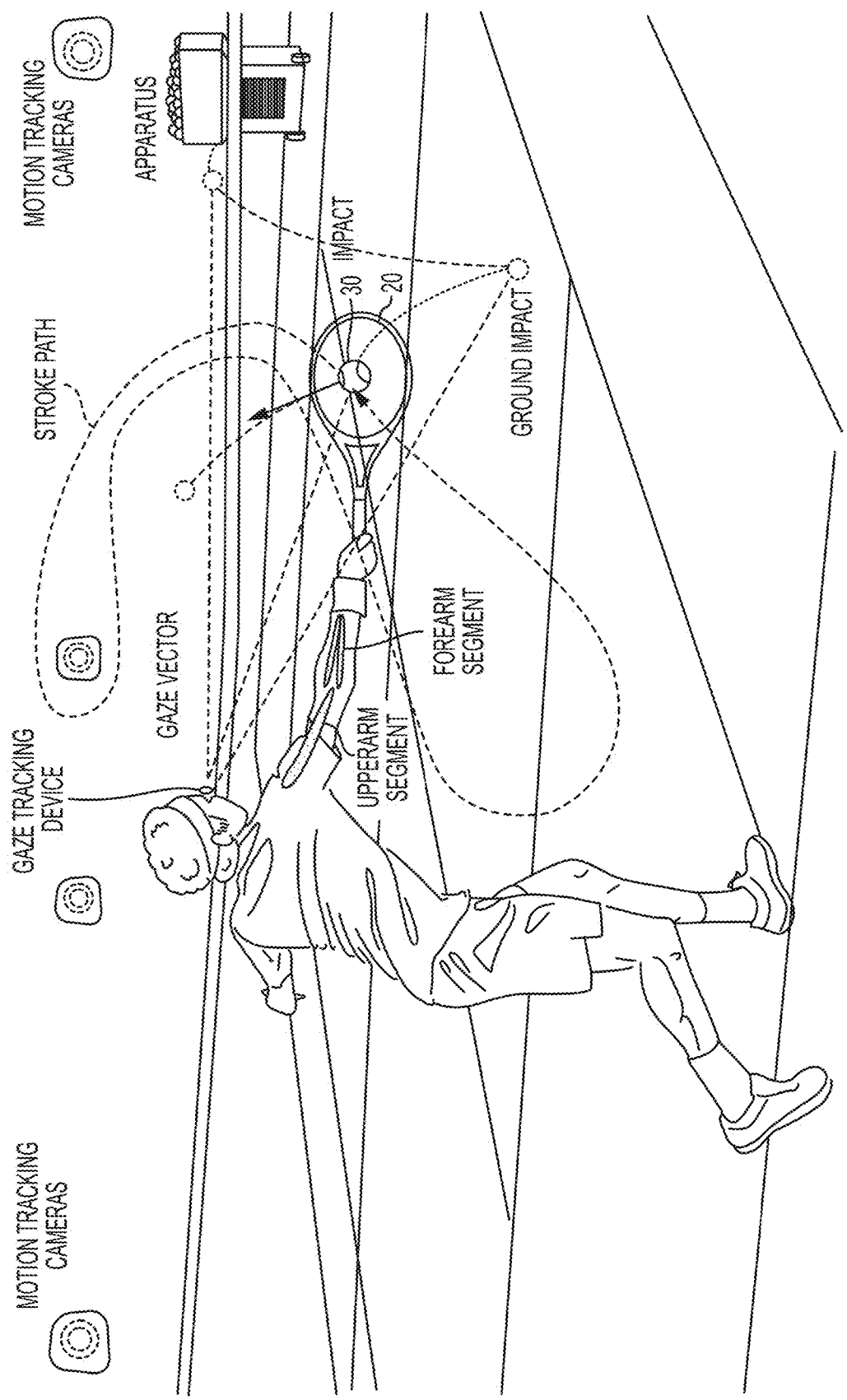
FIG. 2 illustrates an interaction between a stroke motion and the task and environment elements, including the ball trajectory relative to the court, the impact of the ball and its bouncing before the interception with the racket trajectory. The figure also illustrates the gaze of the player along different point of the ball trajectory, and shows a ball machine as an apparatus that can be programmed to enable different forms of interactions.

Analysis of the intrinsic movement structure of the movement technique and functional characteristics can be used for skill analysis. Prior solutions have focused on the interactions of the movement with environment and how operators organize their behavior in relationship to environment and task elements. FIG. 2 illustrates an exemplar motion in the form of an interaction between a user's stroke motion during a tennis game and the task environment elements for a user 10 using a tennis racket 20 to impact a ball 30. One or more motion tracking cameras 210, 210' are provided. The gaze 12 of the user 10 changes at different points depending on the trajectory of the ball 30. The apparatus shown in the same figure can be programmed to enable different forms of interactions. In the tennis example, the apparatus is a ball machine that can be programmed to support the development of specific stroke patterns and therefore can be programmed in conjunction with the cueing system.

In contrast, the systems and devices disclosed augment skills, including, for example:
(1) providing users feedback for training, including providing signals during the performance;
(2) enhancing the athletic experience during performance to help focus;
(3) providing protection from injury by helping users engage in optimal techniques; and
(4) developing training protocols which are directed to developing skills related to the training.

Patterning characteristics are expected in many movement activities. In tennis, for example, the same general stroke pattern can be used to generate different amounts of top spin or pace. However, to maximize these different outcomes, distinct patterns have to be formed to fully use the biological system. For example, a stroke for a top spin or slice have characteristic features in the temporal and spatial arrangement of movement phases. Movement patterning is due to how changes in movement outcomes or task conditions affect movement technique. As the desired outcome or task conditions change, the biomechanics and motor-control must organize differently to best take advantage of the system's capabilities. From a trajectory optimization perspective, the changes in outcome and condition alter the system's "operating point" and result in activation of a different set of constraints. Due to the nonlinearity, this leads to the emergence of a different motion pattern with distinct dynamic characteristics. Patterning corresponds to a tendency for the trajectories in each class of behavior to stay close together in spatial and temporal terms. This closeness can be described formally using techniques from nonlinear time series analysis. Using these techniques, measurement data describing racket state trajectories during a tennis stroke can be aggregated and clustered to identify different stroke patterns.

Such performance data for an activity taken in its totality, for example from measurements of an entire tennis match, results in a repertoire of distinct movement patterns. The repertoire of distinct movement patterns is the result of the optimization of movements technique, i.e., achieving the range of outcomes and conditions required to be proficient in the particular activity. For instance, in tennis an individual will develop a repertoire of different strokes to optimize the necessary outcomes (e.g., type and amount of spin, strength, etc.) and accommodate the range of impact conditions (ball height, speed, etc.). This repertoire essentially plays the role of a vocabulary of motion pattern that an individual can call upon when engaged in a particular activity. The patterning and repertoire, therefore, have important implications for the assessment of skills. The skills of a particular tennis player, for example, can be assessed by:
(1) extracting characteristics about the entire repertoire of strokes, e.g., how well they collectively achieve the range of outcomes and conditions in the activity domain and
(2) determining how well and how consistently each class of strokes in the repertoire achieves associated outcomes
(3) determining how well the strokes adapt to the impact conditions.

The first analysis provides a comprehensive assessment, and the second emphasizes the technical implementation of the motion skills. Understanding human movement control provides a deeper assessment of the movement technique and feedback that helps optimize movement technique.

Skill-based movement behaviors are usually fast, coordinated, multi-dimensional movements. Delays in human's signal transmission and processing limit the role of feedback. Therefore, the biological movement control system has to rely extensively on "open-loop" control, meaning that trajectories are implemented from pre-programmed profiles are largely unconscious. The general motor program (GMP) explains how complex movements are programmed. GMP describe the generalized rules that generate spatial and temporal muscle patterns to produce a movement for the collection of movement patterns in the repertoire. The GMP encompasses the mechanisms needed for adaptation to conditions.

Complex movements frequently involve a sequence of distinct movement phases. Therefore, motor programs encompass mechanisms in order to time and sequence these elements. The movement phases are usually formed to support various functional characteristics, such as biomechanical constraints, task structure and various sensory interactions with the environment. Movement segments can be conceptualized as a movement directed towards a sub-goal, each with its particular biomechanical and sensory-motor constraints. This structure allows the break down complex movements into simpler movement elements. It can also help acquisition of complex movement skills and support the flexibility and adaptability needed to operate in dynamic and uncertain environments.

The bandwidth limitation for closed-loop feedback involving perceptual motor control is somewhere between 0.5 and 2 Hz, depending on the task. Above that bandwidth, intermittent closed-loop can be used. Movement phases typically represent open-loop segments. Corrections can be implemented at specific phase transition. These phase transitions are also associated with functional features, such as when specific elements of information are available. For example, in a tennis stroke, an advanced player already has an idea of the intended outcome and anticipates the conditions of the oncoming ball, at the initiation of the stroke. At the end of the backswing phase, and before the initiation of the forward swing, the player makes adjustments based on the up-to-date information available from the oncoming ball trajectory (see FIG. 2 which illustrates a swing trajectory).

As will be appreciated by those skilled in the art, movement skills often involve extensive interactions with the task and environment elements. For example, in tennis these interactions include producing the desired outcome in the task and dealing with the range of impact conditions. The perceptual system usually provides cues that are used to select the type of motion pattern from the repertoire of learned movement patterns. Signals from the sensory or perceptual system are used to modulate specific aspects of the pattern, such as the timing of the stroke phases based on the tennis ball's perceived speed. Training movement skills, therefore, involves acquiring a comprehensive set of mechanisms. Movements are not simply programs to steer body segments; they encompass numerous functional features. Therefore, skill acquisition also includes learning how to extract relevant signs or cues from the task environment, and developing plans for sequencing individual movement patterns. The basic motor learning concepts are introduced next and will expand in the later sections.

Motor skills are thought of as acts requiring integration of both sensory information and motor responses to attain a particular goal. Goal-directed, deliberate, instrumental or intentional movements are movements characterized by forethought with reference to the consequences they produce. The outcome to be obtained is clear to the performer and determines his organization of the movement pattern. Such deliberate movements contrast reflexes or fixed action patterns. Motor skills are categorized on a continuum defined by the dynamics of the task and environment condition. On one end of the continuum is the open skills, which take place in temporally and spatially changing conditions; on the other end is the closed skills, which take place under fixed, unchanging environmental conditions.

In open skills, a new movement emerging in response to a new aspect of the task environment may not originate as a variation of an existing pattern. Rather, it is presented as a new movement that is formed as a unique new pattern, albeit the new pattern may be reusing components of the original pattern. Therefore, in open skills, the user develops a repertoire of movement patterns that match the range of environmental conditions and task requirements. On the other hand, in closed skills, as the user learns to master the task, the movement performance converges over time to a fixed movement pattern that optimizes the outcome in relationship to the task requirement.

Most complex movements are obtained by combination of motion segments or phases. The high number of degrees of freedom (DOF) in human motion result in redundant movement solutions. For example, racket swinging can be achieved through various combinations of joint motions such as elbow, shoulder, wrist, etc. Each DOF has its own specific displacement range as well as other constraints such as speed or torque. Different executions of the same general movement will cause saturations at different stages of the overall trajectory and will result in a sequence of movement phases. Human users mostly learn through practice; they essentially discover how to best exploit the rich movement space to accomplish the desired outcome. As discussed earlier, skill acquisition proceeds through stages that result in increasing use of the available degrees of freedom.

Typically, a deliberate movement is needed to produce a particular outcome or change in the environment. Many skilled movements involve the control of an end effector such as the hand, foot, or a piece of equipment or instrument. Another important class of skilled motions are characterized by controlling the dynamics of interactions with an environment such as in skiing or surfing. These interaction behaviors involve the performance of particular maneuvers to allow deliberate control of motion. Examples of key maneuvers include turning or stopping. The purpose of movement skill acquisition can be defined as the process used by an individual to learn to change or maintain their state or the state of objects in space.

These end-effector motions encompass a variety of different movement behaviors including reaching motions, such as those used to grab an object or touch something, or interception and throwing or hitting motions. All of these motions guide the end effector along a path to a particular location in space. Most of the reaching motions involve stationary end conditions. Interception and hitting involve more dynamic end conditions. Most skillful end-effector motions involve the precise control of its state at the instant of the action (contact, interception or throw).

Reaching or interception motions rely heavily on visual information. The output side of behavior, i.e., the control of motion, only describes part of the problem. The input side of the behavior, which encompasses the sensory and perceptual mechanisms, is essential for a complete understanding. These movements are in part driven by motor program but functional aspects such as the adaptation of the program to external task elements or dynamics represents a fundamental aspect of the skills. Goal-directed movements, such as swing sports, are organized around a goal state. In tennis, for example, the racket stroke motion is organized around the impact, however it is achieved through a complex coordinated pattern of arm motions that satisfy the constraints of the ball impact and the body and limb biomechanics. In other activities such as skiing, there is no explicit goal. Skiers use gravitational forces and body biomechanics to generate turning motion to steer and control their path. These coordinated movements represent the primary unit of motion. There may be a great variety of movement patterns that satisfy these constraints depending on the configuration and conditions; however, they all typically share characteristic features that enable the movement patterns to be identified and undergo subsequent analysis.

Understanding the acquisition of movement skill requires data that provides a comprehensive description of the movement and task and environment elements. Most movement skills involve many degrees of freedom; tracking movement skills using early techniques meant tediously observing video footage. More generally, limitations in formal systematic skill evaluation and modeling are due to various complexities relating to the fundamental nature of complex movements and other task environment characteristics.

Skilled human movements, such as the tennis stroke, involve the sequencing of complex coordinated motions that are executed based on internal states and external cues. Their successful performance involves managing a range of contributions, including the effects of the tool or equipment (e.g. the tennis racket), the movement biomechanics, the interactions associated with the activity (e.g. tennis ball impact), and the interactions with the environment (e.g. aerodynamics or other medium).

The human motor system evolved to manage these interactions and efficiently handle the variety of uncertainties and disturbances prevailing in the task and environment. However, while the human movement system has tremendous potential, systematic and dedicated training is required for high levels of motor facility. This is similar in any domain of activity, such as athletics, music, or vocational. These factors can be divided into extrinsic and intrinsic factors. Extrinsic factors include the interactions with the environment such as the foot strike or impact of the ball on the racket. Intrinsic factors include the biomechanics, human motor control, and effects arising from the manipulated equipment's dynamics. Most skilled behaviors are so-called deliberate behaviors that are directed at achieving specific outcomes. Therefore, learning skilled behavior in sports or vocational activities involves learning to master these interactions so as to achieve the desired outcomes or goals. The coupling of the human movement system and the task environment have to be considered as a coupled system. If the extrinsic and intrinsic interactions were considered separately, the complexity would be intractable. The key to a tractable solution, therefore, are strategies that structure and organize movement behavior to simultaneously deal with the overall system.

The brain evolved specific organization and functionalities to efficiently work with these complexities. The brain and sensory-motor mechanisms that optimally deal with the coupling of the two domains, and achieve the sufficient level of adaptation, have been determined by evolutionary process. As a result, the specific structure and organization of the brain, including the nervous system and larger biomechanical systems, support natural solutions that enable efficient and adaptive behaviors. Therefore, a portion of the movement system is genetically determined. However, motor skills, especially in deliberate movements, are learned based on repeated interactions within the task and environment and are best acquired early in life when the brain is still developing. Finally, learning movement skills involves changes in the cortex as a result of neuroplasticity. These changes, however, follow a specific process that is dictated by the organization of the various cortical structures (cerebellum, parietal cortex, pre-motor and motor cortices, and the prefrontal cortex).

Three key forms of units of behavior have been described for complex movement behavior. At the top level, motion primitives are related to the concept of "motor equivalence" which has been identified as one of the fundamental characteristics of motor behavior. The idea is that the same movement behavior can be repeated in various contexts and without changing the overall form of the motion. Therefore, segmentation of human movement behavior into motion primitives has been most successful by identifying invariants characteristics. Since complex movements are obtained from a sequence of movement phases, the next level of primitive represents the patterns that can be combined sequentially.

The elements of the movement system are derived from structural features extracted from measurements using pattern analysis. Muscle synergies are obtained from factorization methods (e.g., principle component analysis or non-negative matrix factorization). The general idea is that many movements can be described as variations of a general model and once the general category of movement is specified some of the key mechanisms needed to achieve robust movement performance are those that allow adapting to changes in conditions or transferring to new task or activity.

In contrast to periodic and reflexive movements, which can be generated from low-level brain functions, skilled movements usually involve the deliberate formation of specific goals or outcomes. These movements may be completely self-initiated, e.g. picking up the phone to call someone; they may represent a stage in the context of a larger task, e.g. opening the dish cabinet when preparing food or returning a tennis serve. As seen in these examples, movements are rarely an isolated behavior but are part of a larger set of interactions with the world and therefore are typically part of a chain of behaviors.

Learning deliberate skilled movements involves learning the perceptual cues and motor actions that successfully accomplish the intended goal or outcome (e.g. reaching to grab an object or imparting momentum to a ball). Learning involves iterating on these solutions as the task, or a similar task, is repeated.

As will be appreciated by those skilled in the art, teaching relies on two primary modalities: demonstration and practice. Demonstration in theory should focus on instructions to help the student understand what they need to know about the behavior or movement. Practice refers to the process of performance repetition. Studies have shown that demonstrations too often focus on the task outcome rather than on an analysis of the coordination of movement. Movement skill acquisition could therefore be accelerated by providing specific signals delivered during performance. Two signals in particular would be beneficial. First, signals that highlight the structural elements used in the composition of movement. Second, signals that indicate which characteristics of these elements play a role in movement outcomes. However, these signals have to be adapted to the skill level of the individual and to his or her specific movement technique.

Users form an abstract understanding of movement capabilities in terms of goals and outcomes. Users, for the most part, learn in which contexts to use and initiate movements. Therefore, at the highest level, people can assess how well they do from knowledge of their repertoire of movements. The technical details of movement skills are largely unconscious. This is in part because movement execution is too fast for humans to directly control their technique. Therefore, most learnings follow a trial and error process. Movements that achieve goals are essentially reinforced.

It is difficult or impossible to directly assess movement technique. Users typically only determine technique indirectly through its outcome. Therefore, it is hard to explicitly instruct the technical aspects of the motion skill system. Trainers and coaches increasingly use strategies to help users form sense memory associated with a correct movement technique. A feedback signal that validates correct movement features can, through association, be used to reinforce memory of what such a movement should feel like. This form of feedback should hence accelerate the development and consolidation of a particular skill.

There are three primary forms of feedback which operate at specific levels of the control hierarchy: Real-time feedback, taking place during performance; feedback immediately following an action, such as based on information from the movement outcome; and feedback at the end of a training set or session. Inherent feedback associated with the feel, look, sounds, etc., of movement performance, as well as the movement outcome and interactions with the task and environment, provide a tremendous amount of information that can be used to assess performance and help train. Individuals, however, have to learn to recognize and evaluate those sources of information.

Augmented feedback is information that is supplementary to inherent information about the task or movement. The two major categories of augmented feedback are: knowledge of result (KR) and knowledge of performance (KP). KR represents post-performance information about the outcome or goal achieved. It is sometimes called reinforcement. Note, however, that not all movements have an outcome that is separable from the movement performance. KP represents information about the movement technique and patterning. This information is useful for the acquisition of complex movement skills, such as those requiring high-dimensional spatial and temporal coordination. Previously, it was difficult to measure and track performance in many activities. The advent of MEMS movement sensors has created a wide range of possibilities for using information about movement kinematics and dynamics (kinetics) from measurements.

Several levels of feedback are involved in support of skilled movements. Feedback acts at different levels across the hierarchical organization of the nervous system. The cortical and subcortical functions involved in the formation and implementation of movement patterns and the different feedback structures used to correct and modulate the movement. At the lowest level the spinal and subcortical system used for the physical implementation. This system receives commands from the cortical and subcortical structures. Feedback encompasses the information sensed at the level of the muscles, tendons and joints and modulates at the level of spinal circuits. Between the spinal and subcortical is the system that controls posture. The feedback encompasses information from the vestibular and proprioception combines spinal circuits with cerebellum. At the center of the system is that formation of complex movement patterns, especially the chunking and sequencing of movement phases. Feedback mechanisms use information from cues extracted by visual, auditory, haptic sources. The task of this system is to fine tune and synchronize behavior with external task and environment elements, such as adapting timing of movement phases, or modulating phase profiles. The phases are typically part of a sequence generated by the cortical circuits. The highest structure is the cortical system used for perception, planning and execution. This system combines the various sources of sensory and perceptual information to build representation that can be used to generate plans and monitor the performance and outcomes of the behavior. This system can handle more abstract forms of information such as verbal or written.

Skill-based behavior is driven by signals that carry the proprioceptive information as well as unconscious exteroceptive information. Skill-based behavior involves the automated sensory-motor system. Rule-based behavior is driven by signs or cues, which typically describe a state of the environment, and determines which stored pattern to activate. Knowledge-based behavior is driven by symbols, which describe abstract states related to a conceptual representation and serve as basis for reasoning or planning (see FIGS. 23A-23B).

The human information processing model helps understand the type of feedback information and associated components of movement behavior. Table 1 summarizes the type of signals, cues/signs and symbols in tennis as an example. At the highest level, the knowledge-based behavior corresponds to the type of stroke and body positioning, etc. to use given the information about the overall situational awareness, such as adversary behaviors gained from exteroceptive information. At the intermediate level, cues trigger behavior. At the lowest level, signals are used to modulate muscle responses.

TABLE 1

Example of signals, cues/signs and symbols in tennis.

| | |
|---|---|
| Symbol: | The type/class of stroke as well as the desired ball placement. |
| Cue/sign | When to initiate a stroke phase and the modulation of the stroke pattern based on the predicted ball impact and bounce trajectory, etc. |
| Signal | Coordination of the muscles during the stroke to conform to learned pattern based on proprioceptive feedback. |

At the highest level, the rule-based behavior involves determining which pattern to activate based on the signs or cues typically obtained from the exteroceptive information. At the intermediate level, cues are used for time movement execution. For example, the particular state of the ball extracted visually, such as the impact, may be used to signal the instant to initiate the backswing or the forward stroke, and modulate the strength of the initial acceleration. Finally, at the lowest level, the skill-based behavior corresponds to movement patterns. Signals are primarily the proprioceptive information. The delays and time constants of the sensory-motor system are too large to provide continuous feedback corrections for fast-paced skilled movements. The neuromuscular time constant (time from the signal to go from the motor cortex to the muscle response) is of the order of 20-30 msec; on the other hand, the response time from a visual or auditory stimuli to a physical response is of the order of about 200 msec. Therefore, skilled movements rely on open-loop execution. Feedback is structured, for example, for intermittent actions based on specific cues and controlling the timing of phases. The largely open-loop execution implies that segments have to be learned in order to be reproduced accurately. And mechanisms to predict the outcome of the movement are necessary to enable modulation of the movement at the instant of execution. This general model can be applied to augmentations used to assist or train human movement behavior. In principle, augmentations can be designed across all three levels. Motion skills, however, assuming the outcome is known, primarily involve the skill-based and rule-based behaviors.

The forms of KP feedback that are most useful are those that contribute to the understanding of the task or movement. This explains why providing a reference trajectory, to model after, is not necessarily useful. In that sense, KR has the advantage that it provides objective information about the implicit correctness of a movement.

Since human attention capacity is limited, it is important to select the augmentations that also account for these limitations and possibly organize the augmentation in ways that allows the brain to take advantage of the mechanisms used to operate efficiently with information (e.g. chunking).

Creating KP feedback contributes to understanding the task or movement. This can be achieved by using movement kinematic and dynamic measurements that produce knowledge of performance that is connected to the movement outcomes, as well as organized in terms of timing and form, etc. in ways that are consistent with the movement's functional dimensions, including biomechanics, motor control and sensing or perception mechanisms.

The core component of motion analysis and cueing platform technology is the decomposition of movement into elemental movement units that are grounded in biomechanics and motor control principles including muscle synergies. This makes it possible to generate feedback that connects task outcome to requirements on these elements of performance. At the same time, using feedback that is structured based on movement organization will ostensibly help better overcome attention limitation since the movement units are part of a coherent movement language. With a technology that will reinforce and teach this language, it can help acquire a form of movement intelligence that is difficult to develop using an ad hoc notation system.

By working within natural functional elements and features, it is possible to factor out effects due to individual differences. Focusing on the structural characteristics of movements derived from performance data, and subsequently identifying features within the functional elements that contribute to the outcome, makes it possible to design feedback augmentation that targets individual movement characteristics but generalizes over the range of skill and styles as well as differences that can arise due to injuries and other factors.

Complex movement behavior can be sequenced into movement elements. Most tasks are composed of a series of stages and complex movements are delineated in distinct phases. Therefore, to analyze movement skills, it is necessary to understand how movement elements are composed. First, how complex movements are achieved by sequencing movement segments, and second how the individual segments are achieved through coordination of different body components.

The first is a temporal decomposition into subtasks or subgoals that depends on the elements of the task and environment. The second is a decomposition into spatial components that can be combined in parallel to achieve a library of coordinated movement patterns. The movement patterns themselves often involve a sequence of phases.

Complex human movements are high-dimensional, i.e. their description requires large numbers of state variables (position, velocities, angles). The representational complexity is in part due to 3-dimensional (3D) space which involves 6 degrees of freedom for the linear and angular motions. This number gets multiplied when multiple body segments are involved and becomes exponentially complex once the ligaments and muscles need to be accounted for. In addition, there are the effects of dynamics, which dictate how these state variables evolve over time and interact through the action of forces (both internal effects such as inertial coupling and the external actions such as the muscles or aerodynamics, etc.). For this reason, even tracking a single segment or object in 3D space such as tennis racket or forearm, requires a dozen state variables. Their temporal evolution is described through coupled differential equations. These differential constraints and other constraints on joint configuration, etc. result in geometrical properties which can be exploited for analysis.

From a control standpoint, the formulation of movement programming typically follows the specification of equations of motion, an initial state and a goal state. Such problems can be solved as a dynamic program, or a two-point boundary value problem. The trajectory is obtained by solving for a trajectory that minimizes a pre-specified cost functional (e.g. trajectory duration or energy). This formulation leads to equations which provide conditions for an optimal trajectory. Thus, for a given initial state and goal state (e.g. that specifies the outcome), there typically exists a unique optimal movement trajectory. The control and trajectory optimization framework provides useful tools for the conceptualization and analysis of movement. For example, it is possible to define cost functions that can help characterize human trajectories, such as measuring energy or more general physical performance. Furthermore, the calculus of variation used in trajectory optimization make it possible to investigate relationships between variations in trajectory and outcomes of the trajectory.

The three primary levels of movement organization are:
(i) the movement profiles and their associated outcomes. This level corresponds, for example, to task level description and represents overall movement element or unit such as a tennis stroke in tennis.
(ii) the movement profiles are usually composed of series of multiple phases. This level corresponds to the biomechanical implementation level, i.e., how the limb segments and joints are coordinated to achieve a complex movement.
(iii) the movement phase profiles can then be decomposed into muscle synergies. This level corresponds to the neuromuscular implementation, i.e., how the profiles are achieved by superposition of muscle units. The muscle synergies represent muscle activation patterns.

The first, corresponds to what could be considered the semantic characteristic, i.e. the general movement technique that can be used to achieve the intended outcome, and is related to strategies developed by the brain to partition the workspace and achieve a range of outcomes relevant to a task.

The second, the phase segmentation, corresponds to the internal structure of the movement, and is related to the strategy used by the nervous system to achieve the particular outcome given the available neuro-muscular system.

The third, the muscle synergy, describes how the various muscles are activated to achieve the movement profile at the phase level. The synergies typically provide spatial and temporal components that can be combined to achieve a variety of movement. Therefore, it is expected that same set of synergies can be reused by other movements. Yet, for example, in tennis the arm segments configuration can be very different at different stroke phases, therefore it is likely that different sets of synergies are used in each phase.

Movement measurements, such as from wearable motion sensors or optical motion capture systems, represent non-linear time series. The analysis of time series relies on understanding the structural characteristics of the underlying dynamics. The characteristics associated with the architecture of the movement such as the movement phases in a tennis stroke or golf swing. Insights can be gained using computational visualization tools such as phase space; however, the states may have too many dimensions to be practical. Therefore, the data should be reduced. The behavioral data captured from the available measurements results in a high-dimensional state space. The dynamics driving the behavior, on the other hand, may be lower-dimensional. Dimensionality reduction can be used to discover the dimensions underlying behavior. It belongs to the class of unsupervised learning technique.

For nonlinear time series, the goal is to transform the original movement data, which are described in terms of the high-dimensional time series $x_t$ into a lower dimensional description that preserves the geometric characteristics of the movement dynamics. This can be done, for example, using Taken's embedding theory. Examples of recent applications of dimensionality reduction include gait analysis.

In some applications, movement phase segmentation can be based on pre-existing or empirical understanding of the movement phases. The accuracy of the movement phase decomposition, and the validity of the associated finite-state model, can vary significantly from one individual to another or even on the class of motion considered. Since the movement dynamics and control processes are nonlinear, a broad range of movement patterns can exist for the same intended movement and outcome. The specific movement structure will depend on the individual's skills, technique, the particular body characteristics, biomechanics, and other factors including injury, disease, etc. Therefore, the phase decomposition requires a method to determine the optimal movement segmentation and its finite-state description. FIGS. 15A-15E illustrate the development of movement pattern structure in terms of finite-state model structure for a tennis stroke, as an example.

Although movements are usually high-dimensional behaviors, trained movements typically have specific patterns. Patterns have the useful property that even though the behavior relies on many degrees of freedom (DOF), they can be described by a few, dominant DOFs. The patterns form a lower-dimensional system as a result of the coordination provided by the neuro-motor processes, and other perceptual and control mechanisms. The lower dimensions however can hide a complex geometry and topology.

The movement architecture can be analyzed by focusing on the low dimensional manifold that are associated with the particular movements' dynamics pattern. Using a nonlinear dynamic systems formulation gives access to analysis and modeling tools that under certain conditions can reconstruct the pattern dynamics from measurements of the behavior. The reconstructed dynamics can then be analyzed to determine the structure and geometry which can then be used to determine useful abstractions or models.

Using mathematical tools used for the analysis of nonlinear dynamic systems, the movement patterns can be described by a nonlinear mapping F associated with discrete-time nonlinear dynamics:

$$x_{t+1} = F_t(x_t, t, \in_t) \qquad \text{EQ. 1}$$

where $F_t$ is a map, $x_t \in \mathbb{R}^n$ is the state vector at discrete time $t \in \mathbb{N}$, and $\in_t$ is a time-dependent noise. In the forthcoming discussion it is assumed that the dynamics are autonomous and use a constant map $F_t = F$.

The nonlinear model of movement patterns therefore can be described by a map F. The map captures the combined effects of the biomechanics, sensory, motor-control processes. This model assumes that the movements that are learned result in deterministic dynamics. A continuous time representation could also be used, in this case the dynamics are given as an ordinary differential equation (ODE) $\dot{x} = f(x(t), \in(t))$, which describes a vector field and is typically called the flow. The set of initial conditions which result in the same asymptotic behavior are referred to as the basin of attraction. Such a nonlinear dynamic models can describe a broad range of phenomena. The model could be decomposed into subcomponents giving access to the various contributing systems and processes. For example, it may be possible to explicitly model how the users adjust their movement pattern to changes in conditions such as adjustment of a forehand topspin stroke for changes in ball height at impact. However, at this point in time the behavior is regarded as a closed-loop behavior which abstracts the various internal mechanisms.

The language of nonlinear dynamic systems make it possible to describe the collection of movement patterns that composes a user's repertoire in a particular activity (tennis, skiing, surgery, etc.) by a collection of distinct dynamics or maps $\{F_\alpha, F_\beta, \ldots, F_\gamma\}$. In many nonlinear time series, the movement system state variable x is generally not directly observable. Instead, measurements y are acquired for example through motion sensors. The observations, or measurements can be defined as: $y_t = h(x_t, \eta_t)$, where h is the output map and $\eta_t$ is measurement noise.

A property of movement at the highest level is referred to as "motor equivalence". The fact that the brain generates movements that are equivalent in terms of their accomplished outcomes underscores the idea that at the highest level the brain encodes outcomes and their relationship with task goals. The planning and monitoring functions associated with goals are part of the brain's executive system. For example, in tennis, the player selects a stroke type based on the desired outcome and the conditions (ball state including expected impact height, velocity and spin of ball). Even within the continuum of conditions and outcomes, it is possible to recognize distinct classes of strokes. The invariant characteristics in movement features enables delineation between movement classes, e.g., movements within one particular class can be related through some smooth transformation such as rigid-body translation and rotation, i.e., they are invariant under this class of transformation. The overall movement class can be subdivided into subclasses. For example, a hierarchical decomposition would group movements based on relative similarity.

In tennis, the overall stroke class can be subdivided into dozens of subclasses based on movement where the levels represent different types of features. For this example, a top hierarchical level is called the category level. It differentiates between groundstroke, volleys, serves, etc. The distinction between stroke categories is made primarily based on the height of the impact point. Further, subcategories can be created based on the side of the impact, i.e., forehand or backhand. Even further subclasses can be delineated based on the outcome (topspin, flat, slice), and strength. Beyond these common classes, finer distinctions can then be added based on additional aspects of stroke technique, such as open or closed stance. Most of the stroke characteristics can be determined entirely from the racket trajectory and therefore do not require additional measurements such as the position of the player on the court. Each movement pattern class in a repertoire has a different shape and may occupy a space of different dimension. The shape and dimension is a result of the dynamics, which is given by the transition map F. The repertoire is the collection of these shapes. From a mathematical standpoint, the geometrical characteristics of the movement patterns can be described via embedding theory. The idea is to determine the subspace of DOF that fully describes the movement. The dimensionality of the system and the geometry of the manifold that contains the trajectory describe the movement class structure.

As is often the case in nonlinear system dynamics, the state transition map F (the dynamics), the output map h and the dimensionality of the state vector n are not known. Techniques of nonlinear time series analysis can (assuming deterministic dynamics F and smooth output map h) estimate the dynamics associated with a movement pattern from time series obtained from measurements of the behavior. Repertoire characteristics can provide a variety of information about skill. Movements are typically analyzed in specific classes without considerations about the overall repertoire structure. The movement repertoire for a particular activity domain describes how a user organize the outcomes and technique that task domain. The simplest way to classify movements into repertoire is to extract features from the time series and apply clustering techniques to determine classes.

Movement classifications have been used in other applications unrelated to skill modeling such as activity detection or gesture recognition. Gesture recognition is a growing aspect of natural human-machine interfaces. The general goal in the latter application is to determine motion primitives that provide a low-dimensional description of the various movements that can occur in that domain. The primitives can then be used to classify the movements. The library can then be used by other agents to identify the intent of a human or robotic agent and for example allow collaboration between agents. The emphasis of gesture classification is the identification of semantic characteristics. In the present application the goal is to classification based on characteristics that are related to movement technique and outcomes. Typically, the higher categories of the stroke classification can be considered in a semantic sense (e.g. groundstroke vs. volley or backhand vs. forehand) the lower level classes are related to technique.

A particular ensemble or repertoire of patterns in a domain of activity arise through the effects of biomechanical, neuro-muscular constraints, as well as task related constraints. In the most general sense, the patterns describe how and individual's movement techniques are used to achieve an outcome. An important aspect of the movement characteristics is how they are broken down into phases. Overall movement pattern characteristics, therefore, are the result of the phase structure.

The serial order in behavior and the movement phase structure are distinct. The serial order is associated with the activity level, for example, characteristics related to the activity constraints such as process stages, rules, etc. The movement phase is associated with movement technique and is related to characteristics of the movement system. For example, in tennis, the stages include serving, then moving to the anticipated, making adjustments in the displacements as the ball returns, setting up for the stroke and engaging the ball using the stroke type required for the desired outcome. The overall sequence of stages corresponds to the serial-order of behavior. Each stage can be parsed and the movement associated with it can be analyzed. The phase structure of a movement defines the topological characteristics of the manifold and the dynamics that drive the phases define its geometrical characteristics.

Many complex movements are achieved by combining several movement phases, leading to further temporal structuring of the movement. Examples include the phases in locomotion gait or the phases in a tennis stroke. Phase structuring of patterns typically arise from the intrinsic movement constraints (biomechanics), some aspects of task constraints as well as functional factors related to motor-control and decision mechanisms as discussed elsewhere. For example, in gait, distinct phases are associated with the basic leg biomechanics and mechanics of ground interactions.

In tennis, the general goal of the user is to return an oncoming ball. This is accomplished by imparting forward momentum and spin to the ball when the user hits the ball. The user controls the ball by modulating the amount of linear and angular momentum imparted to the ball. For accomplished players, the overall tennis stroke motion encompasses the kinetic chain formed by the legs, hips, shoulder and elbow and wrist. These segments are coordinated to form a continuous movement starting from the backswing all the way to the follow through and recovery. At closer inspection distinct phases can be recognized. The exact phase characteristics depend heavily on skill level. Beginning players primarily swing the racket from the shoulder without very precise coordination with the rest of the body segments. Advanced players exploit the entire body kinematics to maximize the outcome. Ultimately, the phase characteristics reflect the combination of the body segments' biomechanics and neuro-motor strategies, including the muscle synergies, that achieve the highest outcome reliability with best use of the physical capabilities. Different phases are associated with different biomechanical functions. For example, in walking, synergies that are activated at specific phases of the gait cycle (e.g. forward propulsion, swing initiation, deceleration, etc.) have been identified.

The role of constraints in creating distinct movement phases can be explained using concepts from constraint optimal control. In optimal control trajectory segments are related to the concept of singular arcs, which correspond to segments where different set of constraints are activated by the trajectory. In general, these systems are best controlled using switched control laws. The control law is determined based on a partitioning of the system's state. As the system is driven by the control action, and travels through the different partitions of the state-space the control strategy switches to best account for the local characteristics of the dynamics.

Figure 3:
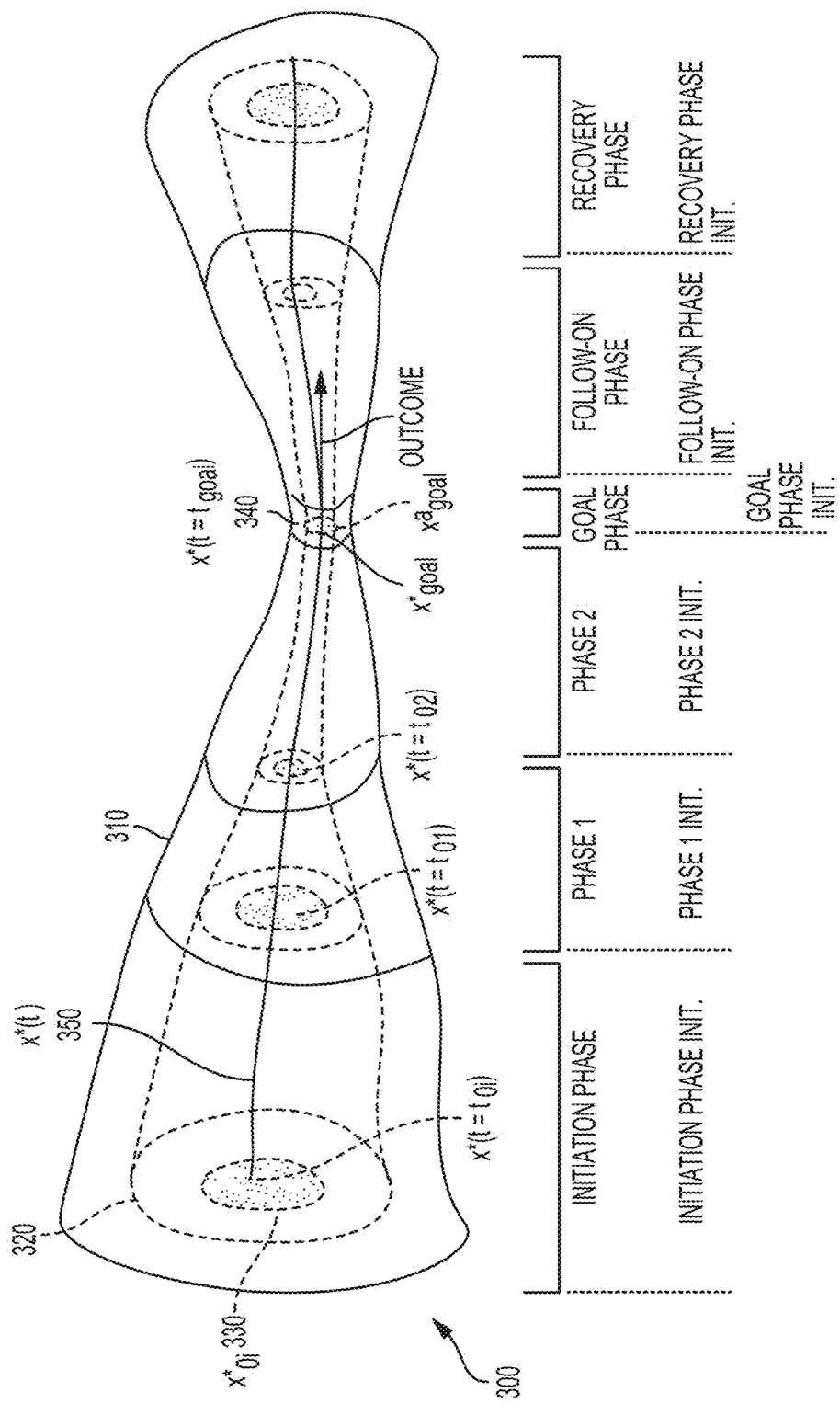
FIG. 3 illustrates a general movement trajectory and associated primary outcome highlighting the movement phases, and showing the optimal trajectory, the admissible envelope, and the feasible envelope across the movement phases resulting from the various movement constraints.

Following the nonlinear dynamic systems description, trajectory phasing can be described mathematically as a sequence of deterministic dynamics $F_1, F_2, \ldots, F_N$. The overall trajectory is obtained by a series of initial values and asymptotic behaviors, where the next set of initial values corresponds to the terminal values of the previous phases (FIG. 3). The dynamics associated with each phase result from different joint and limb segment configuration and force fields. Each dynamics $F_i$, can therefore be assigned a state-space region specified by an initial state set and a goal or subgoal set. For example once the dynamics are initiated from the initial set, the initial dynamics $F_1$ will take the state to its subgoal set $X_1$, and from there, assuming the state satisfies the next initial state conditions for the next dynamics $F_2$ the system will switch to the next phase, etc. The state values associated with the switching between dynamics, e.g. $X_{1i} = X_{0j}$ define the phase transitions. The dynamics associated witch each phase result from different joint and limb segment configurations and force patterns. The force patterns result from the spatio-temporal muscle activation patterns, i.e. muscle synergies.

The synergies describe the coordination between the different muscle groups and limbs segments that are used to implement movements. The synergies are a type of motor primitive which is typically reserved for the neuro-muscular coordination. In examples discussed earlier, various movement profiles observed in an activity can be obtained through the combination of such primitives. Decomposition into synergies therefore can help gain insight into the set of biomechanical and neurological components that participate in movement skill. In turn this information can be used to gain understanding about the biological components, and could be useful for physical performance, injury prevention.

Popular techniques are non-negative matrix factorization. Synergies have been characterized with a variety of measurements, including movement profiles of the end points, joints and/or body segments, as well as muscle and neurological activity such as provided by surface electromyography (EMG). The type of measurements obviously determines the accuracy of the results. For example, simple end point or body segment measurements may not provide synergies that correlate strongly with the neuro-muscular activity. Synergy analysis has not yet been integrated in clinical settings where it could be used for assessment and rehabilitation. Since synergies have been identified at different levels of the neuro-motor hierarchy (motor cortex for grasping, brain stem for posture and spinal cord for locomotion), the muscle synergy analysis can provide a more precise picture of neuro-motor deficits.

Some movements have an explicit outcome or goal. This goal may be the movement's end state, i.e., $X_{goal} = X_N$, or it could be the state at an intermediate phase such as a subgoal. The latter is the case for the tennis stroke. While the ball impact is the primary goal or outcome of the stroke, this phase is not the actual end of the movement. The movement phase following the impact, the follow through, is an important part of the overall movement pattern. Most complex movements involve many body segments or degrees of freedom. Therefore, the state trajectory is a multidimensional state vector and it is necessary to add distinctions between the different state trajectories that participate in the action. Focal and corollary movements are distinguishable; the focal movement is, for example, the finger movement that hits the key; the corollary movement is, for example, the motion of all other fingers that are part of the overall kinematic pattern essential to the task of hitting the key. Although not every movement behavior has an explicit goal or outcome. For example, most of the movements used in skiing have as purpose to control the skiers' speed and direction. From a dynamic system standpoint this goal involves generating a centripetal acceleration though the interaction of the skies with the terrain. Depending on the skier's state and terrain conditions, different motion pattern of the legs and hips, etc. are used to achieve the best outcome (will be discussed elsewhere). For a deterministic autonomous dynamical system, trajectories from a given initial state are unique, and, assuming the system has a stable asymptotic behavior, re-injecting the same initial state will lead to the same trajectory pattern.

It is possible to define an optimal trajectory that takes the system through the phase sequence achieving the goal condition (outcome) while minimizing a performance objective such as jerk or energy. Given the biomechanical constraints, muscle synergies, etc. the optimal trajectory is associated with a specific phase sequence. The conditions at the phase transitions, i.e., the set of initial states, and subgoal states, $X_{1i} = X_{0j}$ as well as the dynamics $F_i$ describing the transitions, represent characteristic features of the optimal trajectory.

Absolute optimal trajectory, which is the global optimal solutions for a given outcome, while the local optimal trajectory is for a given phase structure. The latter, for example represents, situations where due to lack of flexibility, skills or injury, only a limited set of configurations can be achieved as well as limited muscle force fields.

In optimal control theory, perturbation of the initial value leads to neighboring optimal trajectories. This is guaranteed if the initial value is within the so called basin of attraction of the system. A similar idea can be used for perturbations in the dynamics F. Such perturbed dynamics lead to slightly different asymptotic behaviors, however, for small enough perturbations the trajectories stay close enough to the nominal trajectory that these perturbed trajectories belong to the same movement pattern. The range of perturbations in the initial values and dynamics for which the trajectories remain in the basin of attraction defines the admissible envelope. Perturbations in the dynamics and disturbances are captured by the time dependent noise term $\in_t$ FIG. 3 illustrates of a trajectory envelope 300 for a hypothetical movement pattern. The movement in this example includes an intermediate goal set. The trajectory envelope 300 delineates a region of the state-space over time and highlights feasible envelope 310 and the envelope of admissible trajectories 320 as well as the envelope of the optimal trajectory 330 ($x^*_{0i}$) and the optimal trajectory 350 ($x^*(t)$). The structure of the movement both in terms of patterning and the phase segmentation are given by its spatio-temporal characteristics. Movement characteristics are defined by the geometry and dimension of the manifold containing the trajectory. Several phases are shown including: movement initiation, phase 1, phase 2, an intermediate goal phase, a follow-on phase and recovery phase. These movement pattern characteristics are usually determined from the topology of the movement pattern manifold obtained from analyzing the nonlinear time series. A user may choose "admissible movements" that belong to the same movement pattern and still reach the goal conditions or outcome. This could happen due to changes in movement goal conditions (impact height and velocity), or imperfect initiation of the movement. The suboptimal trajectories can still reach the desired end state or outcome, however, they will typically require more physical effort, may cause stress in some of the muscles or joints, or other undesirable effects. The physical performance can be described through models of the musculoskeletal system and cost functions such as for energy consumption.

Movements belonging to the same pattern can therefore be related through perturbations relative to a nominal trajectory. Moreover, the trajectory perturbations also result in perturbations in the primary outcome and any other secondary outcome characteristic such as the different phase outcomes. Using this data, it is therefore possible, for example through regression analysis or sensitivity analysis, to determine relationships between the trajectory perturbations (what correspond to the movement technique) and perturbations in outcomes. This information provides a quantitative basis to generate skill characteristics, such as what aspects of the technique contributes favorably to the outcomes and vice-versa what aspects are detrimental to good outcomes. This knowledge in turn can be used for training and eventually help synthesize feedback laws for real time cueing.

By modeling movement patterns as a sequence of phase segments with distinct dynamics $F_i$, the pattern dynamics can be abstracted as a finite-state model. In the present case, the finite states are the individual phase dynamics $F_i$ which take the system from initial value $x_{i0}$ to the next subgoal state $x_{i1}$. More generally, the initial and subgoal states are represented by sets to account for the variations and disturbances that are typically expected in human behavior. With this model, the overall motion behavior is then given by some finite-state automata which gets triggered from the initial state and initial movement phase. The motion behavior combines both continuous dynamics and discrete variables that capture phase transitions and mode switching which may be associated with discrete decision variables. Hybrid models can be used in many modern engineering applications including robotics such as for autonomous systems, as well as, human-machine systems. Once the structure of the motion is characterized it can be described by finite-state models.

Statistical models, in contrast to deterministic models, where the current state uniquely determines the evolution of the system (i.e., within the disturbance or model uncertainties), describe the evolution of the probability density of future states. Statistical models such as Dynamic Bayesian Networks have become increasingly popular in data-driven approaches. Popular applications in the movement domain are identification of human activities. These approaches typically require learning the phase of activities based on statistical pattern analysis; and subsequently, using this knowledge to discretize the state space into discrete states; and finally, determining the state-transition probabilities. A common model is the Hidden Markov Model (HMM). Most of the notational system focus on the discrete game structure and can be used to analyze game plans but currently do not reach down to the actual movement skill level.

Real-time movement phase estimation can be implemented by someone trained in the art. For example, a multi-layer HMM application to movement could be based on similar models to those used for real time speech recognition. Decoding sound recording for speech recognition typically proceeds in multiple levels. Most of those are associated with the levels of organization of the speech production system. The units of decomposition of speech is based on phones which combine to form the phonemes. The phonemes are the basic building blocks used to form words. The phones are related to features of the vocal movements. Following this model for movement correspond to have, at the top level, a movement phase model which describes the probability distribution over possible sequences of movement phases. At the midlevel, a phase model that describes the composition of the movement phases in terms of movement components (c.f. synergies). And finally, at the bottom level, the movement model that describes the movement components based on features in the available measurements (IMU unit or other sensors).

Because of individual differences in anatomy, style and skill level, movement targeting the same general outcome can be quite different. The differences can manifest in the movement phase structure. For example, for a beginning tennis player, a forward stroke will be a rudimentary movement consisting primarily of a forward swinging motion implemented from the shoulder joint. Over the course of skill acquisition and development, the brain will learn to better take advantage of the physical potential, range of coordination of the body segments, and other movement system components.

Complex movements involve coordination of multiple body segments; some segments are tightly coordinated while others can be independent such as fingers. The evolution in movement technique as movement skill develops is associated with a changes in multiple aspects of the movement system, including, a development of the physical performance (e.g. muscle strength). The most critical for skill analysis is the acquisition of coordination, which involve changes in the central nervous system. As movement skill develops movement patterns undergo profound changes in architecture. Therefore, the analysis of skill has to capture the underlying structural changes. A characteristics of learning complex movements is learning to use and coordinate the large number of degrees of freedom afforded by the body. The structural changes in the movement can be captured by modifying and extending finite-state model. The movement phase structure results among other factor from the effect of various constraints and functional requirements associated with the task. One aspect of the evolution of movement phase structure can be related to the concept of co-articulation that was introduced in speech production. A task that requires a sequence of movement elements, training can lead to the formation of new movement elements (see FIGS. 15A-15E). These are formed through the interaction of neighboring elements. The optimizations of the links between action phases have been studied in simple tasks. The co-articulation, however, mostly focuses on the process linking between elements.

The range of motion sensors, available either as embedded or deployed in the environment, provides measurements of broad aspects of the movement dynamics of users, actors and their equipment. Given the depth of hierarchical levels of the movement system, the scope of motion analysis can be conducted at multiple levels. For example, it could focus on neuro-motor aspects, movement technique and structure, outcomes, all the way up to tactical and strategic levels.

Detailed analysis of movement skill, in particular for open motor skills, quickly become complex. In tennis, for example, the stroke motion is part of a much larger system of coordination and interactions that include the ball trajectory, the footwork, going all the way to court motion, the game tactics, etc. Analysis of the stroke motion usually encompasses the racket trajectory (i.e. end effector or equipment), even though that trajectory is the result of a kinematic chain which involves the upper body and the driving motion that starts from the feet, legs, and hips. Therefore, many elements and body segments should be tracked to provide a complete description of movement performance.

Viewed through direct observation, there is typically significant variability in human performance on repeated trials, making it difficult to apply quantitative models that describe an individual's technique and skill comprehensibly and with specificity. In addition, the movement technique of users is highly individualized due to specific body types, physical fitness and skill level. Therefore, it is essential to be able to capture a user's unique elements and features, and be able to continuously adapt the training method to the user's evolving skill.

Skilled behavior relies on organized strategies and builds on the well-defined hierarchical organization of neurological processes. Therefore, to enable the systematic process, going from the assessment and description of skill to the synthesis of feedback to the user, it is necessary to define a modeling language that captures the structure and organization of movement and is grounded on the fundamental principles and principles of human movement science.

Following this language metaphor, conceptually, the core technology focuses on decoding movement data to extract relevant movement elements that can be used for skill analysis. The relevant elements in natural speech processing are the units of organization of speech production, known as phonemes. The decoded phonemes can then be used to identify words and eventually the meaning of a sound bite. To help extract movement units that are useful for skill analysis and diagnosis of an individual's movement technique, these units are related to the process used for movement production. This analysis can then be translated into instructions and synthesize augmentation systems.

In parallel, the system utilizes an infrastructure to operationalize the various processes. The basis of the infrastructure is a data structure derived from the movement units that support efficient handling, processing, tracking, and managing of motion skill data. In addition, the structure allows codification of skill components and their functional characteristics to design feedback mechanisms that target precise aspects of the movement skill performance and learning. The proposed skill model and accompanying technology accommodates the nuances that naturally occur in human performance, and build on the structural features inherent to the human movement system and its various functional and learning mechanisms. Moreover, the methods capture both the global skill components that give users its versatile performance in an activity domain, and the specific skill components needed for performance and adaptation to the specific task elements and conditions.

FIGS. 4A-4E show examples of movement architecture for the primary movement unit for other movement activities (tennis movement unit 410, golf movement unit 420, baseball movement unit 430, skiing movement unit 440 and running movement unit 450 for a user 10). The drawings also highlight the movement phases and the primary outcome.

The augmented skill platform is configurable to create an integrated environment for training, maintaining and rehabilitating motion skills by combining motion capture technology, skill modeling and analysis tools, and a set of feedback modalities that can target precise aspects of movement performance. The system trains movement techniques to optimize a set of outcomes that are relevant to the activity over its domain of operation.

Any task can be described by environment elements EE, and task elements TE. For example, a person manipulates a device (e.g., tennis racket), end effector or piece of equipment, to interact with the task elements TE (e.g. tennis ball). In addition, there may be miscellaneous accessories Z such as shoes, clothing, that may be relevant for the description of the activity. The workspace W is contained in the environment and is specified by various constraints and rules that characterize the task's success and performance (e.g. the tennis court and tennis game). In tennis, the person is the player (or players); the task environment is the tennis court; the task element is the tennis ball; and the equipment is the tennis racket, and the accessories Z are the shoes and other pieces of attire such as an arm or head band. In addition, a variety of output devices can be included, including graphical displays (e.g. LCD, OLED, etc.), haptic devices (e.g. embedded in the racket grip), speakers. Finally, consider a variety of input devices, including, touch sensitive display (user interface), keyboard, etc. The input and output devices may be integrated in the form of a smart watch, tablet, or a wearable device that can be worn by the person.

The overall elements, agents and other components used, including the measurement, input and output devices, are referred to as the augmented human system or simply the system S. Other examples of systems that have this general setup include a robotic system, a cybernetic system (e.g. a human fitted with a prosthetic), a human-machine system (human operating a robot through tele-operation). For example, a robotic surgical system such as the DAVINCI® Surgical System (available from Intuitive Surgical, Inc.) is a robot that is an example of integrated augmented movement skill system.

Measurements y can be obtained from different components of the human actors, equipment, or system. Typically, instrumentation is designed to obtain measurements that encompass relevant variables for the particular level of analysis. For example, in the analysis of human tennis stroke performance, the states, or a subset of the racket motion may be sufficient. Additional measurements about the body segments (e.g. arm, legs, feet, etc.) are necessary to enable an analysis of the movement on the court, the footwork, or the body motion such as the kinematic chain or other movement units. These measurements can be obtained using a variety of technologies, including inertial motion unit (IMU), visual or optical tracking systems, etc. Examples include the use of video cameras that capture the broader agent behavior and the task environment. Vision processing can also be used to extract information about the motion of individual body segments. An important class of measurements are those that capture physiological quantities. For example, a gaze tracking system to measure the visual attention. Thus, as shown in FIG. 2, a user 10 (or player) holding a tennis racket 20 which impacts a ball 30 during the swing of the racket has a gaze 12 which follows a trajectory which changes during the motion. One or more motion tracking cameras 210, 210' can be provided which capture data related to the user 10, the tennis racket 20, the ball 30, the motion and the environment. Inertial measurement units can be embedded or affixed to the equipment; worn by the agent to measure the movement of body segment; or even placed on the skin or implanted in the body to measure muscle activity or neural signals involved in the control of muscles. See FIG. 5, which illustrates an arm 14 of a user with a surface electromyogram (EMG) sensor 510, an intramuscular electrode 520 and an IMU 530 for illustration purposes. The IMU measures velocity, orientation and gravitational forces using a combination of accelerometers and gyroscopes, and sometimes also magnetometers.

In addition to the measurements, data fusion and state estimation techniques may be implemented to determine states x that are not directly measured. For example, in most applications using IMUs, the orientation of a body segment or piece of equipment requires an attitude estimator which combines angular rate data from the gyroscopes, the accelerations from the accelerometer and the magnetic field strength from the magnetometer. An example of data fusion and estimation is the use of extracted body segment or equipment motion information from a vision-based tracking algorithm, applied to video data from video cameras, and IMU data from a device on either the body segment or equipment. Such a data fusion system can be used to provide an accurate estimation of absolute pose of body segment or equipment. Typical cyber-physical systems are described formally using hybrid system notation. This notation system combines continuous and discrete quantities. For example, the movement of the agent may be governed by physical laws that result in nonlinear continuous time differential equations. Discrete variables may be used to evaluate conditions associated with specific events, such as counting strokes in a tennis game or scoring the game based on ball trajectory relative to the task environment and rules. Categories of state variables include: controlled variables, specific behavioral variables such as the visual gaze vector, and features used as cues by the agent to make decisions.

Actions are typically taken by the user and represent the addition of force or energy to the system. Actions are typically applied to specific locations such as the end effector or equipment. Actions are often motivated by a deliberate desire to achieve a particular outcome. In. In tennis, for example, the player wants to impart a specific effect on the ball (velocity and spin), with the ultimate goal of driving it to a specific location on the opponent's court side. Events can be defined by particular state conditions. For example, in tennis, a major event is the impact of the ball on the racket. Events can be expressed formally by constraints on the system states, e.g. racket acceleration exceeding a threshold due to the impact, or alternatively, the impact can be detected when the ball and racket velocity are equal. Other relevant events in tennis include contact of the ball with the ground and when the ball crosses the net.

Outcomes are defined as quantities that capture the relevant characteristics of the agent's behavior in a task performance. To provide a concise description, outcomes can be categorized hierarchically, e.g. primary outcome, secondary outcomes, etc. The definition of outcomes are a function of the scope and level of the analysis. Expressed formally, outcomes are a subset of the system states (e.g. at specific times, defined by events) or a function of the states. For example, in tennis, primary outcomes are the characteristics associated with the racket-ball impact, such as the spin of the ball when it leaves the racket or the ball's velocity. Secondary outcomes could include the location of the ball on the racket's string bed. Depending on the level of analysis (and available measurements), more comprehensive outcomes include the location of the ball's impact on the court. The skill of an agent A is the effectiveness with which the agent is using its body and/or tool, equipment, etc., to achieve desired task outcomes TO and more generally interact with, and/or adapt to the environment elements EE and task elements TE.

Miscellaneous quantities include task or game rules (e.g. rules of the tennis game). Decision rules if one of the agent or its equipment or accessory is computer controlled, e.g., control laws used to control a prosthetic limb, or for autonomous agents, the rules and algorithms that specify its behavior and actions in the environment and in response to the environment and/or other agent(s).

FIG. 1 illustrates an overview of the system and is followed by a description of the 'augmented human system', and finally, the general motion model, skill model, and the different augmentation modalities. The iterative training process illustrated in FIG. 1 illustrates two primary feedback loops: an assessment loop 100 tracks the skill acquisition process, and an augmentation loop 120 augments the user's human movement behavior during the training and task performance. The assessment loop 100 can be used to track and update information about the user's skills, including motion models and skill models, as well as diagnostic tools used to identify specific deficiencies in movement technique. The identified motion and skill models, combined with the diagnostic assessment provides the basis for generating a set of instructions, which are used to organize the training process, and synthesize cueing laws used to drive the augmentation. A user receives two primary forms of feedback: instructions and real-time cues. The instructions are typically generated during a session at particular intervals, e.g. completion of a training set, or after a training session. Instructions are typically presented in visual form and emphasize more comprehensive aspects of performance and skill.

The augmentation loop can be used to exercise movement by focusing by focusing on movement characteristics that have been identified through the diagnostic tools. The cueing process targets specific characteristics to directly impact movement outcome and performance. The cueing system computes feedback signals using algorithms that are synthesized based on the motion and skill models derived during the assessment. These cues are communicated in real-time to the user. The assessment and augmentation feedback are delivered following the hierarchical organization that takes into account the hierarchical structure of skill development and the temporal characteristics of the movement and skill attributes.

The training assessment loop is managed by a training agent. The augmentation loop is managed by a cueing agent. These agents operationalize the two processes and are able to track progress at these two levels and provide the necessary user functionalities (see FIGS. 1 and 6).

Figure 6:
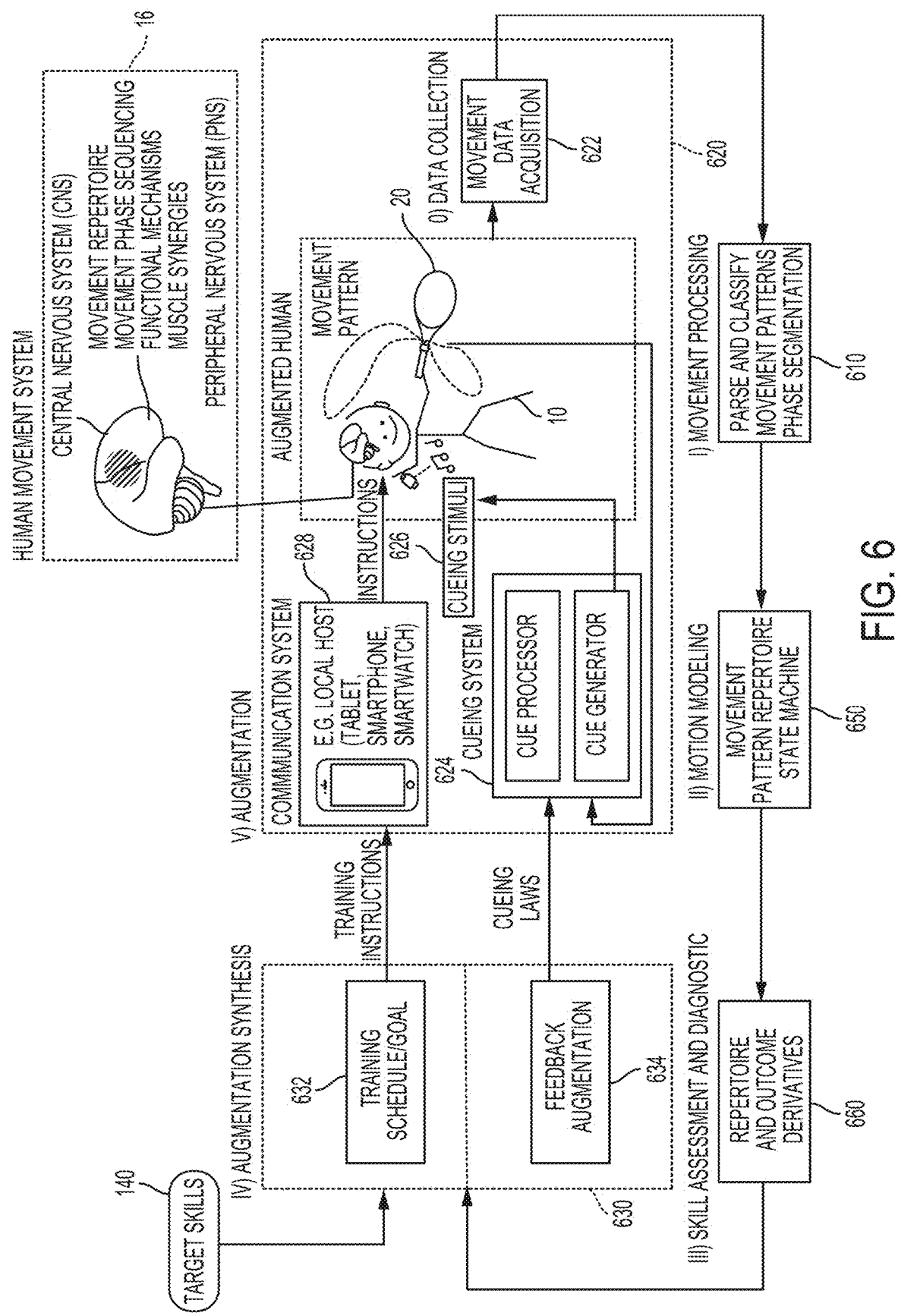
FIG. 6 illustrates components of a platform that a user engages according to the disclosure including the cueing system and communication system that are used to enable user performance augmentation and interactions.

FIG. 6 illustrates the primary components of the proposed platform to target skills 140. The platform depicts a human user 10 (or subject) having a movement system 16 (including a central nervous system and a peripheral nervous system) who exercises his or her movement skills in a particular activity (tennis as shown here) in its corresponding task environment. Some activities include a piece of equipment such as tennis racket 20 and a ball. Movements are used to either produce specific outcomes that are relevant to the activity, or to adapt to environmental conditions. For example, in tennis, the primary outcome is the control of the ball trajectory (it encompasses characteristics such as impact location on the court, the impact velocity, and spin effect determining how the ball will bounce when it lands on the other end of the court). The user is instrumented with some form of motion measurement device such as an inertial measurement unit (IMU) which acquires movement data 622. The motion measurement devices can be distributed on relevant body segments and/or equipment. The user's motion can also be measured using motion capture system such as a vision-based motion-tracking system. In addition, the system can also be configured to monitor the task environment and track relevant elements, such as the motion of the tennis ball relative to the tennis court. Sensor devices can also be embedded in the ball or other relevant elements (e.g. instrumented tennis ball).

Figure 7:
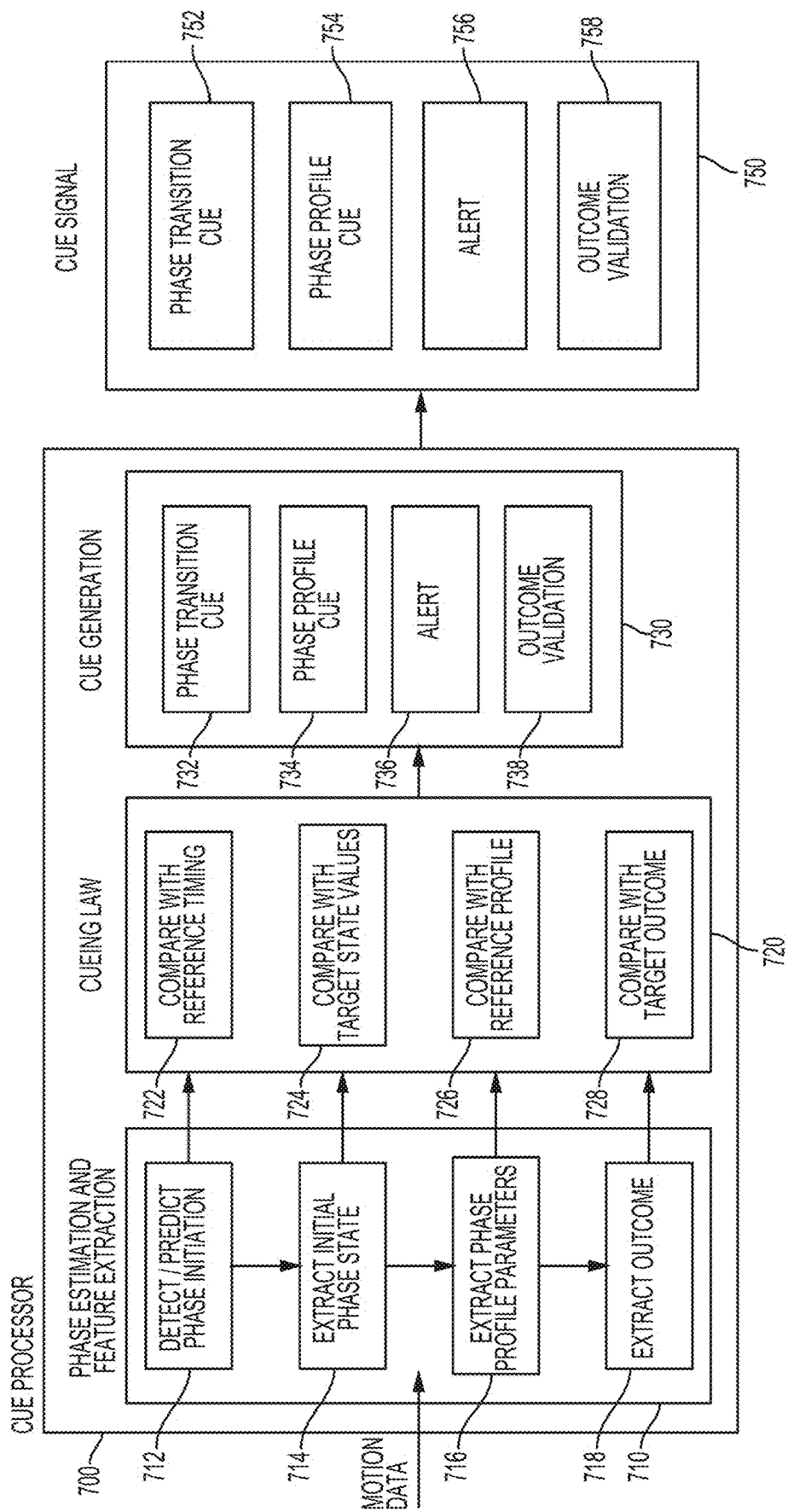
FIG. 7 is a block diagram of cue processor; an overall view of the feedback augmentation processes across four cueing mechanisms: phase transition cues, phase profile cues, alerts and outcome validations.

The real-time feedback augmentation relies on cueing laws that are implemented on a cueing system 624 which has a cue processor (see also FIG. 7). These cueing laws can provide continuous feedback, based on movement profile characteristics, or intermittent feedback, based on discrete movement characteristics via cueing stimuli 626. The signals from the cueing laws are communicated to the user using a cue generator which is part of the cueing system 624, which produces cue stimuli that can be perceived by the user during movement performance. The cueing system 624 and generator can be integrated into wearable devices. Typical cue stimuli include audible, visual, or haptic. The transducers can be integrated in clothing, accessories, etc. The representation of movement skills requires breaking down motion data according to the multiple levels of organization of the movement system. If this representation proceeds based on fundamental properties of human movement system, the representation will provide assessment of skill in a grounded manner that will more easily and directly translate into training interventions. A local host 628 (e.g., tablet, smartphone, smart watch, etc.) can communicate training and cueing information to the user. An augmentation synthesis 630 can include training schedule or goal 632 and feedback augmentation 634. The augmentation synthesis 630 can communicate training instructions to the local host 628 or cueing laws to the cueing system 624. Data that is collected from a user via movement data acquisition 622 can proceed through steps that include movement processing 610, which parses and classifies movement patterns resulting in phase segmentation, motion modeling 650, i.e., the movement pattern repertoire state machine, and skill assessment and diagnostic 660 which provides a repertoire of outcome derivatives. The data resulting from movement processing, motion modeling and skill assessment, is then provided to the augmentation synthesis 630.

FIG. 7 provides additional detail about the operation of the cue processor 700. The cue processor 700 has three main operations: a phase estimation and feature extraction 710, a cueing law 720 and a cue generation 730. The phase estimation and feature extraction 710 further includes one or more of a detect/predict phase initiation 712, an extract initial phase state 714, an extract phase profile parameter 716, and an extract outcome 718. The cueing law 720 further includes one or more of comparing with reference timing 722, comparing with target state values 724, comparing with reference profile 726, and comparing with target outcome 728. The cue generation 730 further includes one or more of phase transition cue 732, phase profile cue 734, alert 736, and outcome validation cue 738. The input to the cue processor 700 is motion data while the output is one or more cue signals. A cue signal 750 is an output of the cue processor 700. The cue signal 750 has one or more of each of a phase transition cue 752, a phase profile cue 754, an alert 756, and an outcome validation 758.

Figure 8:
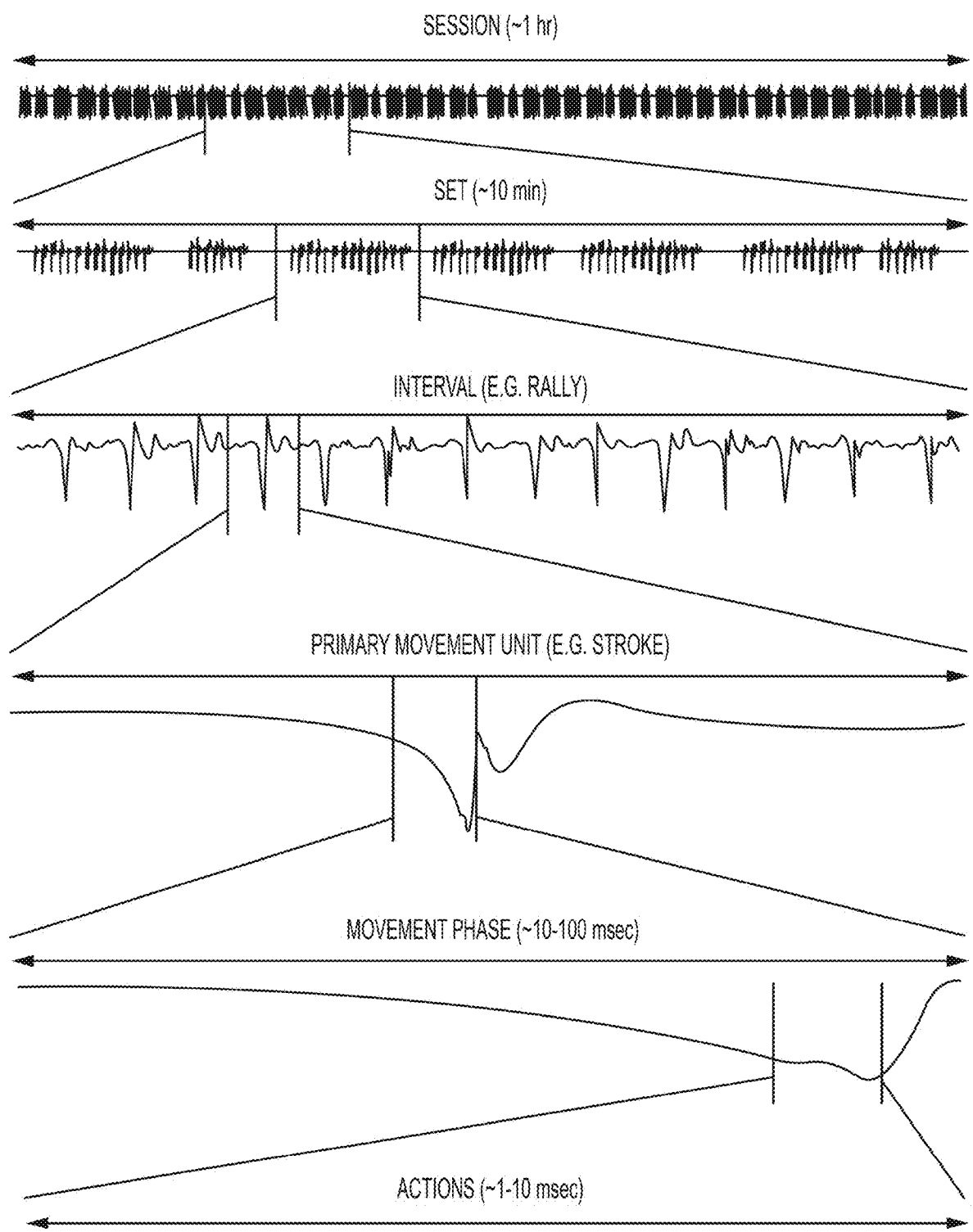
FIG. 8 illustrates a temporal structure of the motion activity data describing the segmentation hierarchy and its typical temporal scales.

FIG. 8 shows the overall temporal structure of movement activity for a session. The figure highlights the primary levels of delineation including session, sets and rallies (consecutive strokes), followed by the primary unit of organization of movement, in this example the stroke, which is further decomposed into phases and finally actions.

The brain's way of organization and control of movement is fundamentally the same for most skilled movement activities. The interaction of a user and task elements and environments results in specific movement architectures. The movement architecture and phase decomposition results from the need to accommodate the biological constraints and the type of outcomes that are specific to the task. However, the same general type of levels of organization and associated movement elements. FIGS. 4A-4E show an example of primary movement patterns and phase decomposition across different movement activities. Many activities share the same basic movement structure and organization. Therefore, the motion model and skill model, as well as skill analysis and augmentation can be used over a broad range of activities.

Skilled movements can be modeled in terms of the three major levels of movement system organization:
(1) the global delineation of movement into distinct movement patterns with their associated primary outcomes, which can collectively be described in terms of the repertoire of movements;
(2) the temporal delineation of the patterns into phase segments;
(3) the phases can subsequently be decomposed in movement synergies.

The movement repertoire describes the collection of movement patterns used by a user to accomplish the range of outcomes necessary to efficiently deal with various environmental and task constraints in the particular activity or adapt to the conditions. The development of repertoires is characteristic of open skills. Complex movements are typically composed of distinct phases. Moreover, the movement phase structure describes the user's movement technique delineating movement phase sequence developed to achieve the outcome associated with each class. Movement or muscle synergies describe how the brain organizes movement to utilize the body's capabilities. The muscle or movement synergies represent the basic building blocks or units of the movement behavior associated with the movement system. The synergies describe how muscle and body segments are coordinated to produce the movement phases that compose the movement patterns. The motion model provides the basis for the analysis of technique and skills.

The motion classification and subsequent mapping describes the range of movement patterns acquired by an individual. Repertoire diversification conveys information about the versatility of the player. Movement patterns are typically associated with primary outcomes and therefore, the repertoire also provides a description of the range of outcomes. Movement patterns are dynamic, therefore, tracking their development provides unique information about how an individual adapts to its environment and task.

The phase decomposition of the different movement classes in the repertoire describes how an individual uses different technique for the different outcomes in the task. The phase segment profiles hold detailed information about how individual users achieve their movement outcome. Since the phase structure results from the functional and biomechanical constraints, the analysis of the movement techniques in terms of features associated with the phases conveys information that is more directly relevant to training. At the same time this representation is sparse compared to the entire time series of a movement pattern. Variability or differentiation of the profiles in the same class conveys information about how the users achieve their outcome and deal with changes in conditions.

Movement phases, such as those found in tennis strokes, involve complex movement coordination. The phase decomposition conveys information about the ability of the user to exploit the natural movement biomechanics and task elements and constraints. Trajectories of each phase are achieved through coordination of numerous muscles and body segments. The decomposition of movement phases allows to identify muscle synergies and biomechanical characteristics. Finally, each phase also has specific mechanisms to achieve adaptive capabilities. For example, phases are part of the sensory-motor structure used to perform under uncertain and dynamics conditions. Movement phases are an essential part of achieving proper timing to synchronize movements to external task and environment elements. Phase are triggered by different sensory cues.

The system is configurable as an augmentation platform that helps train or rehabilitate for a variety of movement applications. The elements of the movement structure and organization just described represent the main elements of a language or codification system that can be used to build an integrated movement processing, analysis and augmentation system. FIG. 6 illustrates how these processes are deployed to enable augmented human movement activity. The elements of the movement structure and organization represent the main elements that are learned and stored by a human user. Therefore, through the effect of skill augmentation, they represent the elements that get operated on through the effect of feedback augmentation. At the assessment loop level, the iterative training process effectively reorganizes the individual's repertoire. At the augmentation loop level, the feedback augmentation reshapes (or reprograms) the movement patterns by manipulating the movement phase characteristics and their relationship to the outcome. The processes I-III are the motion processing functions which are part of the assessment loop. They support the training assessment and update the algorithms that support the augmentation (finite-state model for finite-state estimation, cueing laws, etc.) and include movement processing 610, motion modeling 650, and skill assessment and diagnostic 660. Processes IV-V are the synthesis and realization of augmentation system that support the augmentation loop. They are divided into two levels: instructions and real-time feedback. The instructions are typically implemented on a host equipped with a screen or other means to display symbolic or visual information. The feedback cue is implemented in real-time through the cue processor and generator and is based on signals and cues (see FIGS. 7 and 10).

Figure 9:
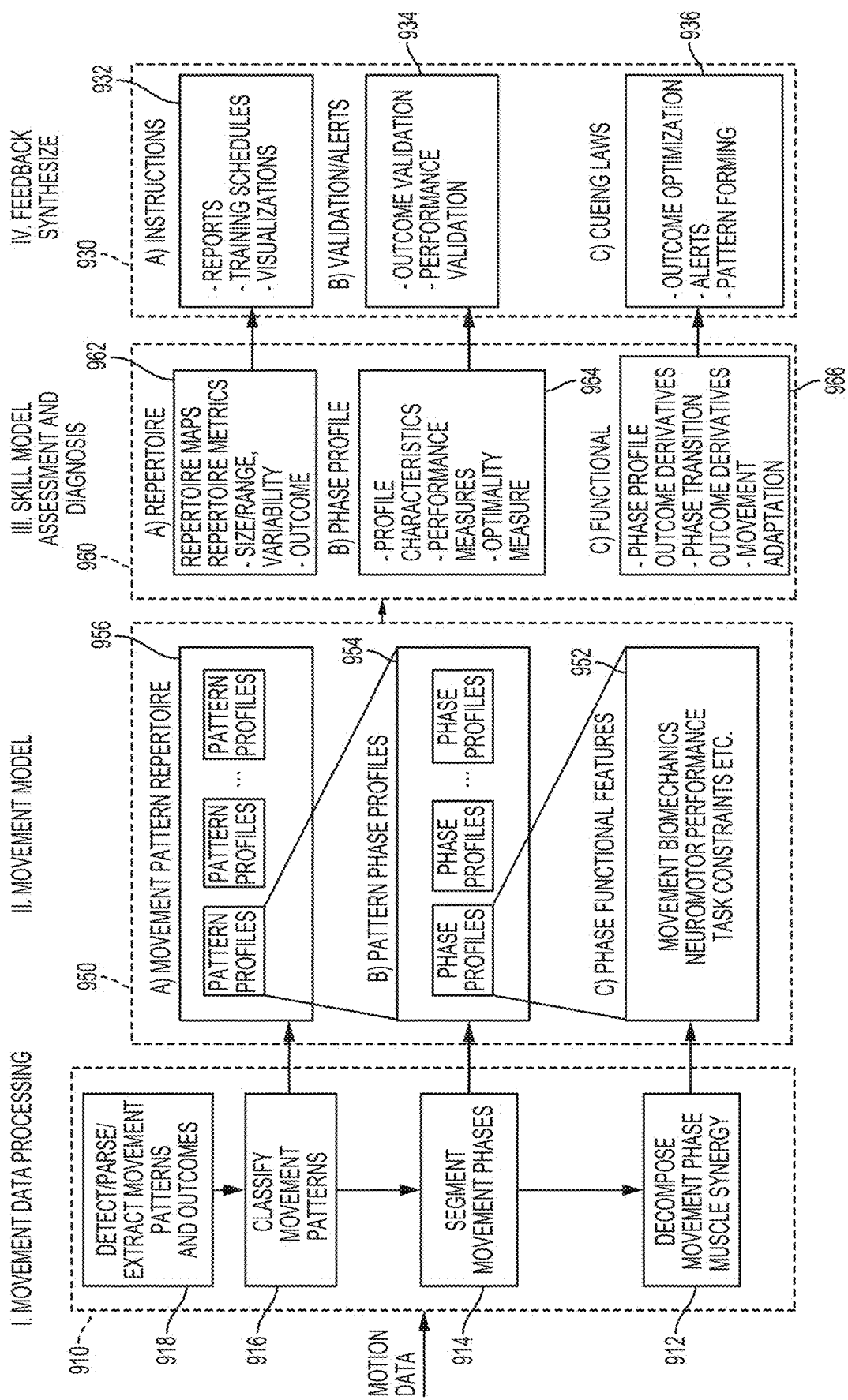
FIG. 9 is a diagram of motion skill processing components which includes movement data processing (I), movement model (II), skill assessment and diagnosis (III), and feedback synthesis (IV)

FIG. 9 illustrates the system integration between the movement components that are extracted from the measurement data and highlights the synergy between the components and processes used for skill assessment and diagnosis and synthesis of various feedback elements. The movement patterns of interest are those that are associated with the primary outcomes for the given activity. They are called motion primitives or primary movement units (MU). The motion skill processing components include movement processing data 910, movement model 950, skill model assessment and diagnosis 960, and feedback synthesis 930. The system input is motion data. The movement data processing 910 includes, detecting, parsing and extracting movement patterns and outcomes 918, classifying movement patterns 916, segmenting movement phases 914, and decomposing movement phase and muscle synergy 912. The movement model 950 including a movement pattern repertoire 956 of one or more pattern profiles, a pattern phase profile 954 of one or more phase profiles, and a phase functional feature 952 which includes movement biomechanics, neuro-motor performance, task constraints, etc. The skill model and assessment diagnosis 960 includes a repertoire 962 (e.g. repertoire maps, repertoire metrics (such as size and variability), and outcomes), phase profile 964 (e.g., profile characteristics, performance measures and optimality measure), and functional 966 (e.g. phase profile outcome derivatives, phase transition outcome derivatives, movement adaptation). Feedback synthesis 930 includes instructions 932 (e.g., data for reports, training protocols), validation alerts 934 (e.g., reinforcement, outcome validation, performance cues, phase alerts), and cueing laws 936 (e.g., real-time feedback, phase reinforcement, outcome feature validation, outcome optimization, phase timing).

Movement measurement data is collected during training, matches or regular performance. This data is processed to extract movement patterns, or primary movement units, relevant to the activity. The motion data is parsed to extract the segments associated with the primary actions and extract information associated with their outcomes. The patterns are classified to extract different categories and classes of motion patterns (see FIG. 11). The movement classes and outcomes form the movement repertoire. Movement patterns are decomposed following the hierarchical organization, including the segmentation of the motion phase, and decomposition of the phase segments according to movement synergies. The different types of primary movement patterns from the movement repertoire and their phase and synergy components collectively form the movement model (see 950 in FIG. 9). The movement model provides data which can be used for skill analysis and diagnosis (see 960 in FIG. 9). Skill analysis and diagnosis encompasses the three levels of the movement model (see FIG. 9). At the repertoire level, information about the range of patterns and outcomes can be assessed relative to the task requirements. At the movement phase level, information about the movement technique and its relationship with the performance and outcome. At the synergy level, the movement components describe relationships between the movement phase profiles and the coordination of body segments and muscles. The proposed framework, based on the organization of movement in terms of the motion model and skill model shown in FIG. 9, makes it possible to organize movement assessment and feedback cueing in a systematic fashion.

An assessment loop tracks the user's longitudinal skill development. A training agent then provides the environment to view and manage training assessments and instructions. Based on the assessments, the training agent provides various outputs to the user to help understand and train movement technique. The two primary outputs are instructions and feedback augmentations. The instructions operate at the knowledge level and are best suited to document medium to long-term aspects in skill development. The feedback augmentation operates at the signal and cue level and is effective in real-time, during performance. Feedback augmentation synthesis 630 shown in FIG. 6 translates results of the analysis and diagnostics into training instructions which are provided to the user during augmentation 620. Examples of the synthesis are provided in the detailed description and the tennis example. Realization refers to the process of translating and communicating instructions into an understandable and actionable form which is presented to the user during augmentation 620. The instructions can be generated at different times: during performance, immediately following a movement, or after the training session. The modalities of communication include symbolic language (spoken, text), cues (visual, audible, haptic) or signals (visual stimuli, audible stimuli, haptic stimuli). The modalities of communication are implemented according to humans' information processing and functional properties associated with the structure and organization of movement.

The instructions can be organized into three levels:
(1) Reinforces the optimal movement features for a particular movement class with feedback or cueing law. The cueing laws account for specific phases in movement pattern segments to perceptual and sensory-motor processes.
(2) Defines "training schedule" based on the organization of the movement repertoire, building the repertoire according to the hierarchical relationships between movement patterns and their associated phase segmentation.
(3) Expands the movement repertoire using an individual's existing movement patterns.

The feedback augmentation is set up to generate stimuli that reinforces the features in the movement technique that lead to outcome improvement. This principle is based on learning theory, such as the Theory of Neuronal Group Selection. The theory essentially states that the behaviors that are associated with good outcomes are selected and reinforced, while those that are detrimental to the outcomes are eliminated. The movement phase structure is also associated with specific functional mechanisms used for adaptation to changing conditions, such as timing and strength. The functional characteristics of motor programs and the associated sensory and adaptation mechanisms provide a basis for training the larger capabilities such as perceptual mechanisms needed for task-level interactions (environment and task elements).

Figure 13:
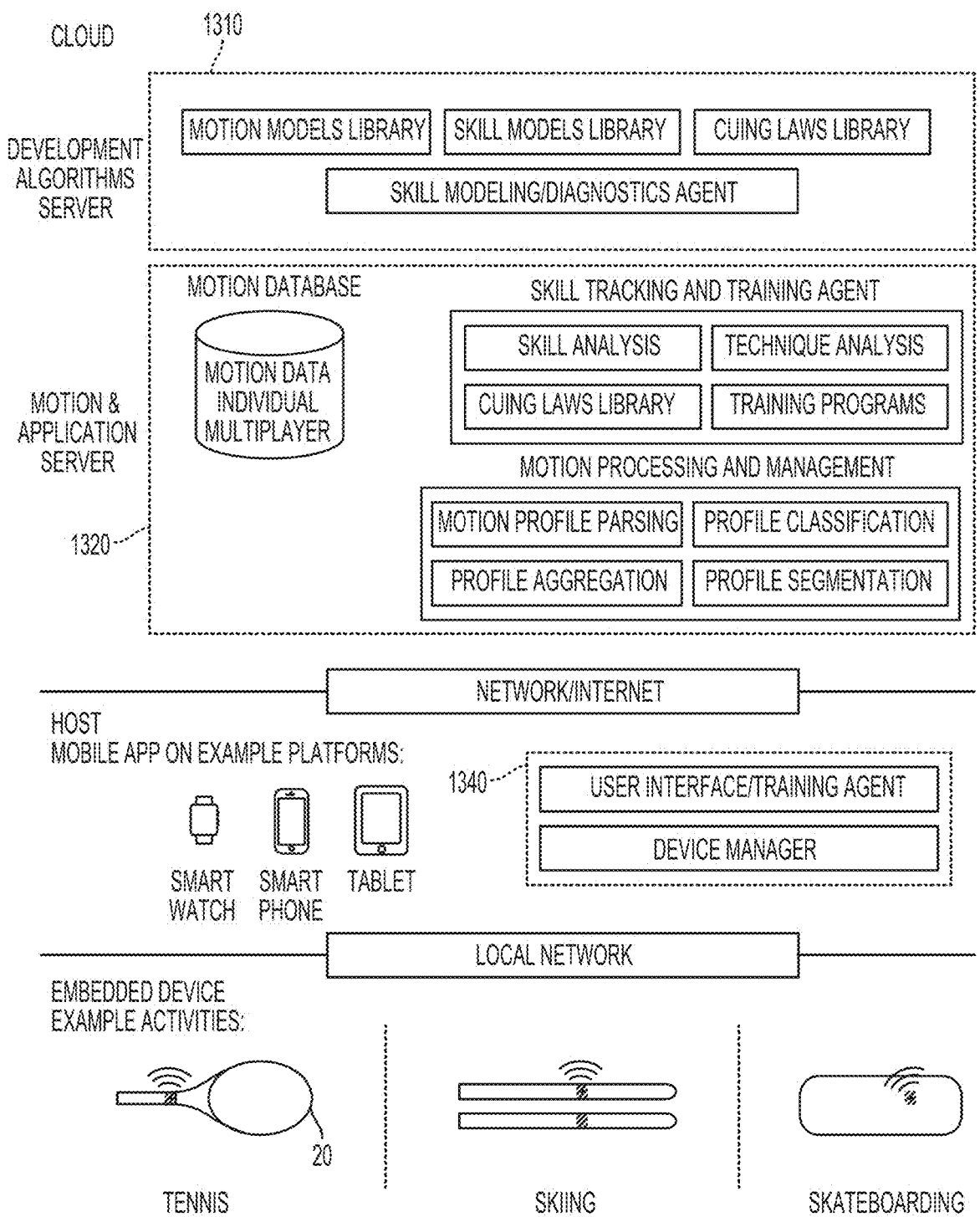
FIG. 13 illustrates an overall platform architecture describing the general functionalities for three example activities (tennis, skiing and skateboarding)

The results of the assessment are presented through the communication system. The training and cueing agent are the systems used to manage the assessment loop and augmentation loop (see FIG. 1). The technology for tracking and training movement skills can employ various information processing and management capabilities. FIG. 13 illustrates an overview of a general platform architecture that organizes and manages a user's movement skills. The platform has a development algorithm server 1310 which can be stored in a cloud computing environment, and a motion and applications server 1320, which can also be stored in a cloud computing environment. A host 1340 can be provided which is, for example, a smart watch, smart phone or tablet, which includes a user interface and training agent along with a device manager. Additionally, embedded devices or sensors can be associated with a piece of equipment (such as a tennis racket 20, skies, or skateboard) associated with the activity (if any). The platform combines components used for communication, user interface, computing and data storage. In particular, it combines cloud computing, which makes it possible to store, manage and process large amounts of data, with embedded sensing and computing, which makes it possible to build the necessary wearable hardware for data collection and real time feedback. Such a system opens opportunities for capabilities that go well beyond what can be achieved with data from a single individual. Data from a population of players opens the possibility to analyze skills from different skill levels and differences in biomechanics, age, health, equipment, etc. Therefore, an important aspect of the platform is the organization and management of the collective motion data, motion models, skill models, cueing laws, etc. A capability enabled by population data is the availability of information about movement technique at different skill levels. This can be used to cross-reference the skill analysis of similarly skilled individuals provides opportunities to borrow technical advantages from one individual to enhance training of a second individual. As will be appreciated by those skilled in the art, the use of a cloud computing environment is just one configuration and other computing environments can be used without departing from the scope of the disclosure.

To enable such large-scale organization and management capabilities, additional levels and control features can be added to the components in FIG. 1.

The movement analysis and cueing and augmentation platform has a plurality of functions, including, for example:
 (i) motion processing function,
 (ii) motion model and assessment functions,
 (iii) feedback augmentation functions, and
 (iv) skill development tracking functions as shown in FIG. 9. The four subcomponents enable: parsing, classification, phase segmentation and decomposition of the movement into synergies. Parsing is the process of segmenting and extracting the data segment that is associated with primary movement patterns, or movement data processing 910. These patterns are the primary movement units in the organization of movement behavior used to accomplish the various primary outcomes in an activity (e.g. stroke in tennis, carving turn in skiing). For example, in tennis, the primary movement outcome corresponds to the racket-ball impact (see FIGS. 4A-4E). Outcomes have distinct features that can be detected. Therefore, for goal-directed movement behaviors, parsing can be performed by detecting features associated with the movement outcome. Reaching movements or other goal-directed movements, as well as throwing or intercepting movements, can be identified similarly. Parsing can also be accomplished by using more general features associated with movement patterns. Other features include, for example, kinematic characteristics such as racket acceleration in the forward swing phase of a tennis stroke. For non-goal directed movements, such as skiing, features of the movement maneuver typically provide sufficient information to parse this behavior into a sequence of movement primitives. For example, in skiing, the turning maneuvers can be detected from kinematics of the apex or the entry phase of the turn. Outcomes are defined based on the activity, and are typically known quantities. In tennis, for example, the outcomes of a stroke are the ball's topspin, speed, direction, etc. The outcomes can be defined at different levels, such as the stroke level and the game level. In tennis, the latter is related to the game structure and scoring scheme. Some outcomes can be directly determined from the measurements, while other need to be estimated from the measurements. Therefore, at the functional level, parsing involves: Discovering features to detect the event(s) associated with MU; Generating a time series description of the MU; Extracting movement outcomes associated with the MU.

The system has inputs which include data streams, and outputs which include time-series descriptions of MUs, their associated features, and the outcome descriptors. Movement skill analysis applications require sampling measurement data at rates significantly higher (100 Hz or higher) compared to activity detection applications (10-25 Hz). Motion can also involve multi-dimensional state variables. Therefore, the measurement time histories result in large quantities of data. Moreover, the measurement data is often expanded to include estimates for unmeasured quantities, such as equipment orientation in space. The situation is further complicated when multiple sensors attached to different body segments. The large data can be challenging to manipulate and analyze, especially for real-time applications. Low-dimensional abstractions are used for efficient, real-time classification. A general approach to classification is to represent the time series through low-dimensional feature vectors. These vectors can then be used to determine movement classes efficiently using data clustering techniques. The movement class-membership information, in turn, can then be used to reconstitute the full-dimensional movement classes in terms of the original time histories. These can then be used to perform movement analysis, such as for evaluating movement techniques or skills.

Figure 14:
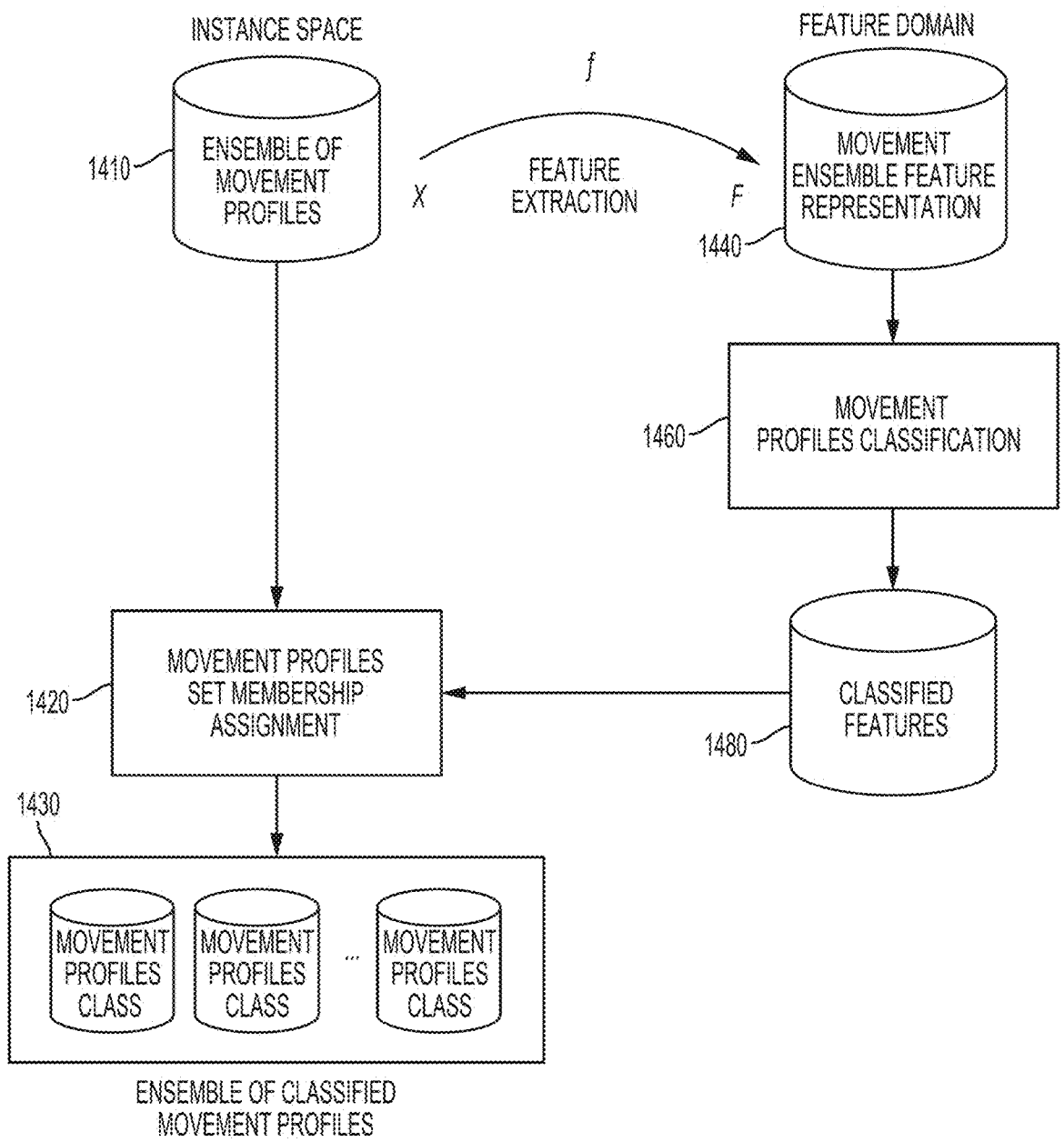
FIG. 14 is a block diagram overview of the movement unit profiles classification using feature representation.

FIG. 14 illustrates an overall classification of the motion pattern profiles. As used in the tennis example, starting from the extraction of stroke features from the movement profiles, and subsequently their use to assign membership of the strokes to the various classes. An ensemble of movement profiles 1410 is generated, which has input into a movement profile, membership assignment 1420, which in turn has input into an ensemble of classified movement profiles 1430. Movement ensemble feature representation 1440, provides input into movement profile classification 1460, which in turn provides input to classified features 1480. The classified features provide input into the movement profile, membership assignment 1420.

The measurement data is typically provided as time series y(t), t∈ℤ. A typical MEMS IMU the measurements typically include the three linear accelerations [$a_x$; $a_y$; $a_z$] and the three angular rates [p; q; r]. The measurements are usually down sampled (period $T_s$) and filtered to yield time histories with appropriate information and size. Most applications involve some form of state estimation (e.g. attitude estimation). Therefore, the classification is typically implemented on state vector data that allows reliable descriptions of the movement performance. The following example assumes the racket movement is described by body acceleration and angular rate.

$$X(t) = \begin{bmatrix} a_x(t) & a_x(t+kT_s) & a_x(t+2kT_s) & \ldots & a_x(t+NkT_s) \\ a_y(t) & a_y(t+kT_s) & a_y(t+2kT_s) & \ldots & a_y(t+NkT_s) \\ a_z(t) & a_z(t+kT_s) & a_z(t+2kT_s) & \ldots & a_z(t+NkT_s) \\ p(t) & p(t+kT_s) & p(t+2kT_s) & \ldots & p(t+NkT_s) \\ q(t) & q(t+kT_s) & q(t+2kT_s) & \ldots & q(t+NkT_s) \\ r(t) & r(t+kT_s) & r(t+2kT_s) & \ldots & r(t+NkT_s) \end{bmatrix} \quad \text{EQ. 2}$$

X is the n×N matrix, where n is the number of states and $N=t_{meas}/T_s$ is the number of samples. For example, a movement profile described by $t_{meas}=2$ second time history, sampled at 1 kHz result in 6×2000=12,000 data samples.

Feature representation involves mapping the movement instances, $X(t) \in \mathcal{X}$ to their feature description F:

$$f_i : |X(t) \in \mathcal{X} \mapsto \mathcal{F}_i$$

where $\mathcal{X}$ is the instance space and $\mathcal{F}_i$ is the feature space. The features are selected to describe the movement profiles $X(t) \in \mathcal{X}$ using a small quantity of data, making efficient processing, classification and analysis possible. FIG. 14 illustrates the mapping from the original data to the feature space, classification and mapping the original data into the class membership. The movement profiles collected in each class can then be used for detailed analysis of the movement technique and skill. Features represent attributes of the time histories that make it possible to distinguish between different movement types. In the following, the features are defined to provide information about the kinematic and dynamic states at selected times over the length of a movement profile. The features can also be selected through more formal approaches, such as based on analyzing ensembles of movement profiles and determining variant and invariant characteristics. The variable characteristics, if they are not due to noise, represent features that will be best distinguished between movement types. Conversely, invariant characteristics carry no information about movement classes. One approach to determine discriminative features is to perform principal component analysis (PCA) on an ensemble of movement profiles. The first eigenvectors, associated with the larger eigenvalues, describe the variance in the data, and hence can help identify data samples that are most informative.

Once a set of features that sufficiently describe a particular type of movement have been defined, these features, or a subset of them, can then be used for classification. For basic classification, features can be selected based on physical or empirical criteria related to the movement mechanics. Alternatively, the features can be selected based on "data-driven" processes such as PCA based feature analysis or K-Means clustering.

Figure 11:
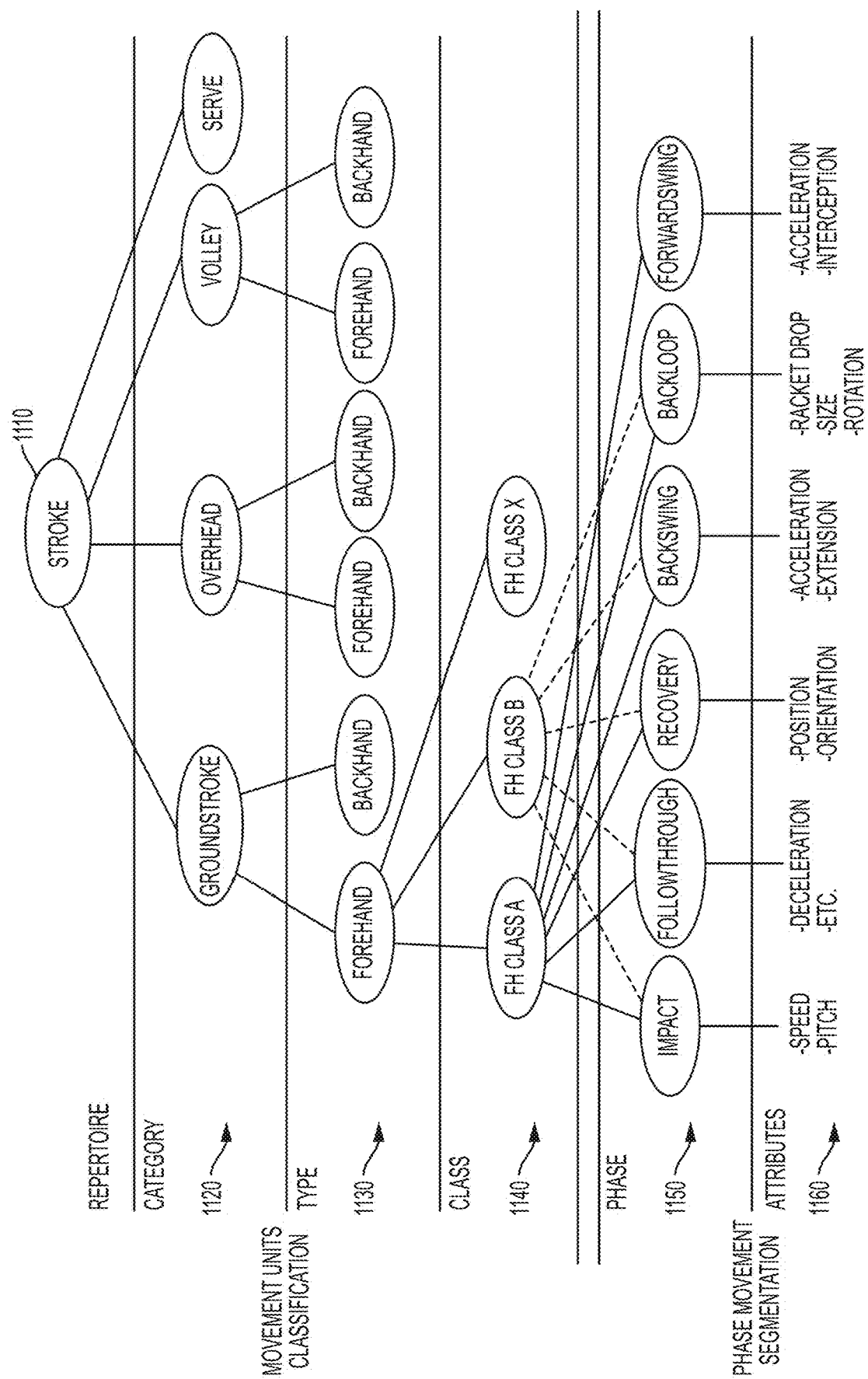
FIG. 11 illustrates a tree structure associate with the tennis stroke highlighting the movement unit classification (into categories, types and classes of strokes) and segmentation (into phases). The phase segments are characterized by profile and transition feature attributes.

For identifying tennis forehand/backhand or slice/topspin, it is possible to determine necessary conditions for these movement types and outcomes. The empirical classification yields a set of pre-defined stroke classes such as shown in the stroke tree (FIG. 11). In contrast, "data driven" classification provides information about the particular structure of an individual's stroke repertoire. Its effectiveness depends on the amount of movement data collected and how well an individual's data spans the players' repertoire. However, individual differences in biomechanics (due to anatomy, injuries, illness, aging, etc.) can result in a repertoire that does not span the typical range of states.

The advantage of predefined classes, e.g. based on domain standards for a task or activity, is that they provide absolute criteria that are useful when comparing multiple players. Predefined classes have the advantage that they are absolute. Individuals can be compared based on the same criteria and also provide a way to assess how well the collected movement data spans a standard repertoire. The classification platform can be configured to combine both approaches. These could represent standardized movement classification criteria for a particular activity. Data-driven classification would be used to gain insights into individual movement patterns. The latter could then be used to define and refine standard class models. This type of analysis corresponds to top-level processes in the platform (shown as skill models and motion models library in the development algorithm server 1310 in FIG. 13). Given the predefined set of features, classification most often only requires a subset of features. Feature analysis and selection is concerned with identifying which subset of features to use from the available features. A common approach for feature analysis and selection is principal component analysis (PCA).

The movement architecture can be modeled as a sequence of dynamics with initial and goal sets. Therefore, the goal is to be able to segment the larger movement units (e.g. the entire tennis stroke) into these subunits or phases as shown in FIG. 11. The phase elements, which can be described by individual phase dynamics $F_i$ and associated initial and sub-goal state sets $\mathcal{X}_{i0}$ and $\mathcal{X}_{i1}$, respectively, emerge from the interaction of the biomechanical system with the task environment and constraints (see e.g. the example of reaching motion). The movement phases typically reflect the biomechanical constraints, as well as factors associated with the dynamics, motor-control and interactions with the environment and task (see FIG. 2). Capturing the movement phase structure makes it possible to better characterize these contributions. Finally, the insights gained from the phase decomposition are used to derive a finite-state model which can be used in the finite-state movement phase estimation. This model describes the overall motion as series of transitions between a finite number of states which represent the motion phases.

Movement phases result from the biomechanical and neuro-motor system as well as functional aspects related to the interactions with the task and environment elements. Further analysis of the movements within the phases can provide detailed information about the physical movement implementation. For example, a tennis stroke combines the body, shoulder, elbow, and wrist motion. A beginner's stroke is mostly achieved by a simple shoulder motion (horizontal abduction and extension). As the player improves, this basic motion combines with elbow and wrist movements to result in a more complex, higher-dimensional movement unit.

Movement synergies are determined from decomposition techniques such as non-negative matrix factorization. The synergies that are determined through mathematical decomposition techniques, such as principle components or matrix factorization, are not necessarily related to muscle activations. Nevertheless, these elements can still provide insights into relevant spatio-temporal characteristics of the movement. This understanding can then be used to characterize skill and feedback augmentation. Synergies can be extracted from a variety of measurements or states, such as the spatial configuration of relevant body segments. The type of insights and understanding that can be derived from synergies depends on the information content of the movement measurements. To obtain muscle synergies that are representative of actual muscle activation patterns, EMG measurements or measurement of the nerve signals are usually required (e.g. see forearm pronation and supination in FIG. 5). Decompositions based on factorization technique still provide valuable information, especially if the results are connected with the biomechanical analysis. Such analysis can be conducted for the primary body segments involved in the phases.

The motion model (see FIG. 9 box II) is derived from the elements that are extracted in movement processing. These elements are derived from the three levels of movement organization. Classification of MU into separate categories. The collection of classes forms the movement repertoire (MR) associated with the user's experience and skill. Segmentation of MU into a sequence of phases and specific phase features that are associated with the phases. Decomposition of the individual segments or phases. The components are related to the muscle synergies or patterns of activation underlying the body segment coordination. The decomposition can be used to relate the movement characteristics and the musculoskeletal constraints.

This collection of elements is incorporated into the motion model 150 and skill model which can be included in the motion model 150 of FIG. 1. The motion model 150 can have a variety of inputs and outputs, including, for example:
 inputs: Collection of time series representation of the MU; and
 outputs: MU organization as data tree, with two levels: the MU types and the phases for
 each MU type; classification features.

Skill can be determined by how movements utilize the natural movement capabilities to accomplish their specific goals or outcomes, and also how these movements achieve adaptive capabilities to compensate for various conditions. The following describes how the movement model (see FIG. 9 box II) can be used to assess skills and target skill augmentation and cueing (see FIG. 9 box III). Motion skill is traditionally assessed in terms of two aspects: knowledge of performance (KP) and knowledge of results (KR). The key question for skill is how these two aspects are related, that is, how movement technique can be used to achieve desired outcome. The stroke technique has to satisfy a variety of constraints including the biomechanical and task constraints, and also requires adapting for changing task conditions. The movement repertoire describes the various patterns used by a user to accomplish the outcomes in the particular activity or adapt to the conditions. The movement phase structure describes the user's movement technique, delineating the movement phase sequence developed to achieve the outcome associated with each class. The movement repertoire formed by those classes for a particular activity domain describes the collection of movement patterns that have been acquired to generate the outcomes necessary to efficiently deal with various environment and task constraints. Movement or muscle synergies describe how the brain organizes movement to utilize the body's capabilities. The muscle or movement synergies represent the basic building blocks or units of the movement behavior associated with the movement system. The synergies describe how the brain coordinates muscles and body segments to produce the movement phases that compose the movement patterns. The user's skills can be assessed based on the characteristics of the repertoire, e.g., how broadly they span behaviors, with measured or estimated outcomes. The motion model captures movement elements and characteristics that reflect the relationship between the task requirements and movement biomechanics. These elements and characteristics can be used to achieve a comprehensive assessment of movement skill and skill acquisition. The approach to this assessment is based on the movement structure and organization and skill development principles.

The component of the movement skill assessment are shown in FIG. 9 (box III) and include:
 (a) At the repertoire level the assessment focuses on the general characteristics of the movement patterns and associated outcomes and how those are organized in relationship to task and environment requirements and elements.
 (b) At the movement phase profile level, the assessment focuses on the movement technique and patterning of motion.
 (c) At the functional level, the assessment focuses on the internal structure of the movement and its detailed functional characteristics including the relationship between technique and outcome, as well the mechanisms used for adaptation to task conditions.

The repertoire represents a discretization of the behavioral space at the task performance level. It reflects how the entire range of behavior is broken up to achieve outcomes under different task conditions while best exploiting the biomechanical, neuro-motor, perceptual and cognitive capabilities. An individual's capacity to exploit the range of conditions, and in turn create distinct categories, is also a reflection of the skill level. The fact that the development of a repertoire requires making categories, which involves recognizing environmental and task conditions, etc. is also a result of the higher level cognitive skills. The different movement patterns that compose the repertoire represent the basic unit of organization associated with the concept of motor equivalences. The extracted classes measure the breadth of the motor repertoire associated with a particular activity as well as the quality of the synergies or movement classes. Given an activity, the goal is to span a large enough repertoire to support versatile performance, i.e., deal with different environmental and task constraints. The patterns that span the repertoire should provide adaptation to uncertainties and disturbances. It is expected that advanced players' repertoires are structured and diversified with a broad range of stroke classes that have distinct characteristics to achieve a range of outcomes. On the other hand, novice players' repertoires are expected to be much less structured with fewer patterns that are themselves less organized. Therefore, the amount of structure and the breadth of patterns and how well they achieve their outcome provide basic elements of systematic skill evaluation.

Movement patterning and specific phase structure is a function of skill level. For example, beginners will adapt existing movement synergies to accomplish the task. As they become more proficient, the number and types of movement phases, as well as the performance in each phase, will change. For example, a beginner tennis player will first use rudimentary stroke techniques that primarily build from a forward swing phase and a backward swing phase. With more experience and training, the stroke patterning will refine to include more phases such as a follow through to optimize the performance after the impact, at recovery, as well as a more sophisticated backswing with a back loop that makes it possible to achieve faster reaction and better satisfy the requirements for the performance of the forward swing leading to the impact.

In contrast to the more global significance of the movement repertoire, each class represents a movement pattern that is acquired to provide specific adaptive performance for a particular environment, task constraint and outcome. While the motion classes in a repertoire span the broad range of conditions, movements within a class require adaptation mechanisms to accommodate changes in task and environmental conditions. The remaining component of variability in a given class, i.e. within motion profiles, is due to motor noise (e.g. $\in_t$). Therefore, once movement patterns have been classified, the analysis of the movement profile characteristics within each class provides detailed information pertaining to the individual's technique and skills (see phase segmentation). For advanced players, the variability displayed within a class is primarily associated with the adaptation to the task requirements such as impact conditions and body configuration. For beginner players, the variability is primarily from motor noise such as due to untrained or poorly coordinated movement patterns. For beginner players, variability also arises from poorly differentiated movement pattern classes, i.e. the user mixes two patterns without a sufficient definition of the category. For example, a user may adapt the same stroke structure to perform topspin and flat shots.

Predictable movement outcome requires precise configuration of body segments during phase transitions and reliable, repeatable pattern of muscle activation and body segment coordination during phase profile. In addition, various correction mechanisms are provided to correct for effects of disturbances or uncertainties at different stages of the movement execution. Movement phases break up the trajectory in a way that allows to best exploit human musculoskeletal and neuro-motor capabilities given task requirements and environment constraints. The phases, therefore, often coincide with important features of the bio-mechanical, motor control or task constraints. The movement patterns once classified represent movements that are equivalent (in the classic sense described elsewhere). Therefore, these trajectories provide precise insights into the various functional aspects related to the movement constraints, including the sensory-motor mechanisms and bio-mechanics. Furthermore, movement skills, in particular open skills result from environment interactions. For example, in tennis, the strokes are determined by the outcome, which is selected based on context such opportunities afforded by the game, and the continuous adaptation to the conditions, including the exact trajectory of the oncoming ball and the movement of the opponent. The stroke architecture is developed to accommodate the task interaction and, in particular, the coordination between information (perception) and movement execution. Therefore, phase decomposition provides information to evaluate how an individual adapts to the conditions and optimizes the outcome. The movement model and associated decomposition technique and data structures can be exploited to generate various outputs that support analysis, visualization and feedback augmentation.

Movement skills diagnostics is aimed at generating actionable information that can be easily used to support the synthesis of training interventions and augmentations. The detailed motion characteristics associated with each phase makes it possible to analyze functional characteristics that have been acquired to attain the outcomes, as well as the mechanisms used for the adaptation to task conditions. In particular, once the movement technique and outcomes have been captured in a concise and sufficiently descriptive form, this information can be combined to analyze the relationship between specific movement features and the movement outcomes. This sensitivity analysis provides the basis for the synthesis of feedback augmentation laws. The general approach is to evaluates features of the movement technique, associated with the MU, that contribute to movements' outcomes and other attributes such as the movement's adaptive capabilities. These include:

(1) Identify movement features for a given movement class that contribute most to the outcome.
(2) Identify movement features for a given movement class associated with an individual's best outcomes. These features define the optimal movement features for the particular movement class and outcome.
(3) Identify movement features for a given movement class associated with adaptation.

Variability in technique of a movement class for a given outcome is associated with adjustments in technique used to compensate for task conditions. Inputs can include motion class; parameters can include outcome or performance criteria; and outputs can include feature vector.

Understanding how feedback can be designed so that it targets specific aspects of the movement techniques and guides the acquisition of skill in a formal analytical framework is needed. In engineering applications, dynamic programming can be used to determine trajectory x(t) to optimize a cost functional J(x(t)) which could be the movement outcome or other aspects of movement performance and results, such as the energy of the movement (i.e., the smoothness or jerkiness of movement). Movement described by a sequence of phases allows to parameterize movement with a much smaller number of variables than would otherwise be necessary. The set of parameters for the proposed movement model includes the movement phase initial and terminal conditions, timing information and the parameters of the phase profile dynamics $F_i$. Profile dynamics are the result of the force field that are produced by the muscle coordination patterns or muscle synergies.

The representation in terms of movement phases also helps better establish a relationship between the outcome and movement characteristics. Namely, the optimization of the outcome can be formulated as a parametric optimization problem, or parametric programming. This is possible because the outcome can be expressed as a function of a finite number of parameters instead of the entire movement trajectory. This model provides a basis for both the functional analysis of movement and the formulation of the feedback augmentation. The formulation of the movement optimization as a parametric optimization problem assumes that the movement outcome (or performance) can be expressed as an objective or utility function $J(x, \Theta)$ that needs to be maximized (or minimized). The quantities x is the optimization variables and $\Theta$ are the parameters. For the movement optimization formulation, $\Theta$ can be used to represent the structure of the movement pattern, i.e., movement pattern configuration parameters, and x are parameters specifying the movement profile within the general pattern, i.e., movement profile features. For example, given a tennis stroke class, e.g., a forehand top spin, the configuration parameters determine the stroke pattern that is associated with the movement structure associated with the individual's stroke (see FIGS. 15A-15E). The movement profile parameters include perturbations within the movement structure such as perturbations in the movement state at phase transitions and/or perturbations about the phase profiles.

The goal of optimization is to determine parameter values that minimize or maximize the objective function. A constraint function $g(x, \Theta) \leq 0$ can be included to describe feasible ranges of movement configuration, as well as a parameter space $\Theta \in v$ to describe the range of values of the movement configuration parameters. A simple solution to the parametric optimization is the gradient descent (or ascent depending on if the goal is to minimize or maximize the objective function). Given a movement pattern structure and profile feature for a trajectory instance, described by $\Theta$ and x, respectively, the objective function can be optimized by iteratively updating the movement by applying small variations in the movement profile features: $x'=x-\gamma \nabla_x J(x, \Theta)$, where $\gamma$ is a step size.

This framework can be used to provide diagnostics of the movement technique, both at the profile feature level and the pattern level. The gradient of the objective function with respect to the profile features x, for a movement structure specified by the movement pattern configuration parameters $\Theta_k$, is given by:

$$\nabla_x J(x,\Theta), \Theta=\Theta_k \quad \text{EQ. 3}$$

which provides information about the sensitivity of the objective or outcome to profile features. Therefore, it is possible to use this analysis to identify the set of features that control the movement outcome. In an example of spin imparted to a ball at impact changes the racket azimuth and elevation at back loop initiation and the elevation and roll rate at forward swing initiation (see FIG. 16B and FIG. 18B).

A similar approach can be used to determine pattern configuration characteristics and their impact on the outcome. The gradient of the objective function with respect to the pattern configuration features $\Theta$, given by:

$$\nabla_\Theta J(x,\Theta), \quad \text{EQ. 4}$$

which provides information about the sensitivity of the objective or outcome to pattern configuration features. However, perturbations in pattern structure may not be sufficiently continuous or smooth to allow numerical sensitivity analysis.

The skill model and diagnostic functions provide information that can be translated into various augmentations (see 930 in FIG. 9). The parametric programming framework demonstrates the basic elements needed for skill diagnostics and synthesis of various forms of feedback augmentation. In practical implementations, the sensitivity analysis and even model can be implemented using the statistical method from machine learning. With this framework, it is possible to use this analysis to identify the set of pattern features for movement outcome. This particular information is useful for the diagnosis of movement pattern and ultimately for designing feedback for reshaping the movement pattern architecture.

The following describes the elements of the skill analysis used to enable a systematic assessment to provide necessary information to synthesize augmentations. Movement data from a motion class in the repertoire and the associated outcome provide information about the range of variations in movement technique acquired by a subject. The comprehensive set of movement profiles can be sorted to determine different subsets based on attributes such as energy, jerk, outcome level, etc. The features associated with a movement pattern and its range of outcome define the current feature envelope of that movement pattern. The envelope describes the functional characteristics within the movement structure and the variations and perturbations associated with the individual's movement performance. Some of the variation is due to motor noise and some is associated with modulation of the movement to control the outcome level and adapt to conditions.

For example, a subset of movement profiles can be identified that are optimal for the subject's current movement technique, where optimality can be assessed using objective function such as energy. This subset provides a reference for the individual's best technique. Therefore, using movement profiles from this set can be used to reinforce movement technique. This can be achieved by providing the player or subject a signal that validates their best technique when it is detected during the movement performance.

Furthermore, within the same class of movement, the different profiles naturally exhibit variations in the level of outcome. Capturing the relationship between movement features and the variations in outcome provides information about the technique used by the individual to modulate the outcome. Similarly, the information about these features can be used to generate feedback signals to help the player understand the outcome modulation.

Information within the set of movement can also provide the basis to help individuals further optimize their movement technique for example to improve smoothness or increase their level of outcome. Following this model, an individual's movement performance can be optimized by generating a signal that provides information about the direction they should modify the movement feature. For example, the parameters extracted from EQ. 3 can describe a set of profile features such as the configuration of the movement at the transitions points between phases, or a specific kinematic characteristic of the phase profiles.

Building on these concepts, a normal and extended envelope can be defined. The envelope captures the features that are associated with the modulation of outcome (see FIG. 16D for the tennis example). The extended envelope corresponds to the features that lead to increase in outcome beyond the range currently achieved by the subject. The extended envelope and their associated features define the range of movement variations that can be exploited for outcome optimization.

One of the challenges of training complex movement skills is the lack of information about the performance or results. Few natural signals exist to help a user know if their movement technique is correct. This knowledge is most effective when delivered during performance. Outcome validation feedback operates as real-time or near real-time assessment. Knowledge of performance (KR) and knowledge of results (KR) can help an individual train. Yet, there isn't an automated system that can deliver feedback signals automatically, in a systematic way, building on the human movement system and human skill acquisition process. The following describes the type of feedback modalities and cueing mechanisms that can be used to augment human performance.

The feedback is delivered within an augmentation system 620 depicted in FIG. 6. The movement architecture and structure represent the main elements that are learned and stored by a human user (see FIG. 6). Therefore, through the effect of the skill augmentation, they represent the elements that are manipulated through the effect of feedback augmentation. Which explains how feedback augmentation can be used to reprogram the human movement system. The feedback is conceived at two primary levels: At the augmentation loop level, the feedback augmentation reshapes (or reprograms) the movement patterns by manipulating the movement phase characteristics and their relationship to the outcome. The augmentation includes both cueing signals or stimuli provided by a cueing system 622 and instructions provided by a communication system 628. At the assessment loop level, the iterative training process effectively reorganizes the individual's repertoire.

Feedback synthesis refers to the process of translating information about the different skill assessment and diagnostic components (FIG. 9 box II and III) into feedback at the different levels of the augmentation hierarchy. The instructions can be generated at different times: during performance, i.e. real-time cues, immediately following a movement (validation cues), or after the training session. The modalities of communication include symbolic language (spoken, text), cues (visual, audible, haptic) or signals (visual stimuli, audible, haptic).

Figure 21:
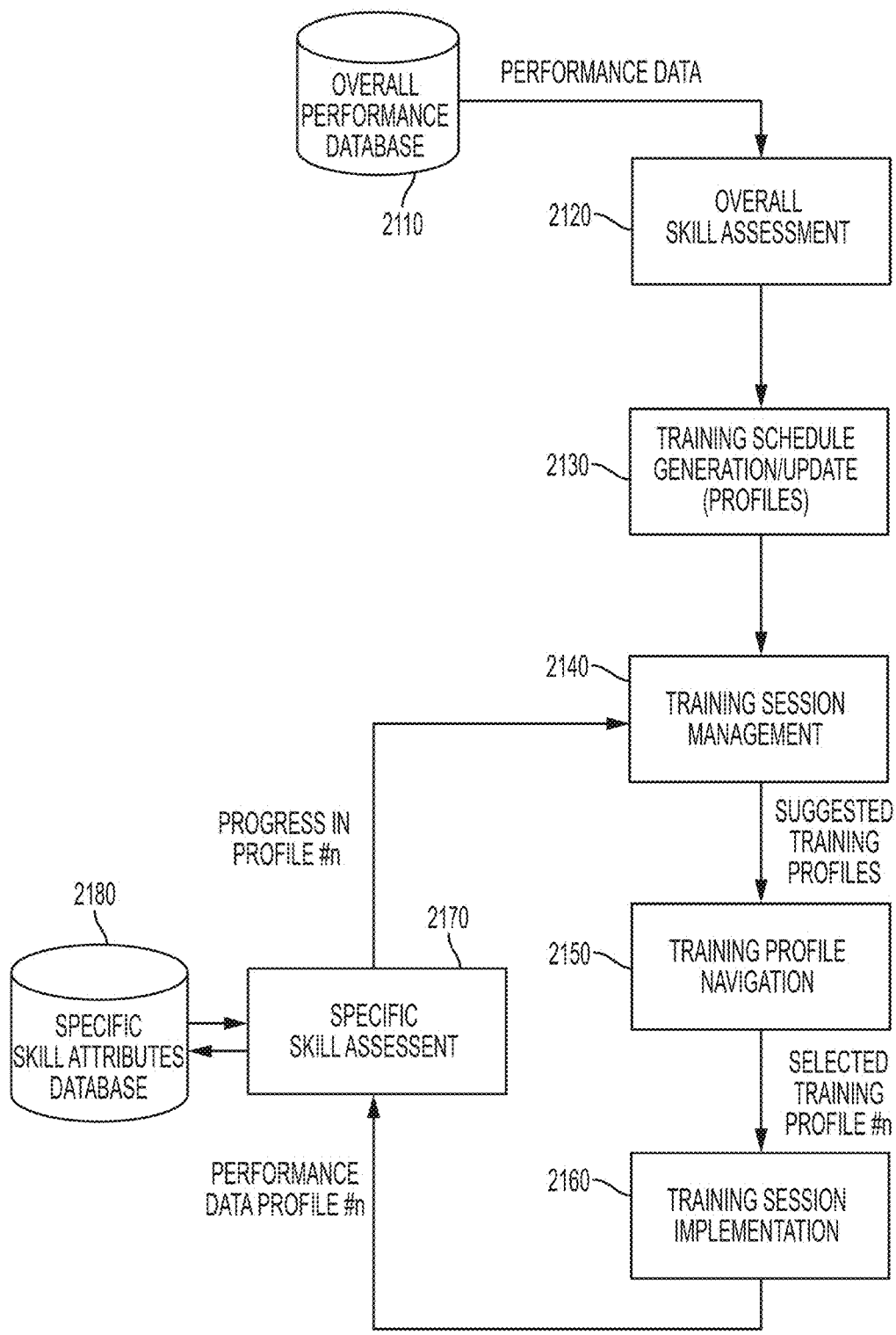
FIG. 21 illustrates a block diagram of the iterative training system process.

FIG. 21 illustrates a block diagram of the iterative training system process. An overall performance database 2110 provides performance data to an overall skill assessment 2120. Training schedules can be generated or updated 2130 which may be provided to a user profile. Additionally, training session management 2140 can incorporate information from the database and other sensors to provide suggested training profiles which are presented as training profile navigation 2150 to a user. The user selects a training profile and a training session is implemented 2160. Following training specific skill assessment 2170 can occur followed by an iterative repeat of the training session management 2140. Additionally, specific skill attributes database 2180 can provide information to the system.

Figure 22:
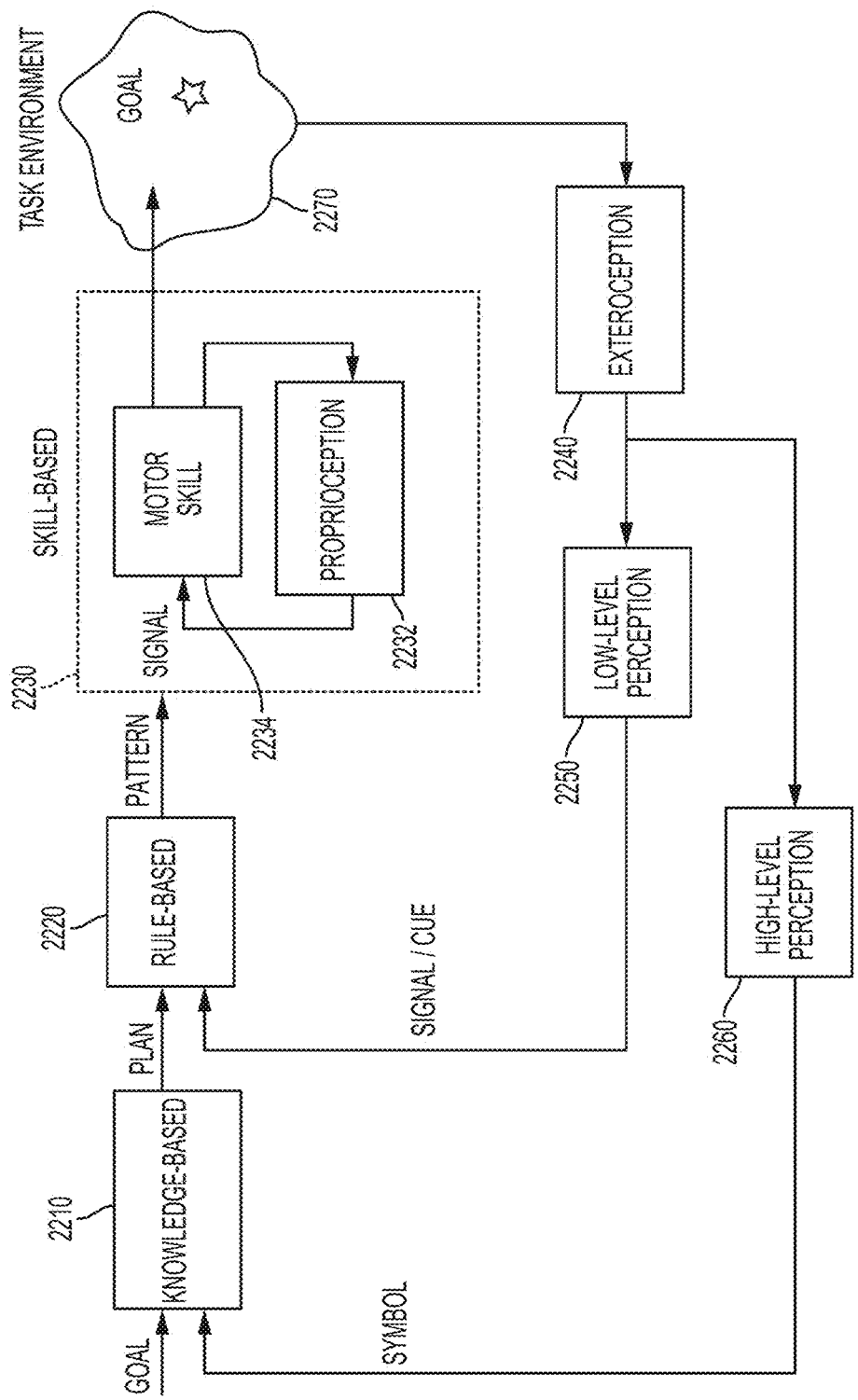
FIG. 22 illustrates the control and information processing hierarchy for human movement behaviors, highlighting the knowledge, rule-based and signal based levels. The figure also illustrates the sensory and perceptual components used to relevant information from the task environment.

The implementation of the augmentation follows the humans' information processing and functional properties associated with the structure and organization of movement as described. The augmentation modalities can also be delineated based on knowledge, cues and signals nomenclature. Post session are typically in the form of visualizations or instructions. They are considered knowledge level. The real-time and near-real-time are typically based on signals and cues (see FIG. 22).

Figure 12:
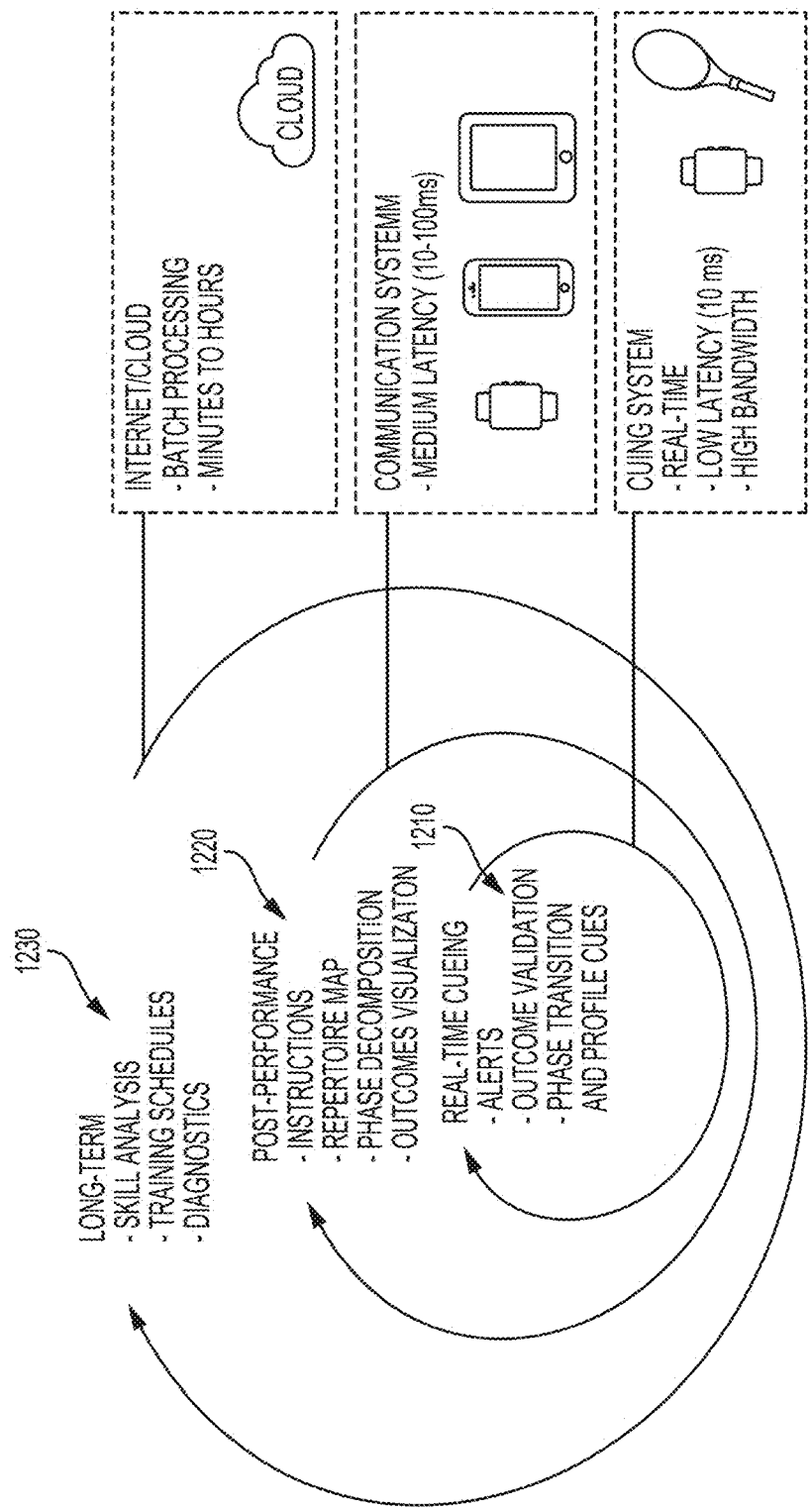
FIG. 12 illustrates an outline of feedback levels nested according to the human information processing organization. The figure also provides examples of devices and system components used to process data and mediate information to the user.

The primary feedback modalities are divided between real-time cues and post session or set illustrated in FIG. 12.

(1) Real-time feedback 1210 for reinforcing the optimal movement features for a particular movement class. The cueing laws account for specific phases in movement pattern segments to perceptual and sensory-motor processes.
(2) Near real-time feedback 1220 provide information to the user about the attributes and outcomes of the current movement.
(3) Post session feedback 1230 are long-term and include "training schedule" based on the organization of the movement repertoire, e.g. expanding the repertoire according to the hierarchical relationships between movement patterns and their associated phase segmentation.

The feedback cueing is based on the functional characteristics associated with the structure and organization of movement described by the motion model. As described the finite-state model provides a sparse representation of the trajectory that is compatible with the human movement system. The movement architecture results from various functional characteristics. This architecture therefore provides the basic structure for the implementation of feedback augmentation.

From the finite-state model, the trajectory is represented by a sequence of sub-trajectories $x_i$, for each phase i and transition conditions that define the initial values for each phase. Following the finite-state notation, features include states at the phase transitions (initial and terminal state $x_{i0}$, $x_{i1}$ shown in FIG. 3 and phase profile characteristics of the phase $x_i(t)$, $t_{i0} \leq t \leq t_{i1}$. The former is related to the initial and terminal (subgoal) conditions in the movement trajectory in FIG. 3. The latter is related to the dynamics, i.e., the force field characteristics associated with muscle synergies. These quantities are ostensibly the type of information the brain encodes for the specification of motor programs.

The phase transition and phase profile structure defines two primary cueing mechanisms. Phase transition cues are cues that are directed at the characteristic of the movement phase at the end of a phase and initiation of the subsequent phase. The phase transitions act as a type of subgoal, therefore, the phase transition cues can, for example, provide information about the intermediate movement configuration over the overall movement pattern. Phase profile cues are cues that are directed at the phase profile characteristics. These cues can help achieve phase profile attributes, such as acceleration or angular rate profile. Phase profile cues also affect the phase transition following the current phase profile.

These cueing mechanisms are used to achieve different cueing goals: validating or reinforcing aspects of the movement; alerting to discourage particular movement features that are detrimental to the outcome or body; and signaling to change movement technique such as for refining the movement technique to maximize an outcome or maximize the effectiveness of the movement technique for a given outcome level.

1) "Outcome validation" provides feedback signals to validate the satisfactory achievement of the movement outcome. Outcome validation cues can be generated immediately following the movement. They act as reinforcement. This function is enabled by assessing the outcome at the instant it is produced.

Consider an outcome z that can, for example, be expressed as a function of the movement state:

$$z = \varphi(x(t=t_{goal})), \quad \text{EQ. 5}$$

and consider the optimal outcome:

$$z \in Z_{goal}^*, \quad \text{EQ. 6}$$

where $Z_{goal}$ represents the set of outcomes that are optimal (w.r.t. to an objective function J). It is possible to discretize the outcome set to define outcome levels A, B, C:

$$Z_{goal}^* = \{Z_{goal}^A, Z_{goal}^B, Z_{goal}^C\} \quad \text{EQ. 7}$$

With this formulation it is possible to define a feedback signal that conveys information about the outcome level. For example, the outcome tiers A, B, C can be mapped to tones which can be generated as audio pulses at the instant of movement outcome.

2) "Outcome feature validation" provides validation of the movement features that are consistent with a given outcome level. The discretized set of outcomes is mapped to the features at the phase transition (or phase profiles). For example, the phase profile at the movement initiation for a level A outcome at phase transition i is given by:

$$x(t=t_{0i}) \in X_{0i}^A \quad \text{EQ. 8}$$

The regions can then be used to generate cues that reinforce the movement technique that is consistent with a desired outcome level. This makes it possible for the user to make associations between the behavior, which is described by specific features of movement phase structure, and the effect of these features on the outcome.

Outcome feature validation provides a feedback signal validating that key movement characteristics meet the required value to achieve the target outcome. This function is enabled by the movement phase decomposition, which allows tracking the movement behavior across various phases and determine if they meet the conditions at the subgoal levels.

The phase transition and profile cues help users develop an awareness of the movement phase structure. The cueing provides information pertaining to both spatial coordination as well as temporal coordination. These forms of cueing therefore can also be regarded as types of proprioceptive augmentation where the proprioceptive augmentation enhances awareness and conscious perception of the movement architecture.

3) "Alerts" can be conceived as the opposite of validation cues. This feedback can be setup to have specific functional roles, such as alerting the user if the movement state trajectory is outside of the feasible region g(x, Θ)≤0 (see FIG. 3). As with other cues, alerts emphasize conditions at phase transitions or during phases (phase profile). Alerts delivered concurrently with the movement features are more effective than at times or attributes that are arbitrary.

Figure 5:
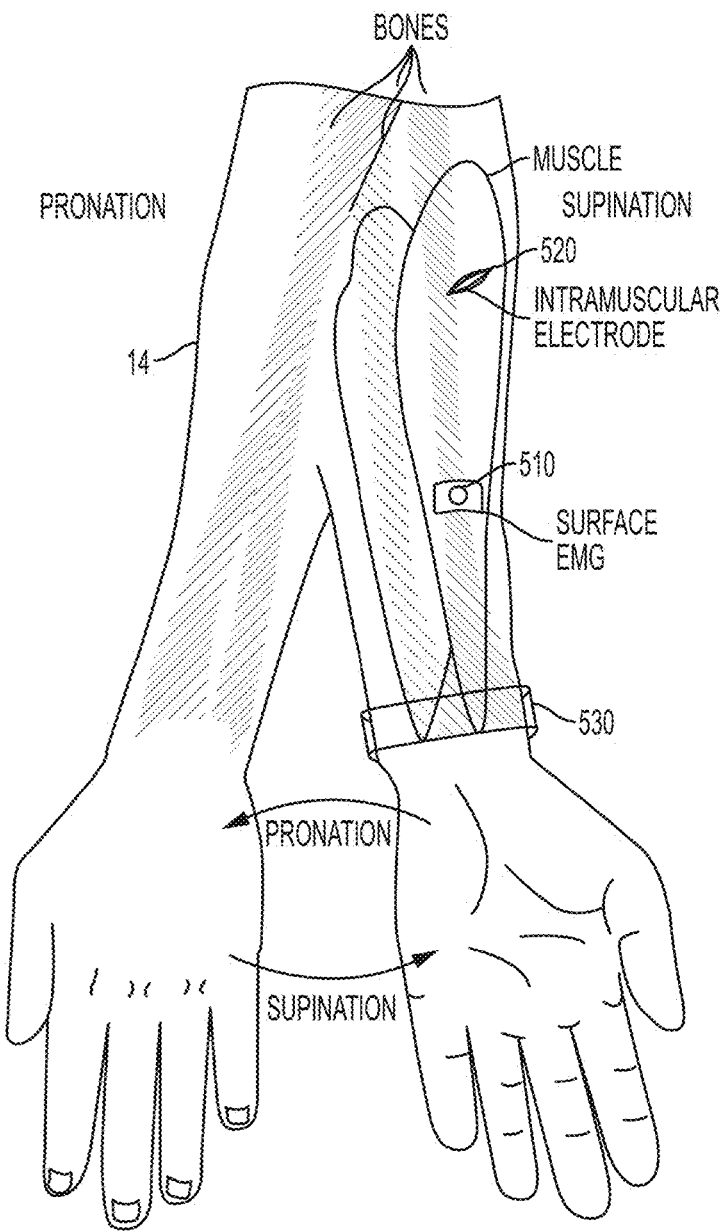
FIG. 5 illustrates a forehand pronation and supination showing basic bone and muscle structures. It also illustrates possible sensors to capture the relationship between forearm movement and musculoskeletal structure.

An alert protecting users from injury or wear can be implemented based on the analysis of the relationship between movement profiles and the biomechanical system. For example, the phase profile during the forward swing and impact can be mapped to the wrist and forearm joint motion and muscle activity (FIG. 5). The synergy decomposition can be used to determine joint deflections and muscle activation profiles. This mapping can then be used to detect when these quantities are exceeding some acceptable values. Similarly, this information can be used to generate phase transition and phase profile cueing to help form movement patterns that are compatible with an individual's musculoskeletal conditions.

4) "Outcome optimization" Following general movement skill acquisition principles, once a basic movement pattern (or architecture) has been acquired, it is refined and eventually optimized. As described, information available for a set of movement data can also provide the basis to help individuals further optimize their movement technique. Optimization of the outcome corresponds to learning to modify the movement to increase the level of outcome. The movement is parameterized by the set of features that influence the outcome. The set of features defines the admissible trajectories. FIG. 3 shows the optimal goal state 340 and the envelope of admissible trajectories 320. A particular combination of features results in the best outcome level for that particular movement pattern.

Given a movement pattern architecture, specified by the finite-state model, the outcome can be defined by a function of the goal phase:

$$z=\varphi(x(t=t_{goal}))=\varphi(x_{goal}). \qquad \text{EQ. 9}$$

The sensitivity of the outcome, with respect to the movement profile, can be described by a sensitivity function $\nabla_{\tilde{x}}\varphi(x, \Theta)$ where $\tilde{x}$ is the set of all phase features. The subset of features that have the highest sensitivity define the control variables that can be used to cue the user to refine phase profiles. Similarly, the sensitivity of the outcome with respect to the movement pattern architecture can be described by a sensitivity function $\nabla_{\tilde{\Theta}}\varphi(x, \Theta)$ where $\tilde{\Theta}$ is the set of all pattern architecture features. The subset of $\tilde{\Theta}$ that has the highest sensitivity defines the control variables that can be used to cue the user to optimize pattern architecture.

Based on this analysis phase timing and initial state characteristics are ideal targets (control variables) for cueing. This corresponds to cueing for the subgoal states (and initial states) of movement phases (FIG. 3). For example, in tennis, this would correspond to guiding the backswing to reach optimal racket orientation (elevation, azimuth and pitch) at the onset of the forward swing.

5) "Movement Refinement": Within an outcome level (EQ. 7), the movement can be refined to achieve better efficiency, lower stress on the body, etc. The optimization of the movement for example to enhance efficiency, follows the same approach as for the outcome optimization but the outcome level is fixed and the objective function captures the qualities that are relevant to refinement such as jerk or energy.

6) "Pattern reshaping": The idea is to extend previously formed patterns by inserting a new phase (see FIGS. 15A-15E). This is a form of pattern refinement that extends outside the movement pattern. This process can be implemented by providing outcome feature validation cues that reinforce new patterns. The cues operate according to the two different forms of phase extensions: either inserting a new phase or breaking up an existing phase in two subphases.

The parametric optimization framework can be used for reshaping movement pattern architecture. For example, given the outcome function J(x, Θ), the gradient of this function with respect to the pattern configuration parameters Θ can help explore effects of variations in pattern architecture. However, this formulation may be ill-posed since an existing trajectory manifold for a user's particular motion pattern class will typically only have one pattern. However, as users progress in their skill acquisition, some elements of new patterns may be available in the data to support the data-driven analysis. Alternatively, simulation tools can be developed from the parameters of user's existing data to discover new patterns. Cueing laws can then be designed to reinforce features that will drive the pattern architecture to the refined architecture.

7) "Pattern formation": The movement structure depends on skill level and evolves with skill development.

Since the phase transition and phase profile cues only have limited to transform the movement structure and organization, the formation of new movement patterns requires different cueing mechanisms.

The cueing formulation introduced earlier is adapted to the skill level, however, phase transition or phase profile cues may not provide sufficient signals to help form new movement patterns. Therefore, it is necessary to design feedback cues that can help form new movement architectures. The following describes cueing mechanisms that can be used to assist the formation and reshaping of movement patterning or phase architecture.

Complex movements, such as the tennis stroke, are dynamic processes, i.e., the temporal and spatial dimensions are coupled. Therefore, to meet the impact conditions at a specific time and space and produce impact conditions that lead to the desired outcome, the execution of these trajectories requires memory of the pattern spatial and state configuration, which is given by the transition points, and memory of the muscle activation patterns (muscle synergies) that enable the dynamic execution of the movement phase profiles and transition between movement phases.

Movement sequence learning theory shows that learning complex sequences starts with an explicit stage emphasizing spatial characteristics followed by an implicit stage focused on the neuro-motor process aspects. The acquisition of spatial movement configuration is usually aided by direct demonstration or through the assistance of a visual display. Once the new movement pattern's spatial configuration is assimilated, the subject has to learn the pattern of muscle activation and body segment coordination to successfully reproduce the movement pattern under dynamic conditions. This process is usually much less conscious and relies on repetition to consolidate in the memory before it can be utilized reliably under typical task conditions.

Cueing mechanisms for outcome feature validation or refinement can help connect the explicit sequence elements and the implicit motor processes, and in turn, should help accelerate the formation and consolidation of movement patterns.

Figure 10:
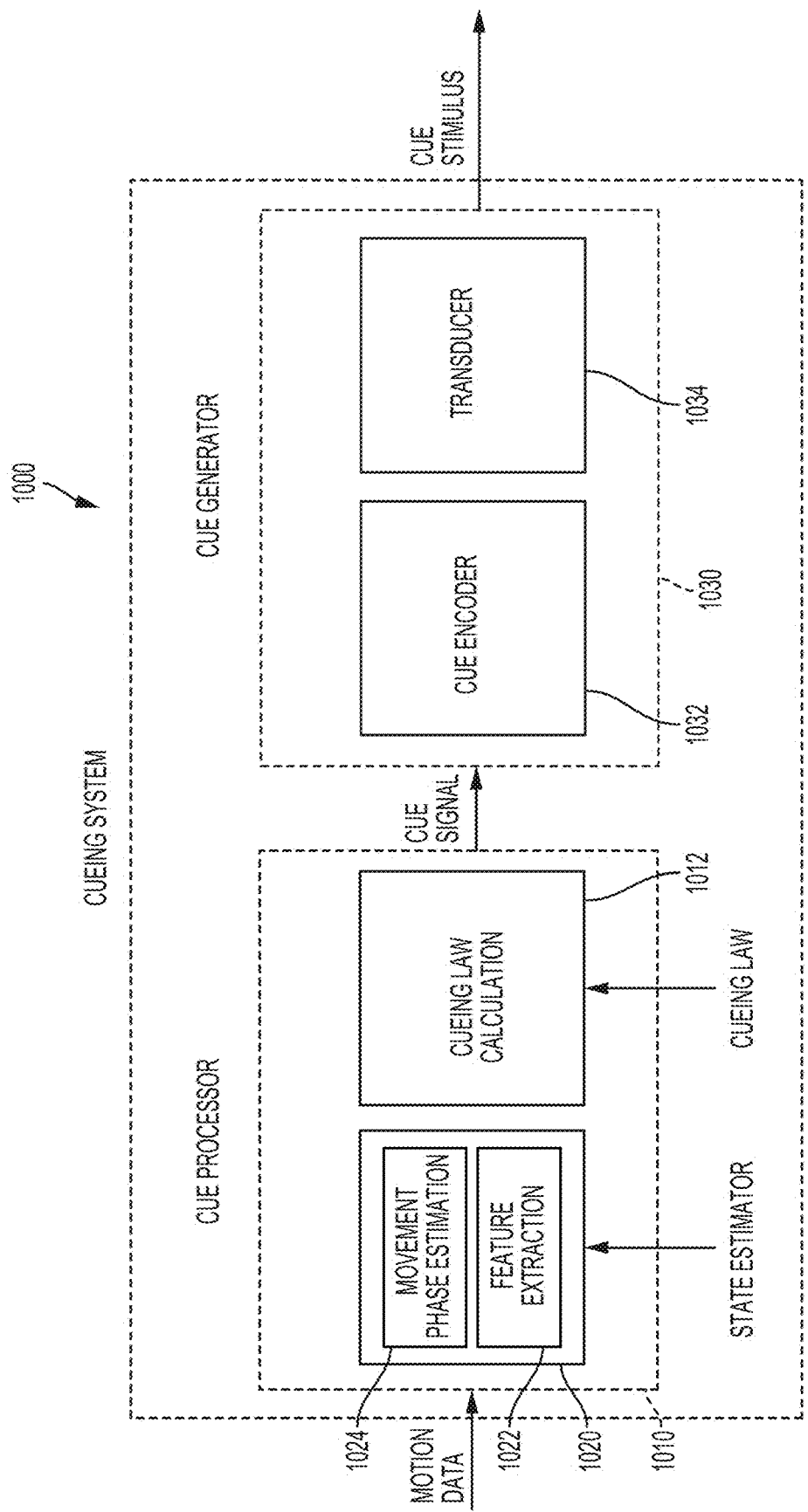
FIG. 10 is a block diagram of cueing system showing exemplar components including the cue processor (movement phase estimator, feature extractor, and a cueing law) and cue generator (cue encoder and transducer)

The real-time feedback augmentation using the cueing mechanisms are implemented by a cueing system. The cueing system 1000 is composed of a cueing processor 1010 and a cue generator 1030 as shown in FIG. 10. The cueing processor 1010 comprises a state machine 1020 and a cueing law 1012. The cue generator comprises a cue encoder 1032 and a transducer 1034. The cueing system 1000 can be integrated into a standalone device, such as an earpiece or a wearable device. The state machine 1020 can be configured to provide a movement phase estimation 1024 and a feature extraction 1022. The input of the cueing system 1000 is motion data while the output is one or more cue stimulus (if necessary). Its primary functions can also be distributed across several physical systems; for example, the cue processor could be on the embedded device and the cue generator could be implemented on a smartwatch. The transducers used to produce the cue stimuli can be integrated in the clothing or other accessories.

As the movement patterns unfold, the finite-state estimator identifies the movement phase and phase transitions. In addition, the knowledge of the movement state across phases makes it possible to extract associated phase profiles and values of the movement state at transition. Based on the knowledge of the skill assessment and skill model and diagnostic, the relevant phase and state characteristics are extracted (e.g. phase outcome derivatives, phase profile outcome derivatives and outcomes). The state estimator uses motion measurements to identify the movement phase with the corresponding initiation times and initial/terminal states at phase transition. The phase estimate can be used to extract relevant information about the movement phase, including, e.g., state information and various derivatives that describe the relationship between the movement characteristics and movement outcome. The cueing law uses this information to compute a cue signal. The cue signal is then transformed into a stimulus by the cue generator.

The cueing system has four main components: phase state estimator, cueing law, cue encoder and transducer. The finite-state model is a key component of the movement phase discrete state-estimation system. Estimation of the movement phase is essential for real-time feedback. Since there is latency in the response, the cues directed at phase transition or phase profile characteristics should be based on prediction of the phase and relevant phase characteristics. The movement phases are identifiable through kinematic or dynamics features at phase transition. Formal detection rules can be formulated for these transition characteristics. These can then be incorporated in estimation schemes, such as a finite-state estimator, that make it possible to automatically segment the movement into phases from the measurements. However, some movements involve subtle structural features and the phase detection requires more sophisticated models. The movement phases can also be determined based on models of the state transition maps extracted from nonlinear time series as discussed earlier. Phase state estimation is also possible with statistical methods such as Hidden Markov Models (HMM).

The cueing law operates similarly to a feedback law. It takes state information and computes a control signal to influence the behavior. The cueing law is grounded in the skill model derived from the assessment and diagnosis process, which identifies the movement characteristics for desired movement performance and outcome. A primary example is the state of the movement at phase transition and its influence on the movement outcome discussed earlier. This relationship can be captured through sensitivity analysis. The signals from the cueing laws are communicated to the user using a cue generator, which produces cue stimuli that can be perceived by the user during movement performance. Typical cue stimuli include audible, visual, or haptic stimuli. The cue generator is composed of a cue encoder, which transforms the cue signal into a codified cue signal, and a transducer, which transforms the cue signal into a cue stimulus.

The purpose of the cue encoder is to create a cue stimulus from the information available in the cue signal that can easily be understood by the user. The encoder is best designed based on the understanding of the type of decoder and internal model that will be used by a user to interpret the cue stimuli. In an audible cue, for example, cue stimuli can be produced by using musical notes from a scale. The musical notes and harmonic principles represent an innate form of the internal model and decoder for the interpretation of the cue stimuli. One way to encode cues is through quantization of the cue signals and assigning values to the quantized signals. This allows the user to recognize different levels in the cue stimulus and associate these levels with relevant information. One approach is to use familiar stimuli codes, such as harmonic or color schemes (red, orange, green), etc. These forms are common enough that users will familiarize with the encoding scheme and progressively more complex cues can be implemented.

The effectiveness of cueing depends on several characteristics including the perception of events, the perception of the structure of movement, and the timing characteristics in natural motor control. The last correction before goal or impact has been estimated to take place at about 290 msec (for visual feedback). That time depends on the feedback modality and is smaller for proprioceptive cues (about 100 msec) and audible cues (about 150 msec). Therefore, little or no benefit is expected for cueing the movement phase profile of phases that are within short time intervals of the primary movement goals. For example, the data from the tennis experiments show little adaptation is visible in the phase about 100 msec before the impact (see, e.g. FIG. 16A which provides an ensemble of racket angular rate profiles highlighting patterns that can be used to identify stroke phases). Real-time cueing, may also require predicting phase transitions and the movement states at the future transitions points.

To achieve systematic, data driven analysis and augmentation, it is necessary to operationalize the training process. The skill augmentation components are synthesized from the hierarchical motion and skill model. The elements needed to realize, track and manage augmented training are introduced following the movement skill model.

The organizational and skill development model for addressing different aspects of a user's skill components such as movement repertoire development and movement pattern phase formation can be broken into a cortical level, subcortical level and spinal level. The cortical level includes movement repertoire (in the long term memory) and executive or high-level perception. The subcortical level includes movement phase pattern formation and reconfiguration, while the spinal level includes physical implementation. These different levels can be targeted through selection of feedback modalities.

The synthesis and realization of augmentation functions is delineated in terms of the knowledge level and the cue/ signal level. FIG. 1 depicts the synthesis and realized components at those two levels. At the knowledge level, the skill diagnostics from the skill model are used to synthesize training schedules and one or more instructions. At the signal and cue level, they are used to synthesize cueing laws.

The training schedule is composed of training elements that specify the patterns and outcomes that needs to be trained (for example refined or optimized). Each training element can be performed under several augmentation modalities. These can be selected as user preferences. Feedback cues are packaged as cueing profile that target the cueing goals (1)-(7) described earlier. Instructions summarize key insights about the individual's movement technique from the diagnostic results, encompassing the various levels of the assessment hierarchy.

In one implementation, the training schedules and instructions are managed by a training agent which provides expert system for managing the long-term training goals. Similarly, the cueing profiles within the training schedules can be managed by a cueing agent, which provides assistance to the user on the selection of cues and tracks their effectiveness. Skill assessments, in particular the outcome phase and profile feature derivatives, provide measurements to determine the best combination of cueing modalities and mechanisms and how these modalities should be used.

The cueing agent tracks the progress in movement technique and outcome for a particular cueing profile and can recommend when to stop or switch to a different profile. In addition, the motion data acquired while a cueing law is active provides further measurements for validation. The cueing law effectiveness is assessed while it is active. Once progress with a cueing profile has reached the expected level, predicted during its synthesis, the training process returns to the training agent.

Figure 15A:
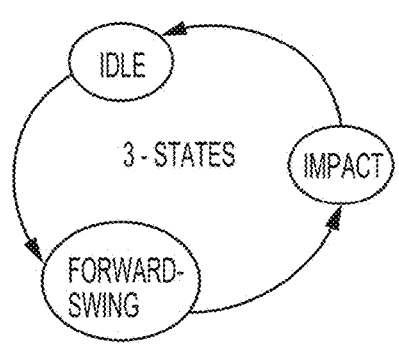
FIGS. 15A-15E illustrates the development of movement pattern structure in terms of finite-state model structure for the tennis stroke example.
Figure 15B:
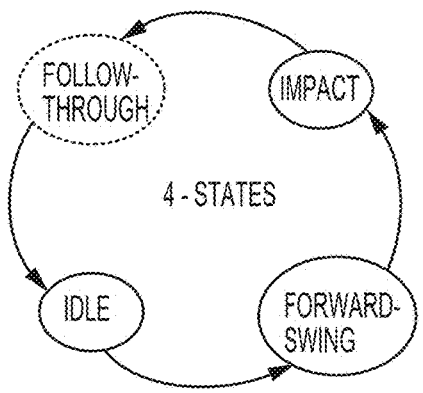
Figure 15C:
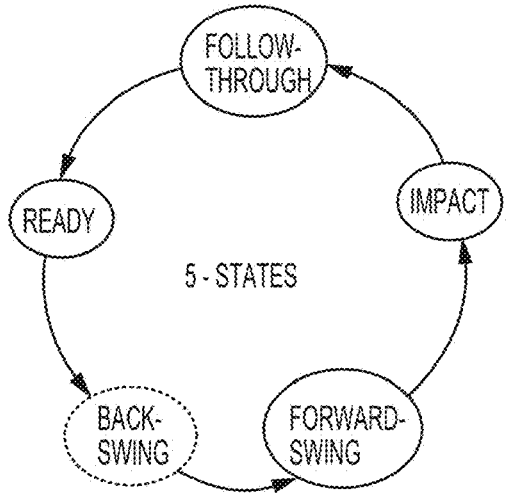
Figure 15D:
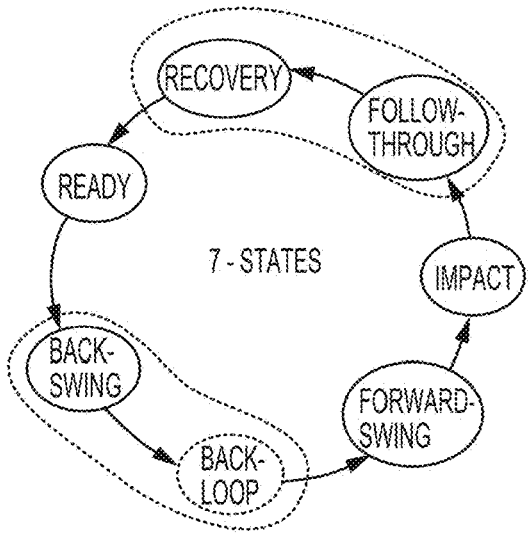
Figure 15E:
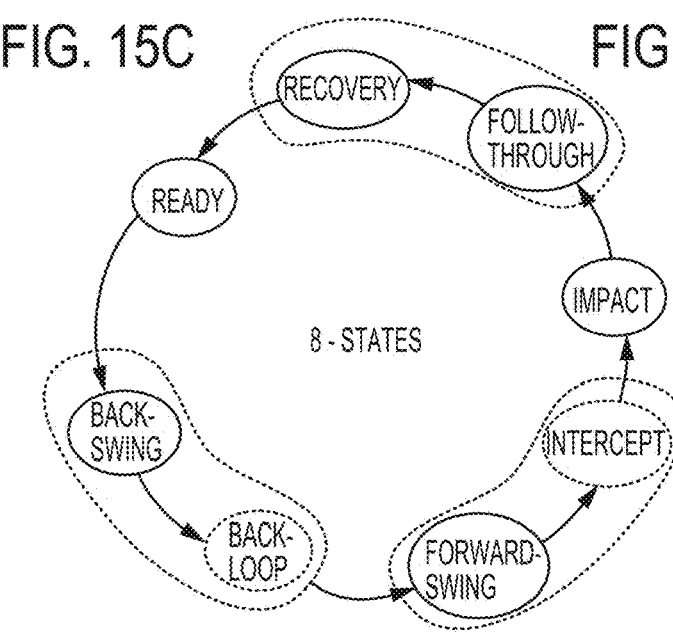

The structure of the finite-state model is expected to change over various stages of skill acquisition (see FIGS. 15A-15E). For example, a beginner primarily focuses on the forward swing and the impact (FIG. 15A). The follow through is a consequence of the impact and the backswing is not integrated in the stroke and is essentially a loading movement. Over time the player learns to integrate the follow through and backswing as part of a coherent stroke motion (FIG. 15B). As users extend their motion into more extensive regions of the state space, additional bio-mechanical constraints and dynamical effects become relevant and therefore need to be accounted for to exploit the extended envelope. As a result, the movement architecture can be quite different and the finite-state model needs to be adapted to these specific characteristics such as the recovery and the back loop (FIG. 15D). Therefore, the goal is to be able to identify the model structure from the data in order to account for individual differences due to technique and the effects of skill. For example, consider the tennis stroke. In beginners, early stroke movements are mostly undifferentiated forward swing motions with the primary goal of intercepting the oncoming ball.

As tennis players continue playing, they begin to differentiate their motion to impart different effects on the ball (comparing strength and spin) and adjust to the impact conditions (comparing trajectory of the oncoming ball). They either discover these new stroke patterns by themselves, through adaptation of their technique, and/or through the direction of a coach. The stroke must be optimized as more specific outcomes and demanding conditions are desired. For example, to achieve strong topspin effects, the stroke trajectory in the phases preceding the impact (backswing and forward swing) must follow a profile that will lead to impact conditions that will generate topspin. For example, the racket head must drop sufficiently low before the forward swing initiation. The optimization of stroke techniques leads to specialization of the movement architecture. As a result of this movement refinement process, the overall movement structure evolves with skill. These characteristics suggest that training schedules, as well as the entire movement analysis, modeling, and feedback augmentation should proceed iteratively, following the differentiation and specialization of the movement structure.

The states of the finite-state model can be conceived as a hierarchical structure that has primary states which are expanded into higher order states. For the tennis example, as shown in FIGS. 15A-15E, the most elementary motion model is composed of three states: the stroke (forward swing), the impact, and ready (or idle). Next, the stroke state can be expanded to include follow through and/or backswing and so on. These three states can then be further expanded: the forward stroke into stroke initiation and interception, the follow through into recovery phases, and the backswing into backswing initiation and back loop. Note that the phase structure, and hence the process of structure refinement is specific to a movement pattern.

The extension of the model follows two basic directions:
(a) addition or insertion of a new primary state such as the case of delineating the swing into a backswing and forward swing,
(b) the refinement or expansion of an existing primary state through the addition of a state such as the case with the expansion of the backswing into a backswing and back loop sub-phases.

The new primary states are shown in FIGS. 15A-15E in dashed lines and the new expanded states are highlighted through a dashed line surrounding these state. The distinction between the addition or expansion is determined by hierarchical movement structure. Primary states are movement sub-units while expansions are determined by factors including movement control mechanisms. In some cases, these distinctions can be ambiguous.

There is a relationship between the movement structure hierarchy and the natural development of skills. Furthermore, primary states are common to a broader class of skills and techniques. For example, they may be shared by different stroke classes, or even be similar from one user to another. Therefore, a low-order motion model can reliably describe a broad population of users. The higher-order models require more detailed understanding of an individual's technique. Therefore, the models can be synthesized through an incremental process, starting with the low-order finite-state model, which can then be refined as data becomes available.

Figure 17:
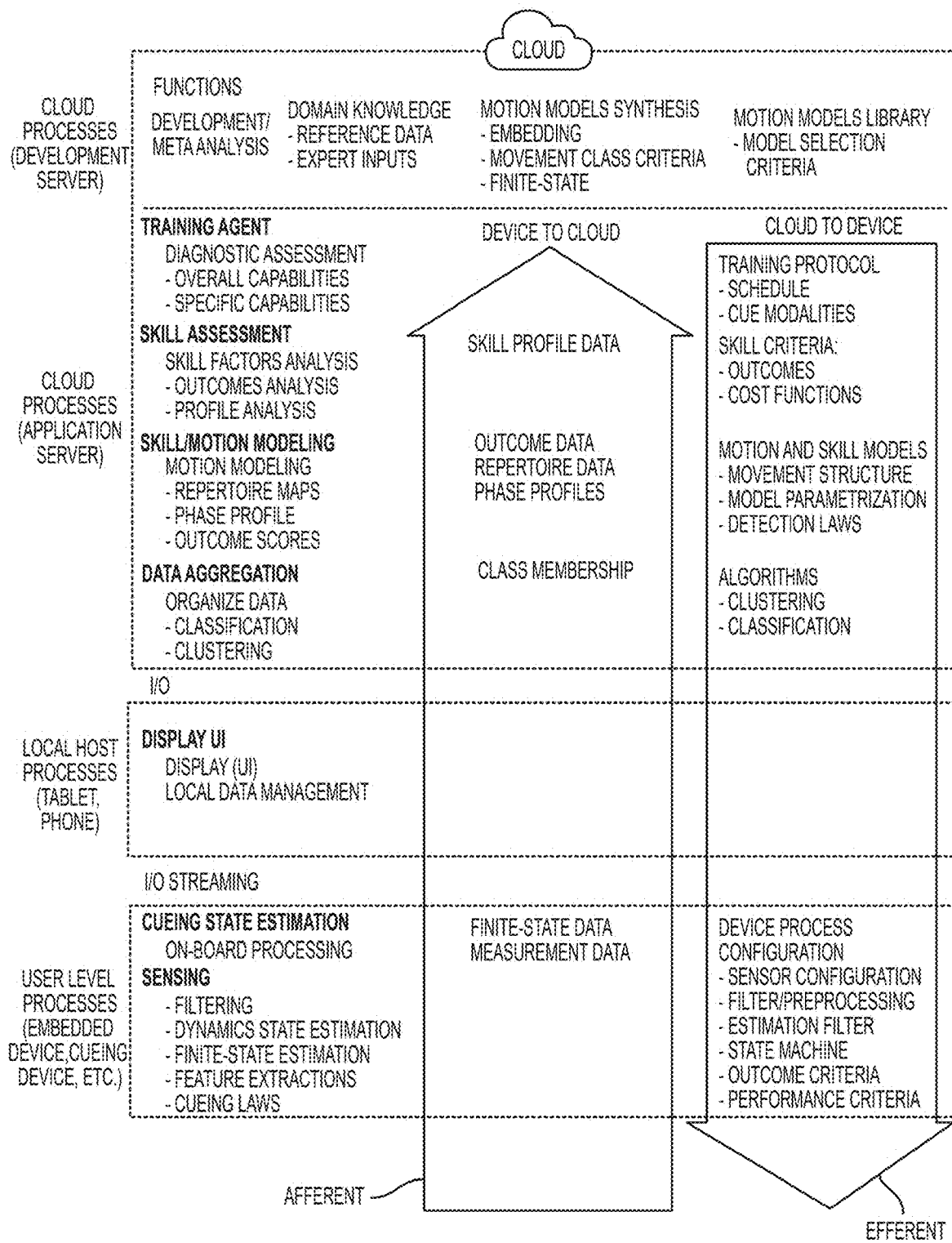
FIG. 17 illustrates an exemplar organization of the data processing and other functionalities across the platform's hierarchy and highlights the information flow across primary component levels and devices.

The movement segmentation and finite-state models for the evolving movement architecture shown in FIGS. 15A-15E can be extracted from individual users in a data-driven fashion. These models can be stored in a library and enable tracking of the skill development process as shown in FIG. 17. With data from a sufficiently broad skill population (both in terms of style and technique), knowledge about the skill acquisition process in terms of pattern formation, associated with movement architecture, etc., it is possible to model long-term skill acquisition. This information can then be use to design long-term training protocols that can account for broad individual characteristics such as morphological and physical characteristics. The understanding of the development of the movement architecture can be applied to refine an individual's motion structure. Capturing the development of the movement architecture through a formal hierarchical model structure makes it possible to design training schedules that allow systematic skill development paths based on the understanding of the refinement in movement architecture.

Capturing movement structure and skills provides a formal basis to track a user's stage in the acquisition process. This understanding can then in turn be used to determine the best forms of interventions, e.g. in the form of feedback augmentation, at each stage along a skill development path. A key characteristic of a successful training framework is the ability to continuously deliver value to a user. Statistics provide most of the information after using the system for a few sessions, but then stop delivering new information. Subtle changes in movement performance are not captured by basic statistics. For example, the four typical outcomes in tennis (impact distribution, racket speed, spin and ball speed) do not provide sufficient direct knowledge of the effect of training, fatigue, injury or even changes in the equipment. Another reason is simply lack of measurements. For example, the role of footwork in the tennis stroke, or the hip motion and core, can only be captured indirectly by measuring the racket motion.

It is possible to access more comprehensive characteristics of the behavior by tracking different aspects of behavior in addition to outcomes. However, extracting knowledge about these still relies on expert interpretation. Tracking these characteristics over time can provide valuable insights such as the onset of fatigue and the effect of specific injuries. These various factors may not sufficiently be picked up in the outcomes since the body can compensate for them. However, tracking movement structure enables monitoring of specific changes in the motion patterns. A persistent problem such as an injury will sufficiently alter the patterns, and thus be quickly identified. It will also be possible to capture subtle changes that occur over time such as effects of feedback augmentation or injury. With this system, it is possible to give comprehensive diagnostics about the health of the user and to continuously deliver information that can be used to provide detailed adjustments to training or other aspects.

As will be appreciated by those skilled in the art, the physical implementation for a typical usage scenario of this system can be realized in a variety of systems and platforms. Following FIG. 1 and FIG. 6, the general usage scenario is to track and assess skill iteratively while providing sets of movement instructions and augmentation cues that enable the user's systematic development of movement skills. This scenario is valid for many movement activities, and is considered here to contextualize the implementation of the platform. In this scenario, the system components and computational processes are implemented in the form of an application that runs on physical components found in the internet-of-things-type (IoT) platform, including: an embedded device, mobile host device, and cloud processor/database. These physical components implement the platform's system components: sensor, host device, User Interface (UI), processing, storage, and augmentation. Delineating between the application, the physical components, and the system components enables flexible deployment across different activity domains and devices.

Most physical activities take place over a defined period of time denoted 'session', possessing a training structure, specified mode(s) of operation, and user interactions. These sessions can include play, game, or training sessions. A typical session is segmented into periods when the user is playing: 'sets' or 'runs'. Sets are delineated by intermissions in activity, when the user pauses to review activity or simply rest. Therefore, a typical session organization consists of cycles of sets and intermissions. During each set, the sensor device captures activity measurements, preprocesses the measurements, and streams the measurement data or a subset of the data to a host device. The host device then further processes the data. Alternatively, the device can stream the data directly to the cloud, possibly relayed via the host device. Different network topologies and architectures can be conceived. For example, a single player can engage with a mobile enabled device that communicates with the internet. Alternatively, two or more players can interact with one or more mobile enabled devices that communicate with the internet. Each player can have an associated sensor device, or each player can have equipment (e.g., tennis racket) with an embedded sensor device. As a sequence of sets unfolds, data can either be continuously processed, batch processed, or processed in a hybrid manner of the two. Processing allows activity review or summarization during an intermission, communicating relevant information to the just-completed activity or future activity. Data can also be available continuously for review, possibly by a trainer. In one implementation, the user interacts with the system via hands-off functionality, such as a natural language interface. For example, in addition to the configuring cueing functions, the player can issue a specific request about training status or current or past performance. Specific training profiles can be selected, based on current skill. A training profile will activate a cueing profile, providing cue signals tailored to the specific goal of that training profile.

The typical user scenario considers a user who regularly performs and trains skills for an activity over a period of months or years, and who wants to track progress and receive instructions for developing, maintaining or rehabilitating movement skill from session to session. More specifically, a user may perform an activity two to three times a week, or even more frequently. The platform aggregates and assesses the user's movement performance data within the assessment loop (see FIG. 1). This process generates a movement repertoire map and skill model which describes the user's current and historical skill states. At any time during the activity, the user can choose to activate feedback augmentation, in the form of instructions and/or feedback cueing (FIG. 12). Even if the user does not enable augmentations, the assessment loop can operate in a passive mode, continuing to collect data whenever the user is engaged in an activity and continually updating the skill model.

In general, the platform's system components can comprise of the following: sensor, host device, User Interface (UI), processing, storage, and augmentation. The sensor is one or more components that acquires movement data. The host ensures that all of the system components are connected and transfers data between them, in either afferent or efferent directions. The host device is typically not involved in data processing or enabling the user interface. The user interface (UI) is the component responsible for user interactions with the platform: recording their interactions, translating the interaction into meaningful processing requests (e.g., start recording, display skill metric, etc.), and delivering the results. The UI does not necessarily have to be graphical in nature, operate completely in real-time, or even implement all of the previously described platform user interactions. The platform's processing component is responsible for processing data from the sensor into relevant information, including, but not limited to, parsed movement data, movement models, skill models, and training or cueing instructions, as detailed elsewhere. In addition to generating relevant information, the processing component prepares data for the storage component, by organizing processed information into a data model and data structure designed for hierarchical and contextual views of movement technique and activity performances. This entire process may consist of various levels of computations; some of these take place in real-time.

At the highest level, the user interface is responsible for executing all end-user requests in processing requests, data requests, system configuration changes, system activations, and many other tasks. More specifically, the user interface (UI) enables users to browse histories of their movement performances, explore skill diagnostics, and engage the assessment and augmentation loops of the training system. The UI allows the end-user to participate in the assessment loop by displaying current skill status, diagnostics, instructions, and repertoire maps. When enabling the augmentation loop, the UI then provides options to select from a variety of cueing profiles enabling and configuring the augmentation component.

Without a coherent data structure, navigation of large amounts of movement performance data is intractable. The design of the UI component therefore is dictated by the skill and movement models for an activity. By ensuring the UI is designed with a specific skill model in mind, the model can most effectively be leveraged to support the user's understanding of their movement technique. The classes and phases that describe a user's skill and motion models can themselves define elements for efficient communication of information and navigation on display systems (e.g., on a smart-phone, tablet, computer screen, etc.).

Specific quantities extracted from the skill model are used to produce visualizations and define an interface, as well as organize the user interactions. These quantities include outputs such as temporal contextual information, ensemble statistics, ensemble motion and phase profiles, and ensemble special motion and phase profiles. These outputs can be mapped to a visualization which includes a navigation interface, a repertoire map, and a phase view, all presented on a user device's display.

The aggregation of the data and its corresponding data structure organization makes it possible to track the development of an individual's movement patterns or changes to the patterns. The long-term aggregation describes the primary movement characteristics of an individual and the short-term aggregation makes it possible to understand the efficacy and impact of a training intervention, cueing law, or other factor such as equipment or physical status, etc. This level of information contributes to the definition of the repertoire map level of the interface.

The motion model's phase segmentation makes it possible to analyze and display relevant quantities for each stroke phase. The phase representation allows concise descriptions focusing on characteristics specific and relevant to that phase. In addition, building on inherent movement architecture, the motion data inherits the hierarchical structure that also provides logical means of navigating and visualizing the data. All three characteristics can be leveraged in the user interface design, determining what information to display as well as what user interactions the system can elicit, at this level. This transparent and logical representation is essential for teaching and broadcasting. Augmentation modality selection can be accomplished via a graphical IO and/or natural language processing UI. During intermissions, or when there is sufficient time to review performance, a smart phone or tablet can provide convenient Graphical User Interface (GUI) interactions. During play, hands-off user inputs and feedback are more practical. For example, in addition to activating cueing functions (e.g., by speaking commands such as "THE SYSTEM: cue me on backhand top spin medium"), the player can receive speech prompts of the training status, as well as make inquiries about movement technique or outcomes (e.g., by speaking commands such as "THE SYSTEM: what was top spin on last stroke?").

Consider the tennis example use case. The tree data structure shown in FIG. 11 allows users to navigate through the different stroke phases from a stroke 1110, for different categories, classes and types where the stroke 1110 can be classified into a category 1120 (e.g., groundstroke, overhead, volley, serve), a type 1130 (forehand, backhand), and a class 1140 (FH Class A, FH Class B, FH Class X). Additionally, the stroke 1110 can be segmented into a phase 1150 (impact, follow through, recovery, backswing, back loop, forward swing) which has attributes 1160. These plots can be used to highlight the corresponding trajectory segment along with the performance and skill attributes that are derived from the characteristic phase features. FIG. 19A shows how this tree structure can be translated into a graphical UI.

In order to enable long-term analysis and feedback on movement performances and skill, historical records are stored. This storage consists of many different entities, objects, and data structures within the platform:
(1) storage of raw motion data and processed motion data into a hierarchical and contextual data structure;
(2) a user's motion model; and
(3) a user's skill model. Information can be stored on any physical component, as long as the information can be accessed by the other relevant components in the system.

A partial basis for the data structure is provided by the hierarchical motion and skill models derived from the inherent movement architecture. As will be appreciated by those skilled in the art, other activities share similar general structure making the platform generalizable to other activity domains.

Changes in proficiency or skill can be assessed via repertoire map, which is part of an ensemble mode. To fill the repertoire map, data must be collected over longer periods (e.g. several months), making it possible to capture the variety of patterns that reflect individuals' technique and skills. Furthermore, movement patterns can be categorized as 'stable', 'unstable' or 'outliers'. For example, from time to time every individual can execute both near perfect as well as catastrophic movements. Once sufficient data has been collected it is possible to differentiate between these characteristics as it relates to an overall general performance or training trajectory.

Different database queries are required to support the different display modes used to investigate performance patterns. These queries include, for example: current set in session; comparing performance of consecutive sets in same session; overall performance during session; comparison of two or more sessions in recent activity history (e.g., when training the same skill in a previous session); overall performance in sessions across specific calendar periods; long-term trends. These queries can be performed across the entire movement repertoire, or focusing on specific categories, types, and/or classes of movements; they can also be focused on certain time ranges or use other selection criteria.

The movement database can also be queried to extract movements with specific characteristics from the repertoire. These movements can then be used as objects to define the user interface. Typical objects include, for example: "optimal" profiles that describe the best stroke in the user's repertoire; or "catastrophic" profiles that can cause injury. The best stroke is determined based on outcome coefficients and trajectory statistics and can be studied over the entire movement profile or within each phase. Information returned in this case might include movement profile statistics, such as mean and variance across relevant state profiles for a given movement type and phase. Other statistics include phase state profile envelopes. This can be used to generate a comparison between stroke instances in a current training set and the optimal strokes from that set, session, or historical results. Movement outliers ("catastrophic" profiles) that describe faulty movement patterns can be used to generate profiles to avoid and associated feedback.

The storage component also enables inter-player comparison of movement skill and technique, via comparing motion models, skill models, or through other criteria. Additionally, reference movements can be used, allowing the incorporation of best practices derived from a particular domain's movement mechanics.

A user's motion model represents the specific details of how a user's data is taken in, processed, and movement units and phase segments are extracted. This model includes information such as finite state models, thresholds, or other parameters and definitions. Depending on the activity, there can be a general template from which each user's motion model is derived from, or a user's motion model can be completely derived from recorded data.

A user's skill model represents their current relationship between movement techniques and outcomes. It also includes information such as which improvements should be prioritized or what has been historically difficult to change. As with a user's motion model, a skill model will have varying degrees of user/activity specificity.

FIG. 11 illustrates a data tree structure associated with the tennis stroke. Other domains tend to have similar general organization of classes and phases of motion. For tennis, the temporal organization can be described as follows. A session starts when a player walks on the court and ends when the player leaves the court. A set is a continuous period of training or play interval. A set ends when the player takes a break, perhaps, during a game or during training to rest or speak to a trainer. A rally is a sequence of consecutive exchanges, typically ending when a player misses the ball or makes an unforced error. Within a rally, strokes are sequenced. A stroke (or swing) is the interval encompassing a time period before the ball impact (stroke preparation), the impact time period, and a time period past the recovery. The period between stroke preparation and following its completion is usually called the 'ready state'. The stroke is described by 'stroke profiles' which represent the measurement time histories. A phase is a segment of the stroke which reflects relevant kinematics, dynamics, or human factors (motor control, perception, decision making) that manifest in the stroke organization. Table 2 describes some of the associated information for tennis.

TABLE 2

Overview of the session data structure.

| Quality | Type | Fields |
| --- | --- | --- |
| Session | Contextual session and player information | Date/time, location, surface, player, opponent, etc. |
| Set | Time indices | Time in 'session' identify the segments when players are in play. |
| Rally | Time indices in 'set' | Start and end of rallies. In game, also include score and server id. |

The highest-level processing is the synthesis of motion models, skill models and cueing laws (see FIG. 10). These processes are part of the algorithm and model development. A function of these models is to provide appropriate movement/skill abstractions, and the continued evolution of these abstractions, as the individual's technique and skill evolves. With sufficient user data from a broad range of applied skills and techniques, a library of movement models can be assembled. At this point, relevant models for a new user can be selected by evaluating the performance of various models from the library. The models will also need to be switched or adapted as a user's skills evolve.

Feedback synthesis refers to the part of processing that generates instructions to improve the outcomes of movement techniques based on a computational assessment of a user's skill status (FIG. 9 box II and III). The instructions generated by feedback synthesis are (computationally) represented as differentials in the movement model which correspond to variations outcomes. From an implementation perspective, the skill model, diagnostic functions, and the movement model and associated phase segmentation can all be used in generating instructions. More specifically, the feedback synthesis process includes the following steps.

(1) Determine the movement features (feature outcome derivatives) from the movement model of a user that the user has the ability to change based on the potential or observed constraints of an instruction (range of motion, ability to accelerate movement, etc.); i.e., determine which movement parameters are free to be optimized.

(2) Determine movement features that display a significant impact on an outcome; i.e., select movement parameters that should be optimized.

(3) Prioritize movement features that are both changeable and have the most significant impact on outcomes; i.e., chose the optimization step.

This analysis becomes the basis for personalized and individualized instructions, used to improve the movement technique and outcomes of a user's movement performance. The output of the feedback synthesis can be transformed into a range of feedbacks including: symbolic language (text, spoken), cues (visual, audible, haptic) or signals (visual stimuli, audible, haptic). The output of the feedback synthesis will be transformed into augmentations by the augmentation system component of the platform.

Computing is generally distributed across the platform, however most computing functions related to movement and skill processing are typically executed in the cloud. These processes require the most computational resources and the most stored data to process, making the cloud a logical location. In some configurations, limited movement and skill processing can be executed at the device and host level. From an implementation perspective, the relationship between the data structure, storage component, and processing component is critical to effectively enabling the vast array of movement skill processing capabilities of the system.

The skill model assumes that the user learns patterns from a general template. The goal therefore is to identify the movement patterns that belong to the distinct schemas that are being learned. The first step is to parse movement patterns that correspond to the learned movement schemas or motor programs. The parsed data can then be aggregated to form the movement repertoire.

Movement classification takes the ensemble data from the movement repertoire and determines a partitioning of this set into subsets of similar patterns. The classification process is based on features that are extracted from the time histories in the ensemble data. These features are then classified using clustering algorithms such as K-Means. The motion profiles associated with the movement patterns can be segmented into phases. Phases are identified from characteristics features which provide the basis for the detection rules that can be used for automatic segmentation. Different classes may display different phases and phase segmentation rules.

Table 3 summarizes some of the relationships between the primary processes, storage operations, and data structure attributes.

TABLE 3

Overview of the primary processes and database operations.

| Processes | Data Structure | Storage |
| --- | --- | --- |
| 1. n/a | Temporal (session/set/etc.) | Contextual Information |
| 2. Time histories stroke parsing/segmentation | Movement Profiles | Datastreams |
| 3. Stroke profile aggregations and statistics | Repertoire, outcomes, associated statistics. | Relational information, statistical information |
| 4. Stroke classification | Category, type, class | Stroke parameters |
| 5. Stroke phase segmentation | Phase segmentation rules | Update stroke data |
| 6. Phase analytics | Technique/skill attributes | Phase reference envelopes |
| 7. Skill modelling and Skill assessment | Repertoire map, Movement class patterns, Outcome quantities | Parameterized user skill status |
| 8. Motion model synthesis | Motion Model | Motion model parameter |
| 9. Augmentation synthesis | Instructions, Cueing Profiles, Cueing Laws | Hierarchical maps relating prioritization of change, methods of changes |

The augmentation system component is responsible for delivering useful information to a user in order to assist the development of the user's movement skills. Augmentation can be packaged in forms such as graphics, text, speech instructions, audible cues, or haptics. Augmentation can be delivered in real time, near real time, or non-real time and is communicated in two primary forms: instructions, which operate at the knowledge level, and feedback cues (see FIG. 6).

The augmentation component of the physical platform implements the feedback modalities synthesized based on the skill diagnostics. Specific types of augmentation, as previously discussed, include: symbolic language (spoken, text), cues (visual, audible, haptic) or signals (visual stimuli, audible, haptic). The purpose of the component is to provide feedback in appropriate forms to help a user meet a desired performance outcome.

FIG. 13 illustrates the organization of the primary functionalities across the platform. Following an IoT type realization of the platform, the hierarchical organization can be divided into three parts: the cloud servers (database, processors), the local processors at a host level (user interface, host), and the device or user level augmented interface (augmentation, sensors). The architecture shown in FIG. 6 also provides a blueprint for the infrastructure. Some configurations will have processes that can be directed toward the cloud (afferent path) and some other processes that can be directed toward the user (efferent path). Additional components and sub-components can be included. The embedded device can have a device manager (with device configuration, which is capable of measurement and preprocessing, data parsing, feature extraction and data streaming), a sampling and pre-processing component (for calibration and filtering sensor characteristics, and sampling or resampling of application requirements), and a motion estimator (which coordinates and transforms data). The mobile host has a mobile app which allows control over interactions with the platform such as training profile selection, diagnostics of performance, and providing performance review. Additionally, the mobile app can assist with movement parsing (e.g., profile feature extraction, impact analysis, stroke profiles and models, classification, aggregation) in some circumstances. The cloud server performs stroke classification, stroke phase segmentation, and technique or skill analysis. Additionally, movement data processing such as phase segmentation, classification, feature extraction, and aggregation are performed by the cloud server. The cloud server also provides activity analysis, motion models, skill analytics, and cueing laws. Statistical information can also be generated in the cloud.

As will be appreciated by those skilled in the art, the assignment of the system components to the three physical components is primarily made to explain the distributed nature of the platform, and different topologies can be used depending on the particular activity and scenario.

The host device is a computing device, of which possible forms include a smartphone, tablet, smartwatch, etc. In general, the host device can be configurable implement the following system components: host, UI, processing, and augmentation. In some configurations, the host device can implement the processing system component. However, since storage and computing power is typically limited on host devices, processing capabilities on a host could be limited. Additionally, depending on the latency between the device and the host acquiring movement data, some real time feedback can be provided.

Host device functionalities can include data routing, request routing, and providing a control layer between the system components. For example, the host device can be responsible for getting data from the sensor to the processing and storage components, as well as returning results from those two components, routing UI requests, and potentially handling feedback configuration. This means that the host possesses knowledge of the sensor and the sensor's data format, as well as knowledge of what data form the storage and processing components expect. The host can manage any required data translation/transformation between these other components. For systems with limited performance where various forms of preprocessing are in use (e.g., compression), the host handles some of this work. The host can also trigger system processes such as: when processing is performed, when data is transferred to temporary or permanent storage, when augmentation configurations are updated, and other system control decisions.

The cloud physical component is a database and application server to implement the storage and processing system components, for a single user and/or a population of users. The cloud archives and organizes movement data, making various data analysis and data management services possible. For example, in the typical IoT deployment of the platform, the stored and processed data can be used to extract relevant information about the user's performance. Centralizing data in the cloud also makes it possible to perform machine learning functions that can be used to determine motion and skill models, cueing laws, etc. and to investigate how these models may fare across a user population. As will be appreciated by those skilled in the art, the function of the cloud component can change during implementation. For example, generation of UI elements can be performed by the cloud component, and some functions attributed to the cloud can instead be implemented on the host or even the device.

The device can be an embedded computer that is able to remotely or via physical attachment observe or record a piece of equipment, the user's body (or portions thereof), or environmental factors. The device can implement the sensor and/or augmentation system components. For many uses, a likely implementation of the device would combine motion sensors (such as an inertial measurement unit, IMU), a processing unit, a memory unit, a wireless radio for transmission and reception of data, and a transducer for generating feedback.

Relevant measurements to capture include a user's movements, the movement of equipment, or the movement of an end effector manipulated by a user. The device can either be attached or embedded in the equipment and/or worn by the user. The sensor captures movement units relevant for analysis and to support augmentations. In addition to motion data, other measurements include surface electromyography (EMG), forces, etc.

The data format will depend on the specific sensors. For IMU based systems, this is commonly time series data of motions. For computer vision systems, relevant quantities can include raw video files, extracted stills, or time series data of extracted skeletal bodies. Data can be either be continuous over entire sessions, limited to regions of interest, or consist of already extracted movement units.

For any data captured, there are corresponding sensor configuration parameters. These parameters include scaling factors, transformations, active sensors, sample rates, measurement units, and other measurement system parameters. In order for data to be processed effectively, knowledge of these parameters is required. However, these parameters can be communicated in a separate piece of information (metadata), embedded within the sensor data, already applied to the data, hard-coded on all ends, or recorded in some other fashion.

The device can also be responsible, in part, for supporting the augmentation system component. This includes an implementation of the cue processor and cue generator, as described in FIG. 10. Such a device also requires some form of transducer capable of generating an audio, visual or haptic signal or stimulus. The type of transducer is determined based on what stimuli can be best recognized by the user while engaged in a particular activity. The cue generator can be integrated with the device or can be part of other accessories or devices such as a smartwatch, eyeglasses, or earpiece. A cue generator can be connectable to the platform components (in particular the device and host) via a wired or wireless connection.

Figure 23A:
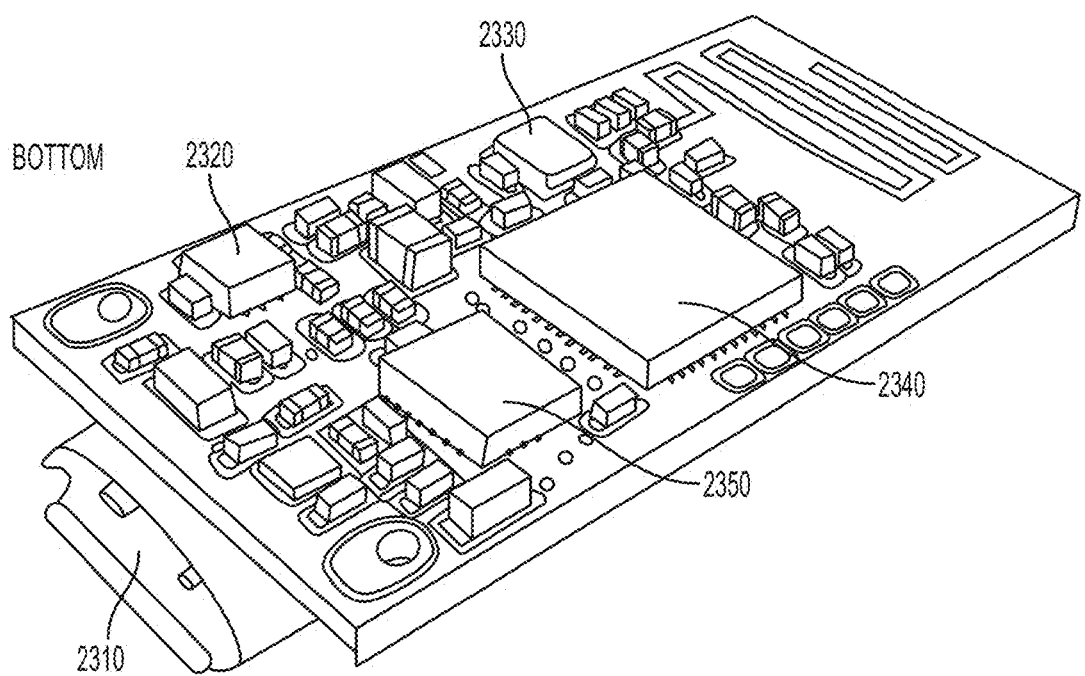
FIGS. 23A-23B illustrate an exemplar embedded sensing and cueing device with the main physical components.
Figure 23B:
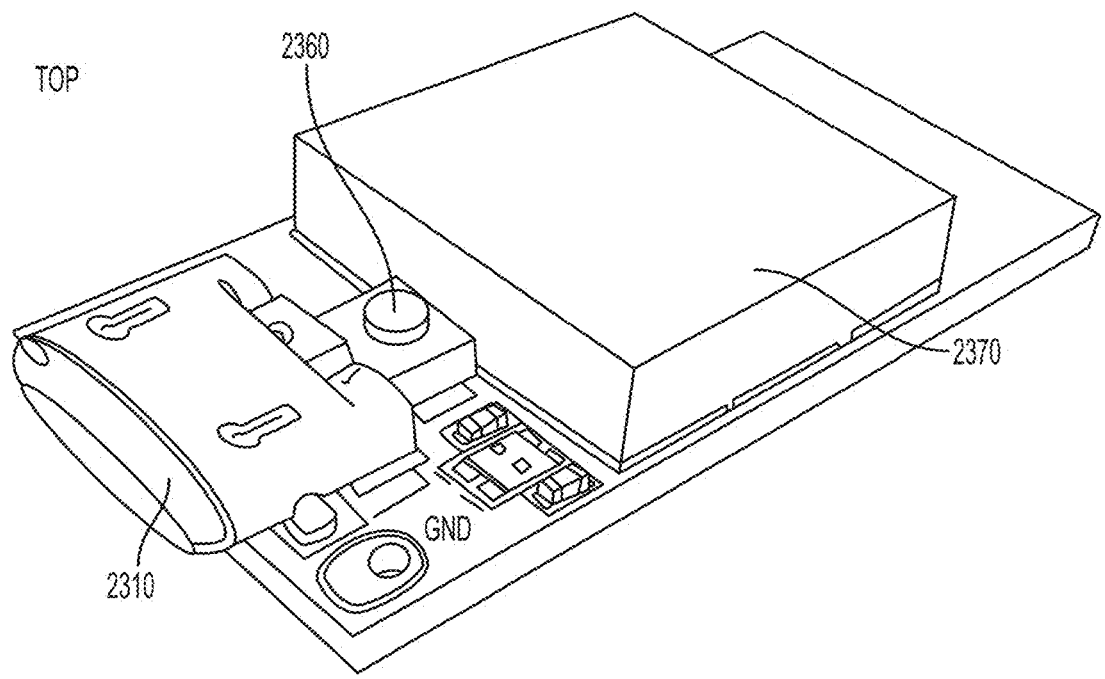

A device including at least one such sensor is shown in FIGS. 23A-23B. Such a device combines inertial measurement unit 2350 (IMU) and other motion sensor device (e.g., GPS, magnetometer, etc.) with a CPU, a radio 2340 for the communication to a host or internet. The sensor component does not have to be a separate device, and can be integrated into the host physical component. Additional components include, for example, an on/off switch 2360, a voltage regulator 2320, a clock 2330, a speaker 2370 (or buzzer), or a USB port 2310.

A variety of configurations of the system components and physical components and devices, based on the commercially available technologies of the IoT ecosystem, can be employed without departing from the scope of the disclosure. The IoT ecosystem combines host, computing resources, sensors, mobile and internetworks, as well as other components such as smartwatches, (near) local distributed computing processors, replicated storage systems, and more. The precise location used for the implementation of the system components of this platform is determined by practical considerations specific to the activity. The assumption for these configurations is that a user will be either performing or training movement skills. Augmentations and feedback is typically scheduled and deployed through a training agent application that embodies the UI, processing, and augmentation system components. The sensor component in these configurations enables measurement and tracking of movements while the UI component gives a user access to training schedules and training sets generated from the skill diagnostics. The training agent application is typically deployed and accessed by the user on the same device as the UI (for example, a mobile phone or smartwatch).

In one implementation of the deployment of the platform system components, the user can activate the application running on a smartwatch to receive a set of instructions, then activate real times cues to guide the performance of a specific movement type during the live performance of the movement. In this usage mode, before the user starts the current or next activity set, or during an intermission from the activity, the user can look at their device display where the application shows a specific set of technique instructions calculated to improve outcomes for the movement type (see FIG. 6).

One configuration has a piece of "smart equipment". The smart equipment provides real time cueing to guide a user's movement technique via measuring the equipment's motion. The piece of equipment (e.g., racket, golf club) contains the physical device, implementing the sensor and augmentation system components. A smartphone implements host and UI system components. The cloud implements processing and storage system components. These three components are in communication through wireless radio technology. For example, the smart equipment communicates with the host via Bluetooth Low Energy (BLE), and the host communicates to the cloud via Wi-Fi or a cellular network.

Another configuration is a stand-alone device with real-time cueing, where the stand-alone device measures the activity movement performance and delivers real time cueing. This essentially separates the device and equipment physical components described in the previous configuration. The device physical component can then exist in various form factors that are appropriate to the requirements of the activity, either worn by the user or attached to equipment. The other system components can be the same as the previous configuration example.

Another configuration is a smartwatch as a real-time cueing device. The smartwatch implements many of the major platform functions. It can be worn by a user during the activity and can provide feedback. The smartwatch serves as the device and host physical components, implementing the sensor, UI, host, and augmentation system components. In such an embodiment, some of the processing system component activities are implemented on the smartwatch based on available system resources such as storage and processing power. The cloud physical component implements processing and storage system components.

An alternate configuration is a stand-alone device as a sensor, with a smartwatch operating as a host and providing augmentation; the device either being worn or embedded into "smart equipment". This configuration allows for the precision of sensors embedded directly into equipment or measuring specific body activities, while providing the convenience of a wearable user interface, display, and audio capabilities available in commercial smartwatches. In such an embodiment, some of the processing system component activities are implemented on the smartwatch based on available system resources such as storage and processing power. The cloud physical component implements processing and storage system components.

EXAMPLES

A. Tennis

The tennis processing follows the organization provided in FIG. 9 and the overall operation is divided between the assessment and the augmentation loops. The data processing for the assessment loop is done on an as-needed basis. Once the motion data has been aggregated, processed, organized into distinct classes and segmented into phases, the information is incorporated in the motion model 950. This model is used to assess and diagnose the individual's technique and skills and ultimately synthesize the instructions and feedback augmentations 930. The former are delivered to the user using a communication system (see 621 in FIG. 6) via a host such as a smart phone or smartwatch. The latter are delivered to the user via the cueing system 622.

Figure 18A:
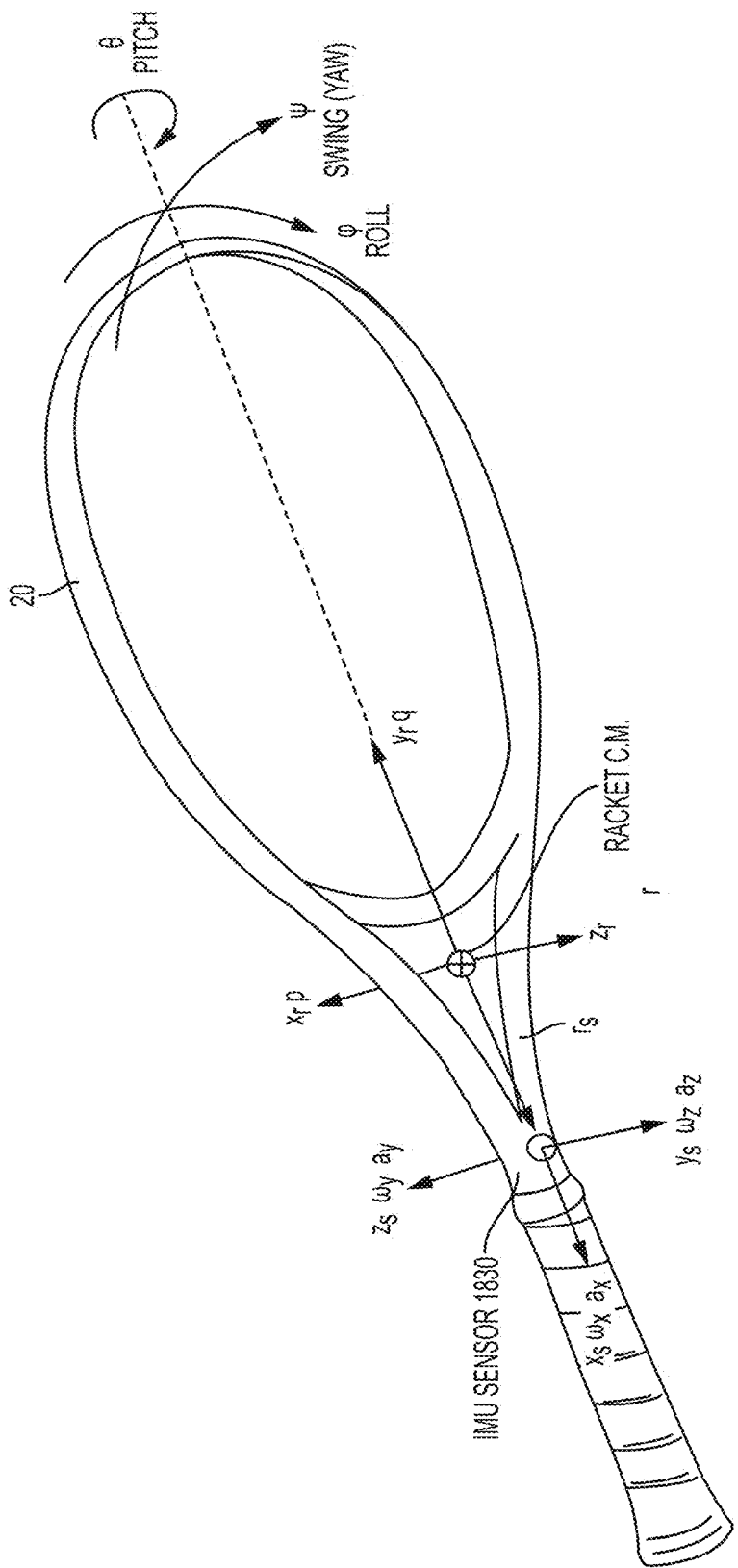
FIG. 18A illustrates the racket and IMU sensor reference frames with key variables including the measured quantities (racket 3 DOF accelerations and angular rates) and primary estimated quantities (roll, pitch, yaw)

The example is used to demonstrate how the processes and analysis techniques using motion data collected from the IMU device 1830 attached to a tennis racket (see FIG. 18A).

For the tennis example, the motion sensors are attached to the racket. The purpose of the sensors is to capture the racquet's motion over the stroke cycle. There are no explicit measurements of the arms or other body segments. In another implementation, additional sensor units, placed at various locations such as feet or arm, can be used to capture the more of the complete movement system behavior, enabling analysis of how the other body segments participate in the stroke movement and potentially identifying other elements relevant to movement technique, such as posture or footwork.

Figure 18B:
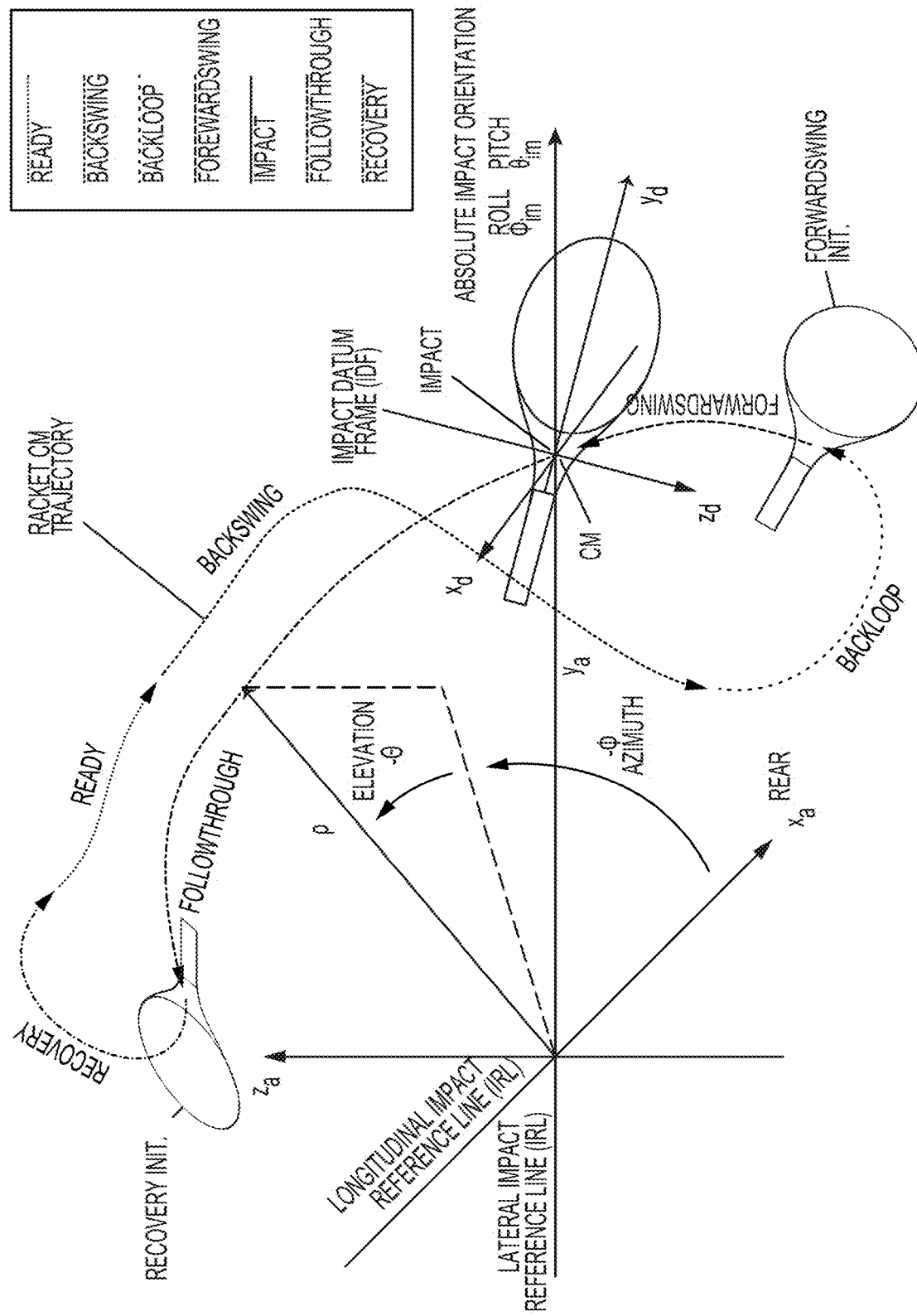
FIG. 18B illustrates the stroke path in terms of absolute spherical coordinates (azimuth and elevation) and exemplar stroke phases over a typical forehand stroke cycle. The figure also illustrates the racket body frame (impact datum frame) and the racket absolute orientation relative to the impact orientation.

FIG. 18A shows the coordinate system for the IMU sensor unit 1830 $\{x_s; y_s; z_s\}$ and the tennis racket frame body coordinate system $\{x_r; y_r; z_r\}$. Note that the orientations of the frames are arbitrary; equivalence to other orientations can be shown. The racket body frame (RBF) coordinate system is shown at the racket's center of gravity. The position vector $r_s$ defines the origin of the IMU's coordinate system relative to the origin of the racket's coordinate system. The accelerometer measures the racket's acceleration along the direction of the $x_s$, $y_s$ and $z_s$ axes and are denoted $a_x$; $a_y$; $a_z$. The angular rate sensor measures the racket's angular rate about the $x_s$, $y_s$ and $z_s$ axes and are denoted $\omega_x$; $\omega_y$; $\omega_z$. The IMU data is filtered and transformed from the sensor frame to the RBF. Additionally, as will be appreciated by those skilled in the art, the sensor's accelerometer and angular rate sensor axes may or may not be on the same device or component (there may be two IMUs). FIG. 18B illustrate impact datum frame for a right-handed user's forehand.

At the most abstracted level of tennis skill analysis, behavioral events are primarily related to game structure and rules that dictate scoring. This level includes events such as shot selection, and patterns of play relating to the game plan. At the intermediate level, the behaviors consist of body motion relating to court positioning and decisions focused on stroke selection and ball placement. These behaviors are primarily determined by the game structure and are considered to be decoupled from the stroke movement.

Below these levels are the core behaviors pertaining to stroke motion skill, namely the organization of the stroke execution in relationship to the ball trajectory and opponent's movement. Further below, behaviors consist of the postural control subserving the stroke, dealing with intrinsic structure of movement implementation and organization and are mostly unconscious. At the stroke level, movement phases unfold dynamically. The transition between the phases is dictated in part by functional elements. For example, the 'forward swing' phase initiation has to be timed based on the estimated impact conditions. This information is determined from perceptual cues extracted from the ball trajectory.

Following an optimal motor programming formulation, specifying the racket trajectory and entire human body movement coordination to accommodate the entire range of possible initial racket state, oncoming ball conditions, etc., a player would need to learn very extensive motor programs. These plans would have to be learned for all the desired outcome conditions (spin, pace, etc.). This movement programming approach would be intractable. Humans exploit invariants in their sensory-motor behavior to mitigate complexity in the interaction with the environment. Therefore, while every stroke has unique characteristics due to the combination of configurations (trajectory of the oncoming ball, its effect on the court and player's positioning, posture, etc.), trained humans will learn efficient sensory-motor strategies to return the ball. Because of the complexity of the infinite range of conditions and the human body's inherent constraints (sensory, perceptual, biomechanics, etc.), the workspace that describes all interactions (sensory and motor behaviors) is discretized in sensory-motor primitives, each covering a specific range of conditions and outcomes.

To analyze a human playing tennis, comprehensive analysis of the unit of behavior should encompass the complete interaction with the environment, including the perception of the environment and task elements (player court position, adversary position, ball position and velocity), as well as the complete body movement (footwork, postural, etc.) (see FIG. 2). Since the sensory-motor behavior is directed at the implementation of the primary unit of behavior in the activity, sufficient details can be extracted through the measurement and analysis of the racket motion alone; these details by themselves already provide useful augmentation and illustrate the platform's capabilities. More sensors could enable analysis of the larger factors that contribute to players' skills over a variety of different activities (see FIGS. 4A-4E). For simplicity, without loss of generality, the following considers the stroke described in terms of the racket trajectory as a primary unit of movement behavior.

The stroke is used to control the ball trajectory on the court. Tennis strokes can be described as cyclic or aperiodic, goal-directed motions. The trajectory of the racket (and possibly other user's body segments) over an entire cycle is called the stroke profile. The motion's primary goal is the controlled impact of the racket and the ball. Therefore, the tennis stroke is a type of interception behavior. The movement phases before the impact are directed at controlling the impact conditions. The stroke phase after the impact is primarily for recovery of the racket trajectory to a resting state. Between consecutive strokes, the periodic motion may be interrupted for a short time, depending mostly on the ball's pace and trajectory and the players' court positioning.

The tennis stroke motions are organized as a sequence of phases (forward swing, impact, follow through, etc.). The movement phases are a common part of teaching and training tennis. However, references to these phases are typically qualitative. Organized stroke segmentation provides an objective, deterministic description of the stroke architecture based on racket motion measurement data. The following analysis first focuses on the description of the stroke characteristics based on the racket's angular rate and acceleration obtained from the IMU's measurements. A primary reference point for building a phase segmentation is the impact. The general stroke architecture can be described based on characteristic kinematic features.

The typical stages or phases of a ground stroke are: Backswing: first stage of a new stroke, the racket accelerates backwards. Back loop: transition between the backward motion of the backswing and the forward motion of the forward swing. During that phase the racket essentially reverses direction following a looping trajectory. Forward swing: acceleration of the racket to gain momentum for the impact. Impact: the time interval during which the ball is in contact with the racket and string bed. Follow through: racket movement following impact, mostly resulting from the racket momentum gained during the forward swing. Recovery: transition from the follow through to the ready state, primarily a deceleration of the racket and a change of orientation before the ready state. Ready state: the "holding state" between the completion of one stroke and the initiation of the next stroke with the racket typically held somewhere between the front and the dominant hand side.

The recorded time series data from the sensor is first parsed into the primary movement units for the activity, which in this example are the tennis strokes. The segments are then aggregated into ensembles and classified according to stroke category. The stroke profiles within each class are then segmented into movement phases that reflect that stroke class's movement architecture. The segments are decomposed into muscle synergies that can be associated with the pattern of muscle activations and biomechanical elements. These steps provide the basis for the data structure used for the motion skill analysis.

The first step in the data processing is parsing the stroke measurement 918 to extract segments that correspond to full stroke profile periods. In the present example, the parsing of the motion data into stroke profiles is performed using features from the ball impact event to detect the motion pattern activity. The impact is identified by finding regions of data where the following evaluates as true:

$$(\|a\| > a_{th_{imp,th}}) \wedge (\|j\| > j_{th_{imp,th}}) \wedge (|H_z| > \dot{H}_{z_{imp,th}}) \quad \text{EQ. 10}$$

Throughout the data stream, each time the above expression is found true, an impact index is created. Starting with the first impact location, the index is recorded in a list of indices. Then the data stream is advanced by a time period (possibly a user/activity/event specific parameter), and the next location where the above expression holds is found and recorded, and the data stream advances again; this process repeats until the entire data stream has been processed. Subsequently, the stroke profiles are extracted by capturing the ranges $(t_{imp} - \Delta T_{pre-imp}, t_{imp} + \Delta T_{post-imp})$ for each recorded index & time. Time intervals are used to define the initiation and termination of the stroke profile, as the physical initiation and termination of the stroke can be more difficult to process. With this technique it is difficult to identify initiations/terminations that are quasi stationary, i.e., that take place at low-speed and low-acceleration. Other techniques that focus on other features can be used depending on the measurements.

Once extracted, these profiles can then be aggregated, classified and further analyzed. The tennis stroke classification is based on a hierarchical tree structure (FIG. 11). The stroke class structure includes: 'categories'={groundstroke, volley, serve}; 'type'={forehand, backhand}; 'spin class'={top spin, flat, slice}; and 'strength class'={strong, medium, low}.

TABLE 4

Overview of the stroke data structure

| Quality | Type | Fields |
| --- | --- | --- |
| Stroke | Time indices in 'rally' and stroke type | Stroke category (ground stroke, volley, serve, etc.), type (forehand, backhand), class (spin and strength). |
| Phases | Time indices in 'stroke' | Phase including forward swing, impact zone, follow through, recovery, ready state, backswing, back loop |
| Actions | Time indices in 'phase' | Actions including, intercept, impact, peak racket response, etc. |

Different incoming ball trajectories, body movement and positioning, and desired end effects on the return ball trajectories lead to a variety of stroke types. After the measurement time histories are parsed the resulting movement profiles are classified 916 to create a user's map of their movement repertoire; more specifically for this tennis example, a stroke map. This representation is the first level of analysis and supports various functionalities such as data management and visualization. The classification method uses features extracted from stroke profile include measurements obtained from motion sensor, which is an IMU, and state estimates including racket orientation. Features make it possible to abstract the large amount of measurement data and therefore enable computationally efficient classification. The feature set extracted from the stroke profiles can then be used to perform clustering of the strokes. Generally, only a subset of feature is needed to delineate between particular stroke types and the classification can also often be performed hierarchically.

Once the stroke profiles have been organized into distinct classes, which share similar characteristics, it possible to proceed with more detailed analysis of the strokes and their outcomes in each class. A central aspect of movement processing is the phase segmentation 914. The detailed information can then be used to support the analysis of a player's techniques and skills.

The strokes are motions that are directed deliberately by the player to produce specific outcomes. The primary purpose of the stroke is to control the ball trajectory, therefore outcomes can be assessed from attributes of the impact and resulting ball trajectory. The outcomes can be measured or estimated from available measurement data. In the present example, the outcomes are estimated from the racket body frame acceleration and angular rate data during the impact phase. The outcomes are described by the following variables: the spin imparted to the ball, the momentum transferred to the ball, as well as, the impact location on the string bed.

Movement structure and organization is central for modeling and analyzing skilled movement. The overall stroke profile depends on several factors including movement biomechanics, neuro-motor, cognitive and perceptual. All these factors will manifest in the form and structure of the stroke. The simplest model of a tennis stroke consists of two phases: a racket's forward motion directed at the ball impact and the backward motion required to "load" the forward motion. Depending on the skill level the stroke can be segmented into additional phases. The tennis literature generally considers the following four phases: backswing, forward swing, impact and the follow through. In this example, the movement architecture (for ground strokes) comprises seven distinct phases. In the forward phase, the segments before and after the impact are the 'forward swing' and the 'follow through', respectively. At both the front and back ends, the stroke motion undergoes a change in direction. The end of the follow through is called the 'recovery' and the end of the backswing and transition to the forward swing is called here the 'back loop'. In addition, a 'ready' phase is considered to describe the resting period between strokes.

The phase segmentation provides a mathematical description of these phases to allow for automatic detection and segmentation. Phases can usually be identified based on kinematic and dynamic characteristics. The phase segmentation uses features from the stroke profiles to detect phases in the stroke execution. Each movement phase is represented by a discrete state in a finite-state model which provides an abstract model of the stroke motion. The finite-state model describes the overall stroke as the transition between a finite number of states. The motion model serves as basis for the motion skill analysis and real-time cueing.

After the stroke have been parsed, i.e. detected and extracted from the measurement time series, they are aggregated in ensembles and classified. In this example, the classification is performed hierarchically based on physical understanding of the major stroke classes illustrated in the stroke tree (FIG. 11).

Information used to classify strokes can be obtained from a set of features extracted from stroke profiles (e.g., RBF angular rates and acceleration). These features capture characteristics of the stroke physics and allow to abstract the stroke and player's technique using a minimal set of parameters. Note that data about the outcomes could in theory also be used. In this example, the outcomes are only used for the skill analysis. The stroke features include:

(1) temporal indices such as those associated with the stroke phases, including the swing rate zero-crossings (are related with the initiation of the forward swing and the ending of the follow through);

(2) state values at those temporal indices; and (3) state values at various time samples before and after the impact.

For example, the swing rate r at t=0.2, 0.1 and 0.02 sec before impact.

The stroke phase features are the features that are used to identify the stroke phases. These features may also provide information for stroke classification. Table 5 summarizes some of the stroke phase features from the angular rate data.

TABLE 5

Stroke Phase Features

| | |
|---|---|
| $t_{imp}$ | impact time |
| $t_{fwd}$ | beginning of forward stroke |
| $t_{rec}$ | end of follow through, beginning of recovery |
| $t_{p-0.0}$ | roll rate zero crossing before impact |
| $t_{p-0.1}$ | roll rate zero crossing after impact |
| $t_{r-0.0}$ | swing rate zero crossing before impact |
| $t_{r-0.1}$ | swing rate zero crossing after impact |

The stroke profile features are chosen to capture the shape of the stroke profiles. Their primary purpose is stroke classification. They essentially are a low-dimensional description of the profile shape. The goal is to use features that are maximally informative to differentiate between stroke types and execution or technique. The phase features sample the RBF acceleration and angular rate measurements over a small number of specific time samples across the stroke profile. These points are chosen to capture important profile characteristics such as the swing rate early in the forward swing and shortly before the impact. Such features can be identified from principal component analysis (PCA) of an ensemble of representative stroke profiles.

The forward swing is the primary motion toward the impact, therefore features extracted from the stroke profiles for that phase are predictive of the stroke type and quality. The stroke kinematic and dynamic characteristics just before impact (interception phase) provide information about the desired impact conditions. Similarly, the follow through profile characteristics provide information about the stroke type and technique. Table 6 summarizes the stroke profile features. The profile features capture the stroke profile characteristics. Finally, external characteristics can also provide valuable information. Table 7 describes peak and statistical characteristics of the stroke profile.

TABLE 6

Stroke Profile Features

| | |
|---|---|
| $p_{imp-0.2\,s}$ | roll rate at the beginning of interception. |
| $p_{imp-0.1\,s}$ | roll rate early in forward swing. |
| $p_{imp-0.02\,s}$ | roll rate just before impact. |
| $q_{imp-0.2\,s}$ | pitch rate at the beginning of interception. |
| $q_{imp-0.1\,s}$ | pitch rate early in forward swing. |
| $q_{imp-0.02\,s}$ | pitch rate just before impact. |
| $r_{imp-0.2\,s}$ | swing rate at the beginning of interception. |
| $r_{imp-0.1\,s}$ | swing rate early in forward swing. |
| $r_{imp-0.02\,s}$ | swing rate just before impact. |
| $a_{x,\,imp-0.2\,s}$ | axial acc. at the beginning of interception. |
| $a_{x,\,imp-0.1\,s}$ | axial acc. early in forward swing. |
| $a_{x,\,imp-0.02\,s}$ | axial acc. just before impact. |
| $a_{y,\,imp-0.2\,s}$ | transversal acc. at the beginning of interception. |
| $a_{y,\,imp-0.1\,s}$ | transversal acc. early in forward swing. |
| $a_{y,\,imp-0.02\,s}$ | transversal acc. just before impact. |
| $a_{z,\,imp-0.2\,s}$ | transversal acc. at the beginning of interception. |
| $a_{z,\,imp-0.1\,s}$ | transversal acc. early in forward swing. |
| $a_{z,\,imp-0.02\,s}$ | transversal acc. just before impact. |

The stroke classes can be characterized hierarchically according to stroke categories (ground stroke, volley, serve), types (forehand/backhand) and classes (spin and strength). There exists a deterministic relationship between the racket motion, as described by the RBF acceleration and angular rate components, and the basic stroke categories, types and classes. In the following example, knowledge of the stroke mechanics is used to determine physical criteria for stroke classification and these criteria are used to determine the necessary features.

TABLE 7

Stroke Statistical Features

| | |
|---|---|
| $\hat{q}_0$ | pitch rate extrema before impact |
| $\hat{q}_1$ | pitch rate extrema after impact |
| $\sigma_{q,\,fwd}$ | pitch rate variance during forward swing |
| $\sigma_{q,\,fol}$ | pitch rate variance during follow through |
| $t_{|ax|<10}$ | time when the longitudinal acceleration drops below 10 m/s² after the impact |
| $\hat{a}_{y,0}$ | transversal acc. extrema during forward swing. |
| $\hat{a}_{y,0}$ | transversal acc. extrema during forward swing. |

The hierarchical classification process based on physical features discussed next. Once the features have been extracted from the stroke profiles the classification first delineates between stroke type (forehand/backhand), second based on the 'spin' class (topspin/flat/slice), third in terms of the stroke strength (high/med/low).

As an example of empirical classification, there is a relationship between racket longitudinal and vertical accelerations $a_x$ and $a_z$, and swing rate r. Features can be extracted from the swing rate r and longitudinal acceleration $a_x$ at 20 msec before impact. The distribution of these features for forehand and backhand strokes at 20 msec before impact illustrates how these features cluster in two groups according to the forehand FH and backhand BH. The simple classification rule (for z down) is given as:

$$FH: r(t=-0.02)<0 \quad \text{EQ. 11}$$

$$BH: r(t=-0.02)>0 \quad \text{EQ. 12}$$

Similar to the FH/BH classification, it is possible to define quantitative criteria for the stroke 'spin' class (topspin, flat and slice). The primary variables that determine the impact spin are the racket roll rate p (sometimes called "windshield wiper" motion) potentially with some contribution of the racket pitch rate q. Therefore, information about these quantities shortly before impact can be used for stroke classification. The following data assumes that the RBF axes configuration with $z_r$ down (see FIG. 18A. In the following example a spin class feature is defined based on the racket roll rate p and swing rate features r 20 msec before impact.

The swing rate distribution can be divided into the FH and BH. The roll rate breaks up in the positive p>0 and negative p<0 roll rate for the backhand (r>0) and two clusters in the forehand. These clusters reflect the amount of slice (or backspin) and top spin. There are also a strokes with low roll rate which are characteristic of a low spin, i.e. flat stroke. A threshold for flat strokes $_p$flat can be used to delineate between flat, topspin and slice.

$$\text{Topspin: } p(t=-0.02)<{_p}\text{flat} \quad \text{EQ. 13}$$

$$\text{Flat: } |p(t=-0.02)|<{_p}\text{flat} \quad \text{EQ. 14}$$

$$\text{Slice: } p(t=-0.02)>{_p}\text{flat} \quad \text{EQ. 15}$$

The threshold value $_p$flat can be set by hand or can be determined from clustering results associated with a player's technique.

Another useful classification is the strength of the stroke based on change in racket momentum during the forward swing. Note that this is not necessarily the same as the impact strength which is related to the magnitude of the racket momentum change at impact. The following emphasizes is on stroke technique, therefore the strength of the stroke based on the stroke characteristics before the impact will be used here. Same ideas can be applied to the impact strength. Two strength thresholds of 50 and 100 m/sec² have been used to delineate between low, medium and high strength classes, which can be seen from the color highlighting.

$$\text{High: } |a_{tot}(t=-0.02)|>a_{med} \quad \text{EQ. 16}$$

$$\text{Medium: } a_{low}<|a_{tot}(t=-0.02)|<a_{med} \quad \text{EQ. 17}$$

$$\text{Low: } a_{tot}(t=-0.02)|<a_{low} \quad \text{EQ. 18}$$

These threshold values are set by hand. Similar to other stroke characteristics these could also be set automatically based on results of data clustering.

The screenshot 1910 in FIG. 19A shows classification results for about 1300 ground strokes that have been classified into 18 stroke classes following the three criteria described in the preceding sections proceeding hierarchically. The strokes are first classified in terms of the type (forehand/backhand), next the spin class (top spin/flat/slice) and subsequently in terms of the strength (high/medium/low).

Once the basic movement patterns (here the tennis strokes) have been parsed and classified, the next step is the decomposition of movement profile data into segments that correspond to movement phases. Typical ground stroke architecture and the movement phases were described earlier.

Phases are associated with the human motor control and biomechanics. These effects manifest in the movement kinematics and dynamic characteristics. Phase segmentation techniques are based on identification of features that are characteristic of phase in particular phase transitions. For example, particular changes in the acceleration and angular rates, such as zero crossings, that indicate a change in movement direction or changes in trajectory curvature.

The phase decomposition enables a more detailed description of the stroke that relates movement characteristics to underlying structural and functional factors. Each phase can be described as discrete states in a finite-state model. This model describes the movement within a phase as continuous dynamics (e.g. the $F_1$ described earlier) transition between the phases based on state conditions that have been identified. The finite-state model is the basis for the formulation of finite-state machine used for finite-state estimation.

Observation from the rate and accelerometer measurements shows that stroke profile ensemble contains distinct patterns that can be related to tennis stroke phases. These patterns are briefly discussed here. More details about feature elements specific to the stroke phases.

Figure 16A:
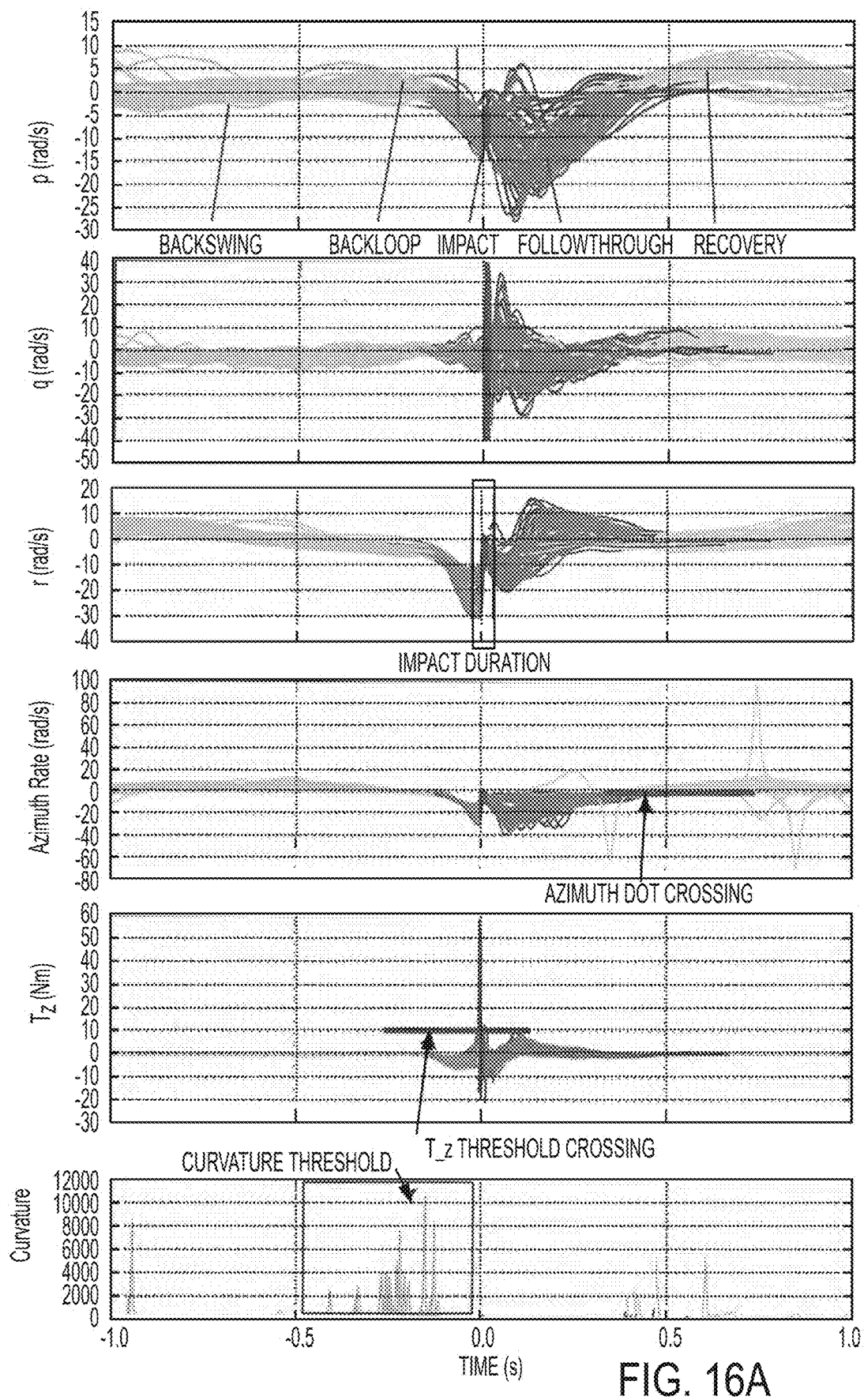
FIG. 16A illustrates an ensemble of racket angular rate profiles highlighting features that can be used to identify stroke phases, including: backswing, back loop, forward swing, impact, follow through, and recovery.

FIG. 16A highlights angular rate features related to the phase decomposition. FIGS. 16C-1 to 16C-2 show the phase portrait of the angular rate vector, which illustrates the 3DOF angular motion associated with the stroke for four stroke classes (BH TS and BH SL, FH TS and FH SL). The angular rate plots highlight that the coupling between rate components is important in delineating the stroke phases. In fact, from the dynamics standpoint the complete angular phase-space is 6 dimensional (3 angular rates+3 angles). From a behavioral standpoint, the stroke angular motion is probably a subspace with less than 6 dimensions. The fact that the sensed body rates describe a well-defined manifold in the 3D plots of FIGS. 16C-1 to 16C-2 indicates that the rates alone are probably sufficient to determine a large part of the stroke behavior.

The angular rate measurements provided by the IMU's gyroscopes are invariant to changes in reference frame. The racket acceleration measurements, on the other hand, are user to the gravitation effect, which require knowledge of the racket's absolute orientation, as well as effects of reference frame relative motion. The magnitude of the racket's inertial acceleration is much larger than the gravitational acceleration, therefore, the racket acceleration may provide additional features for phase detection. The most notable feature is the racket acceleration during impact as well as before and following the impact. These are the stroke's most dynamic movement phases.

The analysis of the data in phase space, such as the description of the three racket angular rates (p, q, r) provide additional insights and criteria for the identification of stroke patterns. FIGS. 16C-1 to 16C-2 show the 3-dimensional phase portrait for the angular rate and acceleration. These plots already incorporate results of the phase segmentation.

The phase portraits describe the periodic patterns associated with the stroke. The plots show that the general shape has distinct and repeatable elements. Even though the individual strokes have varying characteristics there are several prominent features that underscore the concept of motor equivalences associated in movement behavior. As expected the angular rate portraits are more consistent as the acceleration portraits. The trajectories are shown in terms of the individual samples (sampling frequency of 1 kHz), therefore the sample spacing indicates the angular acceleration or jerk for the rate and acceleration portraits respectively. The segments where the sample are spread out correspond to the impact zone. The three-dimensional phase portrait shows how the stroke follows distinct stages. Each stage evolves on a type of orbit in its own two-dimensional sub-space which emphasize various coordination patterns between the angular degrees of freedom.

Figure 20A:
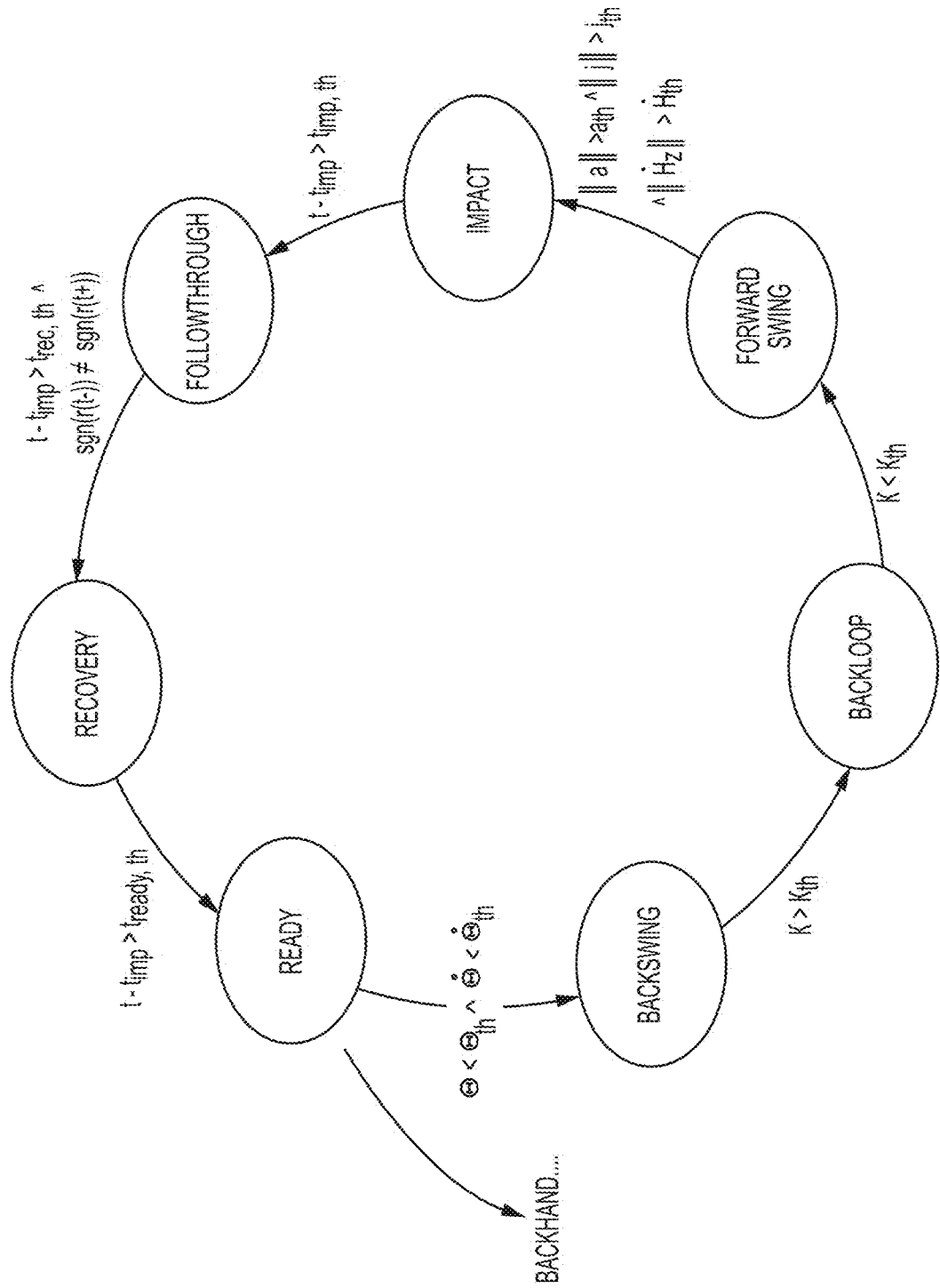
FIG. 20A illustrates a finite-state stroke model.

The phases described in the preceding sections define the primary states of the finite-state stroke model (see FIG. 20A). Each phase is characterized by particular kinematic and dynamic characteristics. These characteristics can be used to formulate detection rules, which can be applied to automatically segment the phases from the motion data. The detection rules also define the state transition in the finite-state model. Note that for many of these rules the measured quantities (here RBF angular rates and acceleration) will give adequate phase transition information only some of the time. Therefore, some phase transition rules also include estimated quantities such as the orientation.

The transition rules between the stroke's finite states are as follows: Ready: the ready state or phase corresponds to the time interval between the end of the recovery to the beginning to the initiation of the next stroke, i.e. the beginning of the backswing until the next stroke. The racket motion during the ready phase is quasi stationary, therefore the ready phase period can be determined from the magnitude of the acceleration and angular rate measurements. Using a threshold on the total acceleration and angular rate:

$$t_{re} = t|_{\|\omega\| < \omega_{re,th} \wedge \|\alpha\| < \alpha_{re,th}}$$ EQ. 19

An alternative approach is to limit the total post impact stroke duration. This rule can be more useful in situations where the racquet does not reach a quasi-stationary state, such as very fast paced games.

$$t_{re} = t_{0,imp} + \Delta T_{dur}$$ EQ. 20

Backswing: the backswing corresponds to the first phase of a new stroke. As the name implies the state is initiated by the racket backswing motion. The initiation of the backswing phase can be detected by using the time the azimuth rate reaches a given threshold and azimuth has reached a threshold. Using azimuth (θ) is preferable to swing rate r as the racquet grip style affects the swing rate.

$$t_{bs} = t|_{\theta > \theta_{bs,th} \wedge \dot{\theta} > \dot{\theta}_{bs,th}}$$ EQ. 21

Back loop: the back loop is used to designate the transition phase between the backswing and the forward swing. This transition represents primarily a rotational motion from the backward swing motion to the forward swing motion. This phase can be extracted from the time interval involving relatively low acceleration but high angular rate, for example by evaluating the (quaternion unit sphere) trajectory curvature.

$$t_{bl} = t|_{\kappa > \kappa_{bl,th}}$$ EQ. 22

Forward swing: the forward swing is the phase that leads to the impact. Therefore, it requires sufficient racket head speed and precise contact conditions. It starts with the angular acceleration of the racket and ends with the ball interception and eventually impact. The start of the forward swing is the time when the high-curvature trajectory of the back loop changes into a low-curvature trajectory as the racquet is set on a ballistic path.

$$t_{bl} = t|_{\kappa < \kappa_{bl,th}}$$ EQ. 23

Note that it should also possible to detect the start of the forward swing phase based on the total translational acceleration $a_{tot}$. This rule will result in different phase delineation and different segments.

$$t_{0,swing}{}^a = t|_{sgn(\|a\|(t-\delta t) - a_{fs,th}) \neq sgn(\|a\|(t+\delta t) - a_{fs,th})}$$ EQ. 24

Before the impact, there is a brief interception phase. Given the neuro-motor constraints (e.g. human neuromuscular constant and the response time) it is impossible to correct for the racket path as the racket closes in on the ball.

Impact: the impact onset is characterized by an impulsive acceleration associated with the momentum transfer that occurs when the ball strikes the string bed. As already described, the ball contact during impact lasts about 5 msec. The start of the impact is detected when the total acceleration ascends through the threshold $a_{th,imp}$:

$$t_{imp} = t|_{\|a\| > a_{th_{imp,th}} \wedge |j| > j_{th_{imp,th}} \wedge |H_z| > H_{z_{imp,th}}}$$ EQ. 25

The impact event is assumed to only last the period of time where the ball and racquet are in contact. Although the impact can be shown to be a nonlinear event (and therefore not guaranteed to be invariant in duration relative to impact strength), empirical study suggests that most impact events have a similar duration. Using duration is also preferable to examining rates/accelerations as it is not affected by racquet vibration modes.

$$t_{fi} = t_{0,imp} + \Delta T_{imp}$$ EQ. 26

Follow through: the follow through primarily involves keeping control of the racket immediately following the impact and slowing the racket. This motion is mostly characterized by the limits on biomechanical range of motion. Similar to the forward swing, the follow through is primarily characterized by the change in racket angular deceleration. The end of the follow through can be detected by the racket swing rate r reversing sign.

$$t_{rec} = t|_{sgn(r(t-\delta t)) \neq sgn(r(t+\delta t))}$$ EQ. 27

Recovery: during the recovery the player takes the racket from the end of the follow through to a resting state which designates the ready position.

The state-transition graph in FIG. 20A shows phases of the stroke where each phase defines a state. Each state is itself represented by its specific kinematics and dynamics and association with biomechanics and sensory, perceptual and motor control elements. These features and associated structure provide the basis for the skill analysis as well as for the design of player feedback mechanisms. The states of the finite-state model are: ready, backswing, back loop, forward swing, impact, follow through, and recovery. Respectively, they are abbreviated as: re, bs, bl, fs, imp, ft, rec.

FIG. 20A illustrates the finite-state stroke model with the seven phases and examples of transition rules. The parameters in the phase transition rules are $\Delta T_{dur}$, $\theta_{bs,th}$, $\dot{\theta}_{bs,th}$, $\kappa_{bl,th}$, $a_{th_{imp,th}}$, $j_{th_{imp,th}}$, $\dot{H}_{z_{imp,th}}$, $\Delta T_{imp}$. These can be determined from statistical analysis.

In general, the stroke phases cannot be measured directly therefore they need to be estimated using a finite-state estimator. When limited to RBF accelerations and angular rates determining the current state for a range of players with different styles and technique can be challenging. Therefore, the processing may not be applicable for these more general cases. Furthermore, athletes might interrupt their motion in mid-stroke, leading to anomalous state transitions. A state estimator to determine racket orientation (attitude) can help make the finite state estimation more robust. Finite-state estimation schemes based in statistical models such as Hidden Markov Models (HMM) generally provide good accuracy and robustness.

The following describes the elements of the skill model and skill assessment for a tennis example. The three main components of the skill model illustrated in FIG. 9, box III:

(a) Movement pattern repertoire, i.e. stroke map.
(b) Pattern phase profiles. And,
(c) the Movement synergies.

Table 8 illustrates the type of attributes that can be extracted from these data for technique and skill assessments.

First, concepts and metrics based on the repertoire. Understanding the relevance of the repertoire requires a brief description of the skill acquisition process focusing on the tennis use case. The typical tennis stroke repertoire comprises multiple classes of distinct swing patterns. These are acquired to achieve the range of outcomes needed to be proficient in a play and deal with the range of impact conditions. The development of a repertoire of movement patterns is typical of open motor skills described. The movements within each class form an ensemble of equivalent strokes that can be adapted to variations in impact conditions (speed, bounce height, spin, etc.) and outcome.

The adaptation of the movement pattern within a given class, however, can only handle a finite amount of variations in impact conditions and outcome. Beyond that admissible range, the stroke performance (e.g. energy or jerk) degrades and eventually reaches the limits of what is feasible within a given movement pattern. These limits are typically biomechanical. To prevent the degradation or saturation, a new pattern has to be developed. Expert players have a broad repertoire of stroke profiles. These patterns are also highly optimized and therefore an expert player will seek to engage the ball using the optimal stroke pattern and within the optimal impact conditions. Using optimal stroke technique requires adequate stroke preparation, which depends on various other facilities, including perceptual mechanisms, footwork and postural adjustments.

A comprehensive stroke repertoire, therefore, gives the subject the ability to use optimized, predictable stroke patterns instead of having to rely on corrections during the stroke. The latter offer only limited amounts of corrective or adaptive range given the various sensory motor constraints such as reaction time and neuromuscular time constant.

Beginners tend to gravitate towards using similar movement patterns and adapting those. Therefore, they exhibit poor pattern definition in their repertoire and movements in each class display large amounts of variability and the strokes are far from optimal.

In tennis, the movement pattern repertoire describes the stroke types acquired by the user to accommodate to the range of oncoming ball trajectories and the range of effects and outcomes. Therefore, the stroke classes reflect both the range of conditions (pace, spin, height of the oncoming ball), as well as, the range of desired stroke outcomes (ball pace, trajectory shape and length, etc.).

Note that the results that are presented in this example only focused on ground strokes category. Note also that stroke maps are not limited to these classes. Given sufficient data, collected under rich play conditions, data driven classification allows identifying broader categories and additional types of classes. The repertoire is given in terms of stroke categories and classes captures the variable and invariable characteristics of someone's strokes.

Processing of the repertoire can be based on different data aggregations. For example, different historical time periods can be mapped such as the past year, month, week, etc. The current session, set, or the past N strokes, etc. It is also possible to aggregate the stroke data based on attributes, such as the strokes for the N best outcomes. These capture different aspect of behavior including identifying deep rooted patterns and allows to track how training strategies, etc. impact behavior at the repertoire level.

Finally, the repertoire assessment depends on the skill level. An advanced player requirement for a repertoire is different to that of a beginner. The advanced player's repertoire has a broader range of patterns and these patterns have a more developed movement structure (see FIG. 15E). Therefore, skill assessments have to be based on skill level. At the repertoire level, the expectations for the range of patterns and the performance of the patterns in terms of the outcomes are based on the movement structure and the task performance level.

TABLE 8

| Quantity | Emphasis | Attributes |
| --- | --- | --- |
| Session | Play characteristics | Total play duration, number of sessions, etc. |
| Set | Session characteristics | Number of rallies, length of rallies, etc. |
| Rally | Exchange characteristics | Number of exchanges in a rally, number of miss hits, etc. |
| Stroke | Stroke repertoire characteristics | Number of stroke categories, types, classes (e.g. spin and strength), etc. |
| Phases | Stroke execution and organization | Phase profile characteristics (e.g. variability) and phase aggregate characteristics (e.g. duration, total variability) etc. |
| Actions | Specific functional aspects | Stroke features (e.g. pitch rate range and statistics at 5 ms post impact, etc.) |

In some applications the movement outcomes are not directly measured and therefore have to be estimated. The following describes how the outcome can be estimated from impact conditions described by racket IMU measurements during the impact phase. The spin and pace of the returning ball are determined by the impact conditions and therefore sufficient measurements of the quantities involved in the impact can be sufficient to accurately estimate the outcomes. In another tennis application, the outcome could be measured using cameras and computer vision algorithms or even instrumenting the tennis ball with IMU sensors.

The ball is controlled by imparting linear and angular momentum from the racquet. Based on Newton's third law, the change in the racket's linear and angular momenta has to be equal to the change in the ball's linear and angular momenta (assuming the player does not impart any force during that phase). Since the collision is short in duration, the change in momenta can be attributed to the impact alone. To capture complete spin and pace values for the tennis ball, a dedicated measurement system such as a vision-based motion capture system is required. When working with limited sensors, such as the racket IMU 1830 (see FIG. 18A), the outcomes can be estimated from the racket motion during the period of impact.

As a stroke includes many velocity/rate changes, there is never a period where linear and angular momenta are constant. Therefore, isolating momentum transfer due to the ball impact, and not the player's input, is challenging. One approach is to filter the data into low frequency and high frequency components. Subtracting the low frequency components from the original signal leaves (approximately) only the impact component of the signals.

With an estimate of the acceleration attributable to impact, $a_{imp}$, and the angular velocity and acceleration attributable to impact, $\omega_{imp}$ and $\alpha_{imp}$, it is trivial to calculate momentum transfer, as it is the integral of force.

$$\Delta L = \int_{t_1}^{t_2} m a_{imp} dt \qquad \text{EQ. 28}$$

$$\Delta H = \int_{t_1}^{t_2} M_{imp} dt \qquad \text{EQ. 29}$$

where m is the mass of the racquet and M is the moment (torque) acting on the racquet, calculated from inertial measurements and knowledge of the racquet's inertia tensor I, defined as:

$$M_{imp} = I\alpha_{imp} + \omega_{imp} \times (I \cdot \omega_{imp}) \qquad \text{EQ. 30}$$

Since the mass and moment of inertia of the ball are significantly smaller than the racket, the racket's state at the onset of the impact dominates the outcome, and the spin outcome can be estimated from the racquet's state alone. The impact location can be calculated from the relationship between translational and angular momentum transfer during the impact.

$$\Delta H_x = m(\Delta L_z r_y - \Delta L_y r_z) \qquad \text{EQ. 31}$$

$$\Delta H_y = m \Delta L_y r_z \qquad \text{EQ. 32}$$

$$\Delta H_z = m \Delta L_x r_y \qquad \text{EQ. 33}$$

Where H, L and, m are as defined above, and r is the position vector from the racquet mass center to the point of impact. Solving the above equations for the components of r gives the impact location. With the impact location known, the ball's spin can be calculated. Assuming a no-slip impact condition (where the ball does not rotate with respect to the racquet), the angular velocity of the ball can be calculated as the sum of the angular velocity of the racquet in the inertial frame and the angular velocity of the ball in the racquet frame; sum of the angular rate of the racquet and the out-of-racquet-plane velocity vector of the point of impact divided by the radius of the ball.

$$^{N}w^{B} = {}^{N}w^{R} + {}^{R}w^{B} \qquad \text{EQ. 34}$$

The angular velocity $^{R}W^{B}$ must then satisfy:

$$v^{r,i} = {}^{R}w^{B} \times r_{ball} \hat{x} \qquad \text{EQ. 35}$$

where $v^{r,i}$ is the velocity of the ball-racquet contact point, in the inertial frame.

For the analysis of tennis stroke skill, the goal is to determine the effect of movement technique on outcome. This requires an analytical framework to describe the relationship between the stroke technique and the stroke outcome. Even if the outcome is determined by impact conditions, the racket state at impact depends on the entire movement characteristics leading to the impact with the ball.

Figure 16B:
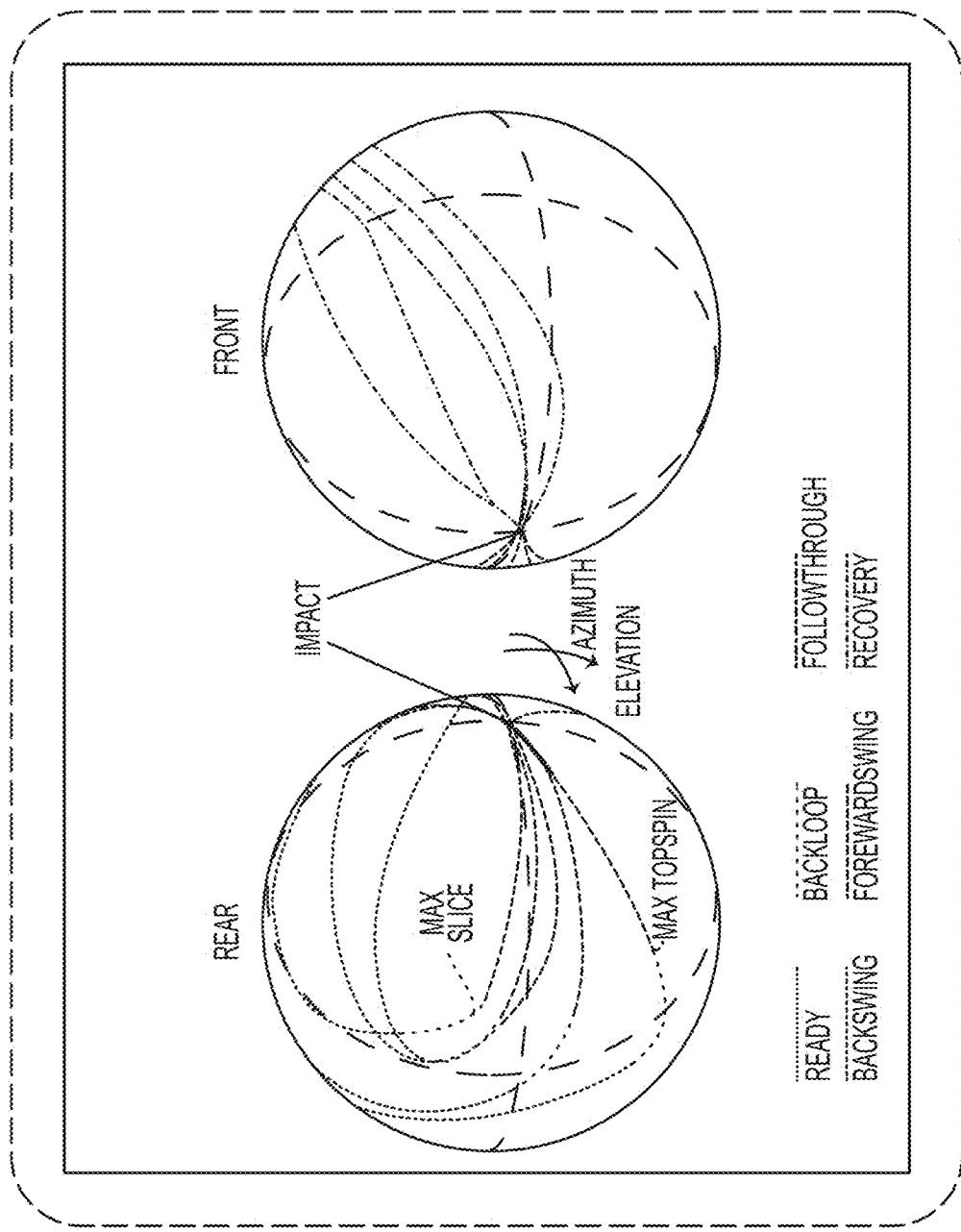
FIG. 16B illustrates racket orientation trajectories (elevation and azimuth) for an ensemble of forehand strokes over a stroke cycle on a unit sphere. The figures also highlight the stroke phases. Two views are presented to provide of the back side and front side of the stroke.
Figures 1, 16C:
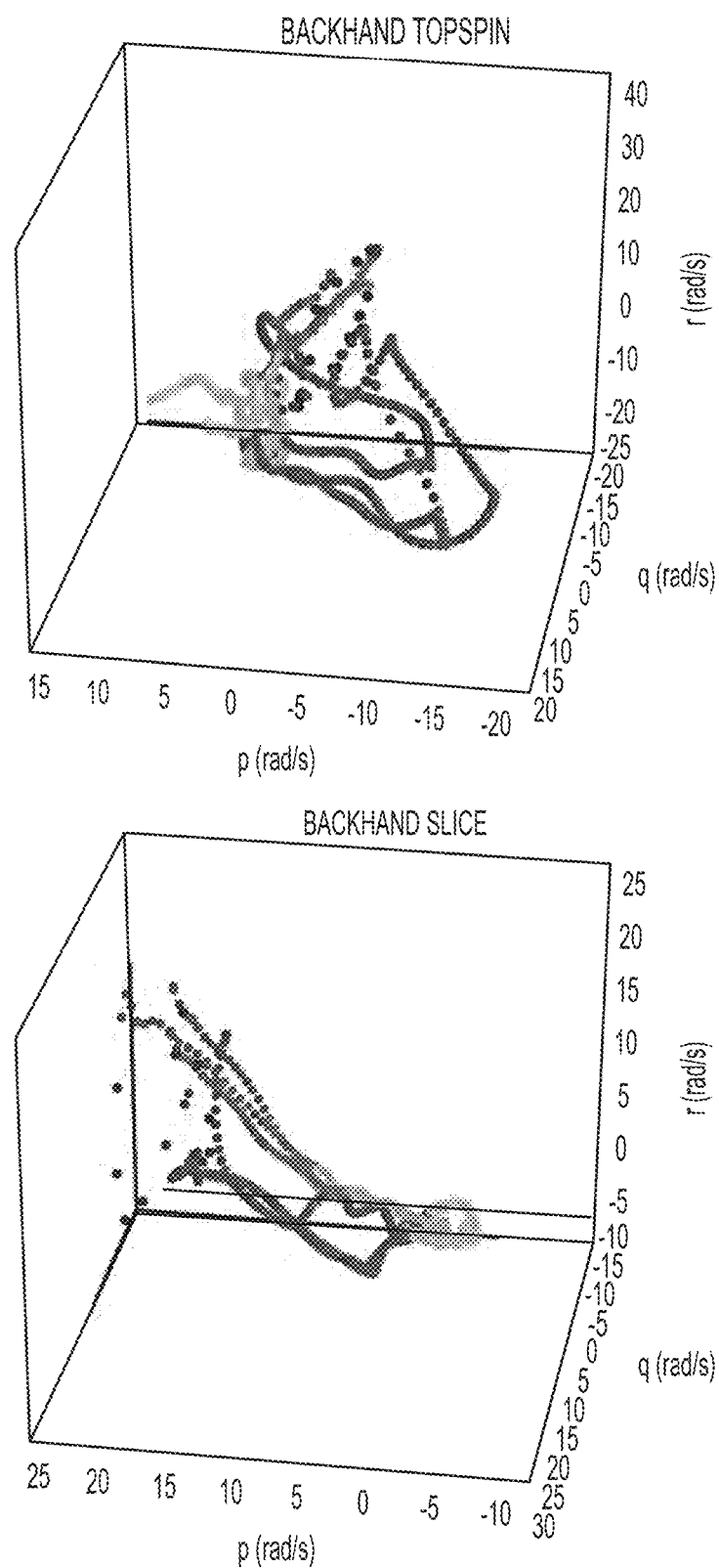
Figures 2, 16C:
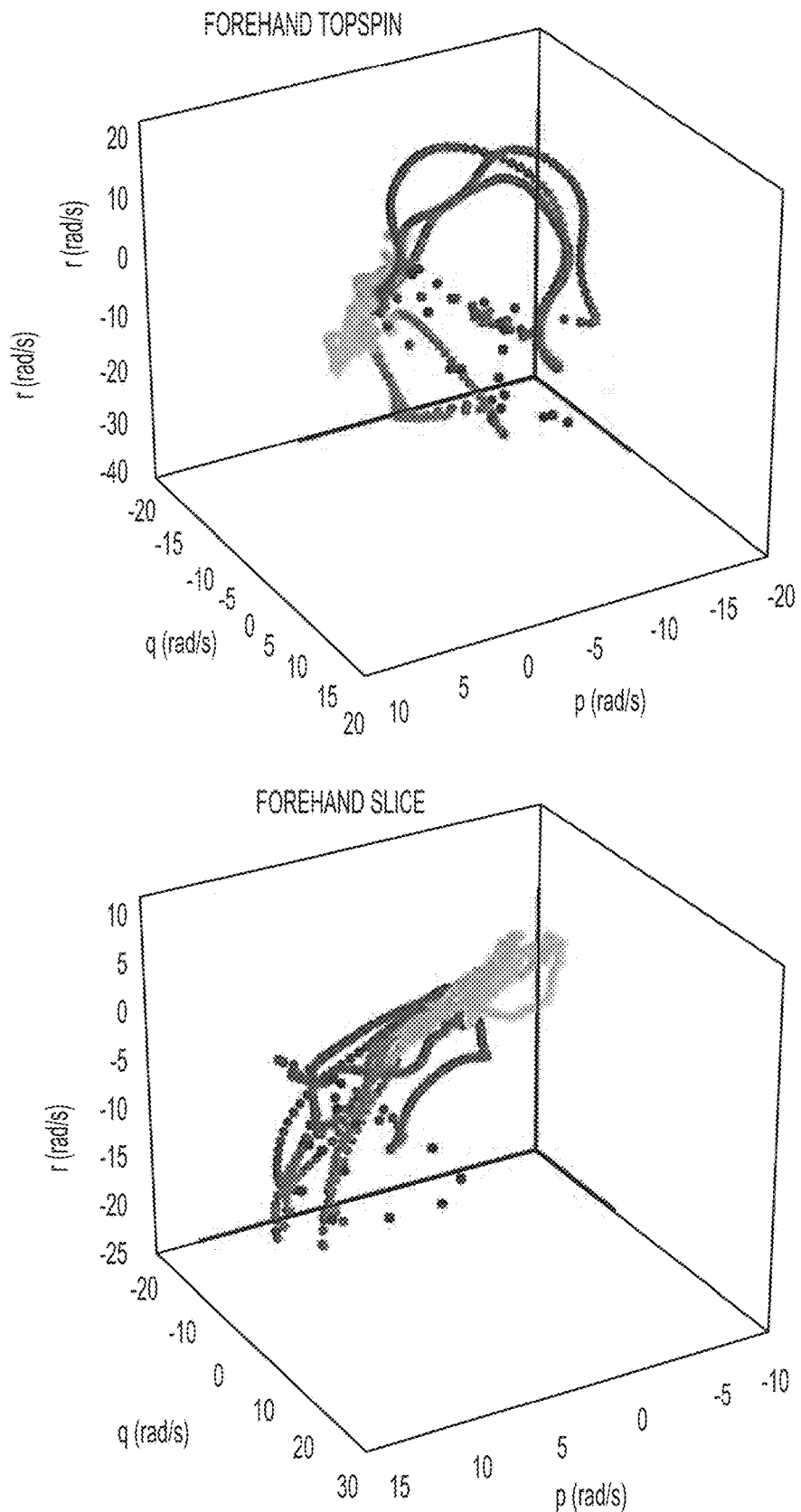

In FIG. 16B, stroke profiles from a forehand stroke class are segmented into phases following movement organization and environment interactions shown in FIG. 2. The phase decomposition describes the particular stroke architecture acquired by a player. The stroke architecture is specific to the outcome and conditions. The tennis stroke phases are similar to typical stroke notation in the literature, with the difference that a segmentation based on movement dynamics provides a quantitative instead of qualitative results. The quantitative approach also results in additional states such as the back loop phase. The phase structure depends on the stroke pattern and the skills.

As visible from the angular rate phase portrait shown in FIGS. 16C-1 to 16C-2, different stroke profiles within the same stroke class are isomorphic. Each class can be recognized through its characteristic state time-history profile (see the overall view of stroke profiles in the stroke map in FIG. 19A).

Figure 16D:
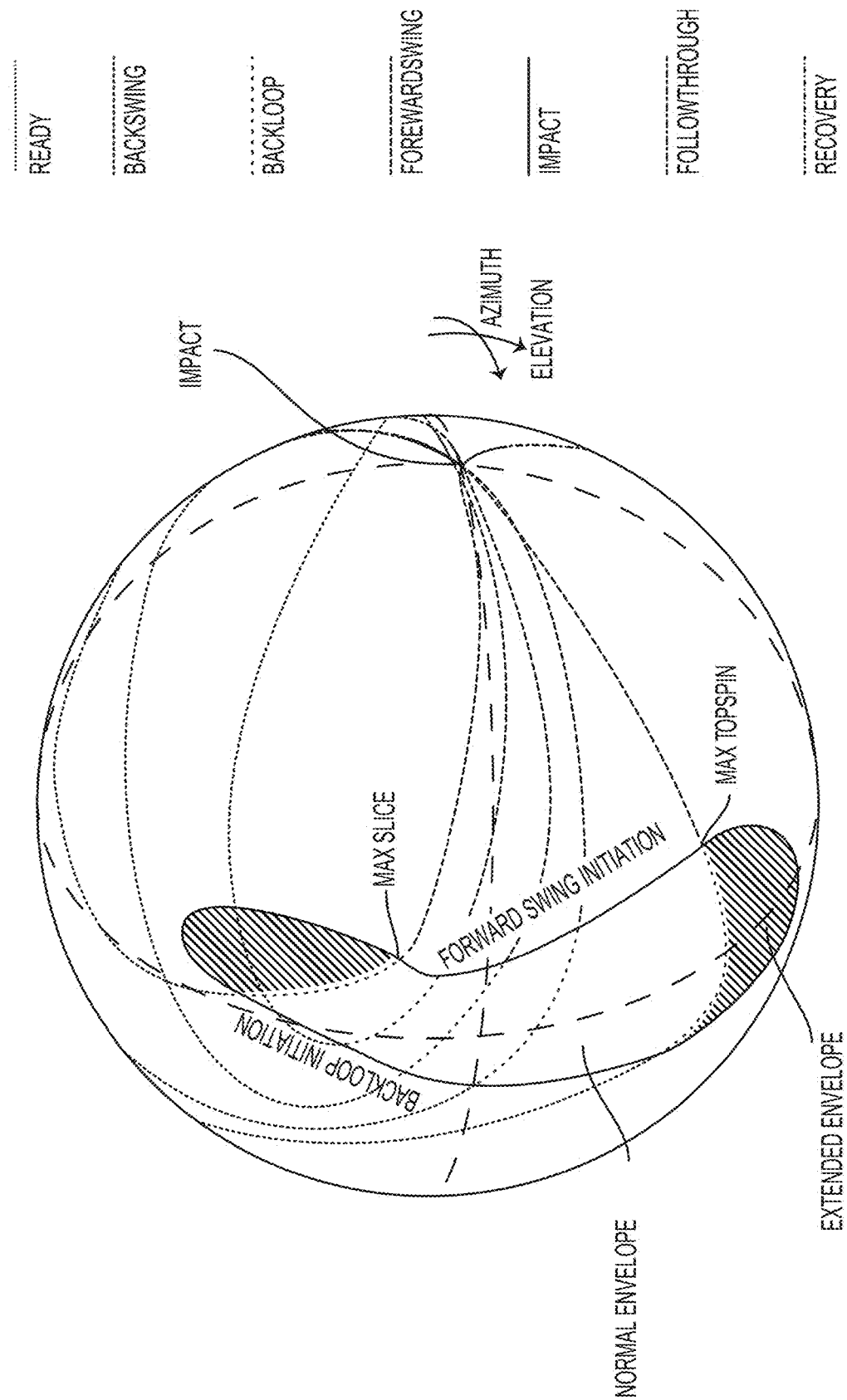
FIG. 16D illustrate an angular motion for several forehand strokes with different topspin and slice outcomes and highlights the stroke phases. The figure also illustrates a normal envelope and an extended envelope associated with the back loop phase.

Given oncoming ball condition (trajectory, height, pace, spin) and desired outcome trajectory (determined by amount of top-spin, strength and momentum transfer), calls for a specific initial racket state at the forward swing initiation FIG. 16D. The initial forward swing state, in turn defines the initial back loop state, etc. Slightly different muscle activation patterns and phase timing are used to modulate the response but the overall stroke patterns preserve their general form. These invariant properties are due to the fact that strokes in each class belong to the same sensory-motor pattern.

The control of the ball trajectory is achieved by precisely controlling the spin and pace of the ball leaving the racket. The tennis example, focuses on such as top spin or pace. The following describes the phase profiles characteristics for the skill assessment FIG. 9 Box III b).

The stroke starts about one second before the impact (see FIG. 16A) when the player initiates the backswing and extends beyond the impact. The backswing is triggered by cues used to anticipate the shot direction. These are extracted visually, e.g., from the opponent's movement behavior, posture, etc. The stroke back loop and forward swing phases are directed at the ball interception and the control of the impact conditions. As noted elsewhere, the forward swing is a consistent motion with invariant conditions at about 200 msec before the impact time FIG. 16A.

The variations within a class are due to compensation for changes in impact conditions and modulation in outcome. FIG. 16B shows the racket orientation phase portrait for forehand strokes with different level of spin outcomes. Variations, of course, are also produced by random motor noise associated with human performance. Variations that are not correlated with changes in the outcome are compensatory. In tennis for example, adaptation is required to accommodate varying impact conditions (pace of the oncoming ball, impact height or spin) and modulating outcome (amount of top spin or pace). Variations that are correlated with the outcome highlight the functional properties of the movement.

The phase decomposition makes it is possible to determine relationships between specific phase segment features and outcomes. FIG. 16D shows an ensemble of phase profile segments for the high-strength, forehand top spin (FHTS) and forehand slice class (FHSL) across the forward swing, impact and follow through phases. The plot highlights the phase profile envelope in terms of the racket yaw rate r, the roll rate p and the elevation E.

These functional characteristics used to modulate outcome and compensation for variations in impact condition can be modeled to determine skill analysis and determine the mechanisms that can be manipulated for the design of cueing or feedback mechanisms.

Movement skill in this tennis example can be defined as the ability of players to effectively use their movement technique to achieve desired outcomes. Therefore, sensitivity analysis can be used to determine how levels of outcome are related to movement technique. As was described this analysis makes it possible to determine specific characteristics of an individual's movement technique that contribute to the outcome.

The movement profiles capture the movement performance and functional characteristics. The state variables in each phase reflect how biomechanics are used to attain the particular outcome and how this strategy is adapted to accommodate impact conditions. Many combinations of variables can potentially influence the outcome, and determining each relationship exhaustively can be inefficient. The movement model makes it possible to extract features that explain the underlying control mechanisms used for adjusting the level of outcome and adaptation to conditions.

The spin imparted to the ball is a function of combination of racket and ball states at the impact, $x_r$ and $x_b$, respectively. The state at the impact is a function of the racket trajectory x, which is given by its states including for example, the racket roll rate, pitch rate, heave rate, azimuth rate and elevation rate:

$$S = f(x_r(t_{imp}), x_b(t_{imp}))  \quad \text{EQ. 36}$$

The racket impact conditions can only be controlled indirectly through the stroke; the ball's state cannot be controlled. The impact condition, and hence the outcome is a function of the racket trajectory $$x_r(t) = x_r(p(t), q(t), r(t), \dot{AZ}(t), \dot{EL}(t), \dots) \quad \text{EQ. 37}$$

Given the model in EQ. 36. In theory, it is possible to determine how perturbations in stroke technique around some optimal trajectory $x_r^*$ changes the outcome. The perturbations are expressed in terms of the model features. Example of features include the initial conditions for the movement phases such as the forward swing or the characteristics of the phase profiles such as the forward swing roll rate. The sensitivity in the outcome relative to these features define the phase transition derivatives and phase profile derivatives.

The following illustrates these derivatives through the sensitivity of the spin outcome to phase transition and phase profile features. The four most sensitive spin outcome phase transition derivatives for forehand are:

(a) azimuth and (b) elevation at back loop initiation, and the (c) roll rate p and (d) elevation at the forward swing initiation.

The corresponding derivatives are:

$$C_{S,\Delta AZ_{BL0}} = \frac{\partial S}{\partial \Delta AZ_{BL0}} \quad \text{EQ. 38}$$

$$C_{S,\Delta EL_{BL0}} = \frac{\partial S}{\partial \Delta EL_{BL0}} \quad \text{EQ. 39}$$

$$C_{S,p_{FSW0}} = \frac{\partial S}{\partial p_{FSW0}} \quad \text{EQ. 40}$$

$$C_{S,\Delta EL_{FSW0}} = \frac{\partial S}{\partial \Delta EL_{FSW0}} \quad \text{EQ. 41}$$

Values for all four coefficients can be extracted through linear regression.

The other important characteristics of movement technique that influence the outcome are the phase profiles. The characteristics are described through phase profiles derivatives. Relevant profiles that change spin imparted to the ball include the peak racket roll rate $\hat{p}_{FSW}$ during the forward swing or the elevation profile $EL_{FSW}$ during the forward swing. The respective derivatives are:

$$C_{S,\hat{p}_{FSW}} = \frac{\partial S}{\partial \hat{p}_{FSW}} \quad \text{EQ. 42}$$

$$C_{S,\Delta EL_{FSW}} = \frac{\partial S}{\partial \Delta EL_{FSW}} \quad \text{EQ. 43}$$

FIG. 16D shows the phase profiles for a range of spin outcomes from the backswing to the impact stroke phases. Inspecting the range of topspin and slice strokes shows clear trends in phase transitions and profiles associated with these outcomes, allowing the aforementioned derivatives to be visually inferred.

For example, at the start of the backswing, the relationship between azimuth and topspin is clear. Strokes that achieve a higher amount of azimuth rotation generate more topspin. There is similar relationship between elevation and topspin. The strokes with the most negative elevation generate the most topspin, and the strokes with the most positive elevation generate the most slice.

At the start of the forward swing, the phase transition derivatives can also be appreciated from FIG. 16D. There is again a clear relationship between the elevation angle and the topspin achieved. The roll rate p is not directly visible on this figure, but examination of the data shows a similar relationship: a higher negative roll rate leads to more topspin and a higher positive roll rate leads to more slice.

During the forward swing, the relevant profiles can also be examined. Analysis of the roll rate p (not shown on the figure) indicates strong correlation between the peak roll rate and the amount of spin imparted to be ball. Generally, the peak roll rate is observed at the end of the forward swing (beginning of the impact), and the peak roll rate at the end of the forward swing corresponds to a unique trajectory. By entering this roll rate trajectory and following the trajectory during the forward swing, the user can enter the impact phase with the highest roll rate, leading to more spin on the ball.

There is a similar relationship between the elevation angle profile during the forward swing and the topspin achieved. While entering the forward swing with the most negative elevation (racket head low) is also related to an increase in topspin, in order to realize that increase, a unique trajectory has to be followed from the start-of-forward swing state to the impact state. Entering and staying on this trajectory leads to more topspin, as shown in FIG. 16D.

The outcome phase transition and phase profile derivatives provide the basis for the design of feedback to help the user maximize their intended outcomes.

These phase profile and phase transition characteristics can be extracted using a variety of numerical analysis techniques. They constitute the functional skill model that is used for the synthesis of instructions and feedback cueing laws.

According to 952 in FIG. 9 the last part of the movement model involves relating the phase profile characteristics to movement biomechanics. The phase profiles are the result of a particular combination of constraints which result from body segment, joint angles and muscle activation. The phase profile characteristics reflect the biomechanics' and other constraints such as motor control and task. Movement phases are achieved by exploiting muscle synergies which determine muscle activation and body segment coordination. Therefore, it is possible to establish a relationship between the biomechanics and extracted stroke characteristics (see 966 in FIG. 9).

In tennis, for example, the general arm motion for the primary stroke phases (from forward stroke through the impact to the follow through) is determine by the wrist, forearm and shoulder biomechanics. The wrist and forearm represent the 'end effector' that provides the fine motor control of the racket, while the gross swing motion is generated through the elbow and shoulder, as well as the entire body (torso, hips and legs).

The forearm pronation and supination (see FIG. 5), as well as, wrist extension and flexion, are an important component of the finer movement coordination necessary during the stroke phases needed to generate the optimal racket swing profiles. For example, the wrist's pronation and supination is a degree of freedom used for the generating the appropriate impact conditions during the impact phase. In advanced players, the arm movement throughout the back loop and transition to forward swing phases, follows very subtle spatial and temporal pattern.

The forearm and wrist motion play a major role in the stroke execution during the forward swing and impact phase. At the impact the wrist is nominally in neutral position or extended. The amount of extension just before impact provides range for flexion that can be used to accelerate the racket head through a whipping motion. If the flexion at impact is too large, the generation of racket head acceleration relies entirely on the elbow, shoulder and body rotation.

With sufficient measurements (e.g. surface EMG electrodes, and body segment instrumentation shown in FIG. 5) it is possible to map phase profiles to joint and body segment motion (which can be described by additional state variables). Decomposition of the profile and body segment variables in synergies provide understanding of how the phase profile is achieved and modulated based on musculoskeletal system.

This information can be used to assess the movement profile and phase transition characteristics taking into account of the individual biomechanical system. In one implementation, this information can provide detailed knowledge of strain on the body structure during the execution of movements and can in turn be used by the cueing system for alerting the player.

The phase analysis at the level of the synergies are used to generate metrics that describe the compatibility of the movement technique with the biomechanical system. At the instructions. Stroke structure is determined from interactions with the task environment which involve perceptual, decision making and information processing mechanisms. Therefore, measurement of additional quantities such as visual gaze (see 12 in FIG. 2) provides to encompass perceptual and decision making into the skill model. The primary decision making and information processing associated with the stroke are: extraction of cues from the task environment, selection of the stroke (outcome), execution of the stroke to target the outcome, and modulation and adaptation to uncertainties and evolving conditions. The primary functional dimensions of the tennis stroke include stroke phases and the states of the oncoming ball (interception, bounce, and impact).

Players select and plan their stroke well before the ball arrives on their side of the court based on observations of the opponent and the tactical considerations. The stroke is initiated based on the expected impact time and location. As the ball is approaching the player, information about the expected impact conditions can be updated. The player uses the up to date information to modulate the stroke, for example, the timing of the forward stroke and the orientation of the racket at onset of the forward swing is adjusted during the back loop, and finally, as the ball is within about 150 msec of the impact, the player initiates the forward swing. No control is possible during the forward swing therefore the initiation of that phase and the consistency of the forward swing profile have to be done with great accuracy.

The impact conditions (location on the string bed, ball spin, relative orientation of the ball relative to the string bed, motion of the racket relative to the ball) which depend on the conditions of the oncoming ball and the player's response and decision about how to engage the ball (see FIG. 2), determine the subsequent motion of the ball and the racket. The analysis of the stroke phases in concert with knowledge of the perceptual cues used by the player and the knowledge of the other task elements can be used to assess the decision making and perceptual mechanisms. These assessments can also be used to synthesize cueing laws to train those mechanisms.

The motion and skill model provide the basis for the synthesis of feedback for the user. The feedback augmentation modalities are delineated according to two primary categories: instructions that are communicated via a communication system and cues that are communicated via a cueing system. The synthesis of instructions and cueing laws follows from the motion model 950 as shown in FIG. 9. Instructions 932 can be derived from various attributes of the skill model; validation cues of outcome and performance characteristics 934 are primarily movement profile characteristics 962 and 964; and cueing laws 936 are derived from the functional characteristics 966.

Feedback cueing mechanisms are synthesized based on the individual skill assessments and skill model. They are designed to target specific aspects of the movement technique using a variety of feedback signals that are generated in real time during the movement.

The example assumes that the user has acquired a range of stroke patterns to achieve a variety of outcomes needed to control the ball trajectory in relationship to the court. These patterns are captured in the repertoire and assessed following the process described earlier. The assessment establishes the individual's skill status which specifies the normal envelope of operation for each pattern, level of outcome and movement technique variations within that pattern.

The parametric analysis framework described provides the relationship between the key movement features and their effects on the outcome in form of derivatives. The range of outcomes for each movement pattern within the normal envelope described can be divided into discrete regions according to the outcome level. For example, assuming a normal distribution in outcome, the mean outcome and the range below one standard deviation of the mean and the range one standard deviation above the mean.

The general goals of training or rehabilitation are to improve the consistency in outcome and expand the level of outcome. Consistency in outcome requires refinement of the movement technique. Improving the outcome requires optimizing the movement technique. As discussed earlier, expanding the outcome may require the formation of a new stroke pattern that best utilize the biomechanical capabilities. The formation of a new movement pattern is either from the beginning, such as for an unfamiliar movement pattern, or can be achieved from the refinement of a prior movement pattern (see FIG. 15E).

The following list describes the synthesis of instructions. Complex movements are hard to comprehend due to their high-dimensionality and dynamic nature. Instructions build on the movement structure. Breaking down the movement in phases helps form an intuitive understanding of movement structure and its basic elements.

The assessments are communicated in the forms of reports that provide an overall summative description of the individual's performance. The reports combine metrics and visualizations. Assessment components organized by level are:

Repertoire: description of the movement repertoire highlights how an individual breaks up the problem space into outcomes. This is an aspect of skilled behaviors in open skills, which require users to develop a variety of patterns to address the broad range of task conditions and outcomes.

Repertoire metrics: (i) range of movement patterns and associated range of outcomes relevant to the domain of activity; (ii) number of differentiated movement classes; (iii) coverage of task domain by outcomes; (iv) success rate in movement class; (v) movement classes with best/worst outcomes.

Movement Phases: decomposition of the movement in each class in terms of movement phases. The goal of assessment at this level is to help individuals understand the organization and structure of movement in the context of a task.

Movement phase metrics: (i) adaptability of movement to uncertainties in activity's task conditions and environment.

In addition, the several physical performance metrics can be derived from the phase segmentation and functional analysis including:

(i) efficiency of the movement technique in achieving their outcome;

(ii) given musculoskeletal constraints, physical stress profiles at various movement phase.

The following describes the embodied implementation of the visual elements of the User Interface (UI) of the platform. These visual elements enable users to build an understanding of their tennis stroke's movement structure, and potentially provide an interface to enable or generate personalized instructions and real time cues (see FIG. 6). This embodiment assumes that the visual elements are deployed via a "mobile app" running on a user's smartphone or smartwatch.

The more complicated interactions with the visual elements will likely take place during breaks in the training or play. The elements are presented over a series of "screens" within the mobile app.

The aggregate screen provides a summary of current or past session data, with an emphasis on highlighting the types, durations, & number of sessions/sets, player info, locations, and types of training performed. The data can be presented as a list or graphically. This screen allows the selection of specific sessions/sets/time periods/outcome ranges/etc. These selections can then be used for comparison with other aggregations or explored on their own, investigating aggregate statistics, trends, or examining the movements in more detail. The screen allows the creation of a "stroke map" of a user's data based on a specific aggregation.

The system can generate a map of a player's tennis stroke repertoire (so-called "stroke map") based on the history of all strokes performed while using the system was capturing data; this stroke map is displayed on the mapping screen. The stroke map enables understanding of the overall repertoire versatility and quality of a user's skills. This organization allows for fast understanding of which techniques produce which outcomes. The mapping enables: mapping of tennis stroke repertoire as the user performs the activity; browsing and navigating the stroke repertoire across sessions of activity; providing outcomes of stroke technique including ball spin, impact location, and direction; and viewing of stroke technique as stroke paths and associated phase segments. As will be appreciated by those skilled in the art, the features illustrated in the mapping screen change for non-racquet related activities.

The general classification structure for a user's tennis stroke repertoire is the tree shown in FIG. 11. The tree informs the user interface interactions relating to exploring the classes. Strokes & their associated information within the different categories 1120 (e.g., groundstroke, overhead, volley, serve), types 1130 (forehand, backhand), and classes 1140 (FH Class A, FH Class B, FH Class X) can be viewed in multiple ways. The tree also allows users to navigate down to and between individual stroke phases. The stroke 1110 can be segmented into phases 1150 (impact, follow through, recovery, backswing, back loop, forward swing) which has attributes 1160. These plots can be used to highlight the corresponding trajectory segment along with the performance and skill attributes derived from the phase features. The embodied example is based on tennis, however, a user interface to enable the navigation of movement performance data for other activities would involve similar general structure, components and modes of interactions.

While the Aggregate Screen was previously described as being used to select the data for the Mapping Screen, the Mapping Screen itself may allow selection of data. Options include: current, displaying only recent strokes (recent either by time, session, or set); historical bests (based on outcomes or other performance metrics). The Mapping Screen allows for exploration of the classification tree by means of specific views. These views are the "Category View", "Class View", "Phase View", and "Feature View". The "Category View" (no example shown) provides the broadest view across stroke classification types. It is functionally similar to the "Class View", covering a broader dataset. The Class View 1910 displays movement categories one level down (in the example, groundstroke subclasses are shown) showing classes of the repertoire for the appropriate aggregation, organized by movement characteristics such as spin (top spin, flat, and slice) and strength (low, medium, and high)

(see FIGS. 19A-19B). The data can be outlined as a matrix, each cell describes a particular category and class. The cells can present basic statistics such as the fraction of different categories and classes (% for the set or session), the number of faulty movements in a class/category (% faults), or statistics on performances and outcomes. Alternatively, the cells can plot the strokes belonging to the current aggregation, presenting the data in a more visual format. This includes trajectory ensembles 1912, in the form of time histories (see FIG. 19A), phase diagrams (see FIG. 16C-1 to 16C-2), 3D movement rotations (see FIG. 16B), histograms, scatter plots, etc. The goal is to provide both intuitive and detailed description of the movement patterns. The user can then choose to go deeper in the analysis and select the particular subclass (in tennis spin class and strength) to bring up a "Phase View" (FIG. 19B).

The goal of the Phase View 1920 is to convey detailed information about the racket movement states, movement phases and movement segments for an ensemble of strokes or single strokes and their relationship to stroke outcomes or stroke phase timing. Displaying an ensemble of strokes, by plotting quantities such as swing rate r, roll rate p and elevation θ, for the 'forward swing', 'impact', and 'follow through' phases, provides detailed descriptions of the phase profiles. Such plots can be viewed either as a function of time or as a function of racket azimuth (Δφ)). Phase portrait representations (e.g. r vs. ΔAZ), which take away the explicit temporal characteristics, highlight the particular phase profile envelopes for these stroke types (forehand vs. backhand) and stroke classes (topspin, slice). The Phase View can highlight the specific phases by assigning unique colors; e.g., red for forward swing, black for impact, indigo for follow through. This type of plot makes it possible to gain detailed insight into the angular motion during those phases (front view see FIGS. 19A-19B). The Phase View can also display similar information as the class view (e.g., 3D movement rotations, histograms, scatter plots, etc.), just applied at the phase level.

Phases can also be related to behavioral aspects (Path View, FIG. 18B), biomechanical aspects (Synergy View showing the change in configuration of relevant biomechanical components FIG. 5 over a phase profile), and functional factors (Feature View, FIG. 16D). The Feature View FIG. 16D provides a detailed representation of the movement features that have been identified from sensitivity analysis. The view can selectively display a set of features that have the strongest impact on the movement outcome. In the example of FIG. 16B, the view is based on the racket orientation (elevation and azimuth) as viewed on a unit sphere, with orientation relative to the impact datum frame (IDF). Such a plot combining the coupling between the azimuth and elevation angles is intuitive for understanding the coordination at the various movement phases.

In one configuration, the user can interact by rotating the sphere in FIG. 16B (shown here using two fingers) to inspect relevant aspect such as the phase transitions. The three panels highlight different views. The "rearview" shows the backswing-backloop-forwardswing transition. The "side view" shows the forward swing-impact-follow through transition. The "front view" shows the follow through-recovery transition. This display highlights features that correspond to variations in outcomes for strokes. The display also shows the regions of "normal envelope" that characterizes the individual range of outcome for this stroke class, and the "extended envelope" that allows the individual to optimize the outcome given the current movement pattern. The Feature View helps to teach the user what aspects of the movement technique should be emphasized during training to best control the level of outcome. In the example configuration, the user can interact by rotating the sphere in FIG. 16B (shown here using two fingers) to inspect relevant aspects such as the phase transitions and associated states.

The Path View FIG. 18B provides a detailed representation of the movement technique by visualizing the motion of the racket center of mass (CM) path in 3D space. A specific movement or stroke can be selected from an ensemble of strokes or from session histories. This 3D representation can be animated to help visualize the racket path or performance of the movement in each of the phases. The Stroke Path view can also be used to depict relevant features of the movement.

Synergy view depicts a relevant body segment during a movement phase. This representation allows the user to understand the implications of a movement technique on the biomechanical system. For example, for the forward swing phase, the synergy view displays the shoulder rotations, elbow extension, forearm pronation and wrist extension (see FIG. 5) during the phase and highlights potential strains or risks of injury that have been assessed from the performance. Through a combination of the assessment and augmentation features of the system, the system can suggest injury alert cues that help prevent the body segments performing at-risk movements in one or more phases.

The app supports a number of user interactions with these visual elements. When viewing strokes, the user can pinch and zoom in on a single stroke or stroke phase segments 1920. Panning and tilting of 3D visualizations can also be performed (see FIG. 16B and FIG. 18B). Additional functionalities include tagging and marking stroke phase segments. A user can also set cues based on the visualized phase segment features (see FIG. 16B, and FIGS. 19A-19B), possibly based off a specific visual prompt, from a selection of relevant cues, or based off a custom user request.

The primary feedback augmentation derived from the motion model and general movement functional characteristics (see 930 in FIG. 9).

Figure 24A:
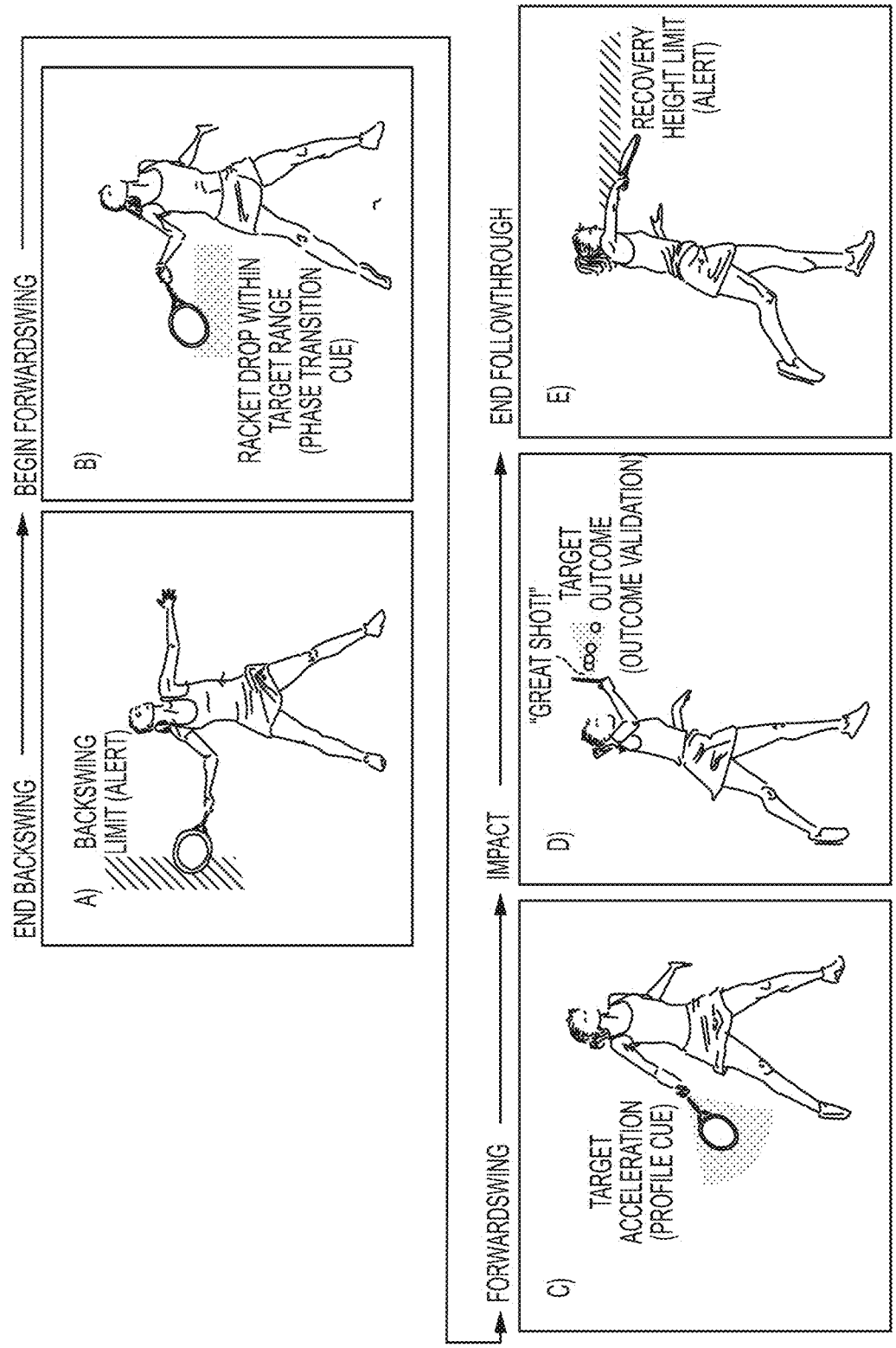
FIGS. 24A-24F illustrate the cueing mechanisms (outcome validation, alerts, and profile and transition cues) at different movement phases for tennis, skiing, golf, running, swimming, rehabilitation.

Outcome validation: real-time feedback signal to inform player that the movement attained the desired target outcome. For example, the target outcome for topspin can be set. Outcome feature validation: real-time feedback signal to inform player that the movement technique for a desired target outcome (see d) in FIG. 24A). Similar to the outcome validation but in addition, a signal is generated to signal movement conformance in terms meeting the features for movement outcome. Potential features include movement state at phase transition and phase profile.

Outcome feature validation are based on the discretization of the outcome levels described earlier. Using the same quantization of the outcome in three tiers as for the outcome validation, for example, a movement technique that produces an outcome at the second level (med) will produce a discrete tone pulse(D) at each the back loop initiation and forward swing initiation (see b) in FIG. 24A). In addition, a pulse (D) is produced at the impact if the outcome reaches the expected medium spin level (see a) in FIG. 24A).

Alerts: real-time feedback cue to signal specific movement features that are detrimental to performance or outcome. They can also be used to protect the user from injury. For example, racket backward during the backswing (see a) in FIG. 24A) or racket elevation at the end of the follow through (see e) in FIG. 24A). The alerts can be used for general movement or for a specific movement pattern.

Outcome optimization: real-time feedback cues to help optimize movement technique for a specified outcome. The mechanism for outcome optimization cueing is derived from the sensitivity analysis. For example, the four derivatives that were illustrated for the diagnostic: the racket roll rate and the racket elevation at the forward swing initiation and the racket elevation and azimuth at the back loop initiation (see FIG. 16D). The general idea is to provide cues to help enforce features that are maximize the outcome. This is achieved by combining feature components based on multivariate derivatives. The selected phase transition features describe specific aspects of the stroke technique that are correlated with the outcome. For the forehand example shown in FIG. 16D, when considering the top spin outcome, these features include the racket elevation and orientation at the back loop initiation, and forward swing initiation. The result can be implemented as a phase transition or phase profile cue (see b) and c), respectively, in FIG. 24A)

An alert cue can be used to help protect the subject from injury or wear can be implemented based on the analysis of the relationship between movement profiles and biomechanical system. For example, the phase profile during the forward swing and impact can be mapped to the wrist and forearm joint motion and muscle activity (FIG. 5). The synergy decomposition, can be used to determine joint deflections and muscle activation profiles. This mapping can then be used to detect when these quantities are exceeding some acceptable values. This information can be used to generate alerts in the form of phase transition and phase profile cueing to help form movement patterns that are compatible with an individual's musculoskeletal conditions.

All of these feedback cues help the player develop "muscle memory" through association between the features of the movement phase and corresponding effects on the outcome. Cueing also helps the players develop understanding of the movement structure and organization.

Note that it is also possible to design more general cue profiles that are not targeting specific outcome. For example, cues that are useful for any forehand or backhand groundstrokes. Such cues emphasize general aspects of the technique, such as the extend of the backswing, the follow through. Some features are common to particular stroke classes, therefore, it is possible to have class specific general cue profiles. Such cueing profiles require identifying the stroke class in order to select the set of cue features appropriate for the class.

Further details of cueing laws are provided as part of the description of the cueing system for the tennis application.

The following describes the system components for the implementation of feedback augmentation. Feedback augmentation is enabled by the cueing system. The cueing system shown on FIG. 10 has two primary components: a cue processor 1010 and a cue generator 1030. The cue processor translates movement data into cue signals. The cue generator translates cue signals into physical stimuli (in the tennis system, audio sound waves).

There is no restriction to the layout of the cueing system components, although certain organizations will be more effective or practical. One such implementation has the cueing system operate entirely on the embedded sensing device. Alternatively, the cue processor can operate on a mobile device and the cue generator on a smart watch, with cue signals transmitted between them. As will be appreciated by those skilled in the art, these different hardware implementations don't affect the functional principles.

Within the cue processor, there are two components: the state machine 1020 and the cueing law calculator 1012. The state machine is further broken down into a movement phase estimator 1024 and a feature extractor 1022.

Figure 20B:
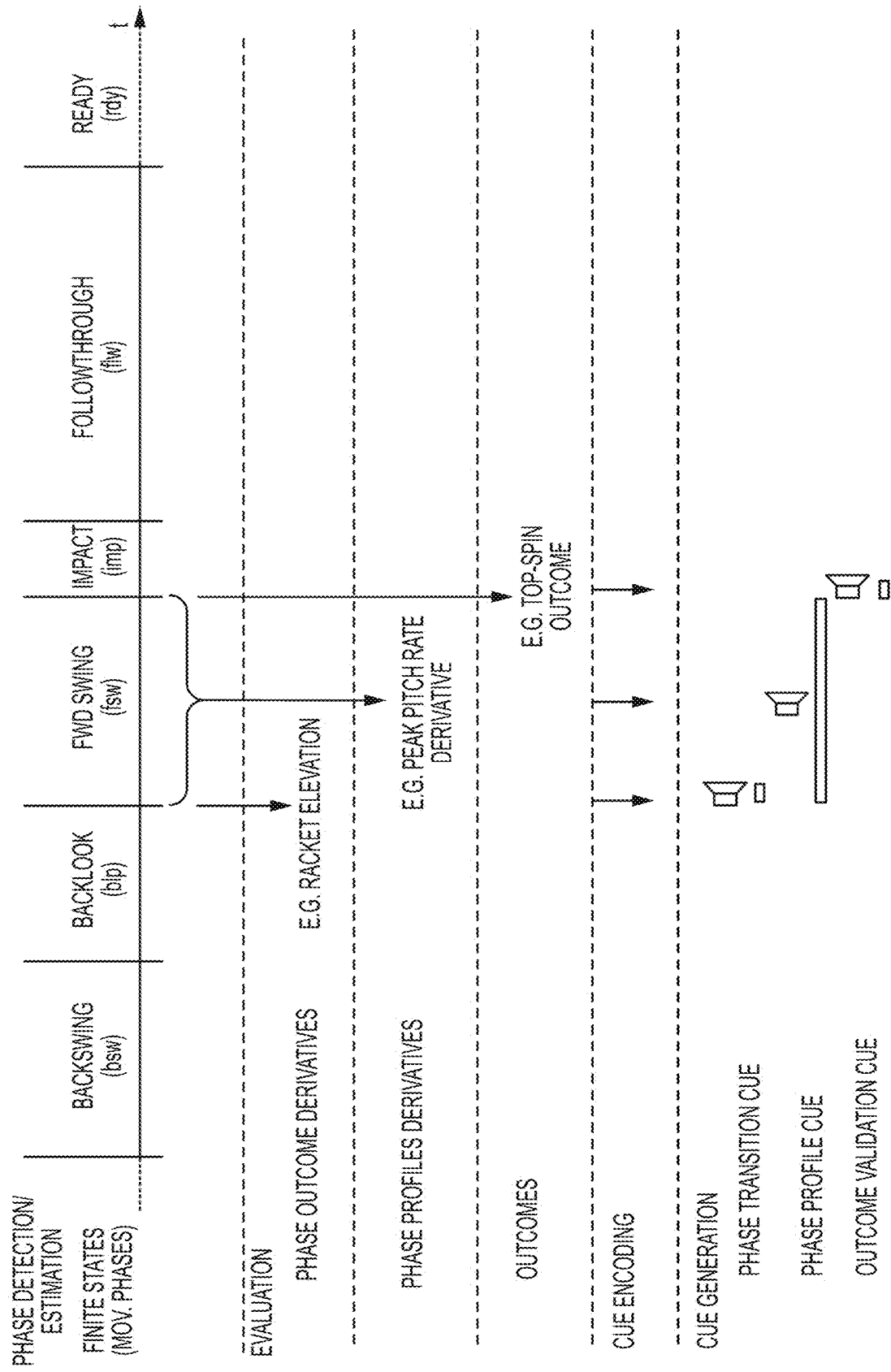
FIG. 20B illustrates the processes of the cueing system for top spin augmentation profile over the stroke cycle, highlighting exemplar phase transition and phase profile derivatives and other quantities extracted for the computation of the feedback cue.

During operation, preprocessed motion data is sent to the cue processor (see FIG. 10 and operations in FIG. 20B). The preprocessing step translates raw sensor data into engineering quantities as well as providing filtering or physical quantity estimation (i.e., orientation). Quantities relevant to tennis were chosen after analyzing recorded sensor data. The finite state estimator operates as a finite-state machine. It's defined by the current phase state vector and has rules governing transitions between states. The state vector of the finite state machine also includes various quantities which are tracked in order to more effectively estimate the current state. From the provided data, it estimates the current phase segment of the racquet and player.

A description of a potential implementation of the finite state estimator follows. As will be appreciated by those skilled in the art, successful phase estimation can be successfully achieved using different classes of approaches (finite state machines, HMMs, etc.) or different parameters for the same approach. This finite state estimator was designed using empirical analysis and is a type of finite state machine. It considers a reduced subset of possible states: ready, backswing, forward swing, impact, and follow through (S=Sr; Sb; Sf; Si; St). An example of its operation is shown in FIG. 20B. The state transitions are governed by the following rules:

Ready: the ready state is left when a significant amount of z-axis rotation has been detected, as determined by integrating the z-axis angular rate.

$$s \rightarrow S_b: |\smallint_{t0c}^{t} r dt| > r_{fthresh} \qquad \text{EQ. 44}$$

Or, the absolute value of the integral of the angular rate r between the most recent time where r crossed 0 and now needs to be greater than a specified threshold. This has the disadvantage of not detecting the state transition until the middle of the backswing (leading to some inaccuracy), but it does reject a number of "false positive" state transitions that would otherwise occur. The latency is not an issue for this transition as cues are typically not delivered on the entry to backswing.

Backswing: the backswing state transitions to the forward swing state when a z-axis rotation rate zero-crossing is detected, or the ready state if excessive time has passed. The forward swing transition is governed by the following rule:

$$s \rightarrow S_r: \operatorname{sgn}(r(t-)) \neq \operatorname{sgn}(r(t+)) \qquad \text{EQ. 45}$$

And the ready state transition is governed by a separate rule:

$$s \rightarrow S_r: t - t_{0c} > t_{bs,max} \qquad \text{EQ. 46}$$

Or, if the time between the start of the backswing and the current time is greater than the maximum allowable time for a backswing, the machine transitions to the ready state, as it is assumed something interrupted the stroke and the impact will not occur.

Forward swing: the forward swing state can transition either into the impact state or the ready state. The transition to the impact state is determined by:

$$s \rightarrow S_i: \quad \Theta(|\dot{H}_z| > \dot{H}_{z,threshold} \wedge |\dot{a}| > \dot{a}_{threshold} \wedge |a| > a_{threshold}) = 3 \qquad \text{EQ. 47}$$

Where $\dot{H}_z$ is the time derivative of the angular momentum vector's z-axis component. The above rule states that the machine transitions to the impact state when all three of these statements are true during the forward swing: the z component of the time derivative of the angular momentum vector is above its threshold, the magnitude of the jerk vector is above its threshold, and the magnitude of the acceleration vector is above its threshold.

While this rule is being checked at each time step, an additional rule is also being checked:

$$S \rightarrow S_r: t-t_{0c} > t_{fs,max} \qquad \text{EQ. 48}$$

This is similar to the "backswing exit" rule, which is that if excessive time has passed, the machine transitions to the ready state.

Impact: the impact state automatically transitions to the follow through state when tested:

$$s \rightarrow S_t \qquad \text{EQ. 49}$$

Follow through: the follow through state will transition to the ready state according to the following rule:

$$s \rightarrow S_r: t-t_i > t_{ft,min} \; \text{sgn}(r(t-)) \neq \text{sgn}(r(t+)) \qquad \text{EQ. 50}$$

Or, the follow through state transitions to the ready state when a minimum amount of time has passed and a zero-crossing for the z-axis rotation rate has occurred after that time passing.

The feature extractor is responsible for combining the phase estimate and the motion data into a feature quantity. As described, features are quantities extracted from the data that have been shown to be relevant to required processing.

For tennis, there are two broad categories of features: continuous and discrete. The phase profile features described are a subset of potential continuous features; phase transition features as described are a subset of potential discrete features. Other discrete features include outcomes, alerts, non-transition related timings or actions, or others.

During operation, the feature extractor has a mapping of phases to features-to-compute. For example, during the backswing phase, the extractor has instructions to compute peak azimuth rate, continuous roll rate, elevation at end-of-phase, as well as others. During the impact phase, the extractor's instructions will include computations for the outcomes.

The relevant features for any given cueing situation will inevitably be a subset of the set of all relevant features for a user, or potentially for all users. However, the set of all relevant features is significantly smaller than the set of all potential features. Furthermore, as previously discussed, the dimensionality of the human movement problem is intractably large. A component which essentially only filters through relevant pieces of information simplifies the system design.

The extracted features and the current state estimate are then provided to the cueing law calculator, which is responsible for interpreting them and generating a cue signal. It has its own parameters used to compute the cue signal. The cueing law calculator's parameters are in part defined by the active cueing profile (as discussed) and by other parameters relevant to the current user.

The cueing profile is in part responsible for this configuration—the selection (by "THE SYSTEM" or by the user) of a profile will determine which cues are currently active. Rather than computing all cues, only computing relevant cues reduces load on the system.

Part of this active configuration is a mapping between phases & features to cue signals and quantization levels. For example, such a mapping would relate starting swing rate (discrete feature) during the forward swing (phase) to a cue signal for outcome feature validation with levels at swing rate={0, 5, 10, 15, 20, 25, inf}. Another example is a mapping relating the elevation rate (continuous feature) during the backswing (phase) to a cue signal for outcome optimization against a target elevation profile, with levels relative to the target profile at {−40%, −20%, ±5%, 20%, 40%}. An alert cue, for example, can be synthesized from the forearm pronation (see FIG. 5) to monitor the safe range of motion for the wrist during the various movement phases. The forearm pronation alert cue maps the relevant quantities to two discrete levels {safe, unsafe}.

Multiple maps across phases, features, signals, and quantization levels can be active at any given time and multiple signals can be generated. The target or reference values/profiles as in 720 will be computed offline, and provided as part of the cueing law parameters.

The cue signal will be a description of what is being cued on, the levels, and whether the signal is continuous or discrete. Both the cueing law calculator within the cue processor and the cue encoder within the cue generator will need to be configured to have shared knowledge of what cue signals are currently defined (e.g., if the cueing law calculator is sending an outcome cue type signal, the cue encoder needs to have provisions to handle such a signal).

A more detailed example for the outcome validation cue signal follows. The cue signal can be encoded based on quantized range of outcome, where quantization levels correspond to outcome quality tiers. Consider a top spin quantization with four tiers (S={(200, 500), (500, 1000), (1000, 1500), (1500, inf.)} rpm:→{low, med, high, very high}). The cue signal is defined as:

$$200 < |S| < 500 \text{ rpm} \rightarrow y_{signal}(\text{low})$$

$$500 \leq |S| < 1000 \text{ rpm} \rightarrow y_{signal}(\text{med})$$

$$1000 \leq |S| < 1500 \text{ rpm} \rightarrow y_{signal}(\text{high})$$

$$1500 \leq |S| < \text{inf.rpm} \rightarrow y_{signal}(\text{very high})$$

and $y_{signal}$ needs to be defined as a "topspin outcome" cue.

These cue signals are used to generate a cue stimulus that can be perceived by the players at the instant of the impact. The cue generator is responsible for generating this cue stimulus. For tennis, stimuli are aural; either pulses, tones, or continuous waveforms.

As shown on FIG. 10, the cue generator 1030 is divided into two functional blocks: the cue encoder 1032 and the transducer 1034. The cue encoder accepts the cue signal and determines what waveform to provide to the transducer. The transducer then converts the waveform into a soundwave for the user to hear.

As described previously, the encoder takes in cue signals and based off its configuration will generate an audio waveform for the transducer. The cue encoder does not require a sophisticated description of how to interpret the signals. Its requirements are to have a mapping between cue signal type, cue signal quantization level, cue signal discrete/continuous and corresponding audio waveforms. Rules for combining mappings are also necessary.

For example, the cue encoder can be configured with a mapping of "outcome feature validation for elevation rate", "{10, 20, 30, inf.}", "continuous" to a set of audio waveforms {WF1, WF2, WF3, WF4}. Another example is a mapping of "outcome optimization forward swing feature transition for swing rate", "{5, 15, 25, 45}", "discrete" to a set of repeating waveform pulses {WFx1, WFx2, WFx3, WFx4}.

The active mappings, both the definition of the cue signal and the resulting waveforms, are set by the cueing profile, and are determined by current goals, current user status, historical user status, and any other relevant information or personal preferences (such as how well a given user can distinguish between audio notes).

A common "language" between the user and waveform characteristics will need to be defined, so the user learns to realize certain tones are positive, or louder signals are negative. Users may have unique requirements on the types of cues they can hear, or on how effective a given cue delivery schema will be for them. For example, some elderly users require different frequencies to be used. Some users react more strongly to volume variations, and others to frequency variations. All of these waveforms can be either pre-computed and stored in audio files, or generated on-the-fly as needed. For continuous cue signals, aspects such as distortion can also encode phase profile variability; if the stroke starts out "rough" the signal may sound awkward or unpleasant, and if the user "smoothens out" the feedback will sound better.

A more detailed example of an encoding schema follows. This encoding maps outcome tiers to tones on a C major scale (C,D,E):

$$y_{signal}(\text{low}) \rightarrow y_{stimuli}(\text{low}) = \text{pulse } (C)$$

$$y_{signal}(\text{med}) \rightarrow y_{stimuli}(\text{med}) = \text{pulse } (D)$$

$$y_{signal}(\text{high}) \rightarrow y_{stimuli}(\text{high}) = \text{pulse } (E)$$

$$y_{signal}(\text{very high}) \rightarrow y_{stimuli}(\text{very high}) = \text{pulse } (C+D+E)$$

An alternate encoding could be mapping to a number of pulses:

$$y_{signal}(\text{low}) \rightarrow y_{stimuli}(\text{low}) = 1 \times \text{pulse}$$

$$y_{signal}(\text{med}) \rightarrow y_{stimuli}(\text{med}) = 2 \times \text{pulse}$$

$$y_{signal}(\text{high}) \rightarrow y_{stimuli}(\text{high}) = 3 \times \text{pulse}$$

$$y_{signal}(\text{very high}) \rightarrow y_{stimuli}(\text{very high}) = 4 \times \text{pulse}$$

The transducer 1034 is responsible for translating the audio waveform into sound waves for the user to hear. As with any such transducer, an electrical signal needs to be provided. The audio waveform generated by the cue encoder may need to be amplified in order for the transducer to have enough power to generate a loud enough sound. The encoder might not necessarily output uncompressed time series data; in this case the transducer component would be responsible for translating the encoder's output into a directly playable waveform. The transducer location may also be relevant on effectiveness. Locating the transducer on the racquet may provide the user more spatial information, but the signal itself will not be as consistent as if the sounds were generated directly in the user's ear (via a headphone for example). Additionally, the transducer need not be in the same physical location as the encoder or the rest of the cueing system; e.g., a wireless speaker. For the tennis example, the transducer can either be on the racquet, on a mobile device attached to or near the user (e.g., smartwatch, smart phone on courtside bench), or on a separate device on the user (e.g., Bluetooth headphones). Finally, the combination of these and other factors (audio transducer design, audio fidelity, power requirements, distance from ear, external noise, etc.) will have an impact on what waveforms should be provided to the transducer. One way to describe an audio waveform is to characterize its envelope with the parameters: attack, decay, sustain, and release; they describe the time to peak, time to steady state, steady state/peak ration, and time from steady state to zero. The above factors will factor into the choice of these parameters.

B. Golf

Motion skills science demonstrates that most movement activities can be analyzed in terms of primary movement units which are the movement patterns used for achieving outcomes in a task or activity. The system is configurable to generalize across many activities and train a wide range of movement types through its ability to extract structure and track patterns and from the performance histories of motion data. The following describes embodiments and implementation examples for the following activities: Golf, Running, Swimming, Skiing, and Rehabilitation.

The golf scenario considers a user who wants to improve their golf performance. Specifically, this includes improving their control over the golf ball across many different club types, swing types, and situations. Increased control over the ball will lead to a lower score, improving the user's golf performance.

A minimal implementation of the cueing system for golf consists of a sensor with an IMU, attached to the user's club. The sensor needs to be aware of what club is currently in use—accomplished by either having the user identify which club is being used, or an electronic tag placed on the club and read by the nearby sensor device. The sensor transmits the IMU data to a mobile phone. The user also wears a smartwatch, and carries their phone on or near them. The user's mobile phone is responsible for processing the sensor's and smartwatch's IMU data, calculating cues, and then either delivering audio cues via speaker on the phone or watch.

A golf session involves the user going to either a driving range, putting green, golf course, or other practice environments. They will configure and prepare their equipment. On their phone they will start the app, creating a session/set/other temporal context. They then may activate certain cues or potentially enable training drill (either action possibly being in response to an app prompt).

The following describes the key processes used in the assessment and augmentation loops (FIG. 1). The processes are implemented according to the processing components described in FIG. 9. The primary movement unit for golf is the swing.

The devices mentioned above allow to capture user motion data including: club orientation, angular rates, angular accelerations; arm and body configuration, rates, and accelerations. Relevant environmental considerations are: GPS location, wind velocity, air temperature, and/or course [ground] conditions. The outcomes recorded include the quantities necessary to describe ball final position and ball flight bath. In one implementation, the user's phone is responsible for computing these quantities; in another implementation, outcome data is acquired via alternate means.

As is the case with other open motor skills there are multiple primary movement patterns; for golf, these are different swing types. For golf, the swing type is primary determined by club selection (which is directly related to the user's current goals). Each club-dependent swing type will also have multiple classifications, based off other intended outcomes.

Figure 4A:
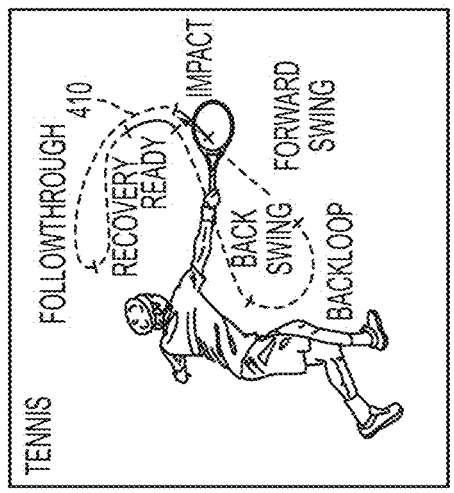
FIGS. 4A-4F illustrate primary movement patterns (or movement unit) along with corresponding phase segments for different movement activities. The drawings also highlight the quantities that can be regarded as primary outcome as a vector (effect of impacts on ball for tennis, golf and baseball, and propulsive force for running and transversal acceleration for skiing)
Figure 4B:
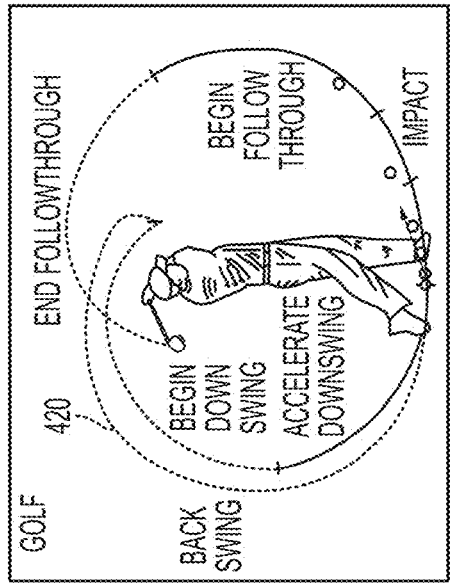
Figure 4C:
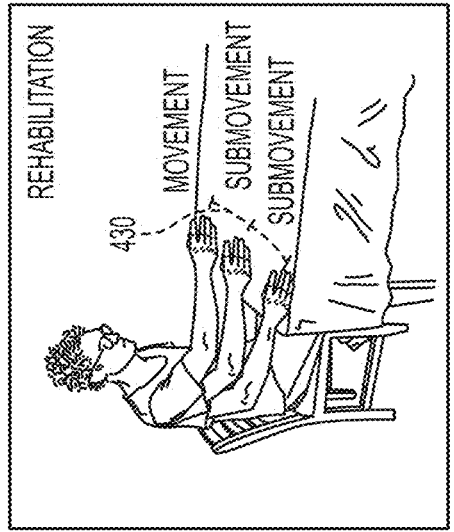
Figure 4D:
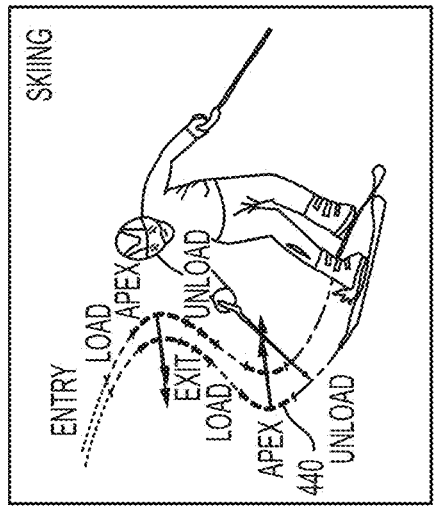

Each classification will have a unique phase segmentation as well. FIG. 4B shows examples of how the phase segmentation will vary based off the type of swing. Some swings will have a backswing, a 2-phase downswing, impact, follow through, and recovery; other swings will have only a backswing, downswing, impact, and upswing. Phase segmentation can be accomplished using a similar approach to what was described for the tennis example.

For golf, the representation of skill is heavily determined by the breadth of the user's repertoire that displays a reasonable amount of performance. Playing a game of golf involves many long shots, short shots, puts, etc. Having no swing or an incredibly poor swing in one area can easily drive up a user's score.

The skill model also encompasses the information described elsewhere in this document, recording: relationships between movement techniques and outcomes; outcome, repertoire, and/or technique trends; effectiveness of cues; and other quantities.

For golf, any of the previously mentioned cueing modalities could be used. Cues include audio feedback from either the user's phone or smartwatch. As golf is a relatively intermittent activity, there is more flexibility in how the information can be encoded. Likely choices are tone (audio note), duration, or repetition; more complicated coding (chords, chord progressions), visual feedback, or verbal feedback are also possible.

Figure 24B:
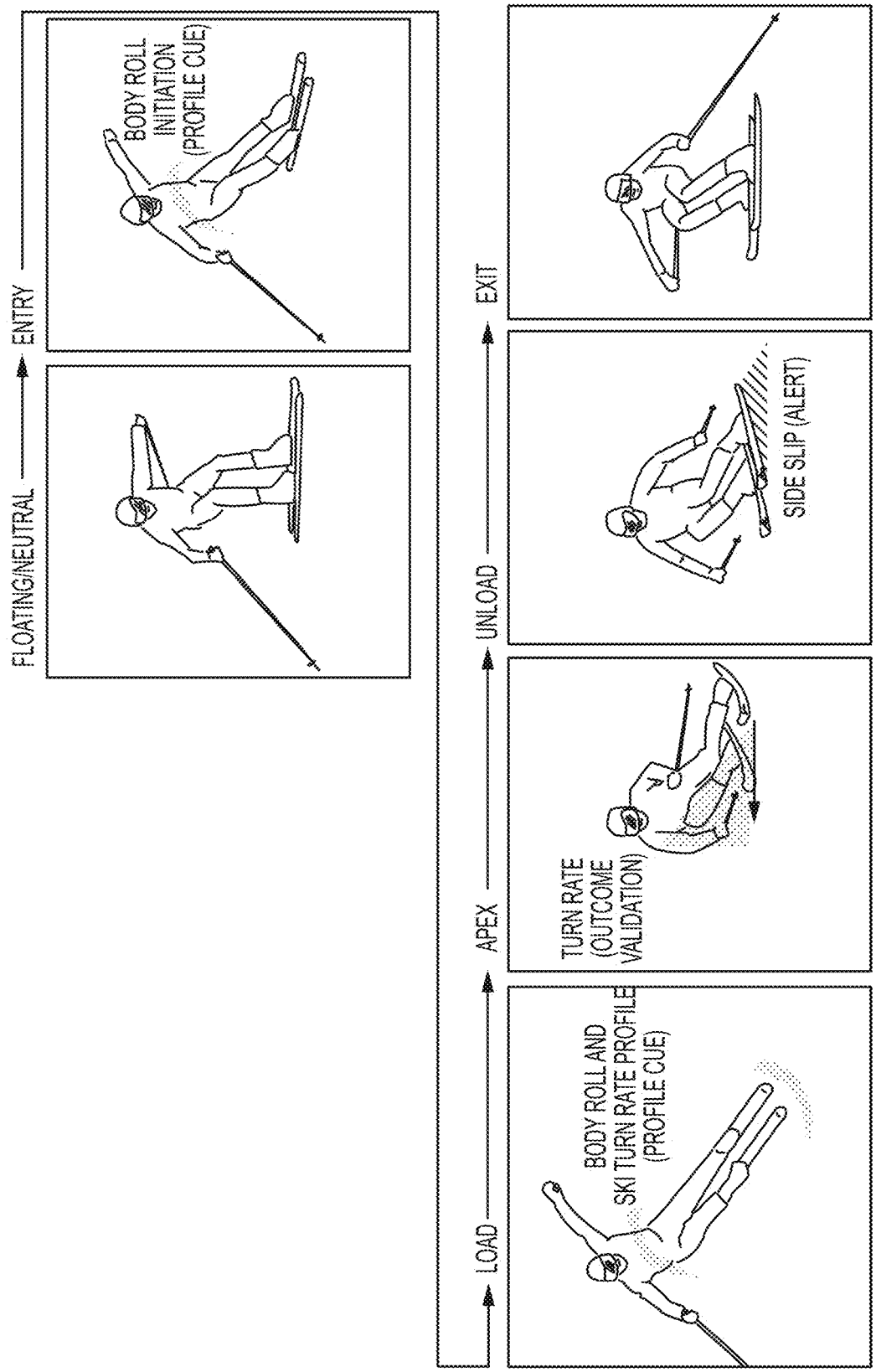
Figure 24C:
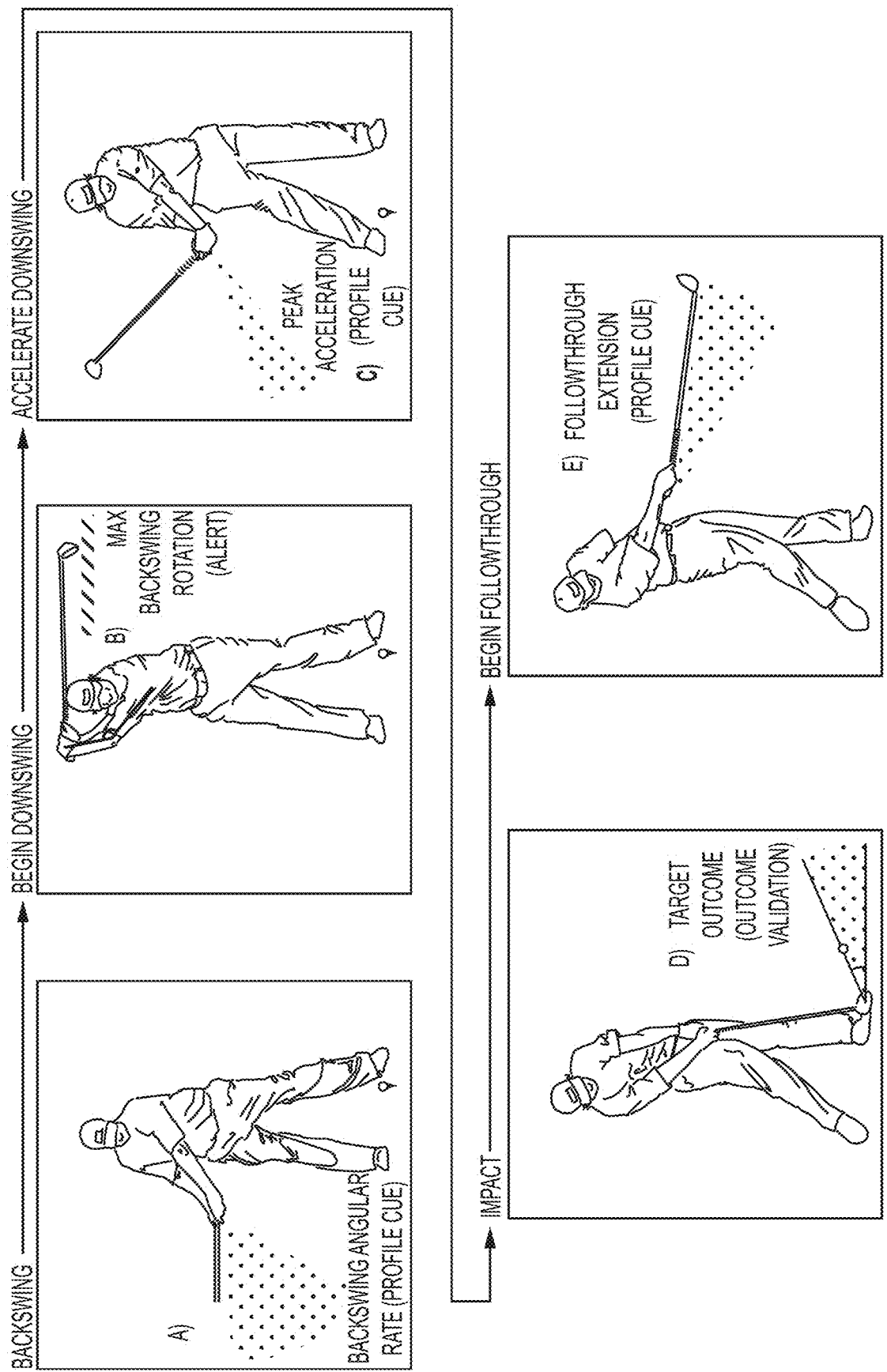

Example cues are shown in FIG. 24C and include: Phase Profile Cue—Backswing Angular Rate. To either improve or reinforce a technique, this cues the user on an appropriate angular rate profile. Alert Cue—Max Backswing Rotation. Raising the club too far back can cause injury; this cue helps the user avoid this action. Phase Profile Cue—Peak Acceleration. In order to maximize distance, the user needs to accelerate their club during the swing to match a target acceleration profile; this cue assists with this. Outcome Validation Cue—Target Outcome. This cue informs the user of the outcome they just achieved when hitting the ball (e.g., strength of shot, angle, etc.). Phase Profile Cue—Follow through extension. Impacting the ball correctly requires the club to be swinging relatively fast. Cueing the user on their follow through helps to build association.

Combinations of cues can be delivered to support technique and outcome development. One potential scenario has primary and secondary cues combined to support a more efficient golf swing trajectory while managing injury risk. An example cueing profile might be: primary cue: Alert Cue—Max Backswing Rotation; secondary cue: Outcome Validation Cue—Target Outcome. As will be appreciated by those skilled in the art, cue profiles can be made of many combinations of cues and the selection of the cue profile will have many factors.

C. Running

The running scenario considers a competitive endurance runner training to win a half marathon type event. The general outcome goal is to increase stride efficiency. Increasing stride efficiency will allow a user to move faster for the same effort, thereby increasing average speed over the course, and reducing time. A minimal implementation of the cueing system for running consists of a sensor attached to a user's foot and a phone or smartwatch attached to a user's arm or body which is in communication with the foot sensor. Both the sensor and the host in this system record movement data from an IMU. The phone or smartwatch capture GPS data. Processing is run on the host, and cues are delivered by the host via audio feedback. A running session involves a user making a decision about the goal of the session. These include training with prompted drills, entering specific routines, or just running without a specific goal.

The following describes the key processes used in the assessment and augmentation loops (FIG. 1). The processes are implemented according to the processing components described in FIG. 9. The primary movement unit of running is one stride of the gait cycle.

The devices mentioned above allow to capture user motion data including: body configuration and speed (angles, CG height, velocity); leg segments configuration and speed (hip/knee/ankle angles and rates). The outcomes of interest are: efficiency ((Energy/Stride Unit)/(Distance/Stride Unit)); maximum possible speed; forces on joints; muscle type usage distribution (division of force between slow & fast muscle fiber types). These outcomes can be computed using a gait motion estimator. These calculations are performed on the user's host device.

Figure 4E:
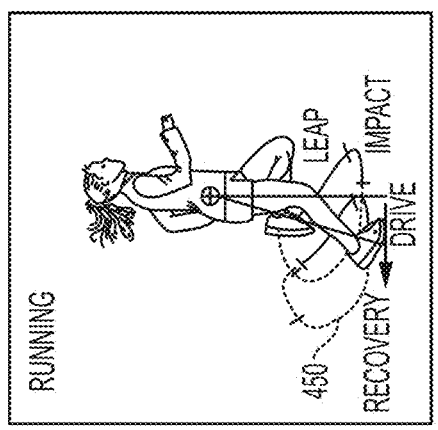

As is the case with other open motor skills the repertoire includes different type of movement patterns. For running, these are different gait cycles. FIG. 4E shows some of these, including walking, jogging, running, and sprinting, as well as their more detailed subclasses, determined by other criteria such as slope or target speed. Each gait cycle class has a unique phase segmentation.

Figure 24D:
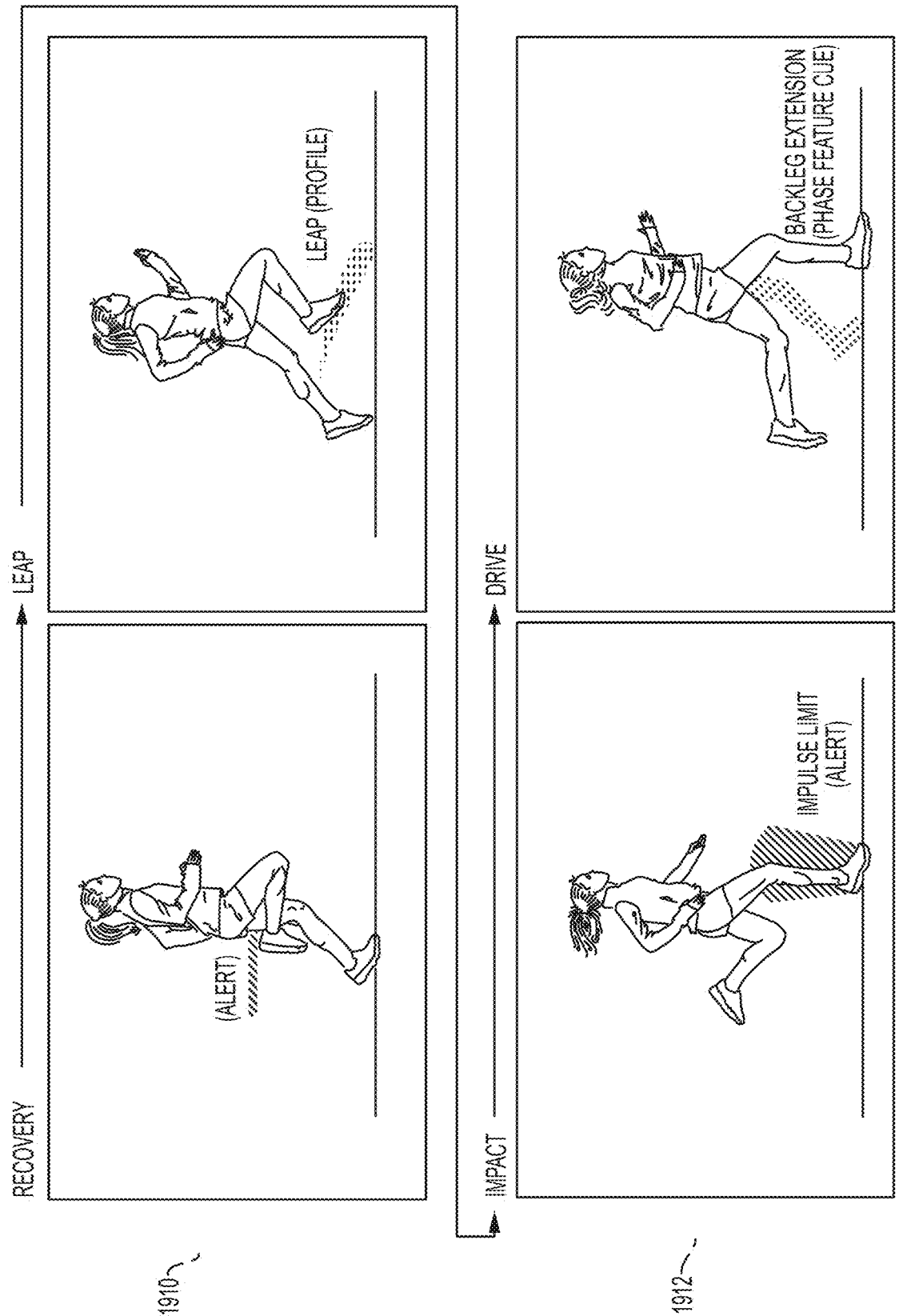

For the fast running level ground gait cycle the phase segmentation is Leap, Impact, Drive, Recovery (FIG. 24D). The phase segments can be identified using existing gait models. The phase segmentation is specific to the gait classes.

The skill model for running, includes the repertoire of gait types (e.g., walking, jogging, running, sprinting) as well as a more detailed class breakdown. For this example, the more important aspect of skill is the performance and not the repertoire breadth. The skill model also encompasses the information described elsewhere in this document, recording: relationships between movement techniques and outcomes; outcome, repertoire, and/or technique trends; effectiveness of cues; and other quantities.

The cueing modalities for running include any of the previously mentioned cueing modalities. Audible cues can be generated from either the user's phone, smartwatch, or either via headphones. The information can be encoded with characteristics such as tone (audio note), duration, or repetition.

Example cues are shown in FIG. 24D and include: Alert Cue—Foot height alert; lifting a foot too high during recovery wastes energy and therefore reduces efficiency. Profile Cue—Foot swing trajectory; having proper coordination of leg segment movements will lead to more efficient, less joint-impact strides. By cueing towards a profile for the foot to follow during the leap phase, target values for leg segment velocity and acceleration can be achieved. Alert—Impulse limit on ground contact cues runner on how hard their feet are hitting the ground on impact. Phase Feature Cue—Drive extension; the duration of the foot-ground contact and the leg extension during the contact period both affect the stride efficiency.

The cue profile provides a combinations of cues that can be delivered to support technique and outcome development. One potential scenario has primary and secondary cues combined to both maximize efficiency. An example cueing profile might be: primary cue: Profile Cue—Foot Swing Trajectory; secondary cue: Phase Feature Cue—Drive Extension. As will be appreciated by those skilled in the art, cue profiles could be made of any combination of cues and the selection of the cue profile will have many factors.

D. Swimming

The swimming scenario considers a competitive swimmer who is working on technique for speed and endurance. Specifically, the user wants to increase the efficiency of their freestyle stroke. A minimal implementation of the cueing system for swimming consists of: a heart rate monitor worn on the chest with an integrated IMU; instrumented gloves worn on the hands containing multiple pressure sensors and IMU; an earpiece which communicates audio cues. Either the chest IMU or the earpiece is responsible for determining position in the pool, via IMU sensors or possibly a connection to the phone (camera, radio strength, other). The phone receives data from all the sensors, process the data, calculate cues, and communicate the audio cues to the earpiece. A swimming session involves a user making a decision about the goal of the session, potentially train with prompted drills, entering specific routines, or just swimming without a specific goal. The training drills might be focused on improving an aspect of skill as determined by the user, the system, or another individual (i.e., coach).

The following describes the key processes used in the assessment and augmentation loops (FIG. 1). The processes are implemented according to the processing components described in FIG. 9. The primary movement unit of swimming is the stroke cycle shown in FIG. 4F. The devices allows capturing user motion data including: wrist/elbow/shoulder angles; position in pool; body roll; pressure on hand (force & sideslip of end-effector). Outcomes of interest are stroke length, stroke duration, and stroke efficiency. The outcomes can be computed from kinematic and dynamic models and sensor fusion algorithms on the user's host device.

Figure 4F:
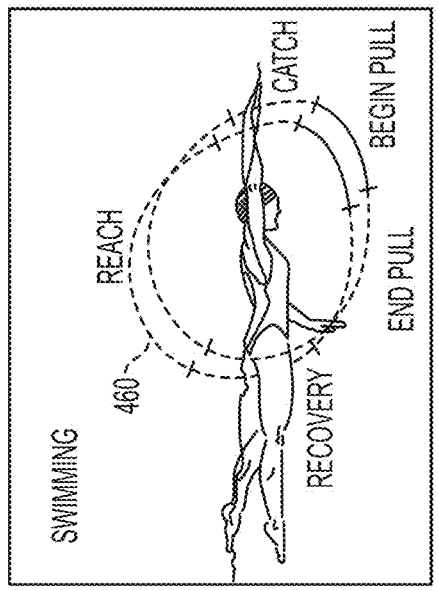

As is the case with other open motor skills, the repertoire includes different type of movement patterns. For swimming, these are the different stroke types, such as freestyle/crawl, butterfly, backstroke, etc. There are also variations in speed for each of these types (e.g., sprint, endurance). Each class has a specific phase segmentation. For the freestyle stroke, the phase segments are: pull, recovery, reach, and catch, as shown in FIG. 4F. The pull is the propulsive segment of the motion. The recovery and reach are the phases that lead to the next pull, and the catch corresponds to the initiation of the next pull. During the pull, the orientation of the wrist relative the forearm is important, as well as the orientation of the forearm in the water. Having the hand & forearm perpendicular to the direction of motion improves the stroke efficiency. Stroke length is in part determined by how far the hand reaches forward during the reach, as well as how far back the hand/forearm move during the pull. Body roll is periodic with the stroke; an appropriate amount of body roll will result in an improved stroke efficiency. Users need to be careful with shoulder movement during the recovery/reach transition. The phase segments can be identified by the shoulder rotation angle, and the amount of force being generated by the hand/forearm (via the pressure sensors) can also contribute. Different classes of movement may have entirely unique phases and phase segmentation rules though.

For swimming, the representation of the skill encompasses the repertoire of "gait" types (e.g., freestyle/crawl, butterfly, breaststroke, backstroke, etc.), as well as, a more detailed class breakdown similar to the tennis stroke class tree in FIG. 11. While the user's goal may be to improve their freestyle stroke, repertoire broadness is still valuable for example when competing in medley events. The skill model also encompasses the information described elsewhere in this document, recording: relationships between movement techniques and outcomes; outcome, repertoire, and/or technique trends; effectiveness of cues; and other quantities.

The cueing modalities for swimming include the same ones as any of the previously mentioned cueing modalities. Cues are audio feedback provided via the user's earpiece. The information can be encoded with characteristics such as tone (audio note), duration, or repetition.

Figure 24E:
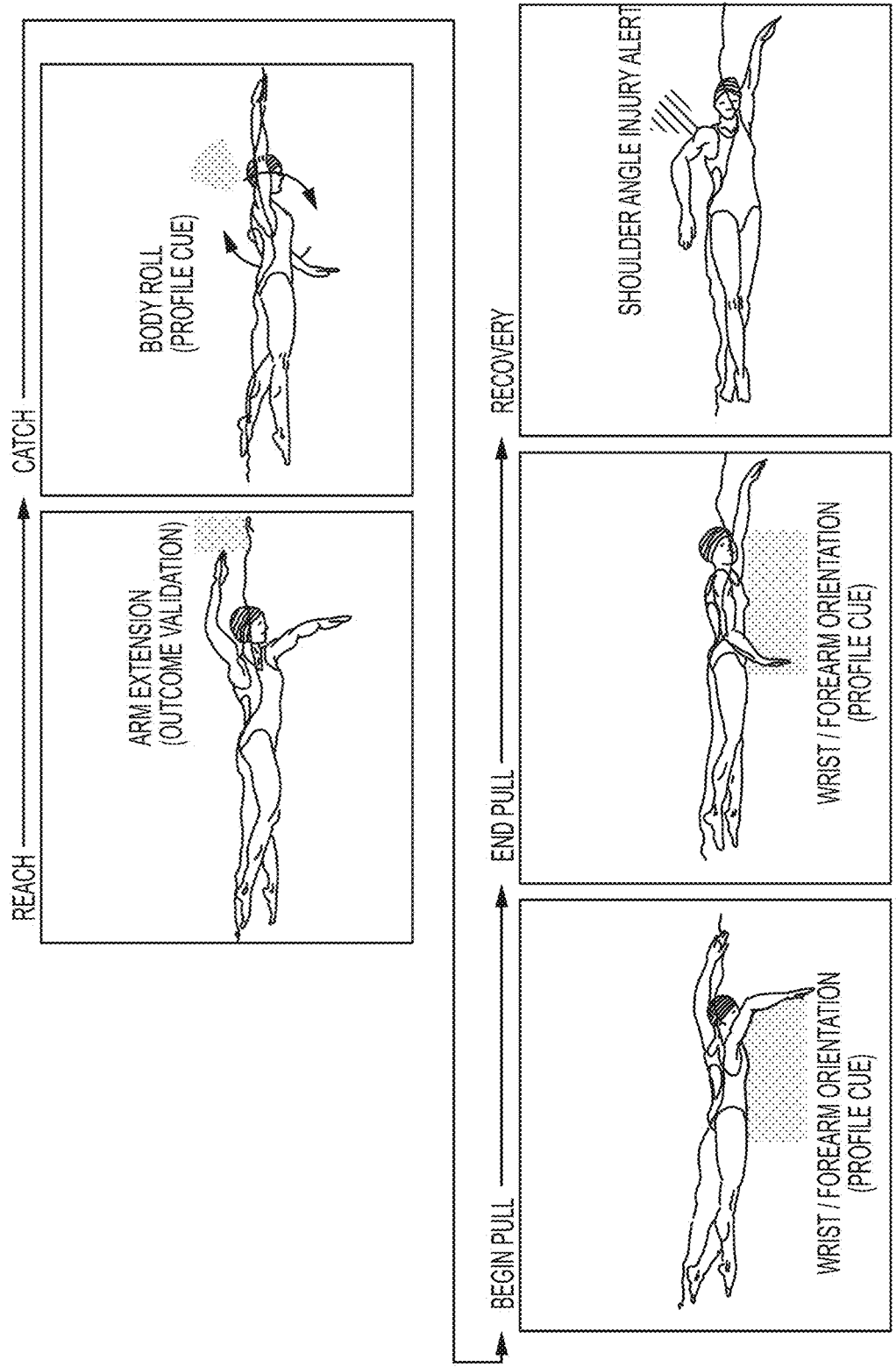

Example cues are shown in FIG. 24E and include: Alert Cue—Shoulder Rotation. Shoulder rotation injury/damage is possible during the recovery phase. Putting an alert limiting shoulder extension during this phase can therefore help prevent injuries. The "high risk" zone are identified from the users' biomechanical properties. Sensor fusion techniques are used to compute the current configuration of the arms, and detect if the shoulder extension is in the high-risk zone. Phase Profile Cue—Body Roll. This cue is used to assist the user maintain target body roll throughout the stroke motion, thereby helping maximize stroke efficiency. Phase Profile Cue—Wrist/Forearm Orientation. Hand/forearm orientation during the stroke is a continuous quantity that affects stroke efficiency that can be cued during the pull phase (phase profile cue). Outcome Validation Cue—Stroke Length. Validation cue for the arm extension at the catch transition to help maximize stroke length.

The cue profile combines cues to support technique and outcome development. One potential scenario has primary and secondary cues combined to both maximize stroke efficiency, and a separate alert cue to prevent injury. An example cueing profile might be: primary cue: Phase Profile Cue—Body Roll; secondary cue: Wrist/Forearm Orientation; alert cue: Alert Cue—Shoulder Rotation. As will be appreciated by those skilled in the art, cue profiles can be made of any combination of cues and the selection of the cue profile will have many factors.

E. Skiing

The skiing scenario considers an amateur skier who wants to improve their control during carving, of turn-in and turn coordination. A minimal implementation of the cueing system for skiing consists of: a sensor with an IMU attached to the ski-boot; the user's mobile phone capturing IMU and GPS location data. The phone receives data from all the sensors, process the data, calculate cues, and communicate the audio cues to headphones or an earpiece.

The following describes the key processes used in the assessment and augmentation loops (FIG. 1). The processes are implemented according to the processing components described in FIG. 9. The primary movement unit of skiing considered here is the carve turn segment (see FIG. 4D). The devices mentioned above allow to capture user motion data including: body, ski, and leg orientations and speeds. The outcomes of interest are: turn rate, side slip and level of turn coordination. These outcomes are computed from the available data; these calculations can be performed on the user's host device.

As is the case with other open motor skills, the repertoire includes different type of movement patterns. For skiing, these are different maneuvers used to negotiate the slope environment, such as following slaloms, carving, or crossing moguls. Each maneuver type and associated motion unit class has its specific phase segmentation. For carving, the phase segmentation consists of: Entry, Load, Apex, Unload (see FIG. 4D). The phase segments can be primarily identified by body and ski roll and yaw rates, as extracted from the sensor data.

For skiing, the skill assessment encompasses the repertoire of maneuver types (e.g., carving, moguls). In this scenario focusing on carving performance, the repertoire describes the carving maneuvers over a range of speeds and turn radii. The skill model also encompasses the information described elsewhere in this document, including: relationships between movement techniques and outcomes; outcome, repertoire, and/or technique trends; effectiveness of cues; and other quantities.

The cueing modalities for skiing, include any of the previously mentioned cueing modalities. Cues are audio feedback delivered from the user's phone via headphones. The information can be encoded with characteristics such as tone (audio note), duration, or repetition.

Example feedback cues are shown in FIG. 24B and include: Phase Profile Cue—Body roll rate profile as the skier enters the turn. Phase Profile Cue—Body roll and yaw rate profile to train proper turn coordination. During loading the skis going into a turn, the body roll angle, ski yaw rate, velocity, and side slip have to be coordinated. Outcome Validation—Turn rate target to provide feedback about turning performance. Alert Cue—Side slip warning to prevent loss of energy during the turn.

Cue profile combine cues to support technique and outcome development. One potential scenario has primary and secondary cues combined to reach target side slip values for different turn radii. An example cueing profile might be: primary cue: Phase Profile Cue—Body Roll and Turn Coordination; secondary cue: Phase Profile Cue—Body Roll. As will be appreciated by those skilled in the art, cue profiles can be of any combination of cues and the selection of the cue profile will have many factors.

F. Rehabilitation

The rehabilitation scenario considers a user who suffered from a stroke, is paralyzed on one side, and is learning to regain the use of their right hand and arm. A minimal implementation of the cueing system for rehabilitation can consist of: three combined IMU/EMG wireless sensors worn on the back of the right hand, the right wrist, and the right upper arm; a mobile phone. The phone receives data from all the sensors, process the data, calculate cues, and output the audio cues.

The following describes the key processes used in the assessment and augmentation loops (FIG. 1). The processes are implemented according to the processing components described in FIG. 9. While the entire rehabilitation process would involve many different types of movement units, the primary movement unit considered in this example is the arm motion for reaching, grasping and lifting the arm and hand.

The devices mentioned above allows capturing the user motion data including: motion of the right arm segments and hand (path and orientation) as well as the relevant muscle activity for these body segments. Outcomes of interest are duration, quality of movement (accuracy, stability).

The primary movement units considered here are segments of arm motion that are characterized by parabolic speed profiles, starting from rest and ending at rest. This allows phases to be defined as the sub-movements in this process. The trajectories are first segmented according to the movement units in the task activity. This process uses the parameters determined during the baseline assessment sessions (which then will likely change over time). For the rehabilitation case, further decomposition of movement and submovement phases into muscle synergies is performed via the sensor's EMGs. This analysis allows analyzing how neuro-motor and/or physical strength are recovering.

The cueing modalities for rehabilitation can include any of the previously mentioned ones. Cues can be audio feedback from the user's phone. The information can be encoded with characteristics such as tone (audio note), duration, or repetition. Since rehabilitation movements unfold more slowly and are more intermittent, there is more flexibility in how the information can be encoded. In some implementations, visual or verbal feedback can be used.

Figure 24F:
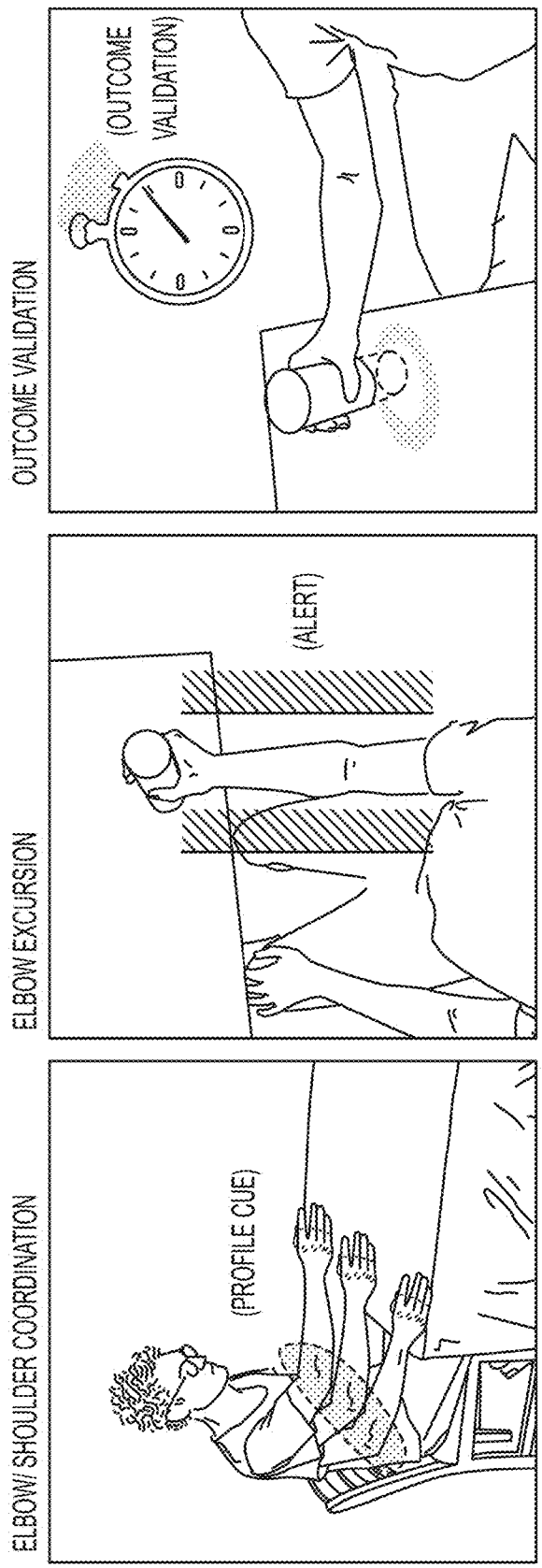

Example cues are shown in FIG. 24F and include: Profile Cue—Elbow/Shoulder Coordination. When reaching for an object, a certain amount of combined shoulder movement and corresponding elbow movement is expected. To help the patient achieve this coordination, cues can be provided to keep them on the correct profile. Alert Cue—Elbow Excursion. As part of rebuilding correct movements, limiting the total amount of variation or excursion from a nominal trajectory is beneficial. An alert cue could warn these situations to the user. Outcome Validation—Time & Accuracy. Regaining functional movement performance includes being able to successfully accomplish tasks in reasonable times. Giving outcome feedback on each action will be beneficial for a user. Combinations of Cues can be delivered to support technique and outcome development. For rehabilitation, user capabilities may vary significantly over time. Cue profiles may be limited to only a primary cue at first, and over time may integrate all the example cues discussed above. Analysis of the performances will strongly impact the available cue profiles.

Before the augmented rehabilitation sessions can be performed, the patient performs several baseline assessment sessions with a physician or physical therapist. These sessions are used to establish initial motion and skill models, baseline statuses, and realistic targets for training schedule based on clinical data. Depending on the user and conditions, these setup sessions include vision-based movement tracking systems to calibrate various algorithms, especially those used in the estimation of the body segments and muscle activations. The rehabilitation process is then organized in half-hour sessions to be completed on a daily basis. Each session can be divided into sets focusing on specific training elements. The training elements are generated from the results of the assessment, overall training goals, or other potentially relevant clinical data.

The training sessions are composed of training elements that emphasize different aspect of the movement rehabilitation. Training elements are reaching exercises. These exercises involve moving the hand between points on horizontal plane at standard table height in front of the subject, and from there to various points on the face including mouth, eyes and nose. The points are designated on a custom table cloth and auditory cues are used to direct the subject during the session, including the designation of the points on the table cloth, the timing of these movements and cueing mechanisms during the reaching movement to help refine the movement patterns. All the training elements are performed "empty handed" or include weights or accessories such as a glass or fork. The accessories are used to change movement conditions.

Following the training session, the system is used to monitor the subject's movement in natural environment interactions, for example while preparing their meal or during their meal. The collected data can also be incorporated by the system to plan the subsequent training sessions. Typical updates in training elements include: Introduction of new reaching patterns to increase the movement repertoire. Movement refinement/optimization exercises to improve outcomes (movement precision, duration, repeatability). Feedback cues are used to target deficiencies in the movement coordination and execution. In particular, to retrain patterns of muscle activation associated with the muscle synergies used in reaching movements. Timing can be changed to increase the speed of the movement patterns and sensory-motor consolidation. New movement patterns can be introduced to address deficiencies in the repertoire. The results from the daily session are also relayed to the physician/therapist who designs the long-term training goals based on clinical data and skill development data from patient with similar skill status and clinical presentations.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A motion analysis and cueing system comprising:
   one or more sensors configured to obtain motion data from a user performing a task in an environment;
   a processor in communication with the one or more sensors, the processor configured to:
   collect the motion data from the one or more sensors;
   parse the collected motion data into one or more movement units and a range of outcomes associated with the one or more movement units;
   delineate the parsed motion data into movement classes;
   model the one or more movement units, wherein a repertoire of prior movement units is formed by aggregating the movement classes;
   analyze one or more of the modeled movement units, wherein a cueing law is synthesized based on the model;
   generate a comparison of the one or more analyzed movement units to the model based on the repertoire of prior movement units used by the user to accomplish the range of outcomes, wherein the model describes reliability and/or efficiency of the one or more movement units in achieving the range of outcomes; and
   identify one or more specific aspects of the parsed motion data for change based on the comparison, wherein the processor computes one or more movement features that relate to variations in the range of outcomes and are predictive of a desired outcome in the range; and
   a cueing system comprising a cue transducer configured to provide feedback to the user based on the cueing law, the feedback selected from visual, audio or haptic stimuli to target one or more of the movement features identified as predictive for the user to achieve or improve the desired outcome in the range.

2. The system of claim 1, wherein the parsed motion data comprise the repertoire of the prior movement units formed by aggregating the movement classes, with the range of outcomes partitioned into families of movement patterns associated with the respective outcomes.

3. The system of claim 1, wherein the one or more sensors comprise a remote sensor.

4. The system of claim 1, wherein the one or more sensors comprise a wearable sensor configurable to sense one or more of a velocity or orientation for the motion data, a gravitational force, and an electrical activity of a muscle of the user, in performing the task.

5. The system of claim 1, wherein the one or more of the movement features identified as predictive impact a quality or outcome of the feedback such that the feedback validates the one or more of the movement features identified as predictive.

6. The system of claim 5, wherein the one or more of the movement features identified as predictive comprise a movement phase transition feature correlated with the desired outcome or a phase profile attribute describing an acceleration or angular rate.

7. The system of claim 6, wherein the feedback provided to the user comprises one or more of a phase transition cue for validating the movement phase transition feature, a phase profile cue for validating the phase profile attribute, and an outcome validation cue for validating the desired outcome.

8. The system of claim 1, wherein the one or more movement units are segmented into movement phases and the movement phases are decomposed into movement components related to muscular activation and body segment motion of the user.

9. The system of claim 8, wherein the feedback comprises an alert cue computed from a map of the one or more movement features to biomechanical features comprising the body segment motion of the user, the alert cue selected to protect the user from injury or wear.

10. The system of claim 8, the processor further configured for decomposing the movement phases into synergies wherein the synergies describe one or more of biomechanical and neuro-muscular relationships between the movement components and the muscle activation and body segment motion.

11. The system of claim 1, further comprising a local host device that communicates one or more of:
    training information comprising a training schedule identifying one or more of the prior movement units to be practiced by the user; and
    cueing information comprising a training profile, wherein the user selects a cueing profile that specifies the feedback as cue signals tailored to a specific goal of the training profile.

12. The system of claim 1, further comprising prioritizing one or more of the specific aspects of the parsed motion data for change based on whether a corresponding feature of the one or more analyzed movement units is changeable and will impact the desired outcome.

13. The system of claim 1, wherein the collected motion data comprise user motion data for the user and device motion data for equipment controlled by the user in performing the task.

14. The system of claim 1, wherein the cue transducer provides the feedback to the user in real time or near real time during performance of the task.

15. The system of claim 1, wherein the cue transducer is implemented within a portable device selected from a smart phone, a smart watch, smart glasses, an earpiece and a tablet.

16. The system of claim 1, wherein the processor is configured to extract movement segments corresponding to movement profiles of the one or more movement units and to delineate the parsed motion data into movement classes according to one or more characteristics of the one or more movement units, interactions with the environment, or the range of outcomes.

17. The system of claim 16, wherein the movement segments define a finite-state model describing the one or more movement units as a sequence of states corresponding to the movement phases.

18. The system of claim 1, wherein the collected motion data comprise population data from a population of users performing such a task, the population data providing information about movement technique used to achieve the desired outcome.

19. The system of claim 18, wherein the processor is configured to analyze different skill levels among the population of users and to cross-reference similarly skilled individuals among the population to borrow technical advantages from one such individual to enhance training of a second such individual.

20. A cue processor comprising:
an input for collecting motion data from one or more sensors, wherein the one or more sensors are configured to obtain the motion data for a user performing a task in an environment; and
a cueing law based on a model of the motion data, wherein the collected motion data are parsed into one or more movement units and a range of outcomes associated with the one or more movement units, and compared to the model based on a repertoire of prior movement units used by the user to accomplish the range of outcomes;
wherein the cue processor is configured to:
generate a movement phase estimation which provides a prediction of a movement phase and an associated movement feature that relates to variation in the range of outcomes, extract the associated movement feature based on the model, and apply the cueing law to the associated movement feature, wherein the model identifies the associated movement feature as predictive of a desired outcome in the range; and
generate a cue signal for a cue transducer based on the cueing law, wherein the model describes reliability and/or efficiency of the one or more movement units in achieving the range of outcomes, and wherein the cue transducer is configured to generate cue stimuli for the user in visual, audio or haptic form selected to target the associated movement feature identified as predictive for the user to achieve or improve the desired outcome in the range.

21. The cue processor of claim 20, wherein the cue processor is incorporated into a stand-alone device comprising the one or more sensors and the cue transducer.

22. The cue processor of claim 21, wherein the standalone device is selected from a smart phone, a smart watch, smart glasses, an earpiece and a tablet.

23. The cue processor of claim 20, wherein the cue signal is prioritized based on whether the associated movement feature identified as predictive is changeable and will impact the desired outcome.

24. The cue processor of claim 20, wherein the cue transducer provides the feedback to the user in real time or near real time during performance of the task.

25. The cue processor of claim 20, wherein the movement phase estimation and movement phase feature extraction include executing one or more of a phase initiation predictor configured to generate the cue signal for a movement phase transition in the movement phase, an initial phase state extractor configured to generate the cue signal based on a phase profile of the movement phase, a phase profile parameter extractor configured to generate the cue signal based on a phase characteristic of the movement phase, and an outcome extractor configured to generate the cue signal based on the desired outcome.

26. The cue processor of claim 25, wherein the cueing law compares the movement phase feature with at least one of a reference timing to generate the cue signal based on the movement phase transition, a target state value to generate the cue signal based on the phase profile, a reference profile to generate the cue signal based on the phase characteristic, and a target outcome to generate the cue signal to validate the desired outcome.

27. The cue processor of claim 26, wherein the cue generator generates one or more of a phase transition cue validating the transition in the movement phase, a phase profile cue validating the profile of the movement phase, an alert cue selected to protect the user from injury or wear, and an outcome validation cue validating the desired outcome.

28. The cue processor of claim 25, further comprising a phase state estimator configured to identify the phase profile and the movement phase transition, and a cue encoder configured for the cue transducer to generate the stimuli as harmonic notes or color schemes.

29. A motion training and cueing program comprising code stored on a non-transitory, computer-readable medium, the code executable on a computer system to perform a method of:
receiving motion data from one or more sensor inputs configurable to collect the motion data responsive to a user performing a task in an environment; and
executing the motion training and cueing program, wherein the computer system is configured to:
parse the collected motion data into one or more movement units and a range of outcomes associated with the one or more movement units;
model the one or more movement units, wherein a cueing law is synthesized based on the model;
generate a comparison of one or more of the movement units to the model based on a repertoire of prior movement units used by the user to accomplish the range of outcomes, wherein the model describes reliability of the one or more movement units in achieving the range of outcomes;
identify one or more specific aspects of the parsed motion data for change, based on the comparison, wherein the computer system computes one or more movement features that relate to variations in the range of outcomes and the model identifies which of the movement features are predictive of a desired outcome in the range; and
present at least one of a training assessment and training instruction to the user, responsive to one or more of the repertoire of prior movement units or a movement synergy describing one or more of biomechanical and neuro-muscular relationships between the movement features and muscle activation and body segment motion of the user;
operating a cueing system configured to provide feedback augmentation to the user in real time or near time based on the cueing law, the feedback augmentation selected from visual, audio or haptic stimuli targeting one or more of the movement features identified as predictive for the user to achieve or improve the desired outcome in the range.

30. The motion training and cueing program of claim 29, wherein the cue system is configurable to provide the stimuli as a plurality of speech prompts to the user performing the task, and to receive inquiries about the collected motion data.

31. The motion training and cueing program of claim 29, wherein the motion training and cueing program outputs a training schedule for the user, the training schedule comprising one or more of the training instructions.

32. The motion training and cueing program of claim 31, wherein the motion training and cueing program is performed iteratively and comprises updating the training schedule upon iteration of the program.

33. The motion training and cueing program of claim 29, wherein the collected motion data comprise user motion data for the user and device motion data for equipment controlled by the user in performing the task.

34. The motion training and cueing program of claim 29, wherein the motion training and cueing program is executed by a training agent providing output comprising the training assessment, the training instruction and the feedback augmentation.

35. The motion training and cueing program of 31, wherein the training schedule identifies one or more patterns in the repertoire of prior movement units to be practiced by the user.

36. A method of motion analysis and cueing based training comprising:
  collecting motion data from one or more sensors, the motion data responsive to a user performing a task in an environment;
  parsing the collected motion data into one or more movement units and a range of outcomes associated with the one or more movement units;
  modeling the one or more movement units;
  analyzing the one or more movement units;
  generating a comparison of the one or more analyzed movement units to the modeling based on a repertoire of prior movement units used by the user to accomplish the range of the outcomes, wherein the modeling describes reliability and/or efficiency of the one or more movement units in achieving the range of outcomes;
  identifying one or more specific aspects of the parsed motion data for change, based on the comparison, wherein one or more movement features that relate to variations in the range of outcomes are computed and the modeling identifies which of the one or more movement features are predictive of a desired outcome in the range; and
  providing feedback to the user during performance of the task, the feedback selected from visual, audio or haptic stimuli targeting one or more of the movement features identified as predictive for the user to achieve or improve the desired outcome in the range.

37. The method of claim 36, further comprising implementing the step of providing feedback to the user with a computer device selected from a smart phone, a smart watch, smart glasses, an earpiece and a tablet.

38. The method of claim 36, further comprising generating a training schedule based on one or more of the specific aspects of the parsed motion data identified for change.

39. The method of claim 36, wherein the one or more movement units are segmented into movement phases and the movement phases are decomposed into movement components related to muscular activation and body segment motion of the user.

40. The method of claim 39, further comprising decomposing the movement phases into synergies wherein the synergies describe one or more of biomechanical and neuromuscular relationships between the movement components and the muscle activation and body segment motion.

41. The method of claim 36, further comprising a local host device communicating one or more of:
  training information comprising a training schedule identifying one or more of the prior movement units to be practiced by the user; and
  cueing information comprising a training profile, wherein the user selects a cueing profile that specifies the feedback as cue signals tailored to a specific goal of the training profile.

42. The method of claim 36, wherein the collected motion data comprise user motion data for the user and device motion data for equipment controlled by the user in performing the task.

43. The method of claim 36, wherein the collected motion data comprise population data from a population of users performing such a task, and further comprising analyzing different skill levels among the population of users and cross-referencing similarly skilled individuals among the population to borrow technical advantages from one such individual to enhance training of a second such individual.

* * * * *